(12) United States Patent
Polakiewicz et al.

(10) Patent No.: US 9,920,110 B2
(45) Date of Patent: Mar. 20, 2018

(54) METHODS AND REAGENTS FOR CREATING MONOCLONAL ANTIBODIES

(75) Inventors: Roberto Polakiewicz, Lexington, MA (US); Wan Cheung Cheung, Lexington, MA (US); John Edward Rush, II, Beverly, MA (US); Sean Andre Beausoleil, Essex, MA (US)

(73) Assignee: Cell Signaling Technology, Inc., Danvers, MA (US)

(*) Notice: Subject to any disclaimer, the term of this patent is extended or adjusted under 35 U.S.C. 154(b) by 0 days.

(21) Appl. No.: 13/416,582

(22) Filed: Mar. 9, 2012

(65) Prior Publication Data

US 2012/0308555 A1 Dec. 6, 2012

Related U.S. Application Data

(60) Provisional application No. 61/450,922, filed on Mar. 9, 2011, provisional application No. 61/560,006, filed on Nov. 15, 2011, provisional application No. 61/566,876, filed on Dec. 5, 2011, provisional application No. 61/594,729, filed on Feb. 3, 2012.

(51) Int. Cl.
| | |
|---|---|
| *C07K 1/14* | (2006.01) |
| *C07K 16/00* | (2006.01) |
| *G01N 33/50* | (2006.01) |
| *C07K 16/08* | (2006.01) |
| *C07K 16/18* | (2006.01) |
| *C07K 16/44* | (2006.01) |

(52) U.S. Cl.
CPC ............ *C07K 16/00* (2013.01); *C07K 16/082* (2013.01); *C07K 16/18* (2013.01); *C07K 16/44* (2013.01); *C07K 2317/21* (2013.01); *C07K 2317/56* (2013.01); *C07K 2317/565* (2013.01)

(58) Field of Classification Search
CPC ............... G01N 33/6848; G01N 33/68; G01N 33/57434; G01N 33/6854; G01N 33/6803; C07K 16/00; C07K 16/18; C07K 2317/565; A61K 2039/505
See application file for complete search history.

(56) References Cited

U.S. PATENT DOCUMENTS

| | | | |
|---|---|---|---|
| 5,969,108 A | 10/1999 | McCafferty et al. | |
| 6,180,370 B1 | 1/2001 | Queen et al. | |
| 6,331,415 B1 | 12/2001 | Cabilly et al. | |
| 6,548,640 B1 | 4/2003 | Winter | |
| 7,485,291 B2 | 2/2009 | Fang et al. | |
| 7,498,024 B2 | 3/2009 | Fang et al. | |
| 8,293,483 B2 | 10/2012 | Yu | |
| 2006/0205041 A1* | 9/2006 | Frye | C12N 9/6424 435/100 |
| 2007/0172887 A1 | 7/2007 | Takacs et al. | |
| 2008/0200658 A1* | 8/2008 | Le Strat et al. | 530/413 |
| 2009/0209737 A1* | 8/2009 | Bradbury | G01N 33/54393 530/413 |
| 2011/0065112 A1 | 3/2011 | Yu | |
| 2011/0312505 A1* | 12/2011 | Reddy et al. | 506/2 |
| 2012/0283134 A1 | 11/2012 | Yu | |

FOREIGN PATENT DOCUMENTS

| | | |
|---|---|---|
| CN | 101679513 A | 3/2010 |
| WO | 91/17271 | 11/1991 |
| WO | 92/01047 | 1/1992 |
| WO | 03/052416 A2 | 6/2003 |
| WO | 2005/084134 A2 | 9/2005 |
| WO | 2008/079914 A1 | 7/2008 |
| WO | 2008/106980 A2 | 9/2008 |
| WO | 2009/065414 A1 | 5/2009 |
| WO | 2009/100896 | 8/2009 |
| WO | 2010/002911 A2 | 1/2010 |
| WO | 2010/083456 A1 | 7/2010 |
| WO | 2011/140433 A2 | 11/2011 |
| WO | 2011/146514 A2 | 11/2011 |

OTHER PUBLICATIONS

Reddy et al (Nature Biotechnology, 2010, 28:965-969 and Online Methods).*
Taipa et al (Journal of Molecular Recognition, 1998, 11:240-242).*
Meier et al (Journal of Biological Chemistry, 1997, 272:30491-30497).*
Obermeier et al (Nature Medicine, 2008, 14:688-693).*
Egan et al. (Proceedings of the Natural Academy of Sciences, 1992, 89:8537-8541).*
Obermeier, B. et al., "Matching of Oligoclonal Immunoglobulin Transcriptomes and Proteomes of Cerebrospinal Fluid in Multiple Sclerosis" Nature Medicine (Jun. 1, 2008) pp. 688-693, vol. 14, No. 6.

(Continued)

*Primary Examiner* — Julie Wu
(74) *Attorney, Agent, or Firm* — Scull, Scott, Murphy & Presser, P.C.

(57) ABSTRACT

In some embodiments, the invention relates to methods for creating a monoclonal antibody that specifically binds to antigen. The method may start from a polyclonal population of antibodies such as a non-specific polyclonal population or a polyclonal population of antibodies that specifically bind to the antigen. The method includes obtaining nucleic acid molecules encoding heavy and light immunoglobulin chains (or variable regions thereof) of multiple immunoglobulins from an animal; obtaining mass spectra information of peptide fragments of a population of polyclonal immunoglobulins that specifically bind to an antigen of choice; comparing and/or correlating the mass spectra information of the peptide fragments of the polyclonal immunoglobulins with predicted mass spectra information of predicted amino acid sequences encoded by the nucleic acid molecules, and then assembling the heavy and light chains to create an antibody (or variable region thereof) that specifically binds to the antigen.

32 Claims, 26 Drawing Sheets

(56) References Cited

OTHER PUBLICATIONS

De Costa, D. et al., "Sequencing and Quantifying IgG Fragments and Antigen-Binding Regions by Mass Spectrometry" Journal of Proteome Research (Jun. 4, 2010) pp. 2937-2945, vol. 9, No. 6.
Schluter, S. F. et al., "Sequence Analysis of Homogeneous Peptides of Shark Immunoglobin Light Chains by Tandem Mass Spectrometry: Correlation with Gene Sequence and Homologies Among Variable and Constant Region Peptides of Sharks and Mammals" Molecular Immunology (Jan. 1, 1990) pp. 17-23, vol. 27, No. 1.
Maciej, A. et al., "Profiling of Polyclonal Antibody Light Chains by Liquid Chromatography/Electrospray Ionization Mass Spectrometry" Rapid Communications in Mass Spectrometry (Jan. 1, 2000) pp. 49-51, vol. 14, No. 1.
Persson, P. et al., "Development of Mass Spectrometry Based Techniques for the Identification and Determination of Compositional Variability in Recombinant Polyclonal Antibody Products" Analytical Chemistry (Sep. 1, 2010) pp. 7274-7282, vol. 82, No. 17.
Cheung, W. C. et al., "A Proteomics Approach for the Identification and Cloning of Monoclonal Antibodies from Serum" Nature Biotechnology (Jan. 1, 2012) pp. 1-8.
International Search Report and Written Opinion dated May 21, 2012 issued in International Application No. PCT/US2012/028501.
Weinstein, J. et al., "High-Throughput Sequencing of the Zebrafish Antibody Repertoire" Science (May 8, 2009) pp. 807-810, vol. 324.
Boyd, S.D. et al., "Measurement and Clinical Monitoring of Human Lymphocyte Clonality by Massively Parallel V-D-J Pyrosequencing" Science Translational Medicine (Jan. 20, 2009) pp. 1-8, vol. 1, No. 12ra23.
Boudinot, P. et al., "New Perspectives for Large-Scale Repertoire Analysis of Immune Receptors" Molecular Immunology (Feb. 1, 2008) pp. 2437-2445, vol. 45.
Damoc, E. et al., "High resolution proteome analysis of cryoglobulins using Fourier transform-ion cyclotron resonance mass spectrometry" Proteomics (2003) pp. 1425-1433, vol. 3.
Omenn, G.S. et al., "Overview of the HUPO Plasma Project: Results from the pilot phase with 35 collaborating laboratories and multiple analytical groups, generating a core dataset of 3020 proteins and a publicly-available database" Proteomics (2005) pp. 3226-3245, vol. 5.
List of 3020 proteins identified in the HUPO Plasma Proteome Project, retrieved from http://www.ccmb.med.umich.edu/PPP in 2012.
Bandeira, N. et al., "Automated de novo Protein Sequencing of Monoclonal Antibodies" Nature Biotechnology (Dec. 2008) pp. 1336-1338, vol. 26, No. 12.
Castellana, N. E. et al., "Template Proteogenomics: Sequencing Whole Proteins Using an Imperfect Database" Molecular and Cellular Proteomics (2010) pp. 1260-1270, vol. 9, No. 6.
Castellana, N. E. et al., "Resurrection of a Clinical Antibody: Template ProteoGenomic de novo Proteomic Sequencing and Reverse Engineering of an Anti-Lymphotoxin Alpha Antibody" Proteomics (Feb. 2011) pp. 395-405, vol. 11, No. 3.
Dekker, L.J. et al., "An antibody-based biomarker discovery method by mass spectrometry sequencing of complementarity determining regions" Anal. Bioanal. Chem. (2011) pp. 1081-1091, vol. 399.
Freeman, J.D. et al., "Profiling the T-cell Receptor Beta-Chain Repertoire by Massively Parallel Sequencing" Genome Research (2009) pp. 1817-1824, vol. 19.
Glanville, J. et al., "Precise Determination of the Diversity of a Combinatorial Antibody Library Gives Insight into the Human Immunoglobulin Repertoire" PNAS (Dec. 1, 2009) pp. 20216-20221, vol. 106, No. 48.
Huse, K. et al., "Purification of antibodies by affinity chromatography" J. Biochem. Biophys. Methods (2002) pp. 217-231, vol. 51.
Instructions for Product Nos. 21901 and 21902, Maleimide-PEG2-Biotin Sulfhydryl-reactive biotin labeling reagent with a polyethylene glycol (PEG) spacer arm, published by Thermo Fisher Scientific Inc. (2008).
Peng, J., "Protein Mixture Analysis by Tandem Mass Spectrometry" In: The Bioinformatics of Brains: From Genes and Proteins to Behaviors (Williams, ed) (2003) pp. 61-68.
Zhang, Z. et al., "Mass Spectrometry for Structural Characterization of Therapeutic Antibodies" Mass Spectrometry Reviews (2009) pp. 147-176, vol. 28.
Reddy, S.T. et al., "Monoclonal antibodies isolated without screening by analyzing the variable-gene reportoire of plasma cells" Nature Biotech (Sep. 2010) pp. 965-969, vol. 28, No. 9.
Scheid, J.F. et al., "Sequence and Structural Convergence of Broad and Potent HIV Antibodies That Mimic CD4 Binding" Science (2011) pp. 1633-1637, vol. 333.
Vanduijn, M.M. et al., "Immune Responses Are Characterized by Specific Shared Immunoglobulin Peptides That Can Be Detected by Proteomic Techniques" The Journal of Biological Chemistry (Sep. 17, 2010) pp. 29247-29253, vol. 285, No. 38.
Verberkmoes, N.C. et al., "Functional Analysis of Natural Microbial Consortia Using Community Proteomics" Nature Reviews Microbiology (Mar. 2009) pp. 196-205, vol. 7.
Yates, J.R., "Mass spectrometry from genomics to proteomics" Trends Genet. (Jan. 2000) pp. 5-8, vol. 16, No. 1.
Essono, S. et al., "Peptide mass-assisted antibody cloning strategy for accurate characterization of potential therapeutic monoclonal antibodies against neurodegenerative diseases" Protein Engineering, Design & Selection (2010) pp. 203-210, vol. 23 No. 4.
Chinese Office Action dated Feb. 16, 2015 received in Chinese Patent Application No. 201280021326.1, together with English-translation.
Hohlfeld R. et al., "The Search for the Target Antigens of Multiple Sclerosis, Part 2: CD8+ T Cells, B Cells, and Antibodies in the Focus of Reverse-Translational Research", *Lancet Neurology* 15:317-331 (Mar. 2016).
Xia Q. et al., "Protein Chemistry and Proteomics", *Frontiers of Modern Biotechnology*, Science Press, Beijing (Apr. 2004), pp. 318-325; together with a partial English-language translation (translation of p. 325).

* cited by examiner

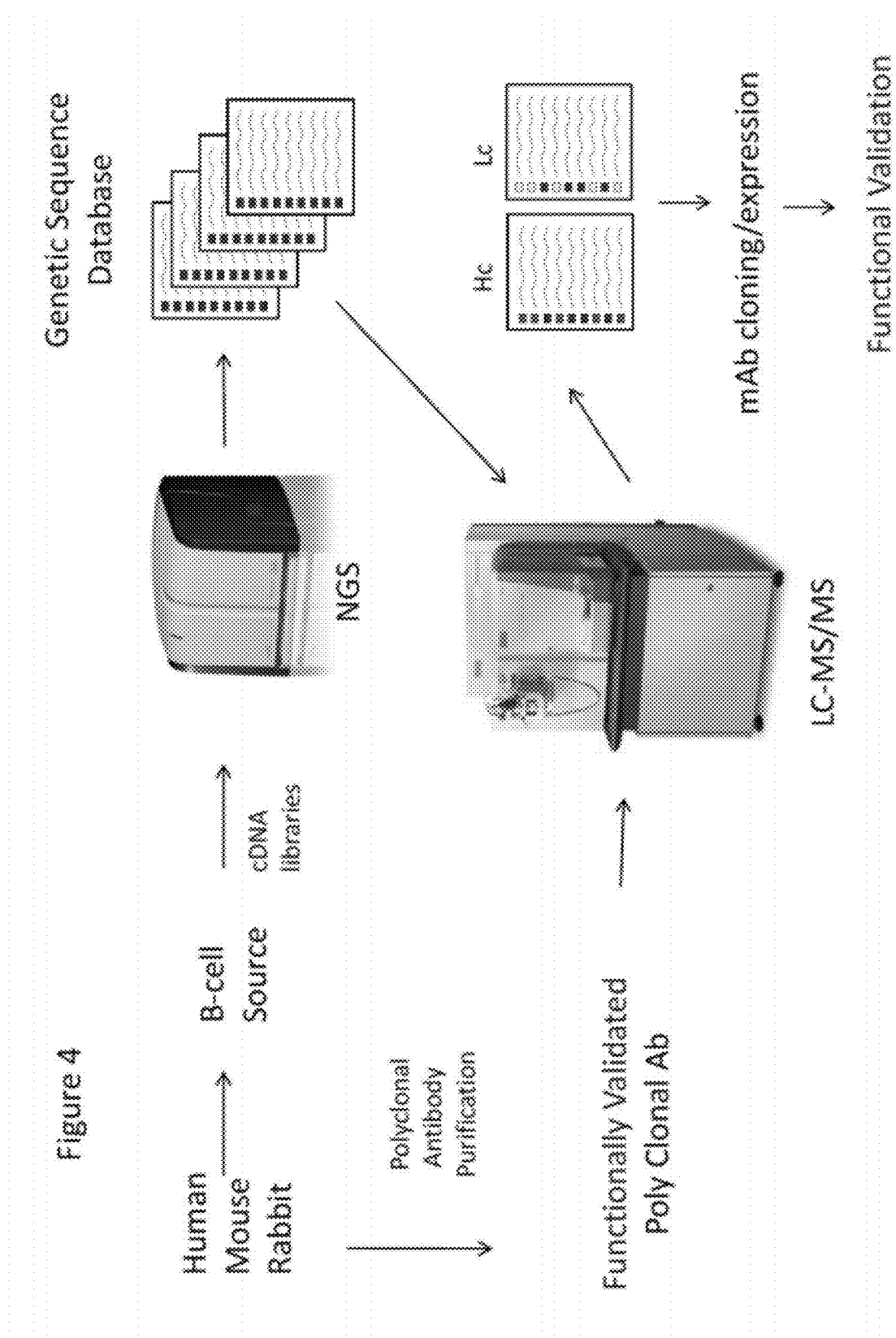

Heavy Chains

| ref | total_peptides | chain | cdr3_count | cdr3 | SEQ ID NO: |
|---|---|---|---|---|---|
| G623FKB01BJOL7 | 153 | heavy | 2 | RGYSGTYVDY | 307 |
| *G623FKB01AF34N* | *148* | *heavy* | *244* | *SRTGIFDY* | *308* |
| *G623FKB01BSNEU* | *131* | *heavy* | *15* | *SRSGIFDY* | *309* |
| *G623FKB01A2ZY4* | *130* | *heavy* | *58* | *RGYYSNTYVDY* | *310* |
| *G623FKB01A0MXT* | *126* | *heavy* | *68* | *LTAYFDY* | *311* |
| G623FKB01AXQN3 | 126 | heavy | 6 | RFYDGSYYFDY | 312 |
| G623FKB01AC4H8 | 122 | heavy | 19 | RGYYADTYVDY | 313 |
| *G623FKB01AB7YA* | *84* | *heavy* | *13* | *HEPLNWFPY* | *314* |
| G623FKB01AUXQW | 69 | heavy | 45 | KYGGGFDY | 315 |
| G623FKB01BO141 | 52 | heavy | 8 | GSAFAY | 316 |
| *G623FKB01BBIXE* | *49* | *heavy* | *5* | *YYRNYGGFDY* | *317* |
| G623FKB01ALSDX | 43 | heavy | 15 | EDYYSDQFAY | 318 |

Light Chains

| ref | total_peptides | chain | NGS_count | cdr3 | SEQ ID NO: |
|---|---|---|---|---|---|
| G623FKB01A3GC7 | 235 | Light | 8 | SQSTHVPWT | 319 |
| G623FKB01AX11C | 199 | Light | 1068 | QQHYSTPPT | 320 |
| G623FKB01ATC8J | 153 | Light | 112 | QQHFSTPPT | 321 |
| G623FKB01BCUK2 | 132 | Light | 597 | QQHYSTPFT | 322 |
| *G623FKB01BY43F* | *74* | *Light* | *532* | *WQGTHFPQT* | *323* |
| *G623FKB01BAZ8V* | *64* | *Light* | *6* | *QQYVSYPRT* | *324* |
| *G623FKB01A58OV* | *39* | *Light* | *20* | *QQSNEDPRT* | *325* |
| G623FKB01A312C | 39 | Light | 384 | QQWSSNPLT | 326 |
| *G623FKB01BADIC* | *31* | *Light* | *258* | *QHFWGTPWT* | *327* |
| G623FKB01ADDWX | 31 | Light | 219 | QQRSSYPFT | 328 |
| G623FKB01A29B2 | 23 | Light | 891 | LQVASYPWT | 329 |
| *G623FKB01BPZWW* | *38* | *Light* | *19* | *QQSKEVPLT* | *330* |

*Bold Italics*: antibody chains that are reactive to the antigen

| Lc ID | Hc ID | AZZY4 A | AZZY4 B | AC4H8 A | AC4H8 B | BJOL7 A | BJOL7 B | ALSDX A | ALSDX B | AUXQW A | AUXQW B | AF34N A | AF34N B |
|---|---|---|---|---|---|---|---|---|---|---|---|---|---|
| | plate 1 | | | | | | | | | | | | |
| BY43F | A | 0.1422 | 0.0986 | 0.0956 | 0.0965 | 0.1142 | 0.0951 | 0.125 | 0.1081 | 0.124 | 0.1346 | 0.1486 | 0.148 |
| | B | 0.3013 | 0.0883 | 0.1651 | 0.1841 | 0.124 | 0.1012 | 0.1195 | 0.0961 | 0.0982 | 0.1429 | 0.1278 | 0.1598 |
| A3GC7 | A | 0.0958 | 0.194 | 0.2652 | 0.4371 | 0.4326 | 0.4051 | 0.2398 | 0.233 | 0.1992 | 0.1144 | 0.2087 | 0.1812 |
| | B | 0.0953 | 0.089 | 0.5074 | 0.4602 | 0.44 | 0.4557 | 0.2844 | 0.2952 | 0.3203 | 0.1075 | 0.1821 | 0.1748 |
| BA28V | A | 0.0966 | 0.084 | 0.2187 | 0.3593 | 0.5384 | 0.3416 | 0.4497 | 0.4084 | 0.3246 | 0.1527 | 0.1331 | 0.1267 |
| | B | 0.0837 | 0.0759 | 0.1215 | 0.3744 | 0.4407 | 0.3472 | 0.3713 | 0.4181 | 0.2386 | 0.0809 | 0.1075 | 0.0982 |
| A313C | A | 0.0973 | 0.0973 | 0.1037 | 0.0944 | 0.1731 | 0.1139 | 0.2151 | 0.1307 | 0.1041 | 0.1071 | 0.102 | 0.1016 |
| | B | 0.0899 | 0.1232 | 0.194 | 0.1527 | 0.1216 | 0.1237 | 0.1262 | 0.0902 | 0.1538 | 0.1891 | 0.1267 | 0.145 |
| | plate 3 | | | | | | | | | | | | |
| A560V | A | 0.1256 | 0.1403 | 0.1049 | 0.1162 | 0.1183 | 0.0843 | 0.091 | 0.0867 | 0.1221 | 0.1369 | 0.6813 | 4.0839 |
| | B | 0.0865 | 0.0923 | 0.0925 | 0.1119 | 0.151 | 0.116 | 0.1443 | 0.095 | 0.078 | 0.1416 | 0.4606 | 4.7606 |
| BPZWW | A | 0.1009 | 0.084 | 0.1061 | 0.1346 | 0.1929 | 0.1688 | 0.1219 | 0.1021 | 0.147 | 0.1143 | 0.1262 | 0.1294 |
| | B | 0.1098 | 0.1563 | 0.1862 | 0.1062 | 0.1875 | 0.1935 | 0.1004 | 0.1742 | 0.1804 | 0.1031 | 0.0813 | 0.1238 |
| ADDWX | A | 0.0917 | 0.0898 | 0.0737 | 0.1389 | 0.2034 | 0.1038 | 0.1136 | 0.1091 | 0.1574 | 0.08 | 0.1027 | 0.1345 |
| | B | 0.0941 | 0.0766 | 0.0868 | 0.1144 | 0.1278 | 0.0779 | 0.1894 | 0.1056 | 0.0974 | 0.0851 | 0.1016 | 0.0867 |
| AXJ1C | A | 0.0996 | 0.0985 | 0.088 | 0.1245 | 0.1463 | 0.1464 | 0.153 | 0.1366 | 0.1708 | 0.1065 | 0.1297 | 0.1081 |
| | B | 0.1233 | 0.0857 | 0.127 | 0.1102 | 0.1855 | 0.139 | 0.1631 | 0.1028 | 0.1296 | 0.1331 | 0.1085 | 0.1783 |
| | plate 5 | | | | | | | | | | | | |
| BCJK2 | A | 0.1191 | 0.1299 | 0.1049 | 0.0994 | 0.1008 | 0.1397 | 0.1856 | 0.1667 | 0.1412 | 0.1237 | 0.1951 | 0.1944 |
| | B | 0.1017 | 0.0901 | 0.0908 | 0.09 | 0.1329 | 0.1093 | 0.1191 | 0.1134 | 0.0902 | 0.1369 | 0.1233 | 0.1771 |
| ATC80 | A | 0.1139 | 0.1023 | 0.1035 | 0.1093 | 0.1077 | 0.1086 | 0.0904 | 0.1018 | 0.104 | 0.1135 | 0.1038 | 0.1455 |
| | B | 0.116 | 0.0864 | 0.1698 | 0.0999 | 0.1153 | 0.1032 | 0.0848 | 0.1091 | 0.0921 | 0.0871 | 0.0897 | 0.1607 |
| BAD1C | A | 0.118 | 0.0915 | 0.0875 | 0.0922 | 0.03869 | 0.0862 | 0.0886 | 0.1082 | 0.1101 | 0.0988 | 4.4611 | 4.4264 |
| | B | 0.1211 | 0.1007 | 0.1083 | 0.0994 | 0.1223 | 0.1087 | 0.0998 | 0.1298 | 0.1193 | 0.11 | 3.7921 | 4.069 |
| A2982 | A | 0.108 | 0.0961 | 0.0886 | 0.1053 | 0.1523 | 0.1132 | 0.1099 | 0.1466 | 0.2152 | 0.1184 | 0.1058 | 0.1696 |
| | B | 0.1896 | 0.1141 | 0.1493 | 0.1354 | 0.1649 | 0.1358 | 0.1706 | 0.1357 | 0.193 | 0.1744 | 0.1836 | 0.3142 |
| | plate 7 | | | | | | | | | | | | |
| A5297 | A | 0.2515 | 0.0869 | 0.1844 | 0.1882 | 0.1441 | 0.1391 | 0.1377 | 0.1882 | 0.2288 | 0.1873 | 0.2154 | 0.2061 |
| | B | 0.1416 | 0.11 | 0.1123 | 0.1112 | 0.1225 | 0.1437 | 0.1244 | 0.1287 | 0.1193 | 0.1406 | 0.1216 | 0.1323 |
| 9106 control | | 1.6764 | 1.4255 | 1.9828 | 1.6363 | | | | | | | | |
| 2ndary alone | | 0.1395 | 0.109 | 0.256 | 0.1528 | 0.1541 | 0.1228 | 0.1033 | 0.1168 | 0.0921 | 0.1133 | 0.1056 | 0.1895 |

Figure 6 continued...

| 3126(pMet) | | | | |
|---|---|---|---|---|
| NGS Sequence ID | Chain | CDR3 sequence | SEQ ID NO: | NGS freq (max 9.12%) |
| GXRYQP201BFGRR | heavy chain | IPSYASSRGYYLIPDRLDL | 331 | 0.03% |
| *GXRYQP201BIQD2* | *heavy chain* | *IPSYVSGRGVYIIPDRFDL* | *332* | *0.19%* |
| GXRYQP201AGL7B | heavy chain | ASDYDSSRGHWLVYNRLDL | 333 | 0.08% |
| *GXRYQP201A97DZ* | *heavy chain* | *KGDPGHPNGLFFTM* | *334* | *0.05%* |
| GXRYQP201ARCKH | heavy chain | IPSYVSSRGYYLIPDGLDL | 335 | 0.02% |
| GXRYQP201A9YV7 | heavy chain | IPSYVSSRGYYLVPDGLDL | 336 | 0.01% |
| GXRYQP201BRYT5 | heavy chain | IPSYVSSRGYYLIPDRLDL | 337 | 0.05% |
| GXRYQP201AK8WL | heavy chain | ISSYVSSRGYWLIPDGLDL | 338 | 0.13% |
| GXRYQP201ANGRW | heavy chain | ISSYVSSRGYYLIPDGLDL | 339 | 0.01% |
| *GXRYQP201BGVA8* | *heavy chain* | *LYNSVVGDDM* | *340* | *0.55%* |
| GXRYQP201AGFK4 | heavy chain | ASDYDSSRGHWLVYDRLDL | 341 | 0.01% |
| GXRYQP201BJROT | heavy chain | LYNSVVGDDI | 342 | 0.03% |
| GXRYQP201A8DBE | heavy chain | LYNSLVGDDI | 343 | 0.22% |
| *GXRYQP201B2QN3* | *heavy chain* | *GMPGSTSGNSNI* | *344* | *0.59%* |
| GXRYQP201ADCZK | heavy chain | GMPASTSGNSNI | 345 | 0.17% |
| *GXRYQP201AZOWE* | *heavy chain* | *GMPGSTSGNSNI* | *346* | *0.59%* |
| | | | | |
| GXRYQP201A1C38 | heavy chain | GVPTNROAM | 347 | 9.12% |
| | | | | |
| 3126(pMet) | | | | |
| NGS Sequence ID | Chain | CDR3 sequence | | NGS freq (max 3.69%) |
| GXRYQP201AAKYU | light chain | AGGYKSSGDTVS | 348 | 0.14% |
| GXRYQP201AG5FC | light chain | QGEFSCRDFDCTV | 349 | 0.11% |
| *GXRYQP201A291T* | *light chain* | *LGGYKTTTDGSI* | *350* | *0.78%* |
| GXRYQP201AD9ZW | light chain | QSYYHNSGTSYIT | 351 | 0.89% |
| GXRYQP201A3ZHW | light chain | AGGYKSTTDGSA | 352 | 0.07% |
| GXRYQP201AJ2IR | light chain | QSYYHNSGNSYIT | 353 | 0.19% |
| GXRYQP201ASGBW | light chain | QSYYYGSGTSYIT | 354 | 0.04% |
| GXRYQP201BP3WS | light chain | AGGYKSSGDTFT | 355 | 0.01% |
| GXRYQP201AY7DW | light chain | LGGYKKTIDGSA | 356 | 0.05% |
| *GXRYQP201BRIWK* | *light chain* | *AGGYKSASDGSA* | *357* | *0.30%* |
| GXRYQP201AYFKS | light chain | QGEFSCDAGVCTL | 358 | 0.07% |
| *GXRYQP201ALDFS* | *light chain* | *QGEFSCRSYDCTV* | *359* | *0.18%* |
| GXRYQP201AATVT | light chain | LQDWSPSYADVA | 360 | 0.06% |
| GXRYQP201APNW9 | light chain | QQGRBSVDVDNV | 361 | 0.05% |
| GXRYQP201AT2TB | light chain | AGGYKTTTDGSI | 362 | 0.02% |
| | | | | |
| GXRYQP201AHXJZ | light chain | QQGYYSNVDNV | 363 | 3.69% |

Bold Italics are the antigen specific antibody chains (Total of 6 heavy chains (italics) and 5 light chains (bold italics) were synthesized, including the highest abundance antibody chains based on NGS frequency)

Figure 8

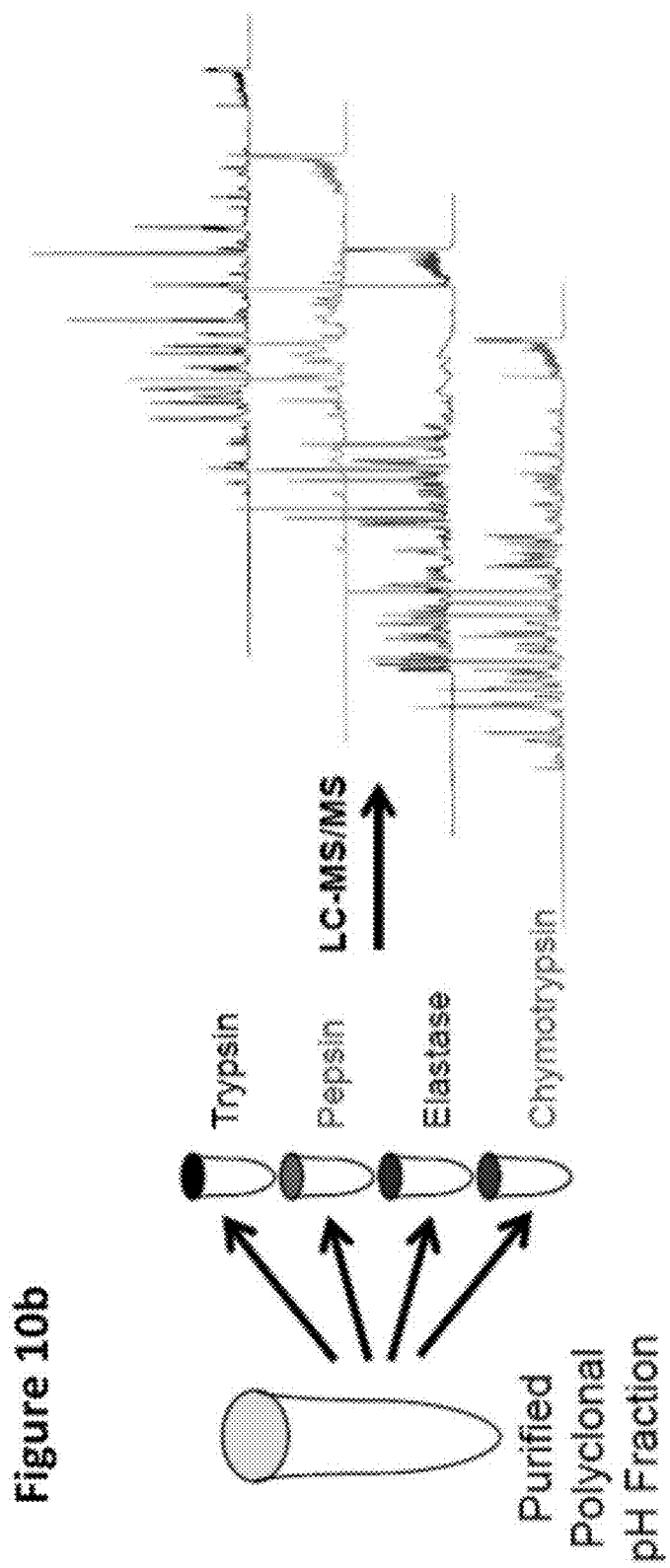

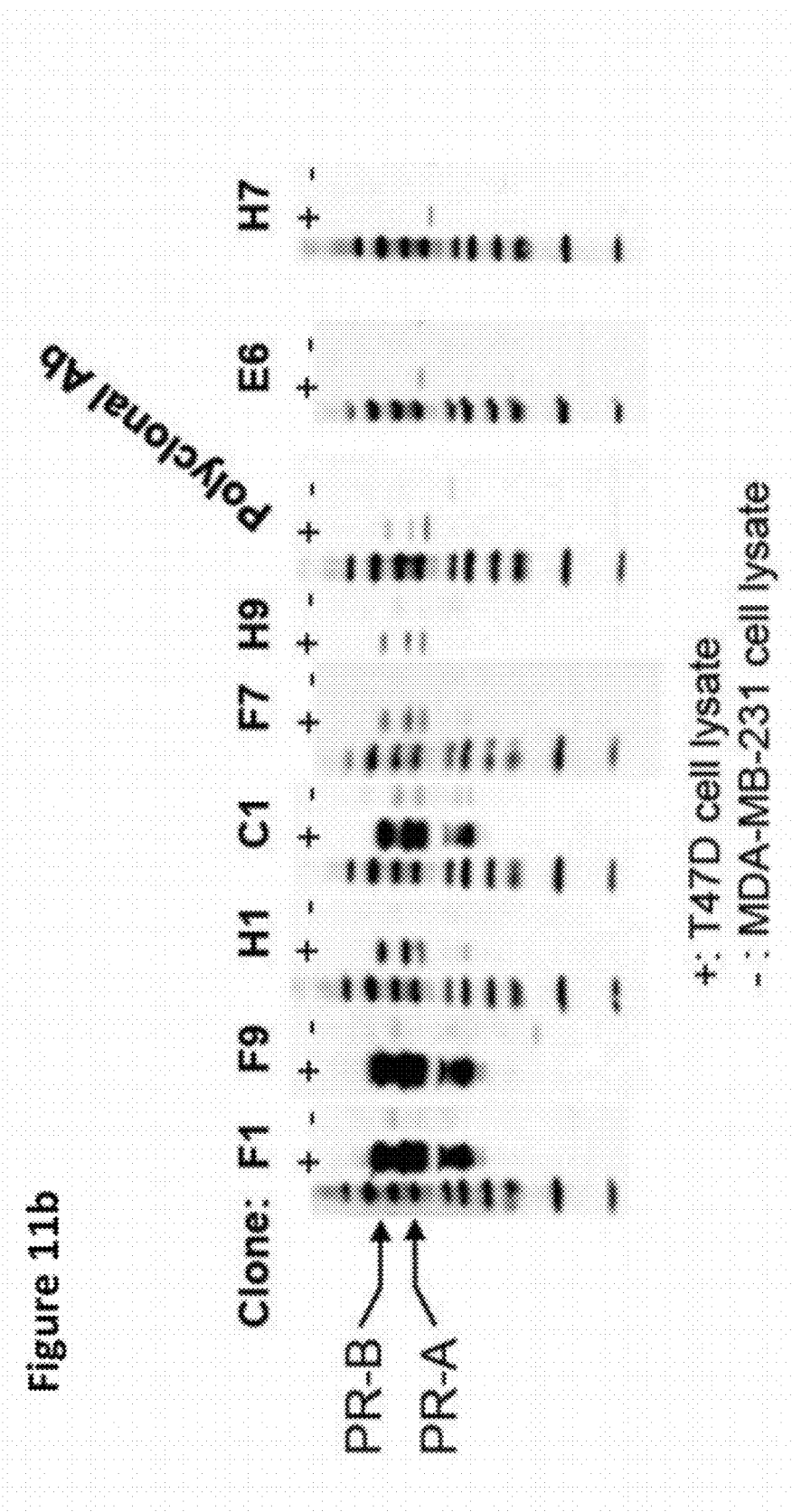

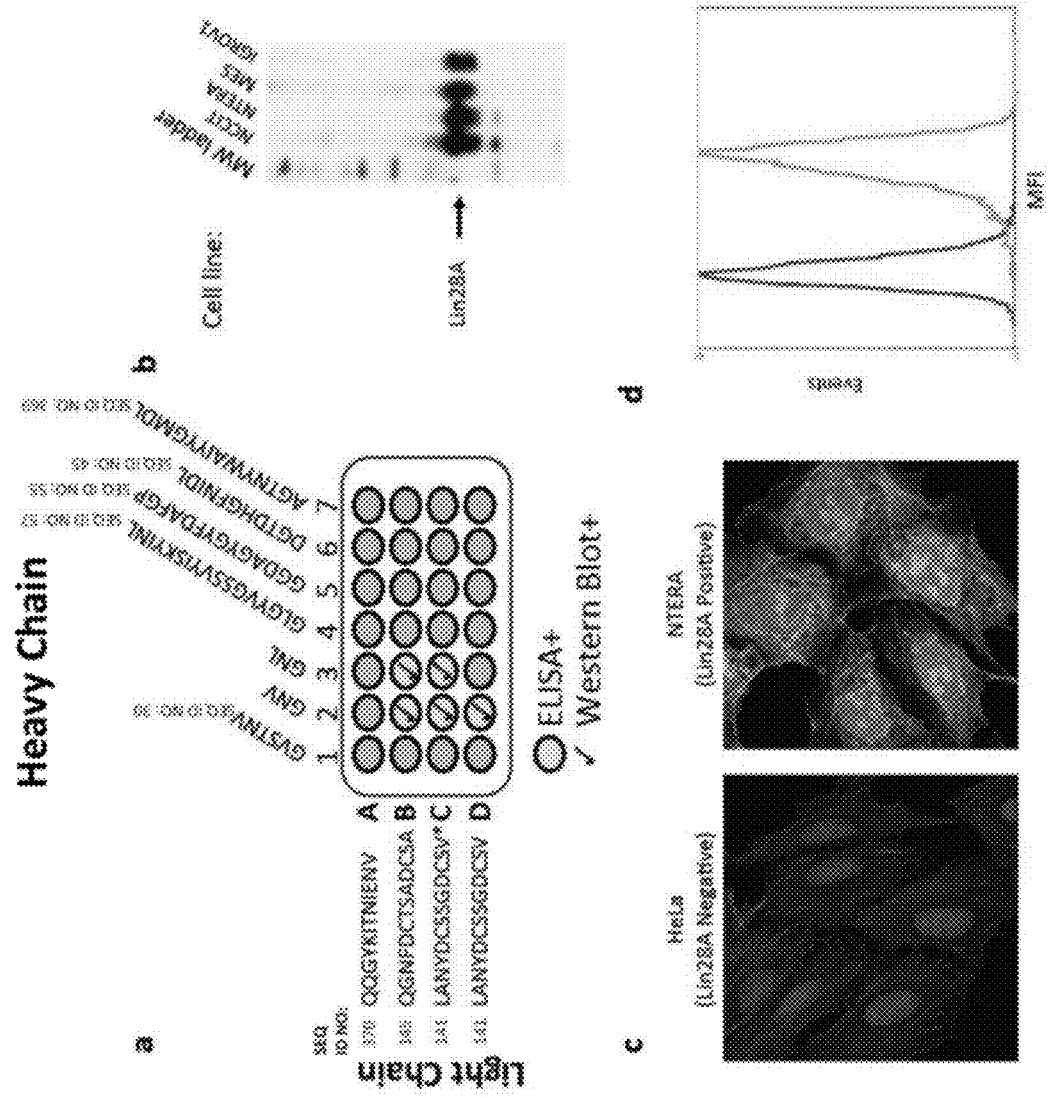
Figures 12a-d

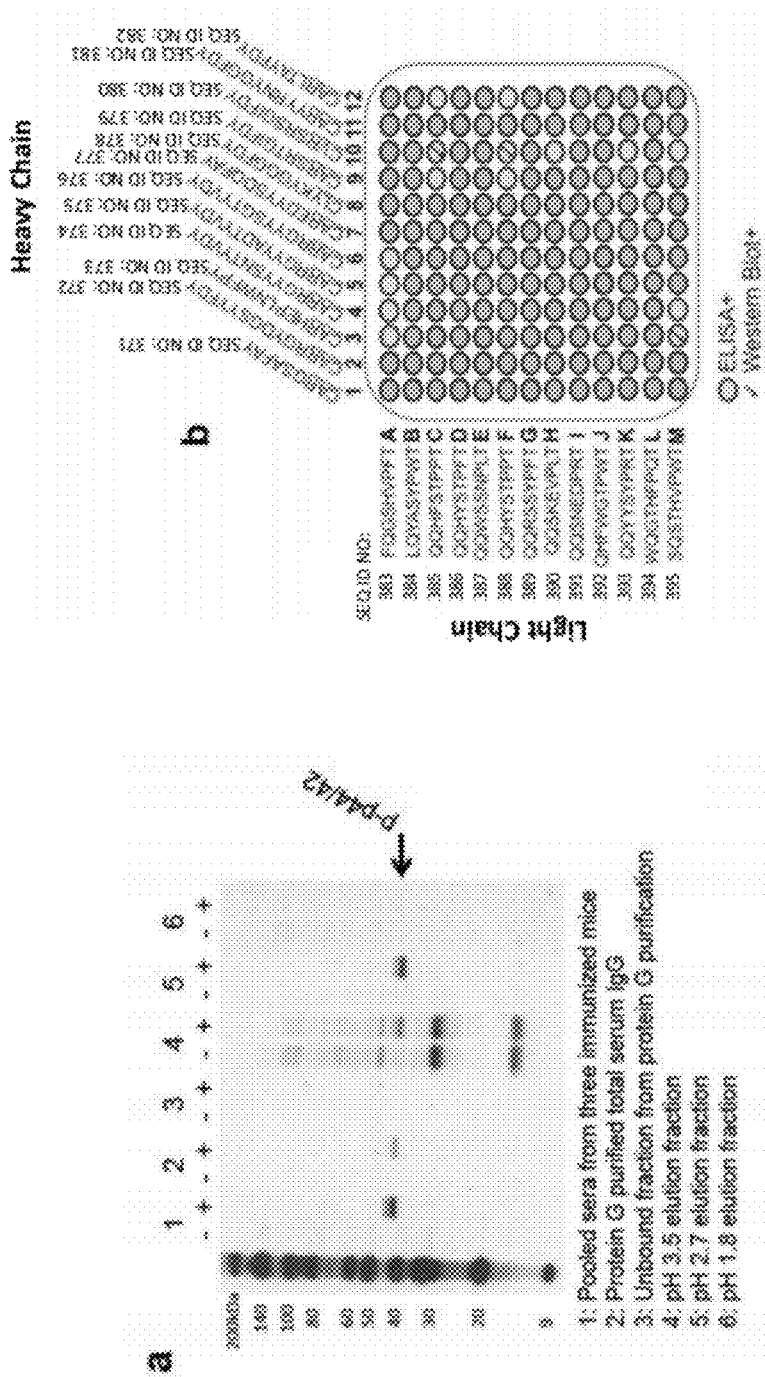
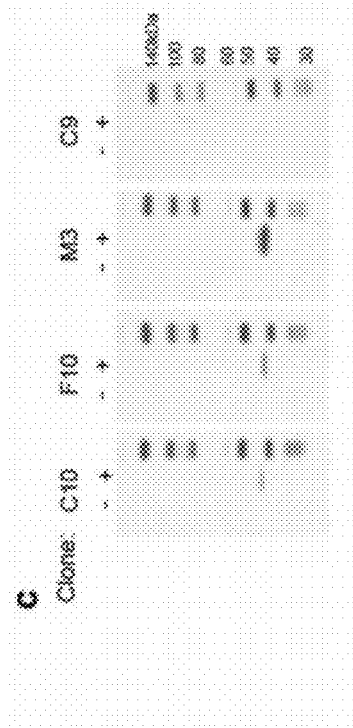
Figures 13a-c

Figure 14

Kappa Chain

| Gamma Chain | | GRAWI | | CHUZK | | EDL1N | | JPSHA | | DO15E | | IKQES | | JQI8X | |
|---|---|---|---|---|---|---|---|---|---|---|---|---|---|---|---|
| | HSP82 | 2.86 | 2.94 | 2.72 | -0.04 | -0.04 | -0.06 | -0.04 | 0.01 | 2.58 | 3.80 | 1.89 | 2.60 | 0.04 | 0.20 |
| | | 2.59 | 2.71 | 0.68 | 0.00 | 0.09 | 0.04 | -0.03 | 0.08 | 3.62 | 2.63 | 2.38 | 0.82 | 0.05 | 0.13 |
| | B1RWB | 0.92 | 0.41 | 0.06 | 0.03 | 2.89 | 3.01 | 0.06 | 0.16 | 0.71 | 0.22 | 0.22 | -0.01 | 0.05 | 0.06 |
| | | 0.07 | 0.05 | 0.03 | 0.01 | 2.83 | 2.85 | 0.08 | 0.09 | 0.04 | 0.02 | 0.00 | 0.33 | 0.03 | 0.05 |
| | BD00L | 0.20 | 0.09 | 1.84 | 1.97 | 0.77 | 0.82 | 1.85 | 2.05 | 0.05 | 0.00 | 1.52 | 1.92 | 1.05 | 1.38 |
| | | 0.18 | 0.15 | 1.89 | 2.11 | 0.85 | 0.83 | 1.91 | 2.16 | 0.06 | 0.03 | 1.72 | 1.87 | 1.06 | 1.43 |
| | H42OK | 0.01 | -0.01 | 0.03 | 0.05 | 0.06 | 0.05 | 0.03 | -0.02 | 0.03 | 0.02 | 0.02 | 0.00 | 0.14 | 0.10 |
| | | 0.02 | -0.01 | -0.02 | 0.04 | 0.05 | 0.10 | 0.06 | 0.09 | -0.03 | 0.00 | 0.05 | 0.06 | 0.09 | 0.06 |
| | CP4Y8 | 0.02 | 0.02 | 0.02 | 0.02 | 0.05 | 0.04 | 0.04 | 0.03 | 0.05 | 0.02 | 0.03 | 0.00 | 2.68 | 2.75 |
| | | 0.04 | 0.06 | 0.04 | 0.04 | 0.06 | 0.06 | 0.05 | 0.07 | 0.04 | 0.04 | 0.02 | 0.03 | 3.71 | 2.60 |
| | GBOGO | 0.06 | 0.04 | 0.06 | 0.04 | 0.05 | 0.03 | 0.06 | 0.05 | 0.06 | 0.05 | 0.04 | 0.05 | 0.08 | 0.08 |
| | | 0.13 | 0.06 | 0.04 | 0.07 | 0.05 | 0.08 | 0.08 | 0.06 | 0.05 | 0.05 | 0.06 | 0.04 | 0.03 | 0.17 |
| | JJESP | 0.15 | 0.05 | 0.10 | 0.12 | 0.04 | 0.10 | 0.07 | 0.15 | 0.06 | 0.07 | 0.14 | 0.08 | 0.05 | 0.10 |
| | | 0.05 | 0.05 | 0.05 | 0.06 | 0.08 | 0.05 | 0.08 | 0.06 | 0.05 | 0.05 | 0.05 | 0.05 | 0.14 | 0.05 |
| | APABY | -0.06 | 0.04 | 0.03 | 0.05 | 0.03 | 0.03 | 0.04 | 0.04 | 0.04 | 0.04 | 0.10 | 0.03 | 0.05 | 0.00 |
| | | 0.05 | 0.08 | 0.09 | 0.04 | 0.08 | 0.05 | 0.04 | 0.04 | 0.05 | 0.05 | 0.07 | 0.13 | 0.04 | 0.04 |
| | H9L3G | 0.75 | 0.71 | 2.33 | 2.59 | 0.97 | 1.27 | 3.55 | 2.83 | 0.67 | 0.74 | 2.57 | 2.63 | 0.21 | -0.32 |
| | | 0.50 | 0.35 | 2.46 | 2.40 | 1.50 | 1.53 | 2.64 | 2.66 | 1.32 | 1.31 | 2.57 | 2.64 | 0.21 | -0.42 |
| | EZKNT | 0.06 | 0.05 | 0.18 | 0.13 | 0.84 | 0.72 | 0.17 | 0.31 | 2.08 | 1.76 | 0.09 | 0.09 | -0.38 | -0.66 |
| | | 0.28 | 0.07 | 0.13 | 0.10 | 0.80 | 1.05 | 0.14 | 0.18 | 2.06 | 1.97 | 0.17 | 0.18 | -0.69 | -0.56 |
| | A9F9Q | 2.60 | 2.47 | 0.23 | 0.10 | 0.05 | 0.07 | 0.11 | 0.25 | 3.01 | 2.90 | 0.08 | 0.17 | -0.46 | -0.69 |
| | | 2.57 | 2.62 | 0.15 | 0.05 | 0.06 | 0.04 | 0.06 | 0.29 | 2.72 | 2.79 | 0.06 | 0.13 | -0.42 | -0.80 |
| | JXGB9 | 0.11 | 0.24 | 0.05 | 0.05 | 0.03 | 0.07 | 0.06 | 0.05 | 0.24 | 0.43 | 0.06 | 0.01 | -1.11 | -0.99 |
| | | -0.04 | 0.03 | 0.01 | 0.02 | 0.02 | 0.03 | 0.03 | 0.03 | 0.06 | 0.05 | 0.06 | 0.03 | -0.25 | -0.80 |
| | JD1J9 | -0.17 | 0.02 | 0.02 | 0.01 | 0.02 | 0.02 | 0.02 | 0.02 | 0.01 | 0.00 | 0.01 | -0.02 | -0.17 | -0.01 |
| | | 0.01 | 0.03 | 0.04 | 0.02 | 0.05 | 0.03 | 0.02 | 0.03 | 0.03 | 0.02 | 0.00 | 0.00 | -0.07 | 0.01 |
| | A6TR9 | 0.01 | 0.03 | 0.03 | 0.03 | 0.04 | 0.02 | 0.03 | 0.04 | 0.04 | 0.05 | 0.02 | 0.05 | -0.02 | 0.02 |
| | | 0.03 | 0.02 | 0.02 | 0.03 | 0.05 | 0.03 | 0.03 | 0.04 | 0.03 | 0.04 | 0.02 | 0.01 | 0.01 | 0.02 |
| | EOZ2F | 0.05 | 0.04 | 0.03 | 0.03 | 0.05 | 0.04 | 0.04 | 0.05 | 0.06 | 0.04 | 0.05 | 0.01 | 0.01 | 0.03 |
| | | 0.06 | 0.06 | 0.04 | 0.04 | 0.05 | 0.06 | 0.05 | 0.04 | 0.03 | 0.05 | 0.05 | 0.03 | -0.04 | 0.03 |
| | ASNDH | 0.05 | 0.06 | 0.04 | 0.04 | 0.04 | 0.05 | 0.05 | 0.05 | 0.05 | 0.03 | 0.05 | 0.02 | 0.00 | 0.02 |
| | | 0.15 | 0.04 | 0.03 | 0.06 | 0.05 | 0.14 | 0.03 | 0.05 | 0.08 | 0.04 | 0.08 | 0.05 | 0.02 | 0.02 |
| | G7MQM | 0.16 | 0.11 | 0.01 | 0.02 | 0.02 | 0.04 | 0.02 | 0.03 | 0.18 | 0.24 | 0.00 | -0.01 | 0.02 | 0.10 |
| | | 0.22 | 0.24 | 0.04 | 0.06 | 0.08 | 0.07 | 0.05 | 0.06 | 0.78 | 0.83 | 0.02 | 0.00 | -0.03 | 0.06 |
| | IJOR6 | 0.02 | 0.04 | 0.04 | 0.04 | 0.05 | 0.05 | 0.03 | 0.03 | 0.05 | 0.05 | 0.04 | 0.01 | 0.05 | 0.06 |
| | | 0.05 | 0.04 | 0.03 | 0.04 | 0.05 | 0.04 | 0.03 | 0.04 | 0.03 | 0.04 | 0.03 | 0.02 | -0.01 | 0.01 |
| | D4LT2 | 0.06 | 0.06 | 0.03 | 0.03 | 0.04 | 0.04 | 0.05 | 0.03 | 0.04 | 0.05 | 0.03 | -0.01 | 0.00 | 0.06 |
| | | 0.04 | 0.04 | 0.03 | 0.04 | 0.04 | 0.05 | 0.07 | 0.05 | 0.05 | 0.06 | 0.04 | 0.02 | -0.05 | 0.02 |
| | EVUGG | 0.06 | 0.05 | 0.04 | 0.06 | 0.03 | 0.04 | 0.04 | 0.05 | 0.05 | 0.05 | 0.04 | 0.03 | 0.03 | 0.17 |
| | | 0.03 | 0.00 | 0.04 | 0.03 | 0.03 | 0.02 | 0.05 | 0.02 | 0.04 | 0.04 | 0.06 | 0.04 | 0.03 | 0.01 |
| | DUIFV | -0.01 | 0.04 | 0.01 | 0.04 | 0.05 | 0.03 | 0.04 | 0.02 | 0.03 | -0.01 | -0.01 | -0.04 | -0.04 | -0.02 |
| | | 0.01 | 0.03 | 0.03 | 0.03 | 0.05 | -0.03 | 0.02 | 0.03 | 0.02 | 0.01 | 0.00 | -0.01 | 0.00 | 0.04 |
| | DTF5S | 0.03 | 0.05 | 0.04 | 0.04 | 0.26 | 0.20 | 0.03 | 0.05 | 0.04 | 0.05 | 0.04 | 0.04 | 0.02 | 0.04 |
| | | 0.03 | 0.03 | 0.03 | 0.03 | 0.25 | 0.20 | 0.03 | 0.03 | 0.04 | 0.04 | 0.03 | 0.00 | 0.02 | 0.04 |
| | DZ3YC | 0.04 | 0.05 | 0.02 | 0.04 | 0.04 | 0.04 | 0.05 | 0.03 | 0.04 | 0.04 | 0.05 | 0.01 | -0.02 | 0.05 |
| | | 0.10 | 0.03 | 0.02 | 0.03 | 0.03 | 0.05 | 0.05 | 0.04 | 0.03 | 0.04 | 0.05 | -0.02 | 0.06 | 0.08 |
| | CIZNS | 0.04 | 0.04 | 0.03 | 0.03 | 0.02 | 0.04 | 0.05 | 0.05 | 0.04 | 0.05 | 0.01 | 0.02 | 0.02 | 0.05 |
| | | 0.05 | 0.05 | 0.03 | 0.04 | 0.05 | 0.05 | 0.03 | 0.04 | 0.07 | 0.07 | 0.08 | -0.01 | 0.01 | 0.03 |
| | | GRAWI | | CHUZK | | EDL1N | | JPSHA | | DO15E | | IKQES | | JQI8X | |

Kappa Chain

Figure 14 (Continued)

Kappa Chain

| Gamma Chain | | HRONB | | BAHZA | | HSHZE | | H6RCI | | FPWBB | | HHFLL | | CRY2A | |
|---|---|---|---|---|---|---|---|---|---|---|---|---|---|---|---|
| | HSP82 | 0.04 | 0.04 | 0.03 | 0.03 | 0.04 | 0.03 | 0.02 | 0.01 | 0.00 | -0.03 | 0.10 | 0.03 | 0.09 | 0.07 |
| | | 0.04 | 0.03 | 0.03 | 0.03 | 0.04 | 0.03 | 0.02 | 0.02 | 0.01 | -0.06 | 0.13 | 0.04 | 0.09 | 0.06 |
| | B1RWB | 0.04 | 0.03 | 0.04 | 0.02 | 0.02 | 0.03 | 0.04 | 0.04 | 0.02 | 0.02 | 0.01 | 0.04 | 0.04 | 0.06 |
| | | 0.03 | 0.02 | 0.03 | 0.03 | 0.03 | 0.03 | 0.09 | 0.07 | 0.03 | -0.02 | -0.02 | 0.03 | 0.04 | 0.05 |
| | BD00L | 1.18 | 1.08 | 0.81 | 1.04 | 1.52 | 1.46 | 2.98 | 2.53 | 0.11 | 0.05 | 0.61 | 1.91 | 1.83 | 1.88 |
| | | 2.06 | 1.51 | 0.59 | 0.95 | 2.01 | 2.05 | 2.85 | 2.68 | 0.15 | 0.00 | 0.57 | 1.79 | 1.98 | 2.07 |
| | H42OK | 2.68 | 2.64 | 0.04 | 0.04 | 0.04 | 0.04 | 0.04 | 0.03 | 0.02 | 0.00 | 0.01 | 0.01 | 0.02 | 0.05 |
| | | 2.46 | 2.35 | 0.04 | 0.03 | 0.03 | 0.03 | 0.02 | 0.01 | 0.01 | 0.01 | 0.00 | 0.01 | 0.01 | 0.01 |
| | CP4Y8 | 0.09 | 0.04 | 0.02 | 0.04 | 0.03 | 0.04 | 0.02 | 0.00 | 0.01 | -0.01 | 0.01 | 0.03 | 0.03 | 0.04 |
| | | 0.19 | 0.14 | 0.03 | 0.03 | 0.03 | 0.02 | 0.03 | 0.03 | 0.01 | 0.00 | 0.03 | 0.02 | 0.01 | 0.04 |
| | G8OGO | 2.22 | 2.36 | 0.05 | 0.03 | 0.03 | 0.03 | 0.04 | 0.04 | 0.03 | 0.00 | 0.03 | 0.02 | 0.05 | 0.05 |
| | | 0.21 | 0.16 | 0.03 | 0.03 | 0.03 | 0.05 | 0.02 | 0.03 | 0.02 | -0.01 | 0.01 | 0.01 | 0.03 | 0.05 |
| | JJESP | 0.07 | 0.08 | 0.03 | 0.02 | 0.03 | 0.03 | 0.05 | 0.06 | 0.03 | 0.00 | 0.03 | 0.06 | 1.96 | 1.97 |
| | | 0.04 | 0.03 | 0.03 | 0.04 | 0.04 | 0.05 | 0.04 | 0.03 | 0.05 | 0.01 | 0.01 | 0.05 | 2.44 | 2.80 |
| | APABY | 0.03 | 0.03 | 0.02 | 0.04 | 0.04 | 0.04 | 0.03 | 0.02 | 0.03 | -0.03 | 0.01 | 0.09 | 0.15 | 0.12 |
| | | 0.04 | 0.03 | 0.03 | 0.04 | 0.03 | 0.04 | 0.03 | 0.01 | 0.03 | 0.03 | -0.03 | 0.01 | 0.01 | 0.07 |
| | H9L3G | -0.33 | 0.38 | -0.11 | 0.20 | 0.37 | 0.35 | 2.34 | 2.44 | 0.27 | 0.16 | 0.19 | 0.27 | 0.12 | 0.15 |
| | | 0.75 | 0.75 | 0.38 | 0.73 | 0.84 | 0.95 | 2.41 | 2.38 | 0.46 | 0.40 | 0.25 | 0.58 | 0.40 | 0.47 |
| | EZKNT | 0.33 | 0.33 | -0.06 | 0.05 | 0.05 | 0.03 | 0.35 | 0.30 | 0.01 | 0.00 | 0.01 | 0.03 | 1.31 | 0.85 |
| | | 0.44 | 0.73 | 0.02 | 0.04 | 0.03 | 0.02 | 0.20 | 0.26 | 0.02 | -0.01 | -0.01 | 0.04 | 1.38 | 1.07 |
| | A9F9Q | -0.30 | -0.18 | 0.03 | 0.02 | 0.03 | 0.03 | 0.07 | 0.07 | 0.00 | 0.01 | 0.04 | 0.04 | 0.02 | 0.06 |
| | | -0.38 | -0.01 | 0.02 | 0.03 | 0.04 | 0.04 | 0.03 | 0.02 | 0.03 | -0.01 | 0.08 | 0.09 | 0.04 | 0.04 |
| | JXGB9 | -0.94 | 0.01 | -0.05 | 0.02 | 0.03 | 0.03 | 0.03 | 0.04 | 0.00 | -0.01 | -0.01 | 0.02 | 0.00 | 0.04 |
| | | -0.02 | 0.03 | 0.02 | 0.01 | 0.03 | 0.02 | 0.02 | 0.01 | 0.01 | -0.08 | -0.04 | 0.00 | 0.01 | -0.01 |
| | JD1J9 | 0.01 | 0.00 | 0.01 | 0.02 | 0.01 | 0.02 | 0.01 | 0.02 | -0.02 | -0.05 | 0.03 | 0.00 | 0.03 | 0.04 |
| | | -0.03 | 0.02 | 0.02 | 0.02 | 0.02 | 0.02 | 0.01 | 0.02 | -0.01 | -0.04 | -0.01 | 0.01 | 0.03 | 0.04 |
| | A6TR9 | 0.03 | 0.03 | 0.02 | 0.02 | 0.02 | 0.03 | 0.04 | 0.03 | 0.01 | 0.01 | 0.03 | 0.02 | 0.03 | 0.04 |
| | | 0.02 | 0.02 | 0.02 | 0.02 | 0.01 | 0.01 | 0.01 | 0.01 | 0.01 | 0.01 | 0.01 | 0.00 | 0.03 | 0.03 |
| | EOZ2F | 0.01 | 0.01 | 0.01 | 0.01 | 0.00 | 0.01 | 0.01 | 0.01 | 0.01 | -0.02 | 0.02 | 0.04 | 0.03 | 0.06 |
| | | 0.03 | 0.01 | 0.01 | 0.02 | 0.02 | 0.02 | 0.00 | 0.02 | 0.01 | 0.01 | 0.04 | 0.04 | 0.02 | 0.02 |
| | A5NDH | 0.01 | 0.00 | 0.01 | 0.01 | 0.01 | 0.01 | 0.02 | 0.02 | 0.00 | -0.04 | 0.03 | 0.02 | 0.02 | 0.04 |
| | | -0.02 | -0.04 | 0.00 | -0.16 | -0.18 | -0.26 | -0.08 | 0.02 | -0.02 | -0.04 | -0.02 | 0.01 | 0.00 | 0.03 |
| | G7MQM | 0.03 | 0.05 | 0.11 | 0.09 | 0.61 | 0.45 | 0.18 | 0.28 | 0.03 | 0.03 | 0.02 | 0.03 | 0.04 | 0.04 |
| | | 0.05 | 0.07 | 0.13 | 0.25 | 0.89 | 0.52 | 0.59 | 0.80 | 0.02 | 0.03 | 0.04 | 0.08 | 0.03 | 0.04 |
| | IJOR6 | 0.06 | 0.06 | 0.03 | 0.04 | 0.01 | 0.02 | 0.05 | 0.05 | 0.04 | 0.04 | 0.03 | 0.03 | 0.03 | 0.04 |
| | | -0.05 | 0.00 | -0.01 | -0.01 | 0.01 | -0.01 | 0.04 | 0.00 | -0.02 | 0.04 | 0.00 | 0.06 | 0.05 | 0.02 |
| | D4LT2 | 0.00 | 0.04 | 0.03 | 0.04 | -0.02 | 0.00 | 0.04 | 0.03 | 0.02 | 0.00 | 0.00 | 0.06 | 0.03 | 0.05 |
| | | 0.00 | 0.01 | 0.05 | 0.00 | 0.04 | 0.05 | 0.05 | 0.06 | 0.06 | 0.06 | 0.02 | 0.03 | 0.02 | 0.03 |
| | EVUGG | 0.04 | 0.06 | 0.04 | 0.07 | 0.04 | 0.05 | 0.06 | 0.06 | 0.06 | 0.06 | -0.01 | -0.02 | 0.00 | 0.05 |
| | | 0.00 | -0.01 | 0.03 | -0.04 | 0.03 | 0.00 | 0.02 | 0.01 | 0.04 | 0.03 | -0.04 | 0.00 | 0.01 | 0.03 |
| | DU1FV | 0.03 | 0.03 | 0.03 | 0.03 | 0.05 | 0.04 | 0.05 | 0.05 | 0.08 | 0.09 | -0.03 | 0.02 | 0.03 | 0.04 |
| | | 0.04 | 0.05 | 0.06 | 0.08 | 0.05 | 0.05 | 0.05 | 0.06 | 0.04 | 0.06 | 0.00 | 0.01 | 0.02 | 0.04 |
| | DTF5S | 0.05 | 0.04 | 0.04 | 0.04 | 0.05 | 0.05 | 0.07 | 0.06 | 0.06 | 0.04 | 0.02 | 0.06 | 0.10 | 0.03 |
| | | 0.04 | 0.05 | 0.05 | 0.03 | 0.04 | 0.07 | 0.05 | 0.06 | 0.04 | 0.03 | -0.02 | 0.01 | 0.06 | 0.04 |
| | DZ3YC | 0.03 | 0.04 | 0.00 | 0.04 | 0.05 | 0.06 | 0.06 | 0.05 | 0.05 | 0.05 | 0.02 | 0.08 | 0.04 | 0.05 |
| | | 0.03 | 0.03 | 0.03 | 0.04 | 0.05 | 0.04 | 0.06 | 0.06 | 0.04 | 0.04 | -0.01 | 0.01 | 0.04 | 0.04 |
| | CIZNS | 0.02 | 0.04 | 0.05 | 0.05 | 0.05 | 0.04 | 0.05 | 0.05 | 0.06 | 0.05 | -0.01 | 0.00 | 0.01 | 0.04 |
| | | 0.03 | 0.02 | 0.02 | 0.05 | 0.03 | 0.03 | 0.03 | 0.02 | 0.06 | 0.11 | -0.03 | 0.01 | 0.02 | 0.02 |
| | | HRONB | | BAHZA | | HSHZE | | H6RCI | | FPWBB | | HHFLL | | CRY2A | |

Kappa Chain

Figure 14 (Continued)

Kappa Chain

| | | ARW3R | | GRBL0 | | JAVSR | | BLP3K | | AE3TS | | GOOZ5 | |
|---|---|---|---|---|---|---|---|---|---|---|---|---|---|
| Gamma Chain | HSP82 | 0.05 | 0.04 | 0.06 | 0.05 | 0.09 | 0.05 | 0.02 | 0.01 | -0.02 | 0.01 | 0.00 | 0.00 |
| | | 0.06 | 0.00 | 0.06 | 0.07 | 0.06 | 0.07 | 0.05 | 0.08 | 0.02 | 0.00 | 0.02 | 0.04 |
| | B1RWB | 0.03 | 0.06 | 0.06 | 0.07 | 0.07 | 0.08 | 0.06 | 0.10 | -0.02 | 0.02 | 0.21 | 0.18 |
| | | 0.03 | 0.08 | 0.09 | 0.17 | 0.06 | 0.07 | 0.06 | 0.08 | 0.01 | 0.12 | 0.08 | 0.18 |
| | BD00L | 2.11 | 2.38 | 2.59 | 2.69 | 2.50 | 2.58 | 0.66 | 0.38 | 0.21 | 0.86 | 0.95 | 0.60 |
| | | 1.86 | 2.12 | 2.53 | 2.61 | 2.53 | 2.38 | 0.49 | 0.42 | 0.14 | 0.63 | 0.91 | 0.35 |
| | H42OK | 0.07 | 0.07 | 0.07 | 0.06 | 0.05 | 0.04 | 0.05 | 0.05 | -0.01 | 0.00 | 0.13 | 0.03 |
| | | 0.03 | 0.05 | 0.03 | 0.03 | 0.03 | 0.04 | 0.04 | 0.05 | -0.11 | 0.00 | 0.01 | 0.01 |
| | CP4Y8 | 0.05 | 0.01 | 0.06 | 0.05 | 0.06 | 0.03 | 0.04 | 0.04 | -0.02 | -0.02 | 0.00 | 0.01 |
| | | 0.04 | 0.05 | 0.08 | 0.05 | 0.05 | 0.06 | 0.00 | 0.00 | -0.01 | 0.00 | 0.01 | 0.01 |
| | G8OGO | 0.06 | 0.00 | 0.06 | 0.07 | 0.08 | 0.08 | 0.06 | 0.06 | -0.03 | 0.00 | 0.00 | 0.01 |
| | | 0.03 | 0.05 | 0.07 | 0.08 | 0.06 | 0.07 | 0.06 | 0.06 | 0.00 | 0.03 | 0.01 | 0.01 |
| | IJESP | 0.04 | 0.06 | 0.08 | 0.08 | 0.08 | 0.07 | 0.08 | 0.05 | -0.01 | 0.04 | 0.01 | 0.04 |
| | | 0.08 | 0.07 | 0.06 | 0.06 | 0.07 | 0.07 | 0.06 | 0.03 | -0.01 | 0.02 | 0.12 | 0.03 |
| | APABY | 0.05 | 0.07 | 0.06 | 0.05 | 0.01 | 0.06 | 0.07 | 0.03 | 0.00 | -0.01 | 0.00 | 0.04 |
| | | 0.04 | 0.02 | 0.00 | 0.02 | 0.00 | -0.01 | 0.01 | 0.04 | 0.03 | -0.04 | -0.03 | 0.01 |
| | H9L3G | 0.30 | 0.58 | 2.22 | 2.39 | 0.36 | 0.51 | 0.04 | -0.05 | 0.09 | 0.17 | 0.20 | 0.28 |
| | | 0.80 | 1.11 | 2.41 | 2.65 | 1.01 | 1.14 | 0.08 | 0.05 | 0.16 | 0.14 | 0.49 | 0.44 |
| | EZKNT | 0.04 | 0.05 | 0.25 | 0.61 | 0.07 | 0.09 | 0.07 | 0.31 | 0.07 | 0.08 | 0.07 | 0.07 |
| | | 0.03 | 0.03 | 0.30 | 0.42 | 0.05 | 0.06 | 0.04 | 0.05 | 0.23 | 0.20 | 0.16 | 0.17 |
| | A9F9Q | 0.04 | 0.05 | 0.12 | 0.14 | 0.05 | 0.09 | 0.06 | 0.05 | 0.13 | 0.09 | 0.09 | 0.10 |
| | | 0.06 | 0.05 | 0.05 | 0.06 | 0.04 | 0.05 | 0.05 | 0.03 | 0.16 | 0.12 | 0.12 | 0.11 |
| | JXGB9 | 0.04 | 0.03 | 0.05 | 0.02 | 0.03 | 0.04 | 0.04 | 0.04 | 0.19 | 0.10 | 0.09 | 0.22 |
| | | 0.00 | 0.02 | 0.03 | 0.02 | 0.02 | 0.03 | 0.04 | 0.07 | 0.13 | 0.06 | 0.07 | 0.08 |
| | JD1J9 | 0.03 | 0.05 | 0.05 | 0.32 | 0.07 | 0.06 | 0.04 | 0.02 | 0.01 | 0.05 | 0.02 | -0.02 |
| | | 0.03 | 0.03 | 0.06 | 0.40 | 0.02 | 0.06 | 0.03 | 0.01 | 0.03 | 0.04 | 0.04 | 0.04 |
| | A6TR9 | 0.03 | 0.03 | 0.04 | 0.05 | 0.07 | 0.12 | 0.05 | 0.03 | 0.17 | 0.04 | 0.05 | 0.01 |
| | | 0.02 | 0.01 | 0.05 | 0.06 | 0.05 | 0.07 | 0.05 | 0.04 | 0.04 | 0.06 | 0.05 | 0.07 |
| | EOZ2F | 0.05 | 0.05 | 0.06 | 0.04 | 0.05 | 0.06 | 0.06 | 0.06 | 0.06 | 0.05 | 0.04 | 0.06 |
| | | 0.04 | 0.05 | 0.06 | 0.05 | 0.05 | 0.05 | 0.05 | 0.01 | -0.02 | 0.03 | 0.04 | 0.05 |
| | A5NDH | 0.04 | 0.04 | 0.07 | 0.29 | 0.04 | 0.06 | 0.07 | 0.07 | 0.04 | 0.03 | 0.08 | 0.06 |
| | | 0.02 | 0.02 | 0.03 | 0.05 | 0.01 | 0.01 | 0.04 | 0.05 | 0.00 | -0.03 | 0.22 | 0.54 |
| | G7MQM | 0.06 | 0.12 | 0.06 | 0.07 | 0.07 | 0.07 | 0.04 | 0.02 | 0.04 | 0.10 | 2.56 | 2.50 |
| | | 0.05 | 0.09 | 0.04 | 0.04 | 0.06 | 0.07 | 0.03 | 0.00 | 0.09 | 0.62 | 2.49 | 2.88 |
| | IJOR6 | 0.04 | 0.05 | 0.05 | 0.04 | 0.07 | 0.08 | 0.03 | 0.02 | 0.03 | 0.03 | 0.09 | 0.15 |
| | | 0.03 | 0.07 | 0.05 | 0.05 | 0.05 | 0.05 | 0.05 | 0.02 | 0.03 | 0.04 | 0.05 | 0.08 |
| | D4LT2 | 0.05 | 0.06 | 0.07 | 0.05 | 0.05 | 0.05 | 0.05 | 0.05 | 0.04 | 0.04 | 0.04 | 0.04 |
| | | 0.04 | 0.04 | 0.05 | 0.04 | 0.06 | 0.05 | 0.04 | 0.04 | 0.02 | 0.04 | 0.03 | 0.04 |
| | EVUGG | 0.03 | 0.05 | 0.04 | 0.04 | 0.04 | 0.04 | 0.04 | 0.03 | 0.04 | 0.05 | 0.04 | 0.04 |
| | | 0.01 | -0.01 | -0.01 | 0.01 | 0.03 | 0.02 | 0.03 | 0.04 | 0.04 | 0.05 | 0.05 | 0.05 |
| | DUIFV | 0.03 | 0.06 | 0.04 | 0.05 | 0.04 | 0.04 | 0.02 | 0.02 | 0.00 | 0.03 | 0.03 | 0.03 |
| | | 0.03 | 0.04 | 0.05 | 0.04 | 0.05 | 0.06 | 0.05 | 0.01 | 0.02 | 0.04 | 0.02 | 0.02 |
| | DTF5S | 0.04 | 0.04 | 0.05 | 0.04 | 0.06 | 0.03 | 0.04 | 0.02 | 0.01 | 0.05 | 0.03 | 0.04 |
| | | 0.05 | 0.05 | 0.06 | 0.06 | 0.05 | 0.06 | 0.05 | 0.04 | 0.03 | 0.03 | 0.04 | 0.03 |
| | DZ3YC | 0.03 | 0.04 | 0.06 | 0.05 | 0.05 | 0.06 | 0.04 | 0.04 | 0.03 | 0.05 | 0.06 | 0.05 |
| | | 0.03 | 0.04 | 0.03 | 0.05 | 0.04 | 0.05 | 0.04 | 0.02 | 0.02 | 0.04 | 0.04 | 0.04 |
| | CIZN5 | 0.01 | 0.03 | 0.05 | 0.04 | 0.03 | 0.02 | 0.03 | 0.04 | 0.02 | 0.04 | 0.03 | 0.03 |
| | | 0.02 | 0.02 | 0.05 | 0.02 | 0.03 | 0.04 | 0.03 | 0.03 | 0.04 | 0.04 | 0.04 | 0.03 |
| | | ARW3R | | GRBL0 | | JAVSR | | BLP3K | | AE3TS | | GOOZ5 | |

Kappa Chain

Figure 14 (Continued)

```
                        SEQUENCE LISTING

<160> NUMBER OF SEQ ID NOS: 412

<210> SEQ ID NO 1
    <211> LENGTH: 60
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 1
ccatctcatc cctgcgtgtc tccgactcag acgagtgcgt gatgtgaagc ttcaggagtc      60

<210> SEQ ID NO 2
    <211> LENGTH: 60
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 2
ccatctcatc cctgcgtgtc tccgactcag acgctcgaca caggtgcagc tgaaggagtc      60

<210> SEQ ID NO 3
    <211> LENGTH: 60
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 3
ccatctcatc cctgcgtgtc tccgactcag agacgcactc caggtgcagc tgaagcagtc      60

<210> SEQ ID NO 4
    <211> LENGTH: 60
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 4
ccatctcatc cctgcgtgtc tccgactcag agcactgtag cagttactct gaaaagagtc      60

<210> SEQ ID NO 5
    <211> LENGTH: 61
    <212> TYPE: DNA
    <213> ORGANISM: Artificial Sequence
    <220> FEATURE:
    <223> OTHER INFORMATION: Description of Artificial Sequence: Synthetic
          oligonucleotide

<400> SEQUENCE: 5
```

```
ccatctcatc cctgcgtgtc tccgactcag atcagacacg gaggtccagc tgcaacaatc    60
t                                                                    61

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccatctcatc cctgcgtgtc tccgactcag atatcgcgag gaggtccagc tgcagcagtc    60

<210> SEQ ID NO 7
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccatctcatc cctgcgtgtc tccgactcag cgtgtctcta caggtccaac tgcagcagcc    60
t                                                                    61

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccatctcatc cctgcgtgtc tccgactcag ctcgcgtgtc gaggtgaagc tggtggagtc    60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccatctcatc cctgcgtgtc tccgactcag tctctatgcg gaggtgaagc tggtggaatc    60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccatctcatc cctgcgtgtc tccgactcag tgatacgtct gatgtgaact tggaagtgtc    60

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 11
cctatcccct gtgtgccttg gcagtctcag tgcagagaca gtgaccagag t            51

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cctatcccct gtgtgccttg gcagtctcag tgaggagact gtgagagtgg t            51

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cctatcccct gtgtgccttg gcagtctcag tgaggagacg gtgactgagg t            51

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cctatcccct gtgtgccttg gcagtctcag tgaggagacg gtgaccgtgg t            51

<210> SEQ ID NO 15
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccatctcatc cctgcgtgtc tccgactcag catagtagtg gatgttttga tgacccaaac   60
t                                                                   61

<210> SEQ ID NO 16
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccatctcatc cctgcgtgtc tccgactcag cgagagatac gatattgtga tgacgcaggc   60
t                                                                   61

<210> SEQ ID NO 17
<211> LENGTH: 58
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 17
ccatctcatc cctgcgtgtc tccgactcag atacgacgta gatattgtga taacccag      58

<210> SEQ ID NO 18
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccatctcatc cctgcgtgtc tccgactcag tcacgtacta gacattgtgc tgacccaatc    60
t                                                                    61

<210> SEQ ID NO 19
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccatctcatc cctgcgtgtc tccgactcag cgtctagtac gacattgtga tgacccagtc    60
t                                                                    61

<210> SEQ ID NO 20
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccatctcatc cctgcgtgtc tccgactcag tctacgtagc gatattgtgc taactcagtc    60
t                                                                    61

<210> SEQ ID NO 21
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccatctcatc cctgcgtgtc tccgactcag tgtactactc gatatccaga tgacacagac    60
t                                                                    61

<210> SEQ ID NO 22
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
```

```
ccatctcatc cctgcgtgtc tccgactcag acgactacag gacatccagc tgactcagtc      60
t                                                                      61

<210> SEQ ID NO 23
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccatctcatc cctgcgtgtc tccgactcag cgtagactag caaattgttc tcacccagtc      60
t                                                                      61

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cctatcccct gtgtgccttg gcagtctcag ccgtttcagc tccagcttg                  49

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cctatcccct gtgtgccttg gcagtctcag ccgttttatt ccagcttggt                 50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cctatcccct gtgtgccttg gcagtctcag ccgttttatt tccaactttg                 50

<210> SEQ ID NO 27
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ccatctcatc cctgcgtgtc tccgactcag tacgagtatg caggctgttg tgactcagga      60
a                                                                      61

<210> SEQ ID NO 28
<211> LENGTH: 51
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 28
cctatcccct gtgtgccttg gcagtctcag cttgggctga cctaggacag t          51

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Val Lys Phe
1

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Val Ser Thr Asn Val
1               5

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Pro Tyr Asp Asp Pro Thr Tyr Arg Gly Tyr Gly Met Asp Leu
1               5                   10                  15

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Pro Ala Val Asn Thr Tyr Ala Ser
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Leu Phe Leu His Phe
1               5

<210> SEQ ID NO 34
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Leu Phe Leu Asn Leu
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Leu Phe Leu Asn Phe
1               5

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Leu Gly Tyr Val Gly Ser Ser Val Tyr Ile Val Lys Tyr Ile Asn
1               5                   10                  15

Leu

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Leu Ile Arg Val Ala Gly Asp Thr Phe Tyr Asp Gly Ala Phe Asn
1               5                   10                  15

Leu

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Arg Tyr Asn Gly Trp Gly Tyr Ser Asn Asp Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 39

Gly Gly Gly Thr Thr Leu Tyr Thr Tyr Phe Asp Leu
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Leu Gly Tyr Val Gly Ser Asp Val Tyr Ile Val Lys Tyr Ile Asn
1               5                   10                  15

Leu

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Tyr Gly Tyr Gly Tyr Gly Asn Thr Asp Phe Asn Leu
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Asp Gly Gly Val Arg Val Asp Phe Asp Leu
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Asp Asp Ser Gly Trp Met Pro Phe Lys Leu
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Val Gly Ser Ser Ser His Tyr Asn Leu Asn Leu
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Gly Thr Asp His Gly Phe Asn Ile Asp Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Thr Phe Arg Asn Ser Tyr Ala Arg Leu Ala Leu
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Pro Tyr Gly Trp Tyr Ser Gly Gly Gly Ala Ala Pro Tyr Phe Asp
1               5                   10                  15

Leu

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Ala Ala Ile Leu
1               5

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Val Ser Asp Asn Gly Tyr Gly Met Tyr Trp Phe Asn Leu
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Glu Leu Ala Gly Tyr Asp Val Gly Val Glu Phe
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Arg Ser Thr Ser Tyr Tyr Ile Asn Leu
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Gly Ser Asp His Gly Phe Asn Ile Asp Leu
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ala Asp Ser Ile Tyr Arg Ile Tyr Phe Asp Leu
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn Val Gly Ser Ser Ser Tyr Tyr Asn Leu Asn Leu
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Asp Ala Gly Tyr Gly Tyr Phe Asp Ala Phe Gly Pro
1               5                   10

<210> SEQ ID NO 56

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Asp Ala Gly Tyr Gly Ser Phe Asp Ala Phe Gly Pro
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Leu Gly Tyr Val Gly Ser Ser Val Tyr Ile Ser Lys Tyr Ile Asn
1               5                   10                  15

Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Pro Trp Thr Gly Gly Ser Gly Asp Ala Arg Leu Thr Arg Leu Asp
1               5                   10                  15

Leu

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Leu Gly Tyr Ala Ser Tyr Ile Gly Tyr Gly Tyr Pro Ser Tyr Tyr
1               5                   10                  15

Phe Lys Leu

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Leu Gly Tyr Ala Ser Tyr Arg Gly Tyr Gly Tyr Pro Ser Tyr Tyr
1               5                   10                  15

Phe Lys Leu

<210> SEQ ID NO 61
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Gly Glu Phe Ser Cys Arg Asp Phe Asp Cys Thr Val
1               5                   10

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Gln Gly Glu Phe Ser Cys Arg Asp Phe Asp Cys Thr Val Phe
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Gly Gly Tyr Lys Ser Ser Gly Asp Thr Val Ser
1               5                   10

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Cys Ala Gly Gly Tyr Lys Ser Ser Gly Asp Thr Val Ser Phe
1               5                   10                  15

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Gly Gly Tyr Lys Ser Thr Thr Asp Gly Ser Ala
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Ala Gly Gly Tyr Lys Ser Thr Thr Asp Gly Ser Ala Phe
```

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Gln Gly Arg Arg Ser Val Asp Val Asp Asn Val
1               5                   10

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Ala Asp Ala Ala Thr Tyr Tyr Cys Gln Gln Gly Arg Arg Ser Val
1               5                   10                  15

Asp Val Asp Asn Val Phe Gly Gly Gly Thr Glu
            20                  25

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gly Glu Phe Asn Cys Asp Gly Val Gly Cys Thr Thr
1               5                   10

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Cys Gln Gly Glu Phe Asn Cys Asp Gly Val Gly Cys Thr Thr Phe
1               5                   10                  15

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Val Arg Asp Trp Gly Asp Ala Leu Asp Leu
1               5                   10

<210> SEQ ID NO 72
<211> LENGTH: 26
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 72

Gly Val Arg Asp Trp Gly Asp Ala Leu Asp Leu Trp Gly Gln Gly Thr
1               5                   10                  15

Leu Val Thr Val Ser Ser Gly Gln Pro Lys
            20                  25

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Tyr Asn Ser Val Val Gly Asp Asp Ile
1               5                   10

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Tyr Asn Ser Val Val Gly Asp Asp Ile Trp Gly Pro Gly Thr Leu
1               5                   10                  15

Val Thr Val Ser Leu Gly Gln Pro Lys
            20                  25

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Tyr Asn Ser Val Val Gly Asp Asp Met
1               5                   10

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Tyr Asn Ser Val Val Gly Asp Asp Met Trp Gly Pro Gly Thr Leu
1               5                   10                  15

Val Thr Val Ser Leu Gly Gln Pro Lys
            20                  25

<210> SEQ ID NO 77
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 77

Gly Met Pro Gly Ser Thr Ser Gly Asn Ser Asn Ile
1               5                   10

<210> SEQ ID NO 78
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Met Pro Gly Ser Thr Ser Gly Asn Ser Asn Ile Trp Gly Pro Gly
1               5                   10                  15

Thr Leu Val Thr Val Ser Leu Gly Gln Pro Lys
            20                  25

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Tyr Asn Ser Leu Val Gly Asp Asp Ile
1               5                   10

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Tyr Asn Ser Leu Val Gly Asp Asp Ile Trp Gly Pro Gly Thr Leu
1               5                   10                  15

Val Thr Val Ser Leu Gly Gln Pro Lys
            20                  25

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Gly Asp Pro Gly His Pro Asn Gly Leu Phe Phe Thr Met
1               5                   10

<210> SEQ ID NO 82
<211> LENGTH: 29
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 82

Lys Gly Asp Pro Gly His Pro Asn Gly Leu Phe Phe Thr Met Trp Gly
1               5                   10                  15

Pro Gly Thr Leu Val Thr Val Ser Phe Gly Gln Pro Lys
            20                  25

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Gly Gly Ser His Ser Gly Ser Ala Ile Tyr Asp Met Asp Pro
1               5                   10                  15

<210> SEQ ID NO 84
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Gly Gly Ser His Ser Gly Ser Ala Ile Tyr Asp Met Asp Pro Trp
1               5                   10                  15

Gly Pro Gly Thr Leu Val Thr Val Ser Ser Gly Gln Pro Lys
            20                  25                  30

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Thr Ser Arg Gly Ser Asp Tyr Arg Leu Asp Leu
1               5                   10

<210> SEQ ID NO 86
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Thr Ser Arg Gly Ser Asp Tyr Arg Leu Asp Leu Trp Gly Gln Gly
1               5                   10                  15

Thr Leu Val Thr Val Ser Ser Gly Gln Pro Lys
            20                  25

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Gly Met Pro Ala Ser Thr Ser Gly Asn Ser Asn Ile
1               5                   10

<210> SEQ ID NO 88
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Met Pro Ala Ser Thr Ser Gly Asn Ser Asn Ile Trp Gly Pro Gly
1               5                   10                  15

Thr Leu Val Thr Val Ser Leu Gly Gln Pro Lys
            20                  25

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Ala Ile Ala Asn Ile
1               5

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Ala Ile Ala Asn Ile Trp Gly Pro Gly Thr Leu Val Thr Val Ser
1               5                   10                  15

Leu Gly Gln Pro Lys
            20

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Lys Trp Met Val Phe Gly Asp Leu Arg Leu
1               5                   10

<210> SEQ ID NO 92
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Asp Lys Trp Met Val Phe Gly Asp Leu Arg Leu Trp Gly Pro Gly Thr
1               5                   10                  15

Leu Val Thr Val Ser Ser Gly Gln Pro Lys
            20                  25

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Gly Arg Thr Tyr Ser Asp Val Ala Asn Val
1               5                   10

<210> SEQ ID NO 94
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Tyr Ser Asp Val Ala Asn Val Phe Gly Gly Gly Thr Glu Val Val
1               5                   10                  15

Val Lys

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Gly Tyr Ser Ser Tyr Asn Val Asp Asn Ala
1               5                   10

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asn Val Asp Asn Ala Phe Gly Gly Gly Thr Glu Val Val Val Lys
1               5                   10                  15

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Gly Tyr Ser Ser Ser Asn Val Asp Asn Ala
1               5                   10
```

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asn Val Asp Asn Ala Phe Gly Gly Gly Thr Glu Val Val Val Lys
1               5                   10                  15

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Gly Thr Tyr Asp Cys Arg Ser Ala Asp Cys Asn Ala
1               5                   10

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ala Asp Cys Asn Ala Phe Gly Gly Gly Thr Glu Val Val Val Lys
1               5                   10                  15

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln His Gly Tyr Tyr Ser Asn Val Asp Asn Ala
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Val Asp Asn Ala Phe Gly Gly Gly Thr Glu Val Val Val Lys
1               5                   10                  15

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 103

Gln Gln Gly Phe Ser Ser Arg Asn Val Asp Asn Ala
1               5                   10

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asn Val Asp Asn Ala Phe Gly Gly Gly Thr Glu Val Val Val Lys
1               5                   10                  15

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gln Gly Tyr Ser Ser Val Asn Val Asp Asn Ala
1               5                   10

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asn Val Asp Asn Ala Phe Gly Gly Gly Thr Glu Val Val Val Lys
1               5                   10                  15

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Gly Tyr Thr Tyr Asn Asn Val Asp Asn Ala
1               5                   10

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Val Asp Asn Ala Phe Gly Gly Gly Thr Glu Val Val Val Lys
1               5                   10                  15

<210> SEQ ID NO 109
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 109

Leu Gly Thr Tyr Asp Cys Arg Ser Gly Asp Cys Asn Val
1               5                   10

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Gly Asp Cys Asn Val Phe Gly Gly Gly Thr Glu Val Val Val Lys
1               5                   10                  15

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Gly Tyr Thr Ser Asn Val Asp Asn Ala
1               5                   10

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asn Val Asp Asn Ala Phe Gly Gly Gly Thr Glu Val Val Val Lys
1               5                   10                  15

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Gln Gly Gln Thr Pro Glu Asn Val Asp Asn Ala
1               5                   10

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asn Val Asp Asn Ala Phe Gly Gly Gly Thr Glu Val Val Val Lys
1               5                   10                  15
```

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Gln Gly Ser Thr Tyr Ser Asp Val Ala Asn Val
1               5                   10

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Tyr Ser Asp Val Ala Asn Val Phe Gly Gly Gly Thr Glu Val Val
1               5                   10                  15

Val Lys

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Gly Ala Thr Tyr Ser Asp Val Ala Asn Val
1               5                   10

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Tyr Ser Asp Val Ala Asn Val Phe Gly Gly Gly Thr Glu Val Val
1               5                   10                  15

Val Lys

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Gln Gly Thr Thr Tyr Ser Asp Val Ala Asn Val
1               5                   10

<210> SEQ ID NO 120
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 120

Thr Tyr Ser Asp Val Ala Asn Val Phe Gly Gly Gly Thr Glu Val Val
1               5                   10                  15

Val Lys

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Gln Gly Tyr Thr Arg Ser Asn Val Asp Asn Ala
1               5                   10

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asn Val Asp Asn Ala Phe Gly Gly Gly Thr Glu Val Val Val Lys
1               5                   10                  15

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Gly Tyr Lys Ser Tyr Gly Asn Ala Asp Ile Asp
1               5                   10

<210> SEQ ID NO 124
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Tyr Gly Asn Ala Asp Ile Asp Phe Gly Gly Gly Thr Glu Val Val
1               5                   10                  15

Val Lys

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 125

Gln Gln Gly Tyr Thr Ser Ser Asn Val Asp Asn Ala
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asn Val Asp Asn Ala Phe Gly Gly Gly Thr Glu Val Val Val Lys
1               5                   10                  15

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Leu Val Ser Tyr Asp Cys Ser Ser Ala Asp Cys Asn Ala
1               5                   10

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Ala Asp Cys Asn Ala Phe Gly Gly Gly Thr Glu Val Val Val Lys
1               5                   10                  15

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln Ala Tyr Thr Ser Ser Asn Val Asp Asn Ala
1               5                   10

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asn Val Asp Asn Ala Phe Gly Gly Gly Thr Glu Val Val Val Lys
1               5                   10                  15

<210> SEQ ID NO 131
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 131

Asp Gly Gly Leu
1

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Gly Gly Leu Trp Gly Pro Gly Thr Leu Val Thr Val Ser Ser Gly
1               5                   10                  15

Gln Pro Lys

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Pro Tyr Asp Thr Asn Thr Ser Leu Asp Ala Leu
1               5                   10

<210> SEQ ID NO 134
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Pro Tyr Asp Thr Asn Thr Ser Leu Asp Ala Leu Trp Gly Pro Gly
1               5                   10                  15

Thr Leu Val Thr Val Ser Ser Gly Gln Pro Lys
                20                  25

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Glu Gly Ser Asp Asp Asp Ser Phe Asp Leu
1               5                   10

<210> SEQ ID NO 136
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 136

Glu Gly Ser Asp Asp Asp Ser Phe Asp Leu Trp Gly Pro Gly Thr Leu
1               5                   10                  15

Val Thr Val Ser Ser Gly Gln Pro Lys
            20                  25

<210> SEQ ID NO 137
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Gly Asp Leu
1

<210> SEQ ID NO 138
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Gly Asp Leu Trp Gly Gln Gly Thr Leu Val Thr Val Ser Ser Gly
1               5                   10                  15

Gln Pro Lys

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly His Trp Ser Ala Gly Ala Thr Leu Tyr Gly Tyr Phe Ser Leu
1               5                   10                  15

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly His Trp Ser Ala Gly Ala Thr Leu Tyr Gly Tyr Phe Ser Leu Trp
1               5                   10                  15

Gly Pro Gly Thr Leu Val Thr Val Ser Ser Gly Gln Pro Lys
            20                  25                  30

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 141

Leu Ala Asn Tyr Asp Cys Ser Ser Gly Asp Cys Ser Val
1               5                   10

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Leu Ala Asn Tyr Asp Cys Ser Ser Gly Asp Cys Ser Val Phe
1               5                   10                  15

<210> SEQ ID NO 143
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Gly Asn Phe Asp Cys Ser Ser Ala Asp Cys Ser Ala
1               5                   10

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Gln Gly Asn Phe Asp Cys Ser Ser Ala Asp Cys Ser Ala Phe
1               5                   10                  15

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Gly Asn Phe Asp Cys Thr Ser Ala Asp Cys Ser Ala
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Gln Gly Asn Phe Asp Cys Thr Ser Ala Asp Cys Ser Ala Phe
1               5                   10                  15

<210> SEQ ID NO 147
<211> LENGTH: 26
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 147

Asp Gly Thr Asp His Gly Phe Asn Ile Asp Leu Trp Gly Pro Gly Thr
1               5                   10                  15

Leu Val Thr Val Ser Ser Gly Gln Pro Lys
            20                  25

<210> SEQ ID NO 148
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Ser Thr Thr Val Thr Leu Gln Met Thr Ser Leu Thr Ala Ala Asp
1               5                   10                  15

Thr Ala Thr Tyr Phe Cys Ala Ser Gly Asn Val Trp Gly Pro Gly Thr
            20                  25                  30

Leu Val Thr Val Ser Ser Gly Gln Pro Lys
        35                  40

<210> SEQ ID NO 149
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Val Ser Thr Asn Val Trp Gly Pro Gly Thr Leu Val Thr Val Ser
1               5                   10                  15

Ser Gly Gln Pro Lys
            20

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Phe Cys Thr Arg Gly Val Lys Phe
1               5

<210> SEQ ID NO 151
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Gly Ser Asp His Gly Phe Asn Ile Asp Leu Trp Gly Pro Gly Thr
1               5                   10                  15

Leu Val Thr Val Ser Ser Gly Gln Pro Lys
```

```
            20                  25

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asn Ala Ala Ile Leu
1               5

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asn Ala Ala Ile Leu Trp Gly Pro Gly Thr Leu Val Thr Val Ser Ser
1               5                   10                  15

Gly Gln Pro Lys
            20

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Arg Ser Thr Ser Tyr Tyr Ile Asn Leu
1               5                   10

<210> SEQ ID NO 155
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Arg Ser Thr Ser Tyr Tyr Ile Asn Leu Trp Gly Pro Gly Thr Leu
1               5                   10                  15

Val Thr Val Ser Ser Gly Gln Pro Lys
            20                  25

<210> SEQ ID NO 156
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Gly Asp Ala Gly Tyr Gly Ser Phe Asp Ala Phe Gly Pro Trp Gly
1               5                   10                  15

Pro Gly Thr Leu Val Thr Val Ser Ser Gly Gln Pro Lys
```

```
                20                  25

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Val Ser Thr Asp Val
1               5

<210> SEQ ID NO 158
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Val Ser Thr Asn Val Trp Gly Pro Gly Thr Leu Val Thr Val Ser
1               5                   10                  15

Ser Gly Gln Pro Lys
            20

<210> SEQ ID NO 159
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asn Val Gly Ser Ser Ser Tyr Tyr Asn Leu Asn Leu Trp Gly Pro Gly
1               5                   10                  15

Thr Leu Val Thr Val Ser Ser Gly Gln Pro Lys
            20                  25

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Val Ser Thr Ser Val
1               5

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Val Ser Thr Asn Val Trp Gly Pro Gly Thr Leu Val Thr Val Ser
1               5                   10                  15

Ser Gly Gln Pro Lys
```

-continued

20

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Gly Tyr Ala Gly Ala Gly Tyr Phe Asp Ala Phe Asn Pro
1               5                   10

<210> SEQ ID NO 163
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Tyr Ala Gly Ala Gly Tyr Phe Asp Ala Phe Asn Pro Trp Gly
1               5                   10                  15

Pro Gly Thr Leu Val Thr Val Ser Ser Gly Gln Pro Lys
            20                  25

<210> SEQ ID NO 164
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asn Tyr Asn Leu
1

<210> SEQ ID NO 165
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asn Tyr Asn Leu Trp Gly Pro Gly Thr Leu Val Thr Val Ser Ser Gly
1               5                   10                  15

Gln Pro Lys

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Asp Gly Phe Ser Thr Asp Arg Tyr Phe Asn Leu
1               5                   10

<210> SEQ ID NO 167

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Gly Phe Ser Thr Asp Arg Tyr Phe Asn Leu Trp Gly Pro Gly Thr
1               5                   10                  15

Leu Val Thr Val Ser Ser Gly Gln Pro Lys
            20                  25

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Arg Gly Thr Gly Ser Gly Asp Tyr Thr Pro Phe Asn Leu
1               5                   10

<210> SEQ ID NO 169
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Ser Gly Asp Tyr Thr Pro Phe Asn Leu Trp Gly Pro Gly Thr Leu
1               5                   10                  15

Val Thr Val Ser Ser Gly Gln Pro Lys
            20                  25

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Ala Ala Ile Leu
1               5

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asn Ala Ala Ile Leu Trp Gly Pro Gly Thr Leu Val Thr Val Ser Ser
1               5                   10                  15

Gly Gln Pro Lys
            20

<210> SEQ ID NO 172
```

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Pro Tyr Val Asp Ser Thr Tyr Tyr Asn Leu
1               5                   10

<210> SEQ ID NO 173
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Pro Tyr Val Asp Ser Thr Tyr Tyr Asn Leu Trp Gly Pro Gly Thr
1               5                   10                  15

Leu Val Thr Val Ser Ser Gly Gln Pro Lys
            20                  25

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Ser Gly Asp Tyr Thr Pro Phe Asn Leu
1               5                   10

<210> SEQ ID NO 175
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Ser Gly Asp Tyr Thr Pro Phe Asn Leu Trp Gly Pro Gly Thr Leu
1               5                   10                  15

Val Thr Val Ser Ser Gly Gln Pro Lys
            20                  25

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Tyr Tyr Asp Gly Ala Asp Tyr His Thr Tyr Asn Leu
1               5                   10

<210> SEQ ID NO 177
<211> LENGTH: 27
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 177

Tyr Tyr Asp Gly Ala Asp Tyr His Thr Tyr Asn Leu Trp Gly Pro Gly
1               5                   10                  15

Thr Leu Val Thr Val Ser Ser Gly Gln Pro Lys
            20                  25

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Glu Phe Gly Asn Asn Gly Trp Asn Ile Asp Leu
1               5                   10

<210> SEQ ID NO 179
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Glu Phe Gly Asn Asn Gly Trp Asn Ile Asp Leu Trp Gly Pro Gly Thr
1               5                   10                  15

Leu Val Thr Val Ser Ser Gly Gln Pro Lys
            20                  25

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Val Glu Tyr Gly Asn Asp Trp Gly Asn Leu
1               5                   10

<210> SEQ ID NO 181
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Val Glu Tyr Gly Asn Asp Trp Gly Asn Leu Trp Gly Pro Gly Thr Leu
1               5                   10                  15

Val Thr Val Ser Ser Gly Gln Pro Lys
            20                  25

<210> SEQ ID NO 182
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 182

Tyr Phe Asp Gly Ala Asp Tyr His Thr Tyr Asn Leu
1               5                   10

<210> SEQ ID NO 183
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Tyr Phe Asp Gly Ala Asp Tyr His Thr Tyr Asn Leu Trp Gly Pro Gly
1               5                   10                  15

Thr Leu Val Thr Val Ser Ser Gly Gln Pro Lys
            20                  25

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Phe Ser Gly Gly Gly Tyr Gly Tyr Asp Leu
1               5                   10

<210> SEQ ID NO 185
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Phe Ser Gly Gly Gly Tyr Gly Tyr Asp Leu Trp Gly Pro Gly Thr Leu
1               5                   10                  15

Val Thr Val Ser Ser Gly Gln Pro Lys
            20                  25

<210> SEQ ID NO 186
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Arg Asp Leu
1

<210> SEQ ID NO 187
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 187

Asp Arg Asp Leu Trp Gly Pro Gly Thr Leu Val Thr Val Ser Ser Gly
1               5                   10                  15

Gln Pro Lys

<210> SEQ ID NO 188
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Leu Asp Leu
1

<210> SEQ ID NO 189
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Tyr Gly Leu Asp Leu Trp Gly Pro Gly Thr Leu Val Thr Val Ser Ser
1               5                   10                  15

Gly Gln Pro Lys
            20

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Tyr Asp Val Asp Ser Val Ser Ala Tyr Asp Leu
1               5                   10

<210> SEQ ID NO 191
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Tyr Asp Val Asp Ser Val Ser Ala Tyr Asp Leu Trp Gly Pro Gly Thr
1               5                   10                  15

Leu Val Thr Val Ser Ser Gly Gln Pro Lys
            20                  25

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 192

Glu Val Val Gly Tyr Asp Tyr Ser Gly Asp Leu
1               5                   10

<210> SEQ ID NO 193
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Glu Val Val Gly Tyr Asp Tyr Ser Gly Asp Leu Trp Gly Pro Gly Thr
1               5                   10                  15

Leu Val Thr Val Ser Ser Gly Gln Pro Lys
            20                  25

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asp Pro Tyr Asp Asp Pro Thr Tyr
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Asp Pro Tyr Asp Asp Pro Thr Tyr Arg
1               5

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Gly Leu Val Lys Pro Gly Ala Ser Leu Thr Leu
1               5                   10

<210> SEQ ID NO 197
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
acgagctacg cacgaactgc aggtrtccac tcc                              33

<210> SEQ ID NO 198
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
acgagctacg cacgaatagc aggtgtccac tcc                              33

<210> SEQ ID NO 199
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
acgagctacg cacgargtac aggtgtccac tcc                              33

<210> SEQ ID NO 200
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
acgagctacg cacgagcyac agmtgtccac tcc                              33

<210> SEQ ID NO 201
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
acgagctacg cacgaactgc aggtgtccwm tcc                              33

<210> SEQ ID NO 202
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
acgagctacg cacgarctrc aggtgtkcac tcc                              33

<210> SEQ ID NO 203
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
acgagctacg cacgagctaw mggtgtccac tcc                              33

<210> SEQ ID NO 204
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
acgagctacg cacgacctca ggtgtccact cc                                     32

<210> SEQ ID NO 205
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
acgagctacg cacgagctac aggtgctcac tcc                                    33

<210> SEQ ID NO 206
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
acgagctacg cacgaactgc aggtgtcctc tct                                    33

<210> SEQ ID NO 207
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
acgagctacg cacgaaytgc aggtgtccay tgc                                    33

<210> SEQ ID NO 208
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
acgagctacg cacgagctam mggtgtccac ttc                                    33

<210> SEQ ID NO 209
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
acgagctacg cacgactcct gtcaktaact kcaggt                                 36

<210> SEQ ID NO 210
<211> LENGTH: 33
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 210
acgagctacg cacgaaactg caggtgtctc tct                               33

<210> SEQ ID NO 211
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
acgagctacg cacgarctrc aggygtccac tct                               33

<210> SEQ ID NO 212
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
acgagctacg cacgaccaag ctgtatcctt tcc                               33

<210> SEQ ID NO 213
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
acgagctacg cacgaccaag ctgtgtcctr tcc                               33

<210> SEQ ID NO 214
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
acgagctacg cacgatgttg acagycvttc ckggt                             35

<210> SEQ ID NO 215
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
acgagctacg cacgatgttc acagcctttc ctggt                             35

<210> SEQ ID NO 216
<211> LENGTH: 34
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 216
acgagctacg cacgatttaa aaggggtcca gtgt                                    34

<210> SEQ ID NO 217
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
acgagctacg cacgataytt taaaargtgt cmagtgt                                 37

<210> SEQ ID NO 218
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
acgagctacg cacgagtttt aaaaggtgtc ctgtg                                   35

<210> SEQ ID NO 219
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
acgagctacg cacgactytt aaaaggkgtc cagwg                                   35

<210> SEQ ID NO 220
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
acgagctacg cacgacyttt amatggtatc cagtgt                                  36

<210> SEQ ID NO 221
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
acgagctacg cacgactttt acatggtttc aagtgt                                  36

<210> SEQ ID NO 222
<211> LENGTH: 34
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 222
acgagctacg cacgaytgtc cctgcatatg tcyt                              34

<210> SEQ ID NO 223
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
acgagctacg cacgaatggc agcwgcycca ag                                32

<210> SEQ ID NO 224
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
acgagctacg cacgatttat caaggtgtgc attgt                             35

<210> SEQ ID NO 225
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
acgagctacg cacgactttt aaaagwtgtc cagkgt                            36

<210> SEQ ID NO 226
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
acgagctacg cacgagtgac agtccttcct ggtag                             35

<210> SEQ ID NO 227
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
acgagctacg cacgacttcc tgatggcagt ggtt                              34

<210> SEQ ID NO 228
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
acgagctacg cacgaagcta caggtatcca atcc                                      34

<210> SEQ ID NO 229
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
cactggtgtg agtcaatgca gacagatggg ggtgtcg                                   37

<210> SEQ ID NO 230
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
cactggtgtg agtcaagacc gatggggctg ttgtt                                     35

<210> SEQ ID NO 231
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
cactggtgtg agtcaacaga ctgatggggg tgttgtt                                   37

<210> SEQ ID NO 232
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
cactggtgtg agtcaagaca gatggggctg ttgtt                                     35

<210> SEQ ID NO 233
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
acgagctacg cacgagacat ywwgatgacc cagtctcc                                  38

<210> SEQ ID NO 234
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
cactggtgtg agtcacagtt ggtgcagcat cagcccg                              37

<210> SEQ ID NO 235
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
cctatcccct gtgtgccttg gcagtcacga gctacgcacg a                         41

<210> SEQ ID NO 236
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ccatctcatc cctgcgtgtc tccgactcag ctagtcactc cactggtgtg agtca          55

<210> SEQ ID NO 237
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ccatctcatc cctgcgtgtc tccgactcag agagcgtcac cactggtgtg agtca          55

<210> SEQ ID NO 238
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ccatctcatc cctgcgtgtc tccgactcag tagagacgag cactggtgtg agtca          55

<210> SEQ ID NO 239
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ccatctcatc cctgcgtgtc tccgactcag cacgctacgt cactggtgtg agtca          55

<210> SEQ ID NO 240
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 240
ccatctcatc cctgcgtgtc tccgactcag tcacgcgaga cactggtgtg agtca      55

<210> SEQ ID NO 241
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ccatctcatc cctgcgtgtc tccgactcag cgcgtataca cactggtgtg agtca      55

<210> SEQ ID NO 242
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ccatctcatc cctgcgtgtc tccgactcag tgatacgtct gggccagtgg aagactgat  60 gg                                                                62

<210> SEQ ID NO 243
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
cctatcccct gtgtgccttg gcagtctcag atcagacacg atggagactg ggctgcgct  59

<210> SEQ ID NO 244
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ccatctcatc cctgcgtgtc tccgactcag tcacgtacta gaagaggagg acagwaggcg  60
c                                                                 61

<210> SEQ ID NO 245
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cctatcccct gtgtgccttg gcagtctcag atggacatga gggcccccc             48

<210> SEQ ID NO 246
<211> LENGTH: 67
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 246
ccatctcatc cctgcgtgtc tccgactcag tacagatcgt cttgttgtcc ttgagttcct    60
cagagga                                                             67

<210> SEQ ID NO 247
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cctatcccct gtgtgccttg gcagtctcag atggcctgca ccccg                   45

<210> SEQ ID NO 248
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ccatctcatc cctgcgtgtc tccgactcag ctgtgcgtcg cagaagacsg atgggccctt    60
ggtgga                                                              66

<210> SEQ ID NO 249
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ccatctcatc cctgcgtgtc tccgactcag acgcgagtat gaagacsgat gggcccttgg    60
tgga                                                                64

<210> SEQ ID NO 250
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ccatctcatc cctgcgtgtc tccgactcag cacgctacgt gaagacsgat gggcccttgg    60
tgga                                                                64

<210> SEQ ID NO 251
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ccatctcatc cctgcgtgtc tccgactcag tgagtcagta tgaagacsga tgggcccttg    60

<210> SEQ ID NO 252
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 252
ccatctcatc cctgcgtgtc tccgactcag atctactgac atgatgaaga csgatgggcc    60
cttggtgga                                                           69

<210> SEQ ID NO 253
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 253
ccatctcatc cctgcgtgtc tccgactcag agtagtgatc tcacagaaga csgatgggcc    60
cttggtgga                                                           69

<210> SEQ ID NO 254
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 254
cctatcccct gtgtgccttg gcagtctcag atggactgga cctggagvat c             51

<210> SEQ ID NO 255
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 255
cctatcccct gtgtgccttg gcagtctcag atggactgga tttggaggrt c             51

<210> SEQ ID NO 256
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 256
cctatcccct gtgtgccttg gcagtctcag atggactgca cctggaggat c             51

<210> SEQ ID NO 257
<211> LENGTH: 51
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 257
cctatcccct gtgtgccttg gcagtctcag atggactgga cctggaggkt c        51

<210> SEQ ID NO 258
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
cctatcccct gtgtgccttg gcagtctcag atggacatac tttgttccac gc       52

<210> SEQ ID NO 259
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cctatcccct gtgtgccttg gcagtctcag atggacacac tttgctacac ac       52

<210> SEQ ID NO 260
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
cctatcccct gtgtgccttg gcagtctcag atgtctgtct ccttcctcat ct       52

<210> SEQ ID NO 261
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
cctatcccct gtgtgccttg gcagtctcag atggggtcaa ccgccatcct c        51

<210> SEQ ID NO 262
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
cctatcccct gtgtgccttg gcagtctcag atggagttkg grctgagctg g        51

<210> SEQ ID NO 263
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
cctatcccct gtgtgccttg gcagtctcag atggagtttk ggctkagctg g    51

<210> SEQ ID NO 264
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
cctatcccct gtgtgccttg gcagtctcag atggaactgg ggctccgctg g    51

<210> SEQ ID NO 265
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
cctatcccct gtgtgccttg gcagtctcag atggarttgg ggctgwgctg g    51

<210> SEQ ID NO 266
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
cctatcccct gtgtgccttg gcagtctcag atgaarcayc tgtggttctt cct    53

<210> SEQ ID NO 267
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ccatctcatc cctgcgtgtc tccgactcag acgacagctc gaagatgaag acagatggtg    60
cagccac    67

<210> SEQ ID NO 268
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ccatctcatc cctgcgtgtc tccgactcag tcgatcacgt gaagatgaag acagatggtg    60
cagccac    67

<210> SEQ ID NO 269
<211> LENGTH: 67
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 269
ccatctcatc cctgcgtgtc tccgactcag tacacacact gaagatgaag acagatggtg      60
cagccac                                                                67

<210> SEQ ID NO 270
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ccatctcatc cctgcgtgtc tccgactcag tgtagtgtga tgaagatgaa gacagatggt      60
gcagccac                                                               68

<210> SEQ ID NO 271
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
cctatcccct gtgtgccttg gcagtctcag atggacatga gggtsccygc tcagctc          57

<210> SEQ ID NO 272
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
cctatcccct gtgtgccttg gcagtctcag atggacatga grgtcctcgc tcagctc          57

<210> SEQ ID NO 273
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
cctatcccct gtgtgccttg gcagtctcag atggaagccc cagcdcagct tctc             54

<210> SEQ ID NO 274
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
cctatcccct gtgtgccttg gcagtctcag atggaaaccc cagcgcagct tctc             54

<210> SEQ ID NO 275
```

```
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
cctatcccct gtgtgccttg gcagtctcag atggtgttgc agacccaggt cttc            54

<210> SEQ ID NO 276
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
cctatcccct gtgtgccttg gcagtctcag atggggtccc aggttcacct cctc            54

<210> SEQ ID NO 277
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
cctatcccct gtgtgccttg gcagtctcag atgaggctcc ytgctcagct cctg            54

<210> SEQ ID NO 278
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ccatctcatc cctgcgtgtc tccgactcag cgtagactag agggcgggaa cagagtgacm    60
gtgg                                                                 64

<210> SEQ ID NO 279
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ccatctcatc cctgcgtgtc tccgactcag cgtagactag agggygggaa cagagtgacc    60 gakg                                                                 64

<210> SEQ ID NO 280
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccatctcatc cctgcgtgtc tccgactcag tctagcgact atagggcggg aacagagtga    60
``` cmgtgg                                                               66

<210> SEQ ID NO 281
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ccatctcatc cctgcgtgtc tccgactcag tctagcgact atagggyggg aacagagtga     60 ccgakg                                                               66

<210> SEQ ID NO 282
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
ccatctcatc cctgcgtgtc tccgactcag tagcgcgcgc tagggcggga acagagtgac     60 mgtgg                                                                65

<210> SEQ ID NO 283
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ccatctcatc cctgcgtgtc tccgactcag tagcgcgcgc tagggyggga acagagtgac     60 cgakg                                                                65

<210> SEQ ID NO 284
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ccatctcatc cctgcgtgtc tccgactcag atagagtact agggcgggaa cagagtgacm    60
gtgg                                                                 64

<210> SEQ ID NO 285
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ccatctcatc cctgcgtgtc tccgactcag atagagtact agggygggaa cagagtgacc    60 gakg                                                                 64

```
<210> SEQ ID NO 286
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
cctatcccct gtgtgccttg gcagtctcag atgacctgct ccctctcct cctca          55

<210> SEQ ID NO 287
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
cctatcccct gtgtgccttg gcagtctcag atggccggct tccctctcct cctca          55

<210> SEQ ID NO 288
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
cctatcccct gtgtgccttg gcagtctcag atggcctggt ctcctctcct cctca          55

<210> SEQ ID NO 289
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
cctatcccct gtgtgccttg gcagtctcag atggcctgga cycctctcct cctcm          55

<210> SEQ ID NO 290
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
cctatcccct gtgtgccttg gcagtctcag atgccctggg ctctgctsct cctsa          55

<210> SEQ ID NO 291
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
cctatcccct gtgtgccttg gcagtctcag atgccctggg tcatgctcct cctga          55

<210> SEQ ID NO 292
```

```
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
cctatcccct gtgtgccttg gcagtctcag atggcctgga ctcctctctt tctgt        55

<210> SEQ ID NO 293
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
cctatcccct gtgtgccttg gcagtctcag atggagaaga agaggagacc tgggg        55

<210> SEQ ID NO 294
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
cctatcccct gtgtgccttg gcagtctcag atggcctgga ccgctctcct tctga        55

<210> SEQ ID NO 295
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
cctatcccct gtgtgccttg gcagtctcag atggcctgga ccgttctcct cctcg        55

<210> SEQ ID NO 296
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
cctatcccct gtgtgccttg gcagtctcag atggcatgga tccctctctt cctcg        55

<210> SEQ ID NO 297
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
cctatcccct gtgtgccttg gcagtctcag atggcctgga tccctctact tctcc        55

<210> SEQ ID NO 298
<211> LENGTH: 55
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
cctatcccct gtgtgccttg gcagtctcag atggcctgga yccctctcct gctcc        55

<210> SEQ ID NO 299
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
cctatcccct gtgtgccttg gcagtctcag atggcatggg ccacactcct gctcc        55

<210> SEQ ID NO 300
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
cctatcccct gtgtgccttg gcagtctcag atggcctgga ccctctctg gctca         55

<210> SEQ ID NO 301
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
cctatcccct gtgtgccttg gcagtctcag atggcctggg tctccttcta cctac        55

<210> SEQ ID NO 302
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
cctatcccct gtgtgccttg gcagtctcag atggcctgga ccccactcct cctcc        55

<210> SEQ ID NO 303
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
cctatcccct gtgtgccttg gcagtctcag atggcctggg ctcctctgct cctca        55

<210> SEQ ID NO 304
<211> LENGTH: 55
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 304
cctatcccct gtgtgccttg gcagtctcag atggcctggg ctccactact tctca          55

<210> SEQ ID NO 305
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Phe Ala Leu Trp Gly Pro Gly Thr Leu Val Thr Val Ser Ser Gly
1               5                   10                  15

Gln Pro Lys

<210> SEQ ID NO 306
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Thr Thr Thr Thr
1

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Arg Gly Tyr Tyr Ser Gly Thr Tyr Val Asp Tyr
1               5                   10

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Arg Thr Gly Ile Phe Asp Tyr
1               5

<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Arg Ser Gly Ile Phe Asp Tyr
```

<210> SEQ ID NO 310
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Arg Gly Tyr Tyr Ser Asn Thr Tyr Val Asp Tyr
1               5                   10

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Leu Thr Ala Tyr Phe Asp Tyr
1               5

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Arg Phe Tyr Asp Gly Ser Tyr Tyr Phe Asp Tyr
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Arg Gly Tyr Tyr Ala Asp Thr Tyr Val Asp Tyr
1               5                   10

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

His Glu Pro Leu Asn Trp Phe Pro Tyr
1               5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 315

Lys Tyr Gly Gly Gly Phe Asp Tyr
1               5

<210> SEQ ID NO 316
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gly Ser Ala Phe Ala Tyr
1               5

<210> SEQ ID NO 317
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Tyr Tyr Arg Asn Tyr Gly Gly Phe Asp Tyr
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Glu Asp Tyr Tyr Ser Asp Gln Phe Ala Tyr
1               5                   10

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ser Gln Ser Thr His Val Pro Trp Thr
1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln Gln His Tyr Ser Thr Pro Pro Thr
1               5

<210> SEQ ID NO 321
```

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Gln His Phe Ser Thr Pro Pro Thr
1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Gln His Tyr Ser Thr Pro Phe Thr
1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Trp Gln Gly Thr His Phe Pro Gln Thr
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gln Gln Tyr Tyr Ser Tyr Pro Arg Thr
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Gln Gln Ser Asn Glu Asp Pro Arg Thr
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

```
Gln Gln Trp Ser Ser Asn Pro Leu Thr
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gln His Phe Trp Gly Thr Pro Trp Thr
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Gln Arg Ser Ser Tyr Pro Phe Thr
1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Leu Gln Tyr Ala Ser Tyr Pro Trp Thr
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gln Gln Ser Lys Glu Val Pro Leu Thr
1               5

<210> SEQ ID NO 331
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ile Pro Ser Tyr Ala Ser Ser Arg Gly Tyr Tyr Leu Ile Pro Asp Arg
1               5                   10                  15

Leu Asp Leu

<210> SEQ ID NO 332
<211> LENGTH: 19
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 332

Ile Pro Ser Tyr Val Ser Gly Arg Gly Val Tyr Ile Ile Pro Asp Arg
1               5                   10                  15
Phe Asp Leu

<210> SEQ ID NO 333
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ala Ser Asp Tyr Asp Ser Ser Arg Gly His Trp Leu Val Tyr Asn Arg
1               5                   10                  15
Leu Asp Leu

<210> SEQ ID NO 334
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Lys Gly Asp Pro Gly His Pro Asn Gly Leu Phe Phe Thr Met
1               5                   10

<210> SEQ ID NO 335
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ile Pro Ser Tyr Val Ser Ser Arg Gly Tyr Tyr Leu Ile Pro Asp Gly
1               5                   10                  15
Leu Asp Leu

<210> SEQ ID NO 336
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ile Pro Ser Tyr Val Ser Ser Arg Gly Tyr Tyr Leu Val Pro Asp Gly
1               5                   10                  15
Leu Asp Leu

<210> SEQ ID NO 337
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 337

Ile Pro Ser Tyr Val Ser Ser Arg Gly Tyr Tyr Leu Ile Pro Asp Arg
1               5                   10                  15

Leu Asp Leu

<210> SEQ ID NO 338
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ile Ser Ser Tyr Val Ser Ser Arg Gly Tyr Trp Leu Ile Pro Asp Gly
1               5                   10                  15

Leu Asp Leu

<210> SEQ ID NO 339
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ile Ser Ser Tyr Val Ser Ser Arg Gly Tyr Tyr Leu Ile Pro Asp Gly
1               5                   10                  15

Leu Asp Leu

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Leu Tyr Asn Ser Val Val Gly Asp Asp Met
1               5                   10

<210> SEQ ID NO 341
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ala Ser Asp Tyr Asp Ser Ser Arg Gly His Trp Leu Val Tyr Asp Arg
1               5                   10                  15

Leu Asp Leu

<210> SEQ ID NO 342
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 342

Leu Tyr Asn Ser Val Val Gly Asp Asp Ile
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Leu Tyr Asn Ser Leu Val Gly Asp Asp Ile
1               5                   10

<210> SEQ ID NO 344
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gly Met Pro Gly Ser Thr Ser Gly Asn Ser Asn Ile
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gly Met Pro Ala Ser Thr Ser Gly Asn Ser Asn Ile
1               5                   10

<210> SEQ ID NO 346
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Gly Met Pro Gly Ser Thr Ser Gly Asn Ser Asn Ile
1               5                   10

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gly Val Pro Thr Asn Arg Asp Ala Met
1               5
```

```
<210> SEQ ID NO 348
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ala Gly Gly Tyr Lys Ser Ser Gly Asp Thr Val Ser
1               5                   10

<210> SEQ ID NO 349
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Gln Gly Glu Phe Ser Cys Arg Asp Phe Asp Cys Thr Val
1               5                   10

<210> SEQ ID NO 350
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Leu Gly Gly Tyr Lys Thr Thr Thr Asp Gly Ser Ile
1               5                   10

<210> SEQ ID NO 351
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gln Ser Tyr Tyr His Asn Ser Gly Thr Ser Tyr Ile Thr
1               5                   10

<210> SEQ ID NO 352
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ala Gly Gly Tyr Lys Ser Thr Thr Asp Gly Ser Ala
1               5                   10

<210> SEQ ID NO 353
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353
```

Gln Ser Tyr Tyr His Asn Ser Gly Asn Ser Tyr Ile Thr
1               5                   10

<210> SEQ ID NO 354
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gln Ser Tyr Tyr Tyr Gly Ser Gly Thr Ser Tyr Ile Thr
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ala Gly Gly Tyr Lys Ser Ser Gly Asp Thr Phe Thr
1               5                   10

<210> SEQ ID NO 356
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Leu Gly Gly Tyr Lys Lys Thr Ile Asp Gly Ser Ala
1               5                   10

<210> SEQ ID NO 357
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Ala Gly Gly Tyr Lys Ser Ala Ser Asp Gly Ser Ala
1               5                   10

<210> SEQ ID NO 358
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gln Gly Glu Phe Ser Cys Asp Ala Gly Val Cys Thr Leu
1               5                   10

<210> SEQ ID NO 359
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 359

Gln Gly Glu Phe Ser Cys Arg Ser Tyr Asp Cys Thr Val
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Leu Gln Asp Trp Ser Pro Ser Tyr Ala Asp Val Ala
1               5                   10

<210> SEQ ID NO 361
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Gln Gln Gly Arg Arg Ser Val Asp Val Asp Asn Val
1               5                   10

<210> SEQ ID NO 362
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ala Gly Gly Tyr Lys Thr Thr Thr Asp Gly Ser Ile
1               5                   10

<210> SEQ ID NO 363
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gln Gln Gly Tyr Thr Tyr Ser Asn Val Asp Asn Val
1               5                   10

<210> SEQ ID NO 364
<211> LENGTH: 125
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Glu Gln Leu Lys Glu Ser Gly Gly Gly Leu Val Thr Pro Gly Gly Thr
1               5                   10                  15
```

-continued

```
Leu Thr Leu Thr Cys Thr Val Ser Gly Phe Ser Leu Ser Ser Val Ala
            20                  25                  30

Met Ile Trp Val Arg Gln Ala Pro Gly Lys Gly Leu Glu Tyr Ile Gly
        35                  40                  45

Ile Ile Ser Gly Gly Gly Asn Thr Tyr Tyr Ala Ser Trp Val Lys Gly
    50                  55                  60

Arg Phe Thr Val Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Ile Pro
                85                  90                  95

Ser Tyr Val Ser Gly Arg Gly Val Tyr Ile Ile Pro Asp Arg Phe Asp
            100                 105                 110

Leu Trp Gly Gln Gly Thr Leu Val Thr Val Ser Ser Gly
        115                 120                 125

<210> SEQ ID NO 365
<211> LENGTH: 116
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ala Thr Phe Ala Ala Val Leu Thr Gln Thr Pro Ser Pro Val Ser Ala
1               5                   10                  15

Ala Val Gly Gly Thr Val Thr Ile Ser Cys Gln Ser Ser Glu Ser Val
            20                  25                  30

Tyr Lys Asn Asn Tyr Leu Ser Trp Tyr Gln Gln Lys Pro Gly His Ser
        35                  40                  45

Pro Arg Leu Leu Ile Ser Ser Ala Ser Thr Leu Ala Ser Gly Val Pro
    50                  55                  60

Ser Arg Phe Ser Gly Ser Gly Ser Gly Thr Gln Phe Thr Leu Thr Ile
65                  70                  75                  80

Ser Asp Leu Gln Cys Asp Asp Ala Ala Thr Tyr Tyr Cys Ala Gly Gly
                85                  90                  95

Tyr Lys Ser Ala Ser Asp Gly Ser Ala Phe Gly Gly Gly Thr Glu Val
            100                 105                 110

Val Val Lys Gly
        115

<210> SEQ ID NO 366
<211> LENGTH: 116
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ala Thr Phe Ala Ala Val Leu Thr Gln Thr Pro Ser Pro Val Ser Ala
1               5                   10                  15

Ala Val Gly Gly Thr Val Thr Ile Ser Cys Gln Ser Ser Glu Ser Val
            20                  25                  30

Tyr Lys Asn Asn Tyr Leu Ser Trp Tyr Gln Gln Lys Pro Gly His Ser
        35                  40                  45

Pro Arg Leu Leu Ile Ser Ser Ala Ser Thr Leu Ala Ser Gly Val Pro
    50                  55                  60
```

```
Ser Arg Phe Lys Gly Ser Gly Ser Gly Thr Gln Phe Thr Leu Thr Ile
 65                  70                  75                  80

Ser Asp Leu Glu Cys Ala Asp Ala Ala Thr Tyr Tyr Cys Leu Gly Gly
                 85                  90                  95

Tyr Lys Thr Thr Thr Asp Gly Ser Ile Phe Gly Gly Gly Thr Glu Val
            100                 105                 110

Val Val Lys Gly
        115

<210> SEQ ID NO 367
<211> LENGTH: 120
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gln Ser Val Glu Glu Ser Gly Gly Arg Leu Val Pro Pro Gly Thr Pro
 1               5                  10                  15

Leu Thr Leu Thr Cys Thr Val Phe Gly Phe Asp Val Ser Ser His Ile
             20                  25                  30

Met Ser Trp Val Arg Gln Ala Pro Gly Lys Gly Leu Glu Trp Ile Gly
         35                  40                  45

Leu Val Asp Ile Gly Lys Ser Ile Lys Trp Tyr Ala Ser Trp Ala Lys
     50                  55                  60

Gly Arg Phe Thr Ile Ser Lys Thr Ser Ser Thr Ile Tyr Leu Lys Leu
 65                  70                  75                  80

Thr Arg Pro Thr Thr Gly Asp Thr Ala Thr Tyr Phe Cys Ser Arg Gly
                 85                  90                  95

Phe Ala Leu Trp Gly Pro Gly Thr Leu Val Thr Val Ser Ser Gly Gln
            100                 105                 110

Pro Lys Ala Pro Ser Val Phe Pro
        115                 120

<210> SEQ ID NO 368
<211> LENGTH: 120
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ala Gln Val Leu Thr Gln Thr Val Ser Pro Val Ser Ala Ala Val Gly
 1               5                  10                  15

Gly Thr Val Thr Ile Asn Cys Gln Ala Ser Pro Ser Val Tyr Gly Asn
             20                  25                  30

Tyr Leu Ser Trp Phe Gln Gln Lys Pro Gly Gln Pro Pro Lys Leu Leu
         35                  40                  45

Ile Leu Asn Ala Ser Thr Leu Pro Ser Gly Val Ser Ser Arg Phe Lys
     50                  55                  60

Gly Ser Gly Ser Gly Thr His Phe Thr Leu Thr Ile Ser Asp Val Gln
 65                  70                  75                  80

Cys Asp Asp Ala Ala Thr Tyr Tyr Cys Leu Gly Ser Tyr Asp Cys Arg
                 85                  90                  95

Ser Asp Asp Cys Asn Val Phe Gly Gly Gly Thr Glu Val Val Val Lys
            100                 105                 110
```

```
Gly Asp Pro Val Ala Pro Thr Val
        115                 120

<210> SEQ ID NO 369
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Gly Thr Asn Tyr Trp Ala Ile Tyr Tyr Gly Met Asp Leu
1               5                   10

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gln Gln Gly Tyr Lys Ile Thr Asn Ile Glu Asn Val
1               5                   10

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Cys Ala Arg Gly Ser Ala Phe Ala Tyr
1               5

<210> SEQ ID NO 372
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Cys Ala Arg Arg Gly Tyr Asp Gly Ser Tyr Tyr Phe Asp Tyr
1               5                   10

<210> SEQ ID NO 373
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Cys Ala Arg His Glu Pro Leu Asn Trp Phe Pro Tyr
1               5                   10

<210> SEQ ID NO 374
<211> LENGTH: 14
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 374

Cys Ala Arg Arg Gly Tyr Tyr Ser Asn Thr Tyr Val Asp Tyr
1               5                   10

<210> SEQ ID NO 375
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Cys Ala Arg Arg Gly Tyr Tyr Ala Asp Thr Tyr Val Asp Tyr
1               5                   10

<210> SEQ ID NO 376
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Cys Ala Arg Arg Gly Tyr Tyr Ser Gly Thr Tyr Val Asp Tyr
1               5                   10

<210> SEQ ID NO 377
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Cys Ala Arg Glu Asp Tyr Tyr Ser Asp Gln Phe Ala Tyr
1               5                   10

<210> SEQ ID NO 378
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Cys Leu Tyr Lys Tyr Gly Gly Gly Phe Asp Tyr
1               5                   10

<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Cys Ala Arg Ser Arg Thr Gly Ile Phe Asp Tyr
1               5                   10

```
<210> SEQ ID NO 380
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Cys Val Arg Ser Arg Ser Gly Ile Phe Asp Tyr
1               5                   10

<210> SEQ ID NO 381
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Cys Ala Arg Tyr Tyr Arg Asn Tyr Gly Gly Phe Asp Tyr
1               5                   10

<210> SEQ ID NO 382
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Cys Ala Arg Leu Thr Ala Tyr Phe Asp Tyr
1               5                   10

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Phe Gln Gly Ser His Val Pro Phe Thr
1               5

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Leu Gln Tyr Ala Ser Tyr Pro Trp Thr
1               5

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385
```

```
Gln Gln His Phe Ser Thr Pro Pro Thr
1               5

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gln Gln His Tyr Ser Thr Pro Phe Thr
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gln Gln Trp Ser Ser Asn Pro Leu Thr
1               5

<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gln Gln His Tyr Ser Thr Pro Pro Thr
1               5

<210> SEQ ID NO 389
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Gln Gln Arg Ser Ser Tyr Pro Phe Thr
1               5

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gln Gln Ser Lys Glu Val Pro Leu Thr
1               5

<210> SEQ ID NO 391
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 391

Gln Gln Ser Asn Glu Asp Pro Arg Thr
1               5

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gln His Phe Trp Gly Thr Pro Trp Thr
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gln Gln Tyr Tyr Ser Tyr Pro Arg Thr
1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Trp Gln Gly Thr His Phe Pro Gln Thr
1               5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Ser Gln Ser Thr His Val Pro Trp Thr
1               5

<210> SEQ ID NO 396
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Lys Leu Gly Leu
1
```

```
<210> SEQ ID NO 397
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gly Phe Ser Leu
1

<210> SEQ ID NO 398
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Asp Leu Gly Asp Leu
1               5

<210> SEQ ID NO 399
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Asp Leu Gly Asn Leu
1               5

<210> SEQ ID NO 400
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Asp Phe His Leu
1

<210> SEQ ID NO 401
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gly Ser Leu Gly Thr Leu Pro Leu
1               5

<210> SEQ ID NO 402
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 402

Gly Phe Ala Leu
1

<210> SEQ ID NO 403
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gly His Asp Asp Gly Tyr Asn Tyr Val Tyr Lys Leu
1               5                   10

<210> SEQ ID NO 404
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gly Phe Thr Leu
1

<210> SEQ ID NO 405
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Leu Ala Gly Tyr Asp Cys Thr Thr Gly Asp Cys Phe Ala
1               5                   10

<210> SEQ ID NO 406
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Leu Gly Gly Tyr Asp Cys Asp Asn Gly Asp Cys Phe Thr
1               5                   10

<210> SEQ ID NO 407
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Leu Gly Thr Tyr Asp Cys Arg Arg Ala Asp Cys Asn Thr
1               5                   10

<210> SEQ ID NO 408
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 408

Gln Ser Thr Leu Tyr Ser Ser Thr Asp Glu Ile Val
1               5                   10

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Gln Cys Ser Tyr Val Asn Ser Asn Thr
1               5

<210> SEQ ID NO 410
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Leu Gly Ser Tyr Asp Cys Arg Ser Asp Asp Cys Asn Val
1               5                   10

<210> SEQ ID NO 411
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Leu Gly Ala Tyr Asp Asp Ala Ala Asp Asn Ser
1               5                   10

<210> SEQ ID NO 412
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Leu Gly Thr Tyr Asp Cys Asn Ser Ala Asp Cys Asn Val
1               5                   10
```

METHODS AND REAGENTS FOR CREATING MONOCLONAL ANTIBODIES

CROSS REFERENCE TO RELATED APPLICATIONS

This application claims priority from U.S. Provisional Application No. 61/450,922, filed Mar. 9, 2011, U.S. Provisional Application No. 61/560,006, filed Nov. 15, 2011, U.S. Provisional Application No. 61/566,876, filed Dec. 5, 2011, and U.S. Provisional Application No. 61/594,729, filed Feb. 3, 2012, the entire contents of each of which are incorporated herein by reference.

FIELD OF THE DISCLOSURE

This disclosure relates to biology, and more specifically, to molecular biology and immunology.

BACKGROUND OF THE DISCLOSURE

Antibodies are biologically and commercially significant polypeptides that bind with great specificity and affinity to a particular target molecule, called an antigen. Antibodies are produced by immune cells of vertebrate animals, and all naturally-occurring antibodies share the same basic structure, namely two identical heavy chains covalently bonded to two identical light chains. The N-terminal regions of a single heavy chain and a single light chain form an antigen-binding site that is particular to each individual antibody. The C-terminal region of the heavy chains determines the particular isotype of the antibody, and the same antibody-producing cell can produce antibodies of different isotypes, where all the antibodies produced by the cell have the same antigen-binding site. The different isotypes typically perform different functions in the animal. For example, antibodies of the E isotype (i.e., IgE antibodies) are involved in the allergic response while antibodies of the A isotype (i.e., in IgA antibodies) can be found in mucosal membrane, saliva, and breast milk. The four-chain antibody molecule can exist by itself (e.g., an IgG antibody) or with additional monomers to form dimers (e.g., an IgA antibody) or even pentamers (e.g., an IgM antibody).

With the basic structure of an antibody well-understood, one can produce recombinant antibodies by manipulating the different regions of an antibody using standard molecular biology techniques. For example, U.S. Pat. Nos. 6,180,370 and 6,548,640 (herein incorporated by reference in their entirety) describe humanizing an antibody that naturally occurs in a non-human animal by manipulating various regions of the non-human antibody using molecular biology techniques. Other methods for manipulating or generating recombinant antibodies using standard molecular biology techniques are described (see, e.g., PCT Publication No. WO91/17271, PCT Publication No. WO92/01047; U.S. Pat. Nos. 5,969,108, 6,331,415, 7,498,024, and 7,485,291, all of which are herein incorporated by reference in their entirety).

During an immune response, an animal will generate numerous different antibodies, each with a different antigen-binding specificity. This population of antibodies is called a polyclonal population of antibodies. If the immune response is directed toward a particular antigen, most (but not all) of the polyclonal antibodies made by the animal will specifically bind that antigen. However, with differences in binding affinity and binding sites on the antigen, some of the polyclonal antibodies are more favored than other polyclonal antibodies. In their Nobel Prize-winning discovery in 1975, Kohler and Milstein discovered a way to isolate and immortalize a single antibody-producing cell, which produces a monoclonal antibody that specifically binds to the antigen of interest, from a polyclonal antibody-producing animal (Kohler and Milstein, Nature 256: 495-497, 1975). This immortalization technology, which involves fusing the antibody-producing cells to an immortalized cell to produce a monoclonal antibody-producing hybridoma, has been the industry standard for making monoclonal antibodies for the past 35 years.

Despite its popularity and its longevity, the Kohler and Milstein hybridoma method has numerous drawbacks. For example, it is very time-consuming and labor-intensive. More relevantly, given how time-consuming and labor-intensive it is, only a small fraction of the antibody-producing cells of the animal are immortalized and screened for their ability to produce an antibody that specifically binds to the antigen. Finally, even once a hybridoma with the desired antigen specificity is isolated, obtaining the amino acid sequence of the antibody to facilitate further manipulation, such as humanization, of the antibody, is arduous and time-consuming.

There is a need for improved methods for creating monoclonal antibodies that specifically bind to a desired antigen.

SUMMARY OF THE DISCLOSURE

The various aspects and embodiments of the invention provide methods and systems to rapidly and accurately create monoclonal antibodies that specifically bind to an antigen of interest. In further aspects and embodiments, the invention provides reagents and compositions for performing the various methods of the invention, and reagents and compositions resulting from the performance of the various methods of the invention. In some embodiments, the methods, reagents, and compositions disclosed herein are useful to create monoclonal antibodies from the circulation of a subject.

In one aspect, the invention provides a method for obtaining the sequences of an immunoglobulin (or variable regions thereof) that specifically binds to an antigen comprising: (a) providing nucleic acid sequences encoding immunoglobulin chains (or variable regions thereof) of multiple immunoglobulins of at least one animal; (b) obtaining mass spectra information of peptide fragments of heavy immunoglobulin chains and light immunoglobulin chains of a population of polyclonal immunoglobulins that specifically bind to an antigen; (c) correlating mass spectra information of the peptide fragments with predicted mass spectra information of the nucleic acid sequences, said predicted mass spectra information derived from predicted amino acid sequences encoded by nucleotide sequences of said nucleic acid sequences, to identify nucleotide sequences encoding immunoglobulin chains (or variable regions thereof) which comprise the peptide fragments; and (d) selecting from the identified nucleotide sequences or amino acid sequences of immunoglobulin chains (or variable regions thereof) based on the amino acid sequence coverage of the immunoglobulin chains or fragments thereof by the peptide fragments, to obtain nucleotide sequences or amino acid sequences of heavy or light chains of immunoglobulins that specifically bind to an antigen.

In some embodiments, a heavy immunoglobulin chain and a light immunoglobulin chain (or variable regions thereof) selected in step (d) are assembled to create an immunoglobulin (or variable regions thereof) that specifically binds to the antigen.

In some embodiments, the nucleotide sequences or amino acid sequences of the immunoglobulin chain variable regions obtained in step (d) are synthesized by recombinant molecular biology techniques or gene synthesis techniques prior to assembly.

In some embodiments, the method further comprises: screening with an immunoassay the immunoglobulin (or variable regions thereof) created to confirm said immunoglobulin (or variable regions thereof) specifically binds to the antigen. In some embodiments, the immunoassay is selected from the group consisting of a flow cytometry assay, an enzyme-linked immunosorbent assay (ELISA), a Western blotting assay, an immunohistochemistry assay, an immunofluorescence assay, a radioimmunoassay, a neutralization assay, a binding assay, an affinity assay, or a protein or peptide immunoprecipitation assay.

In some embodiments, the selection of heavy immunoglobulin chains and light immunoglobulin chains in step (d) is made based on amino acid sequence coverage of a portion of the chains (e.g., the variable region or a complementarity determining region) by the peptide fragments.

In other embodiments, the selection of heavy or light immunoglobulin chains in step (d) is made based on the amino acid sequence coverage of the immunoglobulin chains or fragments thereof by the peptide fragments, in combination with at least one parameter selected from the group consisting of the number of unique peptides mapped, spectrum share, total peptide count, unique peptide count, frequency of the encoding nucleic acid sequences, and clonal relatedness.

In various embodiments, the nucleic acid sequences and information derived from the nucleic acid sequences (including, for example, the nucleotide sequences, the predicted amino acid sequences, and the predicted mass spectra) are located in a genetic material database.

In some embodiments, the animal from which the nucleic acid sequences are obtained is an animal exposed to the antigen.

In some embodiments, the predicted amino acid sequences encoded by said nucleic acid sequences encoding immunoglobulin chains (or variable regions thereof) of multiple immunoglobulins from the animal are obtained by: (1) isolating nucleic acid molecules from white blood cells from said animal; (2) amplifying immunoglobulin chain (or variable region thereof)-encoding nucleic acid molecules using primers specific for polynucleotide sequences adjacent to said immunoglobulin chain (or variable region thereof)-encoding nucleic acid molecules; (3) obtaining nucleotide sequences of said amplified nucleic acid molecules encoding immunoglobulin chains (or variable regions thereof) of multiple immunoglobulins from the animal; and (4) using the genetic code to translate the nucleotide sequences into predicted amino acid sequences.

In some embodiments, the nucleic acid sequences are expressed nucleic acid sequences (e.g., transcribed into RNA and/or translated into protein in cells of the animal).

In some embodiments, the predicted amino acid sequences encoded by the nucleic acid molecules encoding immunoglobulin chains (or variable regions thereof) of multiple immunoglobulins from the animal are obtained by: (1) isolating nucleic acid molecules from white blood cells from said animal; (2) sequencing immunoglobulin chain (or variable region thereof)-encoding nucleic acid molecules using primers specific for polynucleotide sequences adjacent to said immunoglobulin chain (or variable region thereof)-encoding nucleic acid molecules to obtain the nucleotide sequences encoding immunoglobulin chains (or variable regions thereof) of multiple immunoglobulins from the animal; and (3) using the genetic code to translate the nucleic acid sequences into amino acid sequences. In some embodiments, the nucleic acid molecules are RNA molecules and said amplification step includes an initial reverse transcription step.

In some embodiments, the polynucleotide sequences adjacent to the immunoglobulin chain (or variable region thereof)-encoding nucleic acid molecules are selected from the group consisting of genomic DNA flanking immunoglobulin genes, immunoglobulin chain constant region-encoding polynucleotide sequences, and immunoglobulin chain framework region-encoding polynucleotide sequences.

In some embodiments, the predicted mass spectra information is obtained using a method comprising the steps of: (i) performing a theoretical digest of predicted amino acid sequences encoded by the nucleotide sequences of the nucleic acid molecules with one or more proteases and/or one or more chemical protein cleavage reagents to generate virtual peptide fragments; and (ii) creating predicted mass spectra of said virtual peptide fragments.

In some embodiments, the observed mass spectra information of the peptide fragments are obtained using a method comprising the steps of: (i) isolating a population of polyclonal immunoglobulins that specifically bind to the antigen; (ii) digesting the population with one or more proteases and/or one or more chemical protein cleavage reagents to generate fragments; and (iii) obtaining mass spectra information of said peptide fragments. In some embodiments, the population of polyclonal antibodies is isolated using a method comprising the steps of: (1) obtaining body fluid or a fraction thereof (e.g., blood, serum and/or plasma) from an animal; (2) passing the body fluid or a fraction thereof over the antigen under conditions whereby immunoglobulins that specifically bind to the antigen will become attached the antigen; and (3) collecting said immunoglobulins attached to said antigen to obtain the population of polyclonal immunoglobulins that specifically bind to the antigen. In some embodiments, the antigen is attached to a solid support (e.g., the antigen is covalently or non-covalently bound to the solid support). In some embodiments, the solid support may be a bead (e.g., an agarose or a magnetic bead), a wall of a column, or a bottom of a plate (e.g., a tissue culture plate).

In some embodiments, the animal is an animal previously exposed to the antigen. In some embodiments, the animal previously exposed to the antigen is an animal previously immunized with the antigen.

In another aspect, the invention provides a method for obtaining the amino acid sequences of the immunoglobulin chain variable region of an immunoglobulin that specifically binds to an antigen, comprising: (a) providing nucleic acid sequences encoding immunoglobulin variable regions of multiple immunoglobulins of an animal; (b) obtaining mass spectra information of peptide fragments of immunoglobulin chain variable regions of a population of polyclonal immunoglobulins that specifically bind to an antigen; (c) correlating mass spectra information of the peptide fragments with predicted mass spectra information of the nucleic acid sequences, said predicted mass spectra information derived from predicted amino acid sequences encoded by said nucleic acid sequences, to obtain amino acid sequences of immunoglobulin chain variable regions comprising the peptide fragments; and (d) selecting from the identified nucleotide sequences or amino acid sequences of immunoglobulin chain variable regions based on the amino acid sequence coverage of the variable regions by the peptide fragments, to obtain nucleotide sequences or amino acid sequences of variable regions of immunoglobulins that specifically bind to an antigen.

In some embodiments, the method further comprises step (e) screening the amino acid sequences of said immunoglobulin chain variable regions with an immunoassay to isolate an immunoglobulin chain variable region of an immunoglobulin that specifically binds to the antigen. In some embodiments, the nucleotide sequences or amino acid sequences of the immunoglobulin chain variable regions obtained in step (d) are synthesized by recombinant molecular biology techniques or gene synthesis techniques prior to the step (e) screening step. In some embodiments, the immunoglobulin chain variable region produced in step (d) is assembled with a second immunoglobulin chain variable region to create an antibody binding domain of an immunoglobulin that specifically binds to the antigen. In some embodiments, the immunoassay is selected from the group consisting of a flow cytometry assay, an enzyme-linked immunosorbent assay (ELISA), a Western blotting assay, and immunohistochemistry assay, an immunofluorescence assay, a radioimmunoassay, a neutralization assay, a binding assay, an affinity assay, or a protein or peptide immunoprecipitation assay.

In some embodiments, the immunoglobulin chain variable region is a heavy chain variable region or a light chain variable region.

In a further aspect, the invention provides a method for creating an antigen binding domain of an immunoglobulin that specifically binds to an antigen comprising: (a) providing nucleic acid sequences encoding immunoglobulin heavy chain variable regions and light chain variable regions of multiple immunoglobulins from an animal; (b) obtaining mass spectra information of peptide fragments of heavy immunoglobulin chains and light immunoglobulin chains of a population of polyclonal immunoglobulins that specifically bind to an antigen; (c) correlating mass spectra information of the peptide fragments with predicted mass spectra information of the nucleic acid sequences, said predicted mass spectra information derived from predicted amino acid sequences encoded by said nucleic acid sequences, to obtain nucleotide sequences or amino acid sequences of immunoglobulin chain variable regions comprising the peptide fragments; (d) selecting from the identified nucleotide sequences or amino acid sequences of immunoglobulin chain variable regions based on the amino acid sequence coverage of the variable regions by the peptide fragments, to obtain nucleotide sequences or amino acid sequences of variable regions of immunoglobulins that specifically bind to an antigen; and (e) assembling a selected heavy immunoglobulin chain variable region with a selected light immunoglobulin chain variable region to create an antigen binding domain of an immunoglobulin that specifically binds to the antigen.

In various embodiments of all of the aspects of the invention, the animal is a vertebrate animal. In various embodiments, the animal is a mammal. In some embodiments, the animal is a human. In some embodiments, the animal is a rat, a rabbit or a mouse. In some embodiments, the animal is a bird, domesticated animal, a companion animal, a livestock animal, a rodent, or a primate. In some embodiments, the animal is a transgenic non-human animal, e.g., a transgenic non-human animal that expresses human antibody sequences and/or produces antibodies that are at least partly human.

In various aspects, the invention also provides an immunoglobulin (or variable region thereof), or an immunoglobulin chain variable region or an antigen binding domain of an immunoglobulin that specifically binds to an antigen isolated or created in accordance with the various non-limiting embodiments of the invention. In various embodiments, the immunoglobulin (or variable region thereof), or an immunoglobulin chain variable region or an antigen binding domain of an immunoglobulin that specifically binds to an antigen are isolated or recombinant. In various embodiments, the invention also provides a pharmaceutically acceptable carrier and an immunoglobulin (or variable region thereof), or an immunoglobulin chain variable region or an antigen binding domain of an immunoglobulin that specifically binds to an antigen isolated or created in accordance with the various non-limiting embodiments of the invention.

In a further aspect, the invention provides a method of treating an animal having or suspected of having a disease characterized by a disease antigen, wherein the method comprising administering an effective amount of a composition in accordance with various embodiments of the invention, wherein the antigen specifically bound by the immunoglobulin (or variable region thereof), or immunoglobulin chain variable region or an antigen binding domain of the composition and the disease antigen are the same. In some embodiments, the animal is a human. In some embodiments, the animal is a rodent, a livestock animal, a domesticated animal, a companion animal, or a primate.

In a further aspect, the invention provides a method of reducing the likelihood of occurrence in an animal of a disease characterized by the presence in the animal of a disease antigen, wherein the method comprising administering an effective amount of a composition in accordance with various embodiments of the invention, wherein the antigen specifically bound by the immunoglobulin (or variable region thereof), or immunoglobulin chain variable region or an antigen binding domain of the composition and the disease antigen are the same. In some embodiments, the composition further comprises an adjuvant. In some embodiments, the animal is a human. In some embodiments, the animal is a rodent, a livestock animal, a domesticated animal, a companion animal, or a primate.

BRIEF DESCRIPTION OF THE DRAWINGS

FIG. 4 is schematic diagram depicting another example of a non-limiting method of various embodiments of the invention. In this example, a non-limiting B cell source (e.g., splenocytes) and polyclonal antibodies are collected from the same animal (e.g., a human, mouse, or rabbit). Nucleic acid molecules are extracted from the B cell source and are subjected to next generation sequencing (NGS) using the Roche 454 machine using immunoglobulin gene-specific sequencing primers. This information, which can be put into a genetic material database, can be used to generate theoretical mass spectra based on the predict amino acid sequences encoded by the nucleic acid sequence. Also from the animal (e.g., a human, mouse, or rabbit), polyclonal antibodies (or peptide fragments thereof) are loaded into the mass spectrometer for analysis. The nucleic acid sequences are analyzed using Kabat rules to identify the sequences of the variable regions (e.g., one of the CDR regions or FR regions) of the sequence. The sequences of the peptide fragments from the analyzed polyclonal antibodies are then screened to identify which peptides match all or part of the variable region from a predicted amino acid sequence.

FIG. 5 is a table showing heavy and light chain NGS (i.e., next generation sequencing) sequences that had good mass spectrometry correlation and peptide over the variable region. Some of these peptides appeared quite frequently (see, e.g., light chain ref. no. G623FKB01A3GC7) and some had high nucleic acid sequence frequency count (see, e.g., light chain ref. no. G623FKB01AXJ1C). The rows in bold italics represent immunoglobulin chains that, upon testing, were found to contain sequences that specifically bound antigen (see testing results in FIG. 6).

FIG. 6 is a table showing the results of ELISA assays testing antibodies made using a non-limiting method of the invention screened against ELISA plates coated with p-Erk peptides. The different light chains and heavy chains shown in FIG. 5 were randomly combined with each other. As can be seen from FIG. 6, a number of pairings resulted in antibodies that were able to specifically bind to the p-ERK-coated plates (positive antibodies shown in shade).

FIG. 8 is a table showing the sequences of the antibody chains after combining the theoretical (i.e., predicted) mass spectra derived from the nucleic acid sequences with LC-MS/MS data from affinity purified antibody. Antibody chain abundance based on NGS frequency was also displayed. The chains depicted in italics were synthesized and assembled into antibody; and the bold italics chains are those which, upon testing with Western blotting analysis, were found to specifically bind the p-MET antigen.

FIGS. 10a-e. Affinity purification of progesterone receptor-specific polyclonal rabbit IgG. (a) Total IgG from the serum of the immunized rabbit was isolated with Protein A and further affinity purified on immobilized antigen peptides by gravity flow. After extensive washing to reduce non-specific IgG, a sequential elution with progressively acidic pH was used to fractionate the antigen-specific polyclonal IgG. Each fraction was tested for specific activity by Western blotting at matched antibody concentration (21.5 ng/ml) to detect PR A/B in lysates from T47D cells (+). Negative control lysates from HT1080 (−) were also tested. (b). The fraction with the highest specific activity, pH 1.8, was processed with four proteases for LC-MS/MS analysis. (c). An MS/MS spectrum matched by SEQUEST to the V-region full tryptic peptide G<u>FA</u>LWGPGTLVTVSSGQPK (SEQ ID NO: 305) containing CDRH3 (underlined) with an XCorr of 5.560 and a ΔM (observed m/z−expected m/z) of 0.39 ppm. (d). MS/MS spectra were mapped to V-region peptides by SEQUEST and filtered to an FDR of ≤2%. High confidence peptides were then remapped to the V-region database generated by NGS, taking into account the protease used for sample preparation and keeping track of the total number of peptides, the unique number of peptides, the spectrum share, and the amino acid coverage of the entire V-region. High coverage V-region sequences were selected, expressed as monoclonal antibodies, and screened for desired activity. (e). Heavy and light chain sequence identification coverage of clone F9. The depicted V-region sequences, when paired, specifically bind human PR A/B (see FIG. 11a-e). Amino acids mapped by one or more peptides are shown in bold. To maximize V-region coverage and account for highly variable amino acid composition, complementary proteases were used (Chymotrypsin, Elastase, Pepsin, Trypsin.

FIGS. 11a-e. Identification and characterization of functional monoclonal antibodies against progesterone receptor A/B. (a). Combinatorial pairing of heavy and light chains yielded 12 antigenspecific ELISA-reactive clones indicated in yellow. CDR3 sequence is used as an identifier: ✓ indicates Western blot-positive clones (See FIG. 11b). (b). Six clones (F1 F9, H1, C1, F7, and H9) were specific for progesterone receptor A/B detection by Western blotting. Clones E6 (ELISA-negative, Western-negative) and H7 (ELISA-positive, Westernnegative) are shown as controls. +, T47D (PR A/B-positive); −, MDA-MB-231 (PR A/B-negative). All antibodies tested at 21.5 ng/mL. (c). Comparison of specific activity of clone F9 to the affinity-purified polyclonal mixture by immunohistochemistry. 0.4 ug/mL of F9 specifically stained PR A/B-positive tissue or cell lines (T47D and MCF-7), but not a PR A/B-negative cell line (MDA-MB-231). 0.2 µg/mL of polyclonal antibody was used as positive control. (d). Flow cytometry analysis. Blue, T47D cells (progesterone receptor A/B positive cell line); Black, MDA-MB-231 (progesterone receptor A/B negative cell line). Polyclonal antibody signal/noise ratio, 1.69; concentration, 3.7 µg/mL. Monoclonal antibody F9 signal/noise ratio=36.4; concentration 0.5 µg/mL. (e). Confocal immunofluorescence microscopy analysis showed specific nuclear staining pattern on progesterone receptor A/B positive cell line MCF-7 but not on MDA-MB-231 cells at 0.46 µg/mL. No primary antibody was included as background staining control. Polyclonal antibodies were also used as comparison at a concentration of 1.85 µg/mL.

Figure 1:
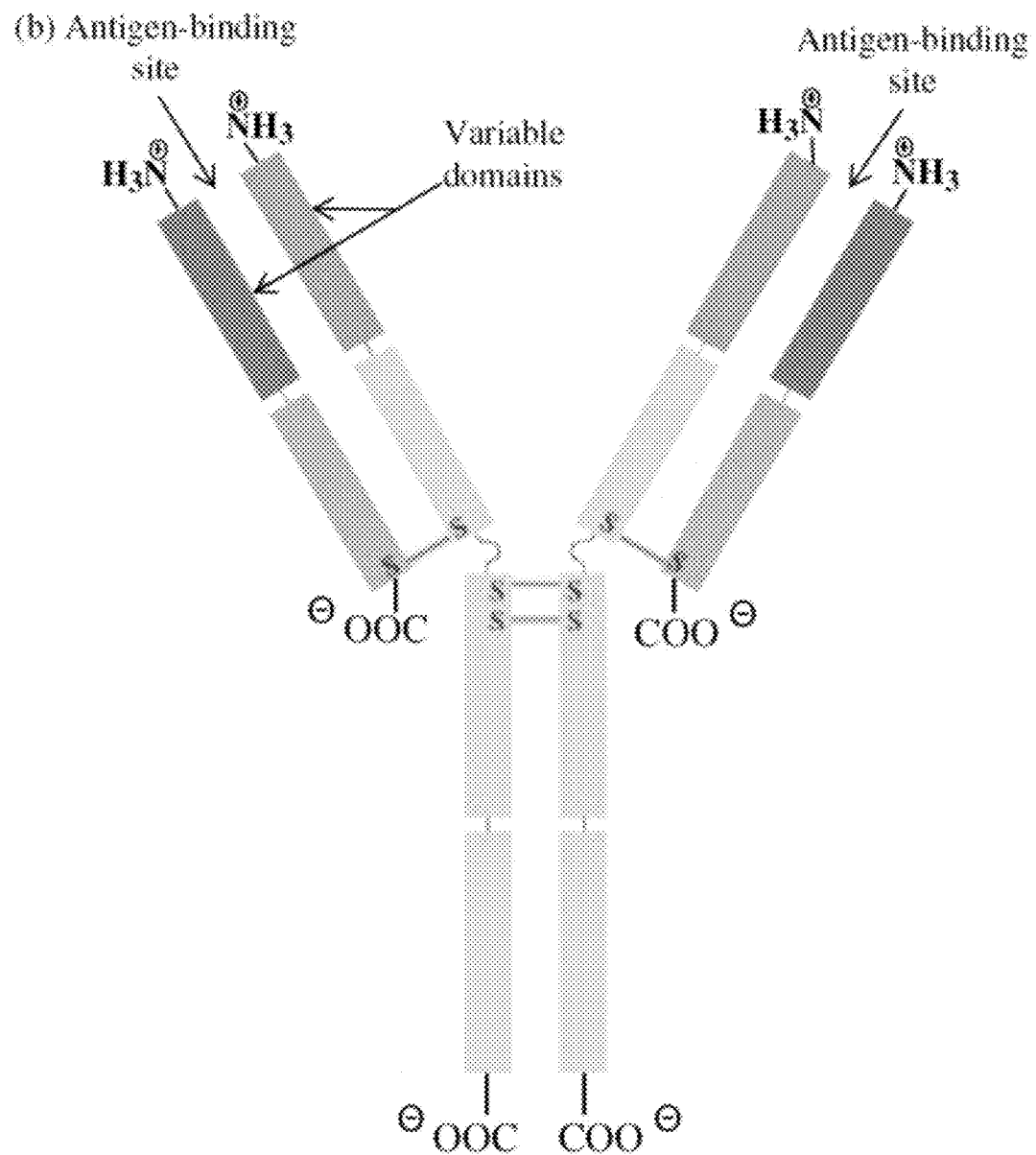
FIG. 1 is a schematic diagram of an antibody comprising two heavy chains and two light chains. The two heavy chains are joined to each other by two disulfide bonds located in the hinge region of the antibody. Each light chain is joined to a heavy chain via a single disulfide bond. The antigen-binding site is created at the N-terminus of the heavy and light chains.

FIGS. 12a-d. Characterization of clone C3 anti-Lin28A monoclonal antibody. (a) Combinatorial pairing of heavy and light chains yielded 5 antigen-specific ELISA-reactive clones indicated in shade. ✓ indicates Western blot-positive clones. CDR3 sequence is used as an identifier. (b) Western blot analysis was performed using various Lin28A positive cell lysates, NCCIT, NTERA, mMES, and IGROV1. (c) Confocal immunofluorescence analysis was performed with Lin28A negative cells (HeLa) and Lin28A positive cells (NTERA). (d) Flow cytometry analysis of monoclonal antibody. Left peak, HeLa cells (Lin28A−); right peak, NTERA cells (Lin28A+). *V-regions had the same CDR3 sequence but not identical V region sequences.

FIGS. 13a-c. Identification and characterization of functional mouse monoclonal antibodies against phospho-Erk. (a) Purification of phospho-Erk polyclonal antibodies from the pooled sera of three mice. The pooled sera, protein G-purified total IgG from the pooled sera, the unbound fraction from the protein G purification, and acid elution fractions of pH3.5, 2.7 and 1.8 were assayed by Western blotting for binding specificity against phospho-Erk in Jurkat cell lysate. +, Jurkat cells stimulated with TPA; −, Jurkat cells treated with U0126. (b) Combinatorial pairing of heavy and light chains yielded 15 clones, indicated in shade, that are reactive by peptide antigen ELISA. ✓ indicates Western blot-positive clones (See (c)). CDR3 sequence is used as an identifier. For the heavy chain sequences the underlined portion indicates the end of Frame Work Region 3. (c) Three clones (C10, F10 and M3) were specific for phospho-Erk detection by Western blotting. Clone C9 (ELISA positive, Western-negative) is shown as a control. All antibodies were tested at 100 ng/mL.

Figure 14:
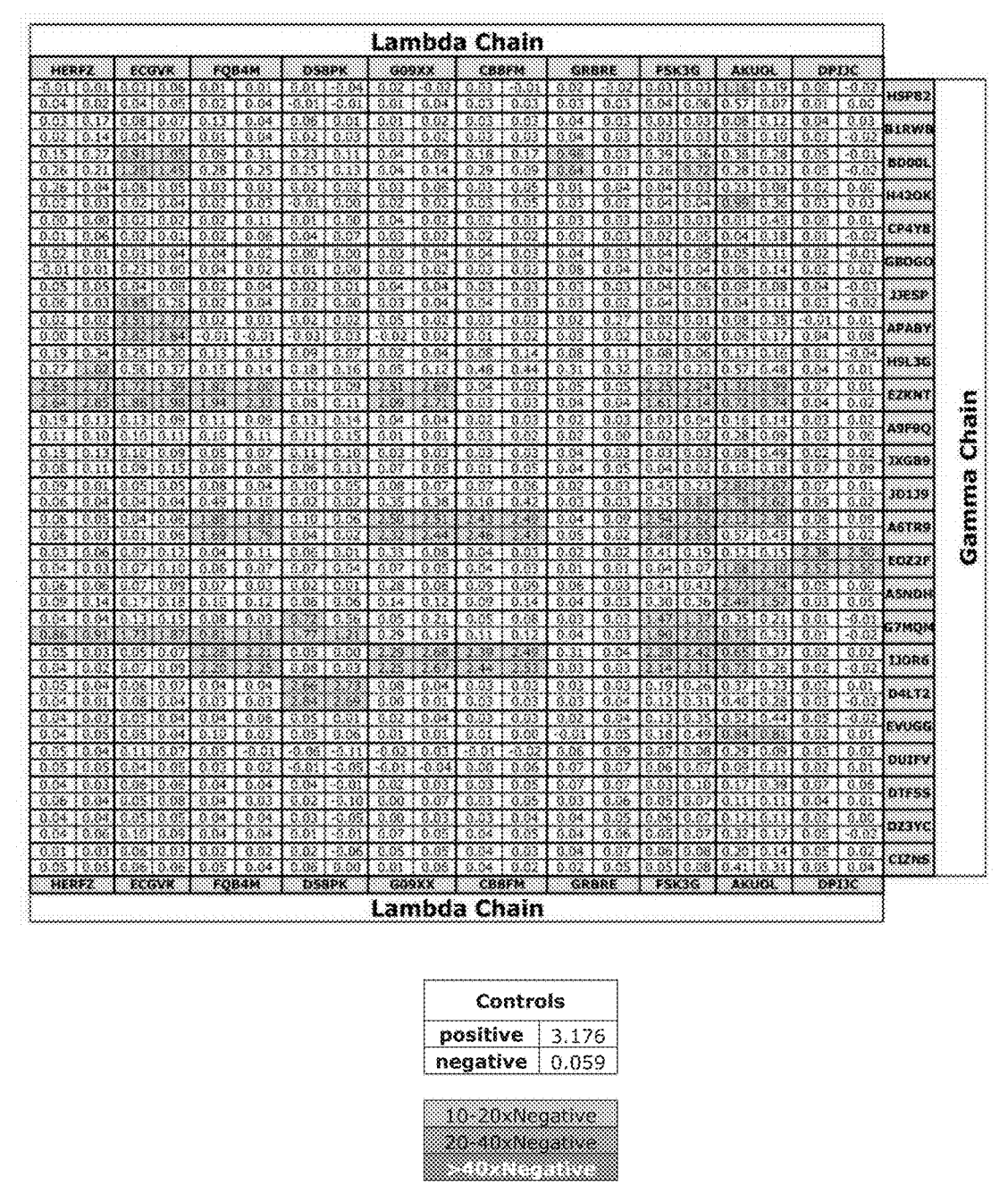

FIG. 14. 24 distinct heavy (gamma) chain variable region clones, 20 distinct kappa chain variable region clones and 10 distinct lambda chain variable region clones were expressed in a combinatorial format by transient transfection of HEK293E cells in standard 96-well tissue culture plates and screened for binding to purified, recombinant hepatitis B surface antigen (HBsAg-adw subtype purchased from Prospec, Ness-Ziona, ISRAEL) by enzyme-linked immunosorbent assay (ELISA). The values obtained from the absorbance of HBsAg plates from which the absorbance of the milk only plates in each well was subtracted.

DETAILED DESCRIPTION

This disclosure is directed to methods and systems for rapidly and accurately obtaining the amino acid sequences (and encoding nucleic acid sequences) of monoclonal antibodies that specifically bind to an antigen of interest. More specifically, the present methodology involves a direct, mass spectrometry-based proteomic investigation of circulating polyclonal antibodies from the serum of an animal, against a genetic material database which is comprised of nucleic acid molecules encoding full length immunoglobulin chains or variable regions. In specific embodiments, the genetic material database is generated from the B cell repertoire of an animal (e.g., the same animal whose serum was collected to obtain the polyclonal antibodies) by utilizing nucleic acid sequencing technologies. Thus, the present approach essentially involves correlating (i.e., cross-comparing or cross-referencing) the information from two sources: mass spectra information from the actual circulating polyclonal antibodies of an animal, and information (including, e.g., predicted mass spectra) from the genetic material database. A list of heavy and light chain DNA sequences can then be identified from the genetic material database that correspond to actual antibodies from the serum. Such heavy and light chains can be expressed in pairs to obtain functional monoclonal antibodies.

In some embodiments, the present methodology does not require B cell immortalization, single cell sorting and molecular cloning, or phage display, and does not involve assembly of antibody sequences based on guesswork. By leveraging the strengths of both mass spectrometry technologies and nucleic acid sequencing technologies (such as Next Generation DNA Sequencing or NGS), the approach of this invention can significantly reduce the amount of time needed to isolate the sequences of antigen-specific monoclonal antibodies from a polyclonal population, thereby enabling a faster transition to recombinant antibodies such as fully human antibodies or humanized antibodies (e.g., humanized murine antibodies) that may be used therapeutically.

Furthermore, the present methodology is capable of identifying rare antibodies likely missed by existing technologies. The inventors have surprisingly found that individual antibodies with very selective specificity (e.g., an antibody that specifically binds to a phosphorylated tyrosine residue within a polypeptide) may occur very rarely within a polyclonal population. Methods that rely on the frequencies of antibody-encoding mRNAs and PCR amplification may miss these antibodies because their variable chains occur with low frequency. In contrast, the present methodology utilizes, for example, mass spectrometry based proteomics analysis of actual peptide fragments derived from a polyclonal antibody population, and therefore does not suffer from the errors of frequency following PCR amplification.

In addition, the present methodology allows for the rapid creation of novel antigen-specific antibodies that may not exist in the starting polyclonal population. For example, the created immunoglobulin molecule that has the highest desired qualities (e.g., highest binding affinity (or lowest KD) for the antigen or a desired isotype (e.g., IgG2a)) may be the result of a light chain from a first antibody in the polyclonal population assembled with a heavy chain of a second antibody (i.e., different from the first antibody) in the polyclonal population.

The methods described herein have applications in basic immunology and therapeutics. For example, the methods can provide the basis for understanding central questions in the field of immunology, including serum antibody diversity, dynamics, kinetics, clonality, and migration of B cells following antigen exposure. The methods can also be used to pursue therapeutically relevant human monoclonal antibodies from immunized, naturally infected, or diseased individuals.

As demonstrated herein, the present methodology has been successfully applied to several different antigens in both laboratory animal species and human, and has led to the isolation of monoclonal antibodies with antigen-specific activities that recapitulate or surpass those of the original affinity-purified polyclonal antibodies found in the serum of immunized subjects.

Accordingly, this disclosure further provides isolated recombinant monoclonal antibodies specific for an antigen, including therapeutic antibodies specific for a disease antigen, as well as therapeutic methods for treating a disease based on administration of therapeutic monoclonal antibodies.

The various aspects and embodiments of the invention are described in more detail below. The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Definitions

As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

By "peptide" or "peptide fragment" is meant a short polymer formed from the linking individual amino acid residues together, where the link between one amino acid residue and the second amino acid residue is called an amide bond or a peptide bond. A peptide comprises at least two amino acid residues. A peptide is distinguished from a polypeptide in that it is shorter. At least two peptides, linked together by an amide bond or peptide bond between the C' terminal amino acid residue of one peptide and the N' terminal amino acid residue of the second peptide, form a polypeptide in accordance with various embodiments of the invention.

By "polypeptide" is meant a long polymer formed from the linking individual amino acid residue, where the link between one amino acid residue and the second amino acid residue is called an amide bond or a peptide bond. A polypeptide comprises at least four amino acid residues; however, multiple polypeptides can be linked together via amide or peptide bonds to form an even longer polypeptide.

By "nucleic acid molecule" is meant a polymer formed from linking individual nucleotides (e.g., deoxyribonucleotides or ribonucleotides) together, where the link between one nucleotide and the other nucleotide is a covalent bond including, for example, a phosphodiester bond. Thus, the term includes, without limitation, DNA, RNA, and DNA-RNA hybrids.

By "nucleic acid sequence" is meant a nucleic acid sequence (or nucleotide sequence complementary thereto) that includes nucleotides that encode all or part of an immunoglobulin chain (e.g., a heavy chain or a light chain). In some embodiments, the nucleic acid sequence is genomic DNA (e.g., exonic DNA with or without intronic DNA). In some embodiments, the nucleic acid sequence is cDNA or some form of RNA (e.g., hn RNA, mRNA, etc.). In some embodiments, the nucleic acid sequence is an expressed nucleic acid sequence that will be either transcribed into a nucleic acid molecule (e.g., DNA transcribed into RNA) or translated into a polypeptide in a cell containing that nucleic acid sequence. Accordingly, an expressed nucleic acid molecule includes, without limitation, hnRNA, mRNA, cDNA, and genomic exon sequences. By "complementary" in terms of nucleic acid molecules simply means that two single-stranded nucleic acid molecules contain nucleotides that will form standard Watson-Crick basepairs to form a double-stranded nucleic acid molecule, whether that double-stranded molecule is DNA, RNA, or a DNA-RNA hybrid.

As used herein, by "B lymphocyte" is meant any white blood cell in which gene recombination (or gene rearrangement) has begun to occur at a locus containing an immunoglobulin chain-encoding gene. For example, human immunoglobulin genes occur on chromosome 14 (heavy chain locus), chromosome 2 (kappa light chain locus), and chromosome 22 (lambda light chain locus). If a human white blood cell has undergone a gene rearrangement event in an immunoglobulin chain locus (e.g., on chromosome 14, chromosome 2, or chromosome 22), that cell is considered a B lymphocyte. Accordingly, B lymphocytes include, without limitation, B cells, pre-B cells, pro-B cells including early pro-B cells (e.g., where the D and J regions of the heavy chain genes have undergone rearrangement but the light chain gene are germline (i.e., are not rearranged)) and late pro-B cells (e.g., where the V, D, and J regions of the heavy chain gene is rearranged but the light chain gene is still germline and where no immunoglobulin proteins are expressed on the cell surface), pre-B cells including large pre-B cells and small pre-B cells, immature B cells, active B cells, germinal center B cells, plasma cells (including plasmablasts), and memory B cells.

Throughout the specification and the claims, the terms "antibody" and "immunoglobulin" are used interchangeably and are meant to include intact immunoglobulin polypeptide molecules of any isotype or sub-isotype (e.g., IgG, IgG1, IgG2, IgG2a, IgG2b, IgG3, IgG4, IgM, IgD, IgE, IgE1, IgE2, IgA) from any species of animal such as primates (e.g., human or chimpanzees), rodents (e.g., mice or rats), lagomorphs (e.g., rabbits or hares), livestock animals (e.g., cows, horses, goats, pigs, and sheep), fish (e.g., sharks), birds (e.g., chickens) or camelids (e.g., camels or llamas) or from transgenic non-human animals (e.g., rodents) genetically engineered to produce human antibodies (see, e.g., Lonberg et al., WO93/12227; U.S. Pat. No. 5,545,806; Kucherlapati, et al., WO91/10741; U.S. Pat. No. 6,150,584; US 2009/0098134; US 2010/0212035; US 2011/0236378; US 2011/0314563; WO2011/123708; WO2011/004192; WO2011/158009); antigen binding domain fragments thereof, such as Fab, Fab', F(ab')$_2$; variants thereof such as scFv, Fv, Fd, dAb, bispecific scFvs, diabodies, linear antibodies (see U.S. Pat. No. 5,641,870; Zapata et al., *Protein Eng.* 8 (10): 1057-1062. 1995); single-chain antibody molecules; and multispecific antibodies formed from antibody fragments; and any polypeptide comprising a binding domain which is, or is homologous to, an antibody binding domain (defined herein elsewhere). Non-limiting antibodies of various embodiments of the invention include but are not limited to polyclonal, monoclonal, monospecific, polyspecific antibodies and fragments thereof, chimeric antibodies comprising an immunoglobulin binding domain fused to another polypeptide, and humanized antibodies such as a non-human antibody (e.g., a rabbit antibody) whose constant and/or FR domains have been replaced with constant and/or FR domains from a human antibody (see, e.g., U.S. Pat. Nos. 5,530,101; 5,585,089; 5,693,761; 5,693,762; 6,180,370; and 6,548,640). Transgenic non-human animals genetically engineered to produce human (e.g., at least partially human) antibodies are available from Harbour Antibodies (Rotterdam, The Netherlands), Ablexis (San Francisco, Calif.), Kymab Ltd (Cambridge, UK), OMT, Inc. (Palo Alto, Calif.), Amgen (Thousand Oaks, Calif.), Medarex (Princeton, N.J.), and Regeneron (Tarrytown, N.Y.).

Naturally-occurring intact antibodies are made up of two classes of polypeptide chains, light chains and heavy chains. A non-limiting antibody of various aspects of the invention can be an intact, four immunoglobulin chain antibody comprising two heavy chains and two light chains. The heavy chain of the antibody can be of any isotype including IgM, IgG, IgE, IgA or IgD or sub-isotype including IgG1, IgG2, IgG2a, IgG2b, IgG3, IgG4, IgE1, IgE2, etc. The light chain can be a kappa light chain or a lambda light chain. For example, a single IgG naturally-occurring (or intact) antibody comprises two identical copies of a light chain and two identical copies of an IgG heavy chain. The heavy chains of all naturally-occurring antibodies, where each heavy chain contains one variable domain ($V_H$) and one constant domain ($C_H$, which itself comprises the CH1 region, the hinge region, the CH2 region, and the CH3 region), bind to one another via multiple disulfide bonds within their constant domains to form the "stem" of the antibody. The light chains of all naturally-occurring antibodies, where each light chain contains one variable domain ($V_L$) and one constant domain ($C_L$), each bind through its constant domain to one heavy chain constant domain via disulfide binding. A schematic of a four immunoglobulin chain antibody (e.g., an IgG antibody) is shown in FIG. 1. In FIG. 1, the three CH domains are shown in light blue, the single VH domain is shown in dark blue, the single CL domain is shown in light pink and the single VL domain is shown in dark pink. As shown in FIG. 1, the VL and the VH domains of the light and heavy chains, respectively, come together to form the antibody binding domain.

In some embodiments, an intact immunoglobulin chain (e.g., a heavy chain or a light chain) may comprise in order from 5' to 3' (for a nucleic acid sequence encoding the chain) or from the amino terminus to the carboxy terminus (for the amino acid sequence of the chain): a variable domain and a constant domain. The variable domain may comprise three complementarity determining regions (CDRs; also called hypervariable regions or HVs), with interspersed framework (FR) regions. The variable domains of both the light chains and heavy chains contain three hypervariable regions sandwiched between four more conserved framework regions (FR), for a structure of 5' (or N')-FR1, CDR1, FR2, CDR2, FR3, CDR3, FR43' (or C'), with the constant region 3' (or C') to the FR4 region. The CDRs form loops that comprise the principal antigen binding surface of the antibody (see Kabat, E. A. et al., Sequences of Proteins of Immunological Interest, National Institutes of Health, Bethesda, Md., (1987) and Wu, T. T. and Kabat, E. A. (1970) *J. Exp. Med.* 132: 211-250 (1970)) with the four framework regions largely adopting a beta-sheet conformation and the CDRs forming loops connecting, and in some cases forming part of, the beta-sheet structure. The CDRs in each chain are held in close proximity by the framework regions and, with the CDRs from the other chain, contribute to the formation of the antigen binding domain.

By "antigen" is meant a target molecule (e.g., a polypeptide or a carbohydrate) that can be specifically bound by an antibody. The portion of an antigen that is specifically bound by the antibody is referred to as an "epitope". An "epitope" is smallest portion of a target molecule capable being specifically bound by the antigen binding domain of an antibody. The minimal size of an epitope may be about three to seven amino acids (e.g., five or six amino acids). There may be multiple epitopes on a single antigen, thus, a single antigen can be specifically bound by multiple different antibodies, all of which antibodies specifically bind the antigen (i.e., all of these antibodies are antigen-specific antibodies) even though each individual antibody specifically binds to a different epitope on the antigen.

By "disease antigen" is meant an antigen which arises in an animal during a disease state. For example, a viral antigen (e.g., an antigen encoded by a nucleic acid molecule of a virus's genetic material) is a disease antigen in animal infected with that virus. Similarly, some diseases (e.g., cancer) are characterized by gene translocations which produce chimeric proteins (e.g., BCR-ABL). Thus, a BCR-ABL protein is a disease antigen. It should be understood that a disease antigen is not necessarily seen only in an animal suffering from that disease.

By "disease" is simply meant any abnormal condition affecting an animal. Non-limiting examples of diseases include, without limitation, autoimmune disease (e.g., rheumatoid arthritis or type I diabetes), cancer (e.g., leukemia, colon cancer, or prostate cancer, etc.), viral infections (e.g., AIDS caused by infection of the HIV virus or chicken pox caused by infection of the varicella zoster virus), parasitic infection (e.g., schistosomiasis or scabies), and bacterial infection (e.g., tuberculosis or diptheria).

By "specifically bind" is meant that an immunoglobulin or antibody interacts with its antigen (i.e., its specific antigen), where the interaction is dependent upon the presence of a particular structure (e.g., an epitope) on the antigen; in other words, the antibody is recognizing and binding to a specific structure rather than to all molecules or structures in general. An antibody that specifically binds to the antigen may be referred to as an "antigen-specific antibody" or an "antibody specific for the antigen". In some embodiments, an antibody that specifically binds to antigen can immunoprecipitate that antigen from a solution containing the antigen as well as other molecules (e.g., a cell lysate). In some embodiments, an antibody that specifically binds to its antigen has a $K_D$ for its antigen of $1 \times 10^{-6}$M or less. In some embodiments, an antibody that specifically binds to its antigen has a $K_D$ for its antigen of $1 \times 10^{-7}$ M or less, or a $K_D$ of $1 \times 10^{-8}$ M or less, or a $K_D$ of $1 \times 10^{-9}$M or less, or a $K_D$ of $1 \times 10^{-10}$ M or less, of a $K_D$ of $1 \times 10^{-11}$ M or less, of a $K_D$ of $1 \times 10^{-12}$M or less. In certain embodiments, the $K_D$ of an antibody that specifically binds to its antigen for its specific antigen is between 1 pM to 500 pM, or between 500 pM to 1 µM, or between 1 µM to 100 nM, or between 100 mM to 10 nM. As used herein, by the term "$K_D$", is intended to refer to the dissociation constant of an interaction between two molecules (e.g., the dissociation constant between an antibody and its specific antigen).

By "variable region of an immunoglobulin chain" or an "immunoglobulin chain variable region" is a polypeptide comprising at least a portion of the variable domain of a heavy (i.e., the VH domain) or a light chain (i.e., the VL domain) of an immunoglobulin, where the portion of the VL and the VH domains form an antigen binding domain of an immunoglobulin (see FIG. 1). Thus, the variable region of an immunoglobulin may include, without limitation, a single CDR (e.g., CDR1), two CDRs interspersed with a single FR (e.g., CDR1, FR2, and CDR2), three CDRs interspersed with two FRs (e.g., CDR1, FR2, CDR2, FR3, and CDR3), or three CDRs flanked by either or both of FR1 and FR4 (e.g., FR1, CDR1, FR2, CDR2, FR3, CDR3, FR4). In some embodiments, the immunoglobulin chain variable region is the region on one of either the heavy or the light chain which, when combined with the immunoglobulin chain variable region of the other chain (i.e., the light or the heavy chain) of the intact immunoglobulin, forms the antigen binding domain.

By "antigen binding domain" is meant the region of a single heavy chain assembled with a single light chain in an immunoglobulin, which retains the specific binding activity of the intact antibody for its specific antigen. Thus, an intact IgG immunoglobulin, which comprises two heavy chains and two light chains, has two antigen binding domains. Likewise, fragmentation of an intact antibody which retains a covalent bond between the heavy chain and the light chain will also result in an immunoglobulin fragment having an antigen binding domain. For example, digestion of an immunoglobulin with the enzyme papain will generate F(ab) fragments, each of which has a single antigen binding domain. Of course the entire F(ab) is not the antigen binding domain; rather, only the portion of the F(ab) fragment which retains the ability to specifically bind the antigen is the antigen binding domain.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of antibody and/or recombinant DNA technologies include Harlow and Lane, *Antibodies: A Laboratory Manual*, Cold Springs Harbor Laboratory Press, Cold Spring Harbor, N.Y. (1988); Sambrook et al., *Molecular Cloning: A Laboratory Manual*, 2nd Ed., Cold Spring Harbor Laboratory Press, Cold Spring Harbor, N.Y. (1989); Coligan et al., *Current Protocols in Immunology*, John Wiley & Sons, New York, N.Y. (1991-2010); Ausubel et al., *Current Protocols in Molecular Biology*, John Wiley & Sons, New York, N.Y. (1987-2010); Kaufman et al., Eds., *Handbook of Molecular and Cellular Methods in Biology in Medicine*, CRC Press, Boca Raton (1995); McPherson, Ed., *Directed Mutagenesis: A Practical Approach*, IRL Press, Oxford (1991); all of which are incorporated by reference in their entirety. Standard reference works setting forth the general principles of pharmacology include Goodman and Gilman's *The Pharmacological Basis of Therapeutics*, 11th Ed., McGraw Hill Companies Inc., New York (2006), which is incorporated by reference in its entirety.

Methods for Obtaining Sequences of Antigen-Specific Immunoglobulins

In one aspect, this invention is directed to a method for obtaining the amino acid and/or nucleic acid sequences of immunoglobulin chains (or variable regions thereof) of a single immunoglobulin from a population of polyclonal antibodies.

According to the present method, a population of polyclonal antibodies of interest is obtained from an animal and fragmented to generate peptide fragments which are analyzed by mass spectrometry. The mass spectra information observed from the peptide fragments is then correlated with predicted mass spectra information derived from a genetic material database comprised of nucleic acid sequences that encode full-length immunoglobulin heavy and/or light chains (or variable regions thereof). As a result of such correlating, immunoglobulin heavy and/or light chains (or variable regions thereof) can be identified from the genetic material database that correspond to immunoglobulin heavy and/or light chains (or variable regions thereof) of immunoglobulin molecules within the starting polyclonal antibody population.

The various aspects of the present method are described in more detail below.

The Starting Population of Polyclonal Antibodies

Immunoglobulins that specifically bind to an antigen of interest may be collected from an animal, which includes any mammal, such as human. Immunoglobulins can be collected from a body fluid sample of the animal including, for example, blood, serum or plasma of the blood, cerebrospinal fluid, synovial fluid, peritoneal fluid, mucosal secretions, tears, nasal secretions, saliva, milk, and genitourinary secretions.

In some embodiments, immunoglobulins need not come from a single individual animal but, rather, may be a cocktail of different antibodies (monoclonal or polyclonal) taken from different individuals. In some embodiments, the immunoglobulins are collected from a transgenic non-human animal, e.g., a transgenic non-human animal that expresses human antibody sequences and/or produces antibodies that are at least partly human.

In some embodiments, these immunoglobulins are specific for an antigen of interest, either because the animal from whom the immunoglobulins are collected was previously immunized with the antigen, or because the animal from whom the immunoglobulins are collected was previously exposed to a condition whereby the animal was likely to generate antigen-specific antibodies. In an example of the latter case, the animal may have been infected with a virus (e.g., Epstein Barr Virus), where the antigen of interest is the EBNA1 protein, which is encoded by the genome of the Epstein Barr Virus.

In various embodiments, the animal whose immunoglobulins are collected (i.e., obtained) is of the same species as the animal whose B lymphocyte nucleic acid sequences are collected to create the reference database. In some embodiments, the animal whose immunoglobulins are collected for the peptide database and the animal whose B lymphocyte nucleic acids are collected for the reference database are the same animal.

Figure 2:
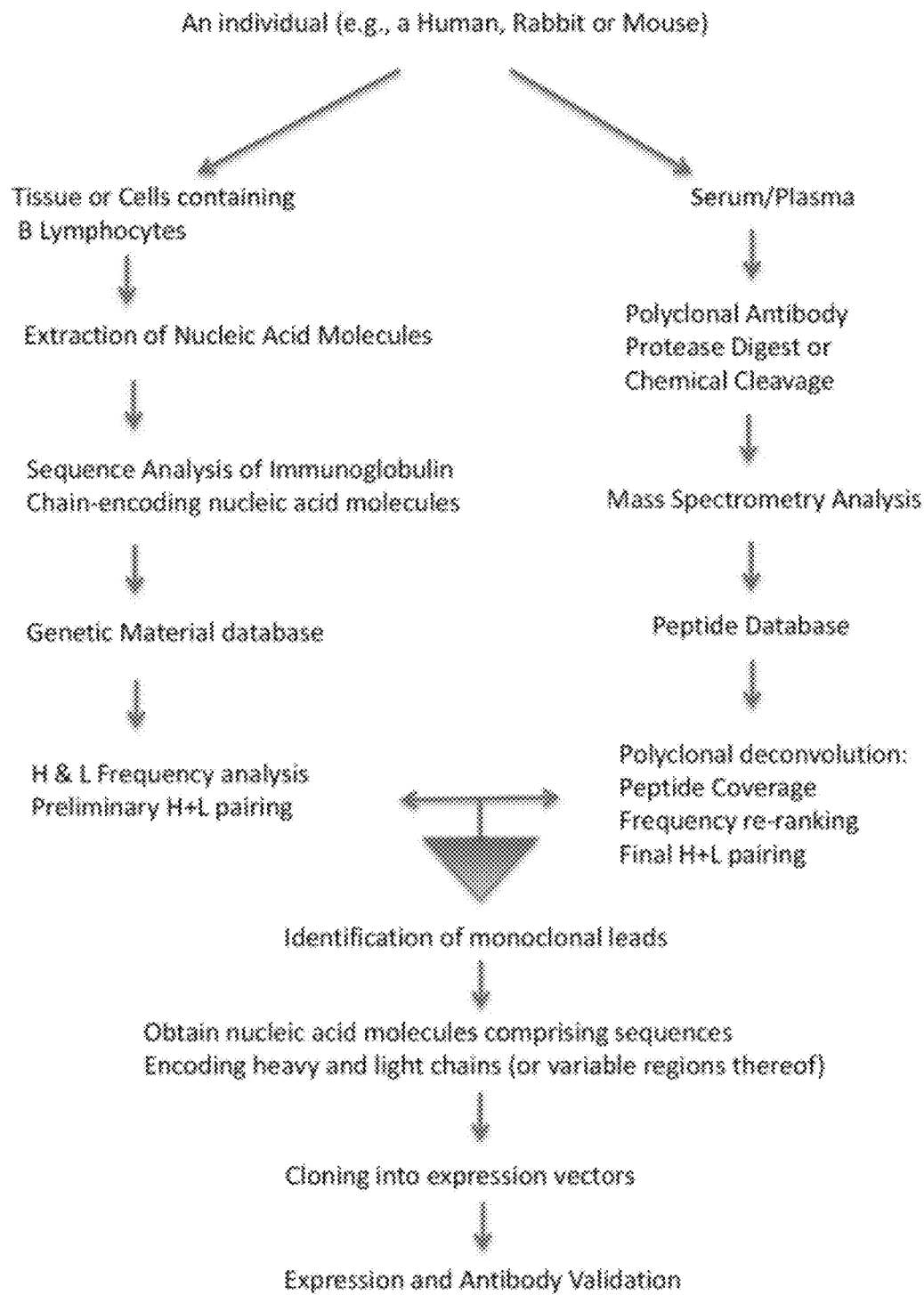
FIG. 2 is a schematic diagram showing an example of a non-limiting method of various embodiments of the invention. In this example, samples comprising B lymphocytes (e.g., a blood sample or a tissue sample) and blood serum and/or plasma are collected from the same animal (e.g., a human, mouse, or rabbit). Nucleic acid molecules encoding immunoglobulin chains (or variable regions thereof) are sequenced and these nucleic acid sequences are used to generate theoretical or predicted mass spectra information based on the predicted amino acid sequences encoded by the nucleic acid sequences. Polyclonal antibodies from the blood sera are proteolytically digested or chemically fragmented and the resulting peptide fragments subjected to analysis by mass spectrometry. The information from the nucleic acid sequences (e.g., the mass spectra) is compared to the mass spectra information of the peptides fragments to identify the sequence of an immunoglobulin chain (or variable domain thereof) of an antibody. This antibody can then be generated recombinantly according to standard methods.

As shown in FIG. 2, where the animal is the same animal, blood taken from the animal can provide both the nucleic acid sequences (e.g., from the cells in the blood) and the polyclonal antibodies (e.g., from the sera or plasma of the blood).

The immunoglobulins collected from the animal form a polyclonal population of immunoglobulins, because different B lymphocytes produced members of the population. It should be noted that in such a polyclonal population, not all of the individual antibodies within that polyclonal population will specifically bind the same antigen. In fact, each of the antibodies within the population may bind a different antigen. However, this polyclonal population still is said to specifically bind a particular antigen if at least one individual antibody, preferably multiple antibodies, of the polyclonal population binds that antigen (see, e.g., Example 3 below). In another example, some antibodies in the polyclonal population may bind the antigen with low affinity. However, a polyclonal population is said to specifically bind an antigen if some (e.g., at least one or more) of the antibodies in that population specifically bind the antigen.

It should be noted that by the phrase "polyclonal antibody (or immunoglobulin) that specifically binds to an antigen" is meant that within the polyclonal population, at least one antibody specifically binds to the antigen, however that one antibody is not necessarily isolated from the other antibodies within the polyclonal population that do not specifically bind to the antigen. Of course in some embodiments, more than one different antibody within the polyclonal population specifically binds to the antigen.

It should also be noted that different antibody molecules are antibody molecules produced by a different B cell. For example, after collecting sera, a polyclonal population of 1000 antibody molecules may be isolated from the sera (e.g., using the antibodies' adherence to a protein A column to isolate the antibodies from the other sera components). Within that population of 1000 antibody molecules, 900 may be identical (i.e., secreted by the same B cell) and thus there are really only 101 different antibodies within that polyclonal population. Regarding a polyclonal population, if all 900 identical antibody molecules specifically bind the antigen, the polyclonal population of 1000 antibody molecules is a polyclonal antibody that specifically binds to the antigen. Similarly, if an additional 5 different antibody molecules of the remaining 100 different antibody molecules also specifically bind to the antigen, the polyclonal population of 1000 antibody molecules is likewise is a polyclonal antibody that specifically binds to the antigen.

The majority of antibody molecules within a polyclonal population need not specifically bind to an antigen for that population to be referred to as a "polyclonal antibody that specifically binds to the antigen". For example, if within a polyclonal population of 1000 antibody molecules, even if only 1 antibody molecule specifically binds to the antigen and 999 antibody molecules do not, that population of 1000 antibody molecules is still a "polyclonal antibody that specifically binds to the antigen" as the term is used herein.

Note also that all of the antibodies in a polyclonal antibody population need not bind the same epitope on the antigen. For example, a polyclonal population can be specific for the antigen where every different antibody within the population specifically binds a different epitope on the antigen.

In various embodiments of the non-limiting methods of the invention, the population of polyclonal immunoglobulins may have, for example, at least two different immunoglobulins within the population, or at least three, or at least five, or at least ten, or at least twenty, or at least fifty, or at least one hundred or at least five hundred different immunoglobulins within the population.

The invention also contemplates collecting a polyclonal population of immunoglobulins from the tissue culture supernatants of B cells grown in vitro (e.g., where the nucleic acid sequences are collected from the B cells themselves). For example, a population of B cells may be collected from an animal that has been subjected to the Epstein Barr virus. The population can be expanded, e.g., to enrich B lymphocytes in the population as compared to other white blood cells. From this cultured media of these cells (into which the polyclonal antibodies are secreted by the cells), the polyclonal population of antibodies can be isolated.

Figure 3:
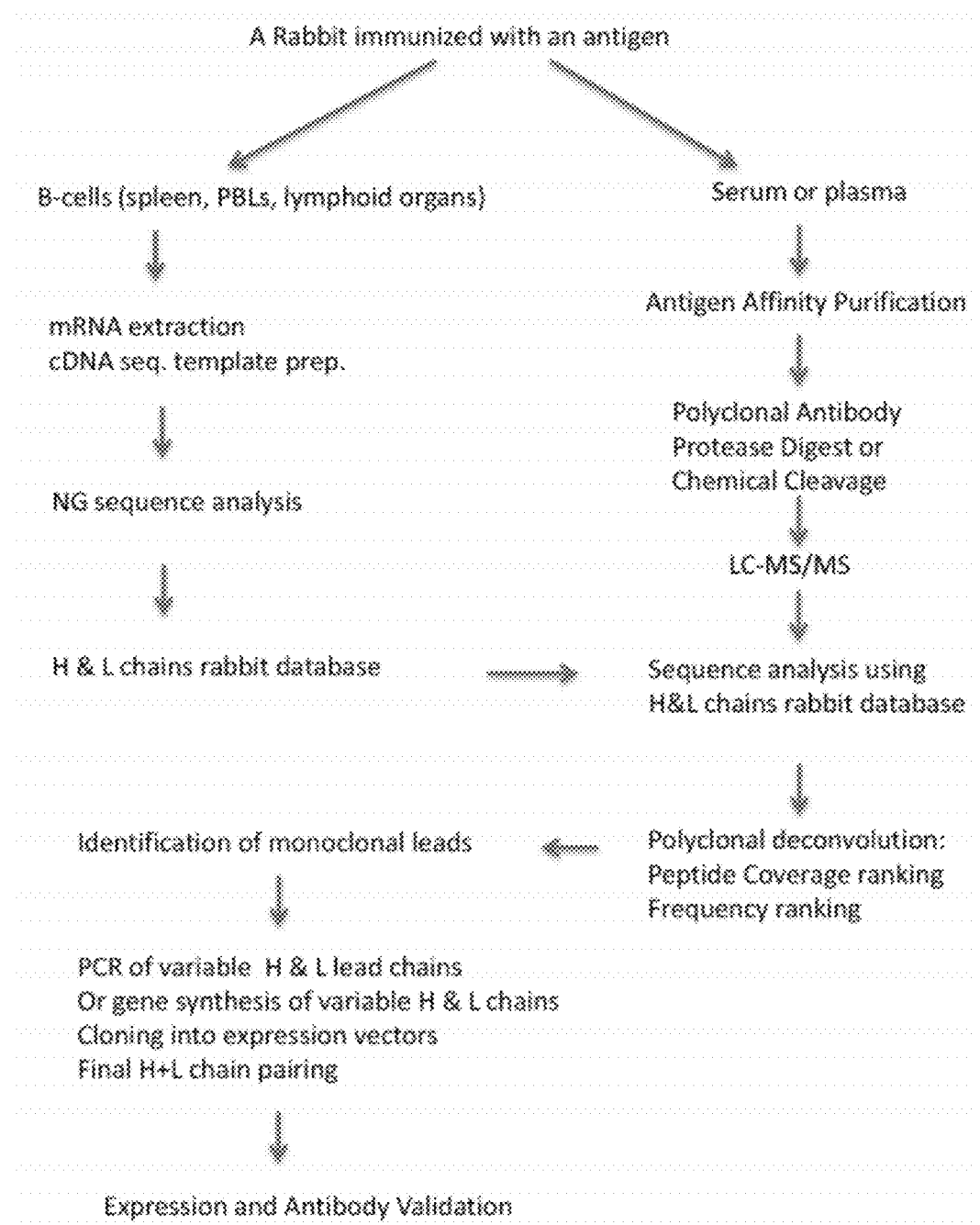
FIG. 3 is a schematic diagram showing another example of a non-limiting method of various embodiments of the invention. In this example, B lymphocytes and blood serum and/or plasma are collected from the same animal (in this case a rabbit). From the B lymphocytes, mRNA is extracted and subjected to sequencing using the Genome Sequencer FLX System machine commercially available from 454 Life Sciences using immunoglobulin gene-specific sequencing primers. This information is used to generate theoretical mass spectra based on the predicted amino acid sequences. From the blood serum and/or plasma, polyclonal antibodies are isolated and subjected to digestion with proteases and/or cleavage with chemical protein cleavage reagents. The resulting peptide fragments are separated by liquid chromatography, followed by mass spectrometry analysis (MS/MS). The mass spectra of the peptide fragments are correlated with the theoretical mass spectra of the nucleic acid sequences to obtain the amino acid sequences of the immunoglobulin chains that include the peptide fragments. A heavy and light chain can then be assembled to create a' recombinant immunoglobulin by cloning nucleic acid sequences encoding the immunoglobulin chains into expression vector(s) and expressing the expression vectors in a cell. The expressed recombinant immunoglobulin is then further characterized.

The polyclonal population of immunoglobulins collected, either from an animal(s) or from tissue culture supernatants of B cells, can be first purified prior to digestion into peptide fragments. For example, the collected polyclonal antibodies can be subjected to a protein A or protein G sepharose column, which can separate antibodies from other blood sera proteins, for example. See, for example, FIG. 2 and FIG. 3. Alternatively or additionally, the collected polyclonal antibodies are subjected to antigen affinity purification to enrich for antibodies with high specific activity. While not entirely necessary, a purification step, especially antigen affinity purification, can reduce the complexity of a polyclonal mixture and ultimately reduce the number of potential false positive or negative candidate immunoglobulins. The collected polyclonal antibodies may be concentrated or buffer exchanged or both, either before or after purification.

In one illustrative embodiment, to collect immunoglobulins that specifically bind to an antigen of interest from an animal, peripheral blood is drawn from the animal, and serum and/or plasma antibodies are collected according to standard methods (e.g., adherence of the antibodies to protein A). The serum and/or plasma antibodies are then purified or screened to enrich for immunoglobulins that specifically bind to the antigen. This screen can be, for example, by coating a solid-phase surface (e.g., a sepharose bead or bottom of a plastic well) with antigen and pass the serum and/or plasma over the antigen-coated surface under conditions where immunoglobulins that specifically bind to the antigen will bind. The bound antibodies may be treated with a protease (e.g., papain) or a chemical protein cleavage reagent that specifically cuts near the hinge region of the immunoglobulin to remove the non-adherent Fc portions. After rinsing away non-binding serum and/or plasma proteins (including non-specific immunoglobulins), the antigen-specific immunoglobulins can be collected and their quantities thus enriched as compared to antibodies that do not specifically bind to the antigen.

Observed Mass Spectra From the Collected Polyclonal Antibodies

To obtain observed (i.e., actual) mass spectra, the collected polyclonal antibodies (or fragments thereof) are analyzed by protein analysis methods (e.g., mass spectrometry, liquid chromatography, etc.).

In some embodiments, observed mass spectra information is obtained from peptide fragments which are generated from the polyclonal antibodies. The polyclonal antibodies can be fragmented, for example, with one or more proteases, and/or a chemical protein cleavage reagent, such as cyanogen bromide.

Certain proteases are known to cleave their substrates at specific sites. Table 1 provides a non-comprehensive list of commonly used proteases and their cleavage sites (in 3 letter amino acid code).

TABLE 1

| Protease | Cleavage Site |
| --- | --- |
| Trypsin | cleaves after (i.e., on the carboxyl side of) Arg or Lys, unless followed by Pro |
| Chymotrypsin | cleaves after Phe, Trp, or Tyr, unless followed by Pro |
| Elastase | cleaves after Ala, Gly, Ser, or Val, unless followed by Pro. |

TABLE 1-continued

| Protease | Cleavage Site |
| --- | --- |
| Endoproteinase Lys-C | cleaves after Lys |
| Pepsin | cleaves after Phe or Leu. |
| Thermolysin | cleaves before Ile, Met, Phe, Trp, Tyr, or Val, unless preceded by Pro. |
| Endopeptidase V8 (alias Glu-C) | cleaves after Glu. |

A more comprehensive listing of proteases that can be used to digest proteins to smaller fragments is given in Tables 11.1.1 and 11.1.3 of Riviere and Tempst (Riviere L R, Tempst P. Enzymatic digestion of proteins in solution. Curr Protoc Protein Sci. 2001 May; Chapter 11:Unit 11.1. PubMed PMID: 18429101; herein incorporated by reference in its entirety).

In specific embodiments, multiple (i.e., two or more) proteases are used (e.g., independently or together) to digest the polyclonal antibodies to maximize V-region coverage and account for highly variable amino acid compositions of immunoglobulins. For example, a combination of chymotrypsin, elastase, pepsin and trypsin can be used, as illustrated in Example 7 herein. In some embodiments, a protease or proteases are chosen on the basis that they do not cleave within predicted CDR3 regions based on analysis of the nucleic acid molecules in the genetic material database.

Proteins may be digested to smaller fragments that are amenable to mass spectrometry by treatment with particular chemical protein cleavage reagents rather than proteolytic enzymes. See for example chapter 3 of G. Allen. Sequencing of Proteins and Peptides, Laboratory Techniques in Biochemistry and Molecular Biology, Vol. 9. Elsevier 1989. Such chemical protein cleavage reagents include, without limitation, cyanogen bromide, BNPS-skatole, o-iodosobenzoic acid, dilute acid (e.g., dilute HCl), and so forth. For example, proteins can be cleaved at Met residues with cyanogen bromide, at Cys residues after cyanylation, after Trp residues with BNPS-skatole or o-iodosobenzoic acid, etc. Protein fragments can also be generated by exposure to dilute acid, e.g., HCl. An example of the use of partial acid hydrolysis to determine protein sequences by mass spectrometry is given by Zhong et al. (Zhong H, et al., *J. Am. Soc. Mass Spectrom.* 16(4):471-81, 2005. PubMed PMID: 15792716, incorporated by reference in its entirety). Zhong et al., supra used microwave-assisted acid hydrolysis with 25% trifluoroacetic acid in water to fragment bacteriorhodopsin for sequencing by mass spectrometry. See also Wang N, and Li L., *J. Am. Soc. Mass. Spectrom.* 21(9):1573-87, 2010. PubMed PMID: 20547072 (herein incorporated by reference in its entirety).

Proteins can be fragmented to make them more amenable for mass spectrometry by treatment with one protease, by treatment with more than one protease in combination, by treatment with a chemical cleavage reagent, by treatment with more than one chemical cleavage reagent in combination, or by treatment with a combination of proteases and chemical cleavage reagents. The reactions may occur at elevated temperatures or elevated pressures. See for example López-Ferrer D, et al., *J. Proteome. Res.* 7(8):3276-81, 2008. PubMed PMID: 18605748; PubMed Central PMCID: PMC2744211 (incorporated by reference in its entirety). The fragmentation can be allowed to go to completion so the protein is cleaved at all bonds that the digestion reagent is capable of cleaving; or the digest conditions can be adjusted so that fragmentation does not go to completion deliberately, to produce larger fragments that may be particularly helpful in deciphering antibody variable region sequences; or digest conditions may be adjusted so the protein is partially digested into domains, e.g., as is done with *E. coli* DNA polymerase I to make Klenow fragment. The conditions that may be varied to modulate digestion level include duration, temperature, pressure, pH, absence or presence of protein denaturing reagent, the specific protein denaturant (e.g., urea, guanidine HCl, detergent, acid-cleavable detergent, methanol, acetonitrile, other organic solvents), the concentration of denaturant, the amount or concentration of cleavage reagent or its weight ratio relative to the protein to be digested, among other things.

In some embodiments, the reagent (i.e., the protease or the chemical protein cleavage reagents) used to cleave the proteins is a completely non-specific reagent. Using such a reagent, no constraints are made may be made at the N-terminus of the peptide, the C-terminus of the peptide, or both of the N- and C-termini. For example, a partially proteolyzed sequence that is constrained to have a tryptic cleavage site at one end of the peptide sequence or the other, but not both, may be used in the various methods described herein.

The resulting peptide fragments can be detected and analyzed using an HPLC coupled to a mass spectrometer from which observed mass spectra are generated. This method may be referred to as a "bottom up" proteomics approach, where proteome components are separated and identified after reducing the proteins to relatively small peptides, e.g., 3 to 45 residues in length.

In other embodiments, an alternative, "top down" proteomics approach can be employed to obtain observed mass spectra, which involves mass spectrometry analysis of intact proteins or large protein fragments or protein domains or large polypeptides. For example, to identify the parts of the antibody variable regions that bestow specific antigen recognition to a particular polyclonal antibody molecule, it is helpful to sequence large portions of the variable regions to identify its CDRs, by direct analysis of fragments large enough that the CDRs remain linked together.

For a review describing both "bottom up" and "top down" strategies, see Han X, Aslanian A, Yates J R 3rd. Mass spectrometry for proteomics. *Curr Opin Chem. Biol.* 2008 October; 12(5):483-90. Review. PubMed PMID: 18718552; PubMed Central PMCID: PMC2642903 (incorporated by reference in its entirety). For a recent review of top-down proteomics applied to determining antibody sequences, see Zhang Z. et al., *Mass Spectrom Rev.* 2009 January-February; 28(1):147-76. Review. PubMed PMID: 18720354 (incorporated by reference in its entirety). For a recent paper showing extensive sequencing of a monoclonal, antibody by top-down proteomics, see Tsybin et al, *Anal Chem.* 2011 Oct. 21. PubMed PMID: 22017162 (incorporated by reference in its entirety).

In some embodiments of the above non-limiting method, while the antigen-specific immunoglobulins are bound to the antigen-coated surface, the immunoglobulins can be digested with either papain or pepsin to generate F(ab) and F(ab)$_2$ fragments, respectively. Since the entirety of an immunoglobulin chain variable region is located on a chain of an F(ab) fragment, this pre-treatment with papain and/or pepsin will enrich for immunoglobulin chain variable regions. After rinsing away the non-binding portions of the immunoglobulins, the immunoglobulin chain variable regions can be collected.

After passage of the immunoglobulin fragments through the mass spectrometer, numerous observed mass spectra will be generated. However, given the potentially large number of different immunoglobulins within a polyclonal population, each with a different amino acid sequence, that are analysed with the mass spectrometer, the resulting observed mass spectra will be difficult to assemble back into a functional immunoglobulin chain variable region. In the methods of various embodiments of the invention, because the underlying nucleic acid sequence is available, there is no need to assemble the observed mass spectra data. Instead, the observed mass spectrum of a single peptide fragment can be correlated with the predicted mass spectra of the nucleic acid sequence to obtain the amino acid (and underlying nucleotide) sequence of the entire immunoglobulin chain (or variable region thereof) of an immunoglobulin that specifically binds to an antigen from a starting polyclonal immunoglobulin population. This correlating step is further described hereinbelow.

In addition to mass spectra information, additional information derived from the peptide fragments of the polyclonal antibodies is useful in various embodiments of the invention. This information includes, without limitation, the mass of each peptide, the length (in amino acid residues) of each peptide, the observed mass spectrum of each peptide (e.g., from tandem mass spectrometry such as the MS2 or MS3 spectrum), the mass to charge ratio of each peptide, the ionic charge of each peptide, the chromatographic profile of each peptide, and the amino acid sequence of each peptide.

Mass Spectrometry Analysis

In the methods of this invention, mass spectra information can be obtained by mass spectrometry analysis of collected immunoglobulins or fragments generated therefrom. A mass spectrometer is an instrument capable of measuring the mass-to-charge (m/z) ratio of individual ionized molecules, allowing researchers to identify unknown compounds, to quantify known compounds, and to elucidate the structure and chemical properties of molecules. In some embodiments, one begins mass spectrometry analysis by isolating and loading a sample onto the instrument. Once loaded, the sample is vaporized and then ionized. Subsequently, the ions are separated according to their mass-to-charge ratio via exposure to a magnetic field. In some embodiments, a sector instrument is used, and the ions are quantified according to the magnitude of the deflection of the ion's trajectory as it passes through the instrument's electromagnetic field, which is directly correlated to the ions mass-to-charge ratio. In other embodiments, ion mass-to-charge ratios are measured as the ions pass through quadrupoles, or based on their motion in three dimensional or linear ion traps or Orbitrap, or in the magnetic field of a Fourier transform ion cyclotron resonance mass spectrometer. The instrument records the relative abundance of each ion, which is used to determine the chemical, molecular and/or isotopic composition of the original sample. In some embodiments, a time-of-flight instrument is used, and an electric field is utilized to accelerate ions through the same potential, and measures the time it takes each ion to reach the detector. This approach depends on the charge of each ion being uniform so that the kinetic energy of each ion will be identical. The only variable influencing velocity in this scenario is mass, with lighter ions traveling at larger velocities and reaching the detector faster consequently. The resultant data is represented in a mass spectrum or a histogram, intensity vs. mass-to-charge ratio, with peaks representing ionized compounds or fragments.

To obtain mass spectra data of a protein sample, the sample is loaded onto the instrument and ionized. Ionization can be done by, e.g., electrospray ionization and matrix-assisted laser desorption/ionization ("MALDI"). See, e.g., Zenobi, "Ion Formation in MALDI Mass Spectrometry", 17 *Mass Spectrometry Review,* 337 (1998). Protein characterization can be done in one of two ways, top-down or bottom-up. The top-down approach involves ionizing intact proteins or larger protein fragments. See, e.g., Allison Doerr, "Top-down Mass Spectrometry", 5 *Nature Methods,* 24 (2008). The bottom-up approach involves enzymatically or chemically digesting the protein into constituent peptides using a protease. See Biran Chait, "Mass Spectrometry: Bottom-Up or Top-Down?", 6 *Science* 65 (2006). The resultant peptides are introduced into the instrument and ultimately identified by peptide mass fingerprinting or tandem mass spectrometry.

In some embodiments, mass spectrometry analysis may be combined with a chromatographic fractionation (e.g., liquid chromatography).

Mass spectra data useful in this invention can be obtained by peptide mass fingerprinting. Peptide mass fingerprinting involves inputting the observed mass from a spectrum of the mixture of peptides generated by proteolytic digestion into a database and correlating the observed masses with the predicted masses of fragments arising from digestions of known proteins in silico. Known masses corresponding to sample masses provide evidence that the known protein is present in the sample tested.

Mass spectra data can be obtained by tandem mass spectrometry. In some embodiments, tandem mass spectrometry typically utilizes collision-induced-dissociation, which causes peptide ions to collide with gas and to fragment (e.g., due to vibrational energy imparted by the collision). The fragmentation process produces cleavage products that break at the peptide bonds at various sites along the protein. The observed fragments' masses may be matched with a database of predicted masses for one of many given peptide sequences, and the presence of a protein may be predicted. See, e.g., Eng, 5 *An Approach to Correlate Tandem Mass Spectral Data of Peptides with Amino Acid Sequences in a Protein Database,* JASMS, 976 (1994).

In another embodiment, tandem mass spectrometry is performed by higher-energy collision induced dissociation (HCD), which on some mass spectrometers shows fragment product ions closer to peptide termini than collision induced dissociation. See Olsen J V, Macek B, Lange O, Makarov A, Horning S, Mann M. Higher-energy C-trap dissociation for peptide modification analysis. *Nat. Methods.* 2007 September; 4(9):709-12. Epub 2007 Aug. 26. PubMed PMID: 17721543.

In another embodiment, tandem mass spectrometry is performed by electron transfer dissociation (ETD), which is based on ion-ion reactions where a distinct reagent chemical ion donates a radical to a peptide ion, which then promptly fragments to form product ions. See Mikesh L M, Ueberheide B, Chi A, Coon J J, Syka J E, Shabanowitz J, Hunt D F. The utility of ETD mass spectrometry in proteomic analysis. *Biochim Biophys Acta.* 2006 December; 1764(12): 1811-22. Epub 2006 Oct. 30. Review. PubMed PMID: 17118725; PubMed Central PMCID: PMC1853258. Certain fragmentation methods, such as ETD, are particularly well-suited to "top down" proteomics strategies. Other fragmentation mechanisms are specific to certain ionization mechanisms, for example, such as post-source decay (PSD) is compatible with matrix-assisted laser desorption ionization (MALDI), and is also well-suited to "top down" proteomics strategies.

Genetic Material Database

In accordance with the present invention, the observed mass spectra information from the starting polyclonal immunoglobulin population is correlated with predicted mass spectra information derived from a genetic material database, in order to obtain the amino acid (and underlying nucleotide) sequences of immunoglobulin chains (or variable regions thereof) of immunoglobulins from the starting polyclonal immunoglobulin population.

As used herein, a genetic material database includes nucleic acid sequences encoding a plurality of immunoglobulin chains (or variable regions thereof). Thus, information which can be obtained or derived from such a genetic material database includes, for example, the nucleotide sequence information of each nucleic acid molecule, the length (in nucleotides) of each nucleic acid molecule, amino acid sequence information of the polypeptides or peptides encoded by each nucleic acid molecule, the mass of a polypeptide or peptide encoded by each nucleic acid molecule, the length (in amino acid residues) of a polypeptide or peptide encoded by each nucleic acid molecule, the mass spectra information of polypeptides or peptides encoded by each nucleic acid molecule (e.g., a predicted mass spectra information based on the amino acid sequence of the polypeptide or peptide), and the amino acid sequence of a polypeptide or peptide encoded by each nucleic acid molecule.

In some embodiments of the invention, the genetic material database contains genetic information of nucleic acid sequences encoding full length immunoglobulin chains (and not just the variable regions thereof). In some embodiments, the nucleic acid sequences are expressed (i.e., transcribed into RNA and/or translated into protein) by the cell from which said sequences are derived. In specific embodiments, the genetic material database includes expressed nucleic acid sequences encoding immunoglobulin chain variable regions of multiple immunoglobulins from an animal. In some embodiments, the genetic material database contains at least one hundred different expressed nucleic acid sequences. In other embodiments, the genetic material database contains at least one thousand different expressed nucleic acid sequences.

Nucleic acid molecules encoding immunoglobulin chains (or the variable regions thereof) are readily obtainable from a population of cells (e.g., peripheral white blood cells) containing B lymphocytes. In some embodiments, the nucleic acid molecules are obtained from splenocytes or mononuclear cells, such as peripheral blood mononuclear cells (PBMCs). In some embodiments, the B lymphocytes are from a naïve animal (e.g., an animal that has not been exposed to the antigen to which an antigen-specific antibody is sought). In some embodiments, the naïve animal has been exposed to very few antigens (e.g., an animal raised in sterile or pathogen-free environment). In some embodiments, the naïve animal is a typical animal that has been exposed to typical antigens, but has not been exposed to the antigen of choice.

In some embodiments, the animal from which the nucleic acid molecules encoding immunoglobulin chains (or the variable regions thereof) are obtained is an animal that has been previously exposed to the antigen. For example, the animal may be an animal immunized with the antigen (e.g., the antigen mixed with an adjuvant or an antigen coupled to an immunogenic carrier such as keyhole limpet hemocyanin (KLH)), may be an animal infected with a pathogen comprising the antigen (e.g., an animal infected with HIV virus when the antigen of choice is the HIV p24 antigen), or may otherwise be previously exposed to the antigen. In some embodiments, the animal is a bird (e.g., a chicken or turkey) or a mammal, such as a primate (e.g., a human or a chimpanzee), a rodent (e.g., a mouse, hamster, or rat), a lagomorph (e.g., a rabbit or hare), a camelid (e.g., a camel or a llama), or a domesticated mammal such as a companion animal (e.g., a cat, a dog, or a horse), or a livestock animal (e.g., a goat, sheep, or a cow).

It shall be understood that the nucleic acid sequences of the various aspects and embodiments of the invention need not come from a single animal. For example, some of the nucleic acid sequences of various embodiments of the invention may come from an animal previously exposed to an antigen, and some of the nucleic acid sequences may come from naïve animal. In some embodiments of the invention, nucleic acid sequences are from animals of a single species. For example, where there are multiple animals from which nucleic acid sequences are obtained, all of those animals may be the same species (e.g., all are rabbits or all are humans). In some embodiments, the nucleic acid sequences are obtained from animals of a single species. In other embodiments, nucleic acid sequences from more than one species of animal may be obtained. For examples, nucleic acid sequences may be obtained from mice and rats, and predicted mass spectra based from these sequences can be used to correlate with and/or compare to the actual mass spectra information of peptide fragment of polyclonal antibodies to create an immunoglobulin (or variable region, antigen binding domain, or chain thereof) that specifically binds to the antigen. In some embodiments, the nucleic acid sequences are obtained from animals of a single gender (e.g., all animals are female).

The animal from whom the polyclonal antibodies are collected and the animal from whom the nucleic acid sequences are collected may be the same animal, or the same species of animal, or syngenic animals (e.g., both are Balb/c mice), or from animals of the same gender (e.g., both are female animals). The MS2 spectra from the antigen-binding components of the polyclonal antibodies can thus be correlated to the theoretical MS2 spectra derived from the nucleic acid sequences obtained from an animal, in order to identify the nucleic acid sequences that encode antigen-binding antibodies.

It shall also be understood that the nucleic acid sequences and the polyclonal antibodies can be collected from cells of an animal where the cells were cultured in vitro following removal from the animal and prior to collection of the polyclonal antibodies (e.g., from the supernatant or cultured media of the cultured cells) and collection of the nucleic acid sequences from the cells. This culturing step is useful, e.g., to expand or enrich B lymphocytes as compared to other blood or tissue cells (e.g., to enrich B lymphocytes over red blood cells or epithelial cells). The number of individual nucleic acid sequences used to create theoretical mass spectra in the various embodiments of the invention is limitless. For example, five or ten or fifty, or one hundred, or one thousand, or one million, or one billion, or one trillion or more different nucleic acid sequences can be obtained and used to create theoretical mass spectra. The nucleic acid sequences may come from any source, and may be from a combination of sources. For example, nucleic acid sequences can be obtained by sequencing expressed nucleic acid molecules encoding immunoglobulin chain variable regions (or the entire full length immunoglobulin chain including the variable regions and constant region) as described herein. Nucleic acid sequences can also be obtained from genomic DNA that may or may not have undergone full V(D)J recombination. Nucleic acid sequences can also be obtained from publicly available sources. For example, numerous amino acid sequences (and nucleotide sequences) of immunoglobulin chain variable regions (and polynucleotides encoding the same) from multiple species of animal are known (see, for example, the following US and PCT patent publications (including issued US patents), the entirety of each of which is hereby incorporated by reference: US 20100086538; WO 2010/097435; US 20100104573; U.S. Pat. No. 7,887,805; U.S. Pat. No. 7,887,801; U.S. Pat. No. 7,846,691; U.S. Pat. No. 7,833,755; U.S. Pat. No. 7,829,092.

The B lymphocytes from which nucleic acid sequences are obtained can be from any blood or tissue source including, without limitation, bone marrow, fetal blood, fetal liver, sites of inflammation (e.g. inflamed joints surrounding synovial fluid in rheumatoid patients), tumors (e.g., tumor-infiltrating lymphocytes), peripheral blood, in lymph nodes, in peyer's patches, in tonsils, and in the spleen or in any lymphoid organ. In some embodiments, the entire tissue (e.g., bone marrow or lymph node) can be processed (e.g., cells separated from one another and lysed), genetic material removed, and the nucleic acid molecules encoding immunoglobulin chains (or variable regions thereof) sequenced.

In some embodiments, B lymphocytes are enriched from tissues or a population of cells (e.g., peripheral blood) containing them prior to isolating genetic material from the B lymphocytes. In accordance with various embodiments of the invention, methods for enriching B lymphocytes from an animal are well known. B lymphocytes can be found in many organs and areas of the body including, without limitation, bone marrow, fetal blood, fetal liver, sites of inflammation (e.g. inflamed joints surrounding synovial fluid in rheumatoid patients), tumors (e.g., tumor-infiltrating lymphocytes), peripheral blood, in lymph nodes, and in the spleen. From these tissue samples (e.g., peripheral blood or the spleen of an animal), white blood cells may be isolated according to standard methods (e.g., using the Ficoll-Paque PLUS or Ficoll-Paque PREMIUM reagents commercially available from GE Healthcare, Piscataway, N.J., according to manufacturer's instructions). B lymphocytes themselves can then be further isolated from other white blood cells using, for example, cell surface markers found on B lymphocytes. B lymphocyte cell surface markers include, without limitation, cell surface expressed immunoglobulin chains (e.g., lambda light chain, kappa light chain, and heavy chain such as IgM or IgG). Additional B lymphocyte cell surface markers include, without limitation, CD21, CD27, CD138, CD20, CD19, CD22, CD72, and CD79A. Yet additional B lymphocyte cell surface markers include, without limitation, CD38, CD78, CD80, CD83, DPP4, FCER2, IL2RA, TNFRSF8, CD24, CD37, CD40, CD74, CD79B, CR2, IL1R2, ITGA2, ITGA3, MS4A1, ST6GAL1, CD1C, CD138, and CHST10.

These B lymphocyte surface markers can be used sequentially to enrich for B lymphocytes. For example, antibodies specific to a B lymphocyte cell surface markers (e.g., CD19) can be coupled to magnetic beads (e.g., Dynabeads commercially available from Invitrogen Corp., Carlsbad, Calif.), and cells adhering to the beads (e.g., CD19 positive cells) isolated from non-CD19 expressing cells. B lymphocytes can be further enriched from the CD19 positive cells by, for example, flow cytometry sorting of cells expressing immunoglobulin chains at their cell surface. These enriched B lymphocytes can thus be isolated for use in the methods of various embodiments of the invention.

Antigen specific B lymphocytes can also be purified directly using the desired antigen as bait to isolate B cells expressing the antigen specific B cell receptor (membrane immunoglobulin). For example, B cells can be added to a column to which is adhered the desired antigen. The antigen-specific B cells will flow through the column more slowly than non-specific B cells or other cells (e.g., red blood cells, macrophages, etc.). The antigen-specific B cells can thus be enriched using this method.

Enriched or non-enriched B lymphocytes from an animal (e.g., enriched by various methods) can also be subjected to in vitro cell culture for 1 or 2 or 3 or 4 or more days prior to nucleic acid extraction. Such culture in vitro may expand the number of B lymphocytes and thus enrich them over non-B lymphocyte cells. In one non-limiting example, CD27 isolated human B lymphocytes can be subjected to various cytokine and extracellular molecule cocktails (such as but not limited to activated T cell conditioned medium, or any combination of B cell growth, and/or differentiation factors) prior to nucleic acid extraction in order to stimulate growth and/or differentiation of the B lymphocytes prior to nucleic acid extraction from the B lymphocytes. Other biological molecules can also be added to the tissue culture media during the in vitro culturing to assist in growth, differentiation, and/or in vitro immunization, and/or any combination of the above.

From these isolated, enriched, or stimulated B lymphocytes, nucleic acid sequences (e.g., genomic DNA, hnRNA, mRNA, etc.) can be extracted using standard methods (e.g., phenol: chloroform extraction; see Ausubel et al., supra). This nucleic acid can then be subjected to sequencing analysis using a variety of methods for sequencing.

In some embodiments, the nucleic acid sequences can be directly sequenced from the biological material (i.e., without being amplified prior to sequencing). Services and reagents for directly sequencing from nucleic acid sequences are commercially available, for example, from Helicos BioSciences Corp. (Cambridge, Mass.). For example, Helicos' True Single Molecule Sequencing allows direct sequencing of DNA, cDNA, and RNA. See also U.S. Pat. Nos. 7,645,596; 7,037,687, 7,169,560; and publications Harris et al., *Science* 320: 106-109, 2008; Bowers et al., *Nat. Methods* 6: 493-494, 2009; and Thompson and Milos, *Genome Biology* 12: 217, 2011 (all of which patents and publications are incorporated herein by reference in their entireties).

In other embodiments, the nucleic sequences are amplified (e.g., by polymerase chain reaction (PCR)) prior to obtaining sequence information.

In one non-limiting example, an oligo dT PCR primer is used for RT-PCR. In another non-limiting example, gene-specific RT-PCR is performed using the PCR primers described herein, such as the 454 specific fusion mouse primers, the 454 rabbit immunoglobulin chain fusion primers or the variable heavy and variable light region primers. In another example, PCR primers against heavy chain and light chain populations in a mouse have sequences set forth in PCT publication no. WO2010/097435, herein incorporated by reference.

With or without B cell enrichment, purified genetic materials (DNA or mRNA) can be amplified (e.g., by PCR or RT-PCR) following standard procedures (see, e.g., Ausubel et al., supra) to prepare a library before NGS sequencing.

Isolated B lymphocytes mentioned above by various means can also be subjected to single cell encapsulation by using method in the art such as oil emulsion encapsulation or by commercial instrument such as RainDance technology (RainDance Technologies, Inc., Lexington, Mass.). These encapsulated B lymphocytes can then be fused with an appropriate single cell RT-PCR reagent (e.g., the reagent sold by Qiagen, as Cat #210210) with the appropriate amplification primers to generate linked Heavy and Light chain PCR products from each single B cells. Ligation or overlap PCR is known in the field and is practiced routinely for various molecular biology applications to stitch 2 DNA pieces into one (see, e.g., Meijer P. J. et al., *J. Mol. Biol.* 358(3):764-72, 2006 for overlap PCR). This approach allows for cognate pairing preservation and identification during sequencing.

DNA Sequencing Methods

Methods for DNA sequencing that are well known and generally available in the art may be used to obtain the nucleic acid sequences of the various embodiments of the invention. The methods may employ such enzymes as the Klenow fragment of DNA polymerase I, SEQUENASE® (US Biochemical Corp, Cleveland, Ohio), Taq polymerase (Invitrogen), thermostable T7 polymerase (Amersham, Chicago, Ill.), DNA ligase (e.g., from T4) or combinations of recombinant polymerases and proofreading exonucleases such as the ELONGASE Amplification System marketed by Gibco BRL (Gaithersburg, Md.). The process may be automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Applied Biosystems).

Non-limiting methods to sequence nucleic acid molecules and thus generate nucleic acid sequences (e.g., to populate a genetic material database) of various embodiments of the invention include the Sanger method (see, e.g., Sanger et al, *Nature* 24: 687-695, 1977), the Maxam-Gilbert method (see, e.g., Maxam and Gilbert, *Proc. Natl. Acad. Sci. USA* 74: 560-564, 1977), and pyrosequencing (see, e.g., Ronaghi et al., *Science* 281 (5375): 363, 1998 and Ronaghi et al., *Analytical Biochemistry* 242 (1): 84, 1996). Pyrosequencing, another non-limiting sequencing method that can be used to obtain polynucleotide sequences, uses luciferase to generate light for detection of the individual nucleotides (either dATP, dTTP, dGTP, or dCTP, collectively "dNTPs") added to the nascent DNA, and the combined data are used to generate sequence read-outs.

In some embodiments, the nucleic acid sequences are obtained using deep sequencing or next generation sequencing. One rate-limiting step in conventional DNA sequencing arises from the need to separate randomly terminated DNA polymers by gel electrophoresis. Next generation sequencing devices bypass this limitation, e.g., by physically arraying DNA molecules on solid surfaces and determining the DNA sequence in situ, without the need for gel separation. These high throughput sequencing techniques allow numerous nucleic acid molecules to be sequenced in parallel.

Thus, thousands or millions of different nucleic acid molecules can be sequenced simultaneously (see Church, G. M., *Sci. Am.* 294 (1): 46-54, 2006; Hall, N., *J. Exp. Biol.* 210(Pt. 9): 1518-1525, 2007; Schuster et al., *Nature Methods* 5(1): 16-18, 2008; and MacLean et al., *Nature Reviews Microbiology* 7: 287-296, 2009). A variety of different methods and machines for performing next generation sequencing exist, any of which can be used to generate nucleic acid sequences. See Lin et al., *Recent Patents on Biomedical Engineering* 1:60-67, 2008 for an overview of numerous next generation sequencing technologies.

For example, Shendure, J. et al., *Science* 309(5741): 1728-32, 2005 and U.S. Patent Publication No. 20070087362, describe the polony next generation sequencing method which uses a ligation-based sequencing method (see also U.S. Pat. No. 5,750,341). The SOLiD technology commercially available from Applied Biosystems (a LifeTechnolgies Corp. company, Carlsbad, Calif.) employs sequencing by ligation. Using the SOLiD technology, a library of DNA fragments to be sequenced are amplified by emulsion PCR, and of the multiple fragments in the library, a single fragment species will be attached to a single magnetic bead (so called clonal beads). The fragments attached to the magnetic beads will have a universal P1 adapter sequence attached so that the starting sequence of every fragment is both known and identical. Primers are then selected that hybridize to the P1 adapter sequence within the library template. A set of four fluorescently labeled di-base probes compete for ligation to the sequencing primer. Specificity of the di-base probe is achieved by interrogating every 1st and 2nd base in each ligation reaction.

Another next generation sequencing method that of Margulies et al., *Nature* 437: 376-380, 2005 and U.S. Pat. Nos. 7,211,390; 7,244,559; and 7,264,929, which describe a parallelized version of pyrosequencing which amplifies DNA inside water droplets in an oil solution (emulsion PCR), with each droplet containing a single DNA template attached to a single primer-coated bead. Using the sequencing machine (the Genome Sequencer FLX System machine commercially available from 454 Life Sciences, a Roche company, Branford, Conn.), oligonucleotide adaptors are ligated to fragmented nucleic acid molecules and are then immobilized to the surface of microscopic beads before PCR amplification in an oil-droplet emulsion. Beads are then isolated in multiple picoliter-volume wells, each containing a single bead, sequencing enzymes, and dNTPs. Incorporation of a dNTP into the complementary strand releases pyrophosphate, which produces ATP, which in turn generates light that can then be recorded as an image for analysis.

U.S. Pat. No. 7,115,400 describes another technique for solid-phase amplification of nucleic acid molecules. This allows a large number of different nucleic acid sequences to be arrayed and amplified simultaneously. This technology is embodied in the Genome Analyzer system commercially available from Solexa (Illumina, Inc.). In this technology, DNA molecules are first attached to primers on a slide and amplified so that local clonal colonies are formed (bridge amplification). Four types of ddNTPs are added, and non-incorporated nucleotides are washed away. Unlike pyrosequencing, the DNA can only be extended one nucleotide at a time. A camera takes images of the fluorescently labeled nucleotides then the dye along with the terminal 3' blocker is chemically removed from the DNA, allowing a next cycle.

Polynucleotide sequences encoding immunoglobulin chain variable regions may be extended utilizing a partial nucleotide sequence and employing various methods known in the art to detect upstream sequences such as promoters and regulatory elements. For example, one method that may be employed, "restriction-site" PCR, uses universal primers to retrieve unknown sequence adjacent to a known locus (Sarkar, G., *PCR Methods Applic.* 2: 318-322 (1993)). In particular, genomic DNA is first amplified in the presence of primer to linker sequence and a primer specific to the known region. Exemplary primers are those described in Example 4 herein. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al., *Nucleic Acids Res.* 16: 8186 (1988)). The primers may be designed using OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al., *PCR Methods Applic.* 1: 111-119 (1991)). In this method, multiple restriction enzyme digestions and ligations may also be used to place an engineered double-stranded sequence into an unknown portion of the DNA molecule before performing PCR. Another method which may be used to retrieve unknown sequences is that described in Parker et al., *Nucleic Acids Res.* 19: 3055-3060 (1991)). Additionally, one may use PCR, nested primers, and PROMOTERFINDER® libraries to walk in genomic DNA (Clontech, Palo Alto, Calif.). This process avoids the need to screen libraries and is useful in finding intron/exon junctions.

It shall be understood that the nucleic acid from B lymphocytes may be further screened for those nucleic acid molecules encoding immunoglobulins prior to sequencing. To do this, primers specific for immunoglobulin-encoding nucleic acid molecules (or specific for regions adjacent thereto) may be employed.

As used herein, by "primer" is meant a nucleic acid sequence that may be at least about 15 nucleotides, or at least about 20 nucleotides, or at least about 30 nucleotides, or at least about 40 nucleotides in length. A primer specific for a particular nucleic acid molecule is meant to include a primer that hybridizes to a portion of the nucleic acid molecule under PCR annealing conditions (e.g., 60° C. for thirty seconds). In some embodiments, a primer specific for a particular nucleic acid molecule is one that is complementary to that nucleic acid molecule.

Primers used for sequencing the nucleic acid sequence may be referred to as Sequencing Primers. Primers used for amplification of a target nucleic acid sequence by the polymerase chain reaction (PCR) may also be referred to as PCR primers or amplification primers (see description of PCR, for example, in Sambrook et al., supra and Ausubel et al., supra) the entire disclosure of which is hereby incorporated herein by reference.

In one non-limiting example for obtaining nucleic acid sequences in accordance with various embodiments of the invention, total nucleic acid from B lymphocytes may be rendered single-stranded (e.g., by heating the nucleic acid to 94-98° C. for at least one minute. The single-stranded nucleic acid may then be passed over a solid support (e.g., a column or gel) to which are adhered single-stranded primers that are specific for non-variant regions of immunoglobulin-encoding nucleic acid molecules or non-coding regions adjacent thereto (e.g., immunoglobulin gene promoters, enhancers, and/or introns). Some non-limiting examples for these non-variant regions of immunoglobulins include the constant region of the heavy chain, and the constant region of the light chains, and the FR1 region of either the heavy chain or the light chain. The nucleic acid is allowed to hybridize to the solid-phase support-bound primers, and the non-hybridizing nucleic acid removed. After removal, the hybridized nucleic acid (which is enriched for immunoglobulin-encoding nucleic acid molecules) is released from the primers by, for example, addition of heat or increasing the concentration of EDTA in the buffer.

In another embodiment of the invention, regardless of whether the nucleic acid from the B lymphocytes is enriched for immunoglobulin-encoding nucleic acid molecules, the immunoglobulin-encoding nucleic acid molecules may be amplified to increase their copy number. This amplification can be performed, for example, by PCR amplification using primers specific for non-variant regions of immunoglobulin-encoding nucleic acid molecules or non-coding regions adjacent thereto.

In all of the above methods for obtaining nucleic acid sequences in accordance with the various embodiments of the invention, it will be understood that the primers (e.g., sequencing or PCR primers) used to generate the immunoglobulin chain variable region-encoding nucleic acid sequences may be universal (e.g., polyA tail) or may be specific to immunoglobulin-encoding sequences.

In some embodiments, the starting material from which the immunoglobulin gene-encoding nucleic acid sequence information is obtained is genomic DNA. For example, if the immunoglobulin chain variable regions are from humans, primers (e.g., sequencing primers and/or PCR primers) may be selected to be identical to or hybridize to an immunoglobulin chain gene promoter. For example, the human genome sequence is known. Since the heavy chain-encoding gene occurs on chromosome 14 and the light chain-encoding gene occurs on chromosome 22 (lambda light chain) and 2 (kappa light chain), it would be routine for the ordinarily skilled biologist to design primers that hybridize to regulatory elements of the heavy chain-encoding gene and the light chain-encoding gene. Such regulatory elements include, without limitation, promoters, enhancers, and introns.

Immunoglobulin variable region-specific primers can likewise be readily determined for mice immunoglobulins since the murine kappa light chain gene is known to be located on chromosome 6 and the murine heavy chain gene is known to be located on chromosome 12.

In another non-limiting embodiment, the starting material from which the immunoglobulin gene-encoding nucleic acid sequence information is obtained is mRNA or cDNA reversed translated from the mRNA. In this example, to obtain immunoglobulin variable region-encoding nucleic acid sequences, primers can be selected to be identical to or hybridize to the polyA tail of an mRNA or the complementary TTTT (SEQ ID NO: 306)-rich sequence of the mRNA's corresponding cDNA. Alternatively, or in addition, primers can also be selected to be identical to or hybridize to the FR1-encoding nucleic acid sequences. Alternatively, or in addition, primers can also be selected to be identical to or hybridize to a portion of (or all of) one of the CH regions (i.e., CH1, CH2, or CH3) and/or the VH region-encoding nucleic acid sequences.

Sequencing errors can arise from using universal degenerate primers to sequence nucleic acid molecules encoding immunoglobulins from hybridomas. For example, Essono et al, *Protein Engineering, Design and Selection*, pp. 1-8, 2009 describe a method combining sequencing with peptide mass spectrometry fingerprinting of the corresponding Ig chain to determine the correct sequence of a monoclonal antibody produced by a hybridoma clone. However, in the non-limiting methods of various embodiments of the invention, the presence of sequencing errors will merely increase the number of different nucleic acid sequences. Unlike Essono et al., supra, since the methods of various embodiments of the invention allow the creation of a single antibody (both heavy and light chains or variable regions thereof) from a starting polyclonal population of antibodies (where the created antibody may not actually occur within the starting polyclonal population of antibodies), having a large number of sequences in the genetic material database with which to correlate the observed mass spectra data of the peptide database is an asset.

Predicted Mass Spectra Information from the Genetic Material Database

In accordance with various embodiments of the invention, once nucleotide sequences of the nucleic acid molecules are generated, additional information may be generated based on the nucleotide sequence information alone. For example, the nucleotide sequence information can be translated into predicted amino acid sequences using the genetic code. Although the ordinarily skilled artisan can readily translate nucleotide sequences into amino acid sequences using the genetic code, several automated translation tools (which are publicly available) can be used, such as the ExPASy translate tool from the Swiss Institute of Bioinformatics or the EMBOSS Transeq translation tool from EMBL-EBI.

Similarly, predicted mass spectra information of the predicted amino acid sequences encoded by the nucleic acid sequences can be readily determined by the ordinarily skilled artisan. For example, following virtual (i.e., in silico) digestion of the predicted polypeptides encoded by the nucleic acid sequences, predicted mass spectra of the peptide fragments can be generated by using standard publicly available software algorithm tools including, without limitation, the Sequest software (from Thermo Fisher Scientific, Inc., West Palm Beach, Fla.), the Sequest 3G software (from Sage-N Research, Inc., Milpitas, Calif.), the Mascot software (from Matrix Science, Inc., Boston, Mass.; see also Electrophoresis, 20(18) 3551-67 (1999)), and the X!Tandem software (opensource from The Global Proteome Machine Organization, whose use is described in Baerenfaller K. et al., Science 320:938-41, 2008).

As used herein, the words "predicted," "theoretical," and "virtual" are used interchangeably to refer to nucleotide sequences, amino acid sequences or mass spectra that are derived from in silico (i.e., on a computer) transcription and/or translation (for the predicted nucleotide and amino acid sequences) or in silico digestion and/or mass spectrometry analysis (for the predicted mass spectra) of information from the nucleic acid sequences. For example, nucleic acid sequences are derived from genomic nucleic acid molecules obtained from B lymphocytes as described herein. The nucleotide sequence of, for example, mRNA derived from genomic DNA is predicted following in silico translation of the genomic DNA. This predicted mRNA (or cDNA) may then be translated in silico to produce predicted amino acid sequences. The predicted amino acid sequences may then be digested in silico with proteases (e.g., trypsin) and/or chemical protein cleavage reagents (e.g., cyanogen bromide) to produce predicted (or theoretical or virtual) peptide fragments. The virtual peptide fragments can be then analyzed in silico to produce predicted mass spectra information. Thus, predicted mass spectra information, predicted peptide fragments, predicted amino acid sequences, and predicted mRNA or cDNA sequences can all be derived from the nucleic acid sequences collected from B lymphocytes (e.g., from an animal).

In certain embodiments, the protease(s) and/or the chemical reagents used to digest predicted polypeptides to generate predicted peptides fragments and ultimately predicted mass spectra is the same protease(s) and/or reagent(s) used to digest the starting population of polyclonal antibodies, as described above.

Correlating Observed Mass Spectra with Predicted Mass Spectra

As described above, passage of the fragments derived from the starting polyclonal population of antibodies through a mass spectrometer generates numerous observed mass spectra. Given the potentially large number of different immunoglobulins within a polyclonal population, each with a different amino acid sequence, that are analyzed with the mass spectrometer, the resulting observed mass spectra will be difficult to assemble back into a functional immunoglobulin chain variable region. In the methods of various embodiments of the invention, because the encoding nucleic acid sequences are available, there is no need to assemble the observed mass spectra data. Instead, the observed mass spectra are correlated with the predicted mass spectra derived from the nucleic acid sequences of the genetic material database to obtain the amino acid (and underlying nucleotide) sequences of full-length immunoglobulin chains (or variable regions thereof) of an immunoglobulin that specifically binds to an antigen from a starting polyclonal immunoglobulin population.

Also as described above, the genetic material database can be derived from nucleic acid molecules isolated from the B-cell repertoire of an immunized animal, including nucleic acid molecules encoding full length immunoglobulin heavy and light chains and variable regions thereof. Attempts to identify nucleic acids encoding antigen-specific immunoglobulins based solely on the information from the genetic material database (e.g., frequency rankings of variable region sequences) may miss those immunoglobulins that occur at low frequencies yet manifest superior antigen-specific activities. In accordance with the various embodiments of this invention, however, by correlating the predicted mass spectra information from the genetic material database with the observed mass spectra information from the actual circulating polyclonal antibodies as disclosed herein, those immunoglobulin chains (or variable regions thereof) in the genetic material database can be selected that correspond to immunoglobulins within the circulating polyclonal antibodies.

By "correlating" it is meant that the observed mass spectra information derived from the starting polyclonal antibodies and the predicted mass spectra information derived from the genetic material database are cross-referenced and compared against each other, such that immunoglobulin heavy and/or light chains (or variable regions thereof) can be identified or selected from the genetic material database that correspond to immunoglobulin heavy and/or light chains (or variable regions thereof) of antigen-specific immunoglobulins in the starting polyclonal population.

In specific embodiments, the correlating process involves comparing the observed mass spectra information with the predicted spectra information to identify matches. For example, each of the observed spectra can be searched against the collection of predicted mass spectra derived from the genetic material database, with each predicted spectrum being identifiably associated with a peptide sequence from the genetic material database. Once a match is found, i.e., an observed mass spectrum is matched to a predicted mass spectrum, because each predicted mass spectrum is identifiably associated with a peptide sequence in the genetic material database, the observed mass spectrum is said to have found its matching peptide sequence—such match also referred to herein as "peptide spectrum match" or "PSM". Because of the large number of spectra to be searched and matched, this search and matching process can be performed by computer-executed functions and softwares, such as the SEQUEST algorithm (Sage-N Research, Inc., Milpitas, Calif.).

In some embodiments, the search and matching is directed to functional domains or fragments of immunoglobulins, such as variable region sequences, constant region sequences, and/or one or more CDR sequences. For example, the observed spectra are only searched against predicted mass spectra derived from V regions (and/or CDR3 sequences) of immunoglobulins to identify V-region (and/or CDR3) PSMs. In other embodiments, the search and matching is directed to full-immunoglobulin heavy or light chain sequences.

After the search and matching has been completed, immunoglobulin heavy or light chains in the genetic material database are analyzed and selected based on one or more of the following parameters: the number of unique peptides, the spectrum share, the amino acid sequence coverage, the count of peptides (either total peptide count or unique peptide count), frequency of the encoding nucleic acid sequences, and clonal relatedness.

The term "coverage" in referring to a sequence or region (e.g., a heavy or light chain sequence, a V-region sequence, or a CDR sequence) is defined as the total number of amino acids within the sequence that have been identified in peptides which map to the sequence or region and which have a matching observed spectrum, divided by the number of amino acids in the sequence or region. The higher the coverage, the more likely the sequence or region appears in the actual polyclonal population.

By "number of unique peptides" it is meant the number of distinct peptides observed mapping to a single protein sequence (e.g., a single immunoglobulin heavy or light chain or a variable region thereof). The higher the number, the more likely the immunoglobulin chain is present in the polyclonal population. In specific embodiments, selection of an immunoglobulin chain is made based on a number of unique peptides of at least 5, 6, 7, 8, 9, 10, 11, 12 or more in the immunoglobulin chain or its variable region.

"Spectrum share" is determined by dividing the total number of peptides mapped to the sequence by the total number of confident PSMs mapped to the entire genetic database. Spectrum share provides a human readable count of peptides expressed as the percentage of PSMs that map to a specific V-region sequence.

The term "peptide count" in referring to a protein sequence (e.g., a CDR3 region or a variable region) means the number of times a peptide is identified from the observed mass spectra that matches the protein sequence. For example, the count of a CDR3 region means the number of times a peptide is identified from the observed mass spectra that matches the CDR3 region. The count of a variable region means the number of times a peptide is identified from the observed mass spectra that matches the variable region. "Total peptide count" in referring to a protein sequence means the number of times any peptide (unique or non-unique) is identified from the observed mass spectra that matches the protein sequence. "Unique peptide count" means the number of times a unique peptide is identified from the observed mass spectra that matches the protein sequence. If the same peptide has been identified multiple times from the observed mass spectra, the total number of times this peptide is observed will be considered in determining the total peptide count, yet this peptide will be counted only once for determining the unique peptide count.

In specific embodiments, an immunoglobulin heavy or light chain is selected based on sequence coverage. In other embodiments, the selection is made based on a combination of sequence coverage with one or more other parameters, including the number of unique peptides, spectrum share, total peptide count, unique peptide count, frequency of the encoding nucleic acid sequence, or clonal relatedness.

The above parameters can be independently determined with respect to a full-length heavy or light chain, or with respect to one or more portions of an immunoglobulin heavy or light chain, e.g., the variable region, and a CDR (e.g., CDR1, CDR2, or CDR3, especially CDR3). In certain embodiments, selection of immunoglobulin chains (or variable regions thereof) is made based on the V-region coverage and/or CDR coverage (e.g., CDR3 coverage).

The selection of immunoglobulin heavy or light chains (or variable regions thereof) can be made based on the absolute value of one or more parameters, or based on the ranking of absolute values for a relevant parameter. Where ranking for a particular parameter is considered, the top ranked 10, 20, 30, 40, 50, 60, 70, 80, 90, 100 or more sequences can be selected irrespective of the absolute values of that parameter. Where the value of a parameter is considered, e.g., the percentage of sequence coverage, in some embodiments, selection of immunoglobulin chains is made based on a CDR coverage (such as CDR3 coverage) of at least 10%, 15%, 20%, 25%, 30%, 35%, 40%, 45%, 50%, 55%, 60%, 65%, 70%, 75%, 80%, 85%, 90%, 95%, 98% or higher; additionally or alternatively, based on a V-region coverage of at least 5%, 10%, 15%, 20%, 25%, 30%, 35%, 40%, 45%, 50%, 55%, 60%, 65%, 70%, 75%, 80%, 85%, 90% or higher.

In some embodiments, a phylogenetic analysis is performed to determine clonal relatedness of the heavy chain variable region, light chain variable region, or one or more CDR's (e.g., CDRH3 or CDRL3). Changes or mutations of nucleic sequence of heavy and light chains compared to germline sequence can provide evidence of affinity maturation of antibodies following antigen exposure. Clonal relatedness can be used as a factor in selection of antibody sequences. A phylogenetic analysis can be performed by methods known in the art, e.g., those described in Dereeper et al., 2008, *Nucl. Acids Res.*, 36(Web Server issue):W456-459; Dereeper et al., 2010, *BMC Evol. Biol.*, 10:8, and available online at www.phylogeny.fr/version2_cgi/index-.cgi. In some embodiments, the entire heavy or light chain variable regions are grouped by homology, then further grouped by CDR (e.g., CDR3) homology.

The selected heavy and light chain sequences can then be expressed in pairs to assemble into monoclonal antibodies which are analyzed to confirm antigen-specific functionality. The pairing of selected heavy and light chain sequences can be entirely random, or can take into consideration of one or more parameters described above, including sequence coverage, unique number of peptides, spectrum share, total peptide count, and unique peptide count.

In some embodiments, the abundance of a population of antibodies having a particular peptide sequence can be determined using a heavy isotope labeled (e.g., AQUA) peptide. See, e.g., WO 03/016861 and Gerber et al., 2003, 100:6940-45. These methods employ the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. The peptide can be unique to one species of antibody or found in multiple (e.g., clonally-related) antibodies. In some embodiments, the peptide can include at least a portion of a CDR (e.g., CDR3). Quantitation of the abundance of antibody populations can be useful in methods of monitoring serum antibody composition, e.g., following vaccination of a subject.

It should be noted that the immunoglobulin that specifically binds to the antigen whose amino acid sequence (or nucleic acid sequence) created using the non-limiting methods of various embodiments of the invention need not actually be present within the starting polyclonal population of immunoglobulins. Rather, the non-limiting methods of various embodiments of the invention simply allow the rapid creation of an immunoglobulin that specifically binds the antigen whether or not that immunoglobulin actually existed in the starting polyclonal population. For example, the created immunoglobulin that has the highest desired qualities (e.g., highest binding affinity (or lowest KD) for the antigen or a desired isotype (e.g., IgG2a)) may be the result of a light chain from a first antibody in the polyclonal population assembled with a heavy chain of a second antibody (i.e., different from the first antibody) in the polyclonal population. The resulting created immunoglobulin can be further characterized (e.g., binding affinity for the antigen or isotype) according to standard methods.

Method of Making Recombinant Antibodies

Once the nucleotide sequence of an immunoglobulin chain (or variable region thereof) of an antibody that specifically binds to the antigen is elucidated, a nucleic acid molecule comprising that sequence can be generated.

For example, if the starting population from which the immunoglobulin chain (or variable region thereof)-encoding nucleic acid molecules is obtained is a cDNA library, the nucleic acid molecule comprising the elucidated sequence can be readily obtained from the library (e.g., by screening the library with a primer identical to or capable of hybridizing to a portion of the elucidated sequence) or by PCR amplifying the nucleic acid molecule from the library using primers designed to amplify the elucidated nucleic acid sequence.

Alternatively (or in addition), nucleic acid molecules comprising the elucidated nucleotide sequence can be generated by simply artificially generating the nucleic acid molecule using a standard DNA synthesis machine. Numerous DNA synthesis machines are commercially available including, without limitation, the MerMade series of synthesizers (e.g., MerMade 4, Mermade 6, MerMade 384, etc.) available from BioAutomation, Plano, Tex.; the various DNA/RNA synthesizers commercially available from Applied Biosystems (now part of Life Technologies, Corp., Carlsbad, Calif.). Several companies also offer DNA synthesis services (e.g., BioPioneer, Bio S&R, Biomatik, Epoch BioLabs, etc.)

Methods to express nucleic acid encoding heavy and light chains of an immunoglobulin to produce recombinant immunoglobulins are known (see, e.g., U.S. Pat. Nos. 6,331, 415; 5,969,108; 7,485,291; US 2011-0045534; and PCT Publ. No. WO 2011/022077). Recombinant immunoglobulins can be made in a variety of cells including, without limitation, insect cells (e.g., SF9 cells), hamster cells (e.g., CHO cells), murine cells (e.g., NIH-3T3 cells), primate cells (e.g., COS cells), human cells (e.g., Hela cells), and prokaryotic cells (e.g., E. coli cells). In some embodiments, the cells expressing the recombinant immunoglobulins of various embodiments of the invention are able to add secondary modifications (e.g., glycosylation) to the recombinant immunoglobulin in a manner similar to that of the species from which the immunoglobulin was originally derived. For example, where the population of polyclonal antibodies whose fragments were used to generate the observed mass spectra data are collected from a human, human cells (or cells which glycosylate proteins similarly or identically to human cells) may be used.

To obtain expression of the nucleic acid sequences of a recombinant immunoglobulin (or antigen binding fragment thereof) that specifically binds to the antigen in a cell, the nucleic acid sequences may be ligated into a vector (e.g., a plasmid or a retroviral vector) containing appropriate regulatory sequences such that the inserted nucleic acid sequences are expressed in the cell into which the nucleic acid sequence are introduced. Such regulatory sequences include, for example, promoters, enhancers, intron acceptor elements, poly adenylation sites, etc. Any method can be employed to introduce the nucleic acid sequences of a recombinant immunoglobulin (or vector containing the same) into a cell including, without limitation, electroporation, transfection by chemical means (e.g., CaPO4, DEAE-dextran, polyethylenimine), infection, transduction, liposome fusion, etc. (see methods, e.g., in Ausubel et al., supra).

In accordance with some embodiments of the invention, the heavy immunoglobulin chain and the light immunoglobulin chain are randomly selected to be assembled into an immunoglobulin (or variable region or antibody binding domain thereof). For example, correlation of the actual mass spectra from a peptide fragment of the polyclonal antibodies with the predicted mass spectra of a predicted peptide encoded by the nucleic acid sequences will be used to obtain the nucleotide sequence or predicted amino acid sequence of an immunoglobulin chain comprising the peptide fragment. The obtained nucleotide sequence of the immunoglobulin chain can then be randomly co-expressed and/or with a second similarly obtained nucleotide sequence of an immunoglobulin chain, where the second nucleotide sequence encodes the other chain of an intact antibody under conditions where the two encoded immunoglobulin chains will assemble into an intact antibody.

Conditions for co-expressing two nucleotide sequences (e.g., in cells) each encoding an immunoglobulin chain such that an intact immunoglobulin is assembled are known (see, e.g., U.S. Pat. Nos. 5,969,108; 6,331,415; 7,498,024; 7,485, 291; and US Pat. Pub. No. 20110045534, all herein incorporated by reference in their entireties). Because of the number of different nucleotide sequences that can be obtained using the methods described herein, the invention contemplates the use of robotics and high-throughput methods to screen the encoded immunoglobulins to create an immunoglobulin that specifically binds to the antigen.

As used herein, by "assembled" or "assembling" is meant that a light chain of an antibody (or a fragment thereof) and a heavy chain of an antibody (or a fragment thereof) are combined together in a manner in which the two chains join to create an antibody (or a fragment thereof). In some embodiments, in the assembled antibody (or fragment thereof), amino acid residues from both the heavy chain and light chain contribute to the antigen binding domain of the assembled antibody (or fragment thereof). In some embodiments, the assembled antibody (or fragment thereof) comprises a light chain (or fragment thereof) covalently bonded to a heavy chain (or fragment thereof). In some embodiments, the assembled antibody (or fragment thereof) comprises a light chain (or fragment thereof) non-covalently bonded to a heavy chain (or fragment thereof).

In some embodiments, the nucleotide sequences or amino acid sequences of the immunoglobulin chains (or variable regions thereof) identified in the proteomics analysis described above are synthesized by recombinant molecular biology techniques or gene synthesis techniques prior to assembly of recombinant antibodies. For example, the nucleotide or amino acid sequences may be synthesized on a nucleotide or peptide synthesis machine prior to assembly. Or, the nucleotide or amino acid sequences may be expressed recombinantly by cloning the nucleotide sequences into an expression vector (e.g., pcDNA3.1 from Invitrogen, Carlsbad, Calif.), and expressing the encoded polypeptide in a cell (e.g., HeLa cells, CHO cells, COS cells, etc.) transfected with the expression vector. In some embodiments, the assembly step occurs in the transfected cell (e.g., a single cell is transfected with one or more expression vectors comprising nucleic acid sequences encoding one heavy and one light chain, where the heavy and light chain will be expressed as polypeptides in the transfected cell).

In various embodiments of the invention, the recombinant antibodies are isolated. As used herein, by "isolated" (or "purified") is meant an antibody is substantially free of other biological material with which it is naturally associated, or free from other biological materials derived, e.g., from a cell that has been genetically engineered to express the antibody of the invention. For example, an isolated recombinant antibody is one that is physically separated from other components of the host cell (e.g., the endoplasmic reticulum or cytoplasmic proteins and RNA). Likewise, a purified antibody from blood sera and/or plasma is an antibody that is isolated from other serum or plasma components (e.g., albumin or cells) (using, for example, adherence of the antibodies to protein A, where the non-antibody sera components will not adhere to protein A). Thus, an isolated antibody (or isolated immunoglobulin) of the present invention includes an antibody that is at least 70-100% pure, i.e., an antibody which is present in a composition wherein the antibody constitutes 70-100% by weight of the total composition. In some embodiments, the isolated antibody of the present invention is 75%-99% by weight pure, 80%-99% by weight pure, 90-99% by weight pure, or 95% to 99% by weight pure. The relative degree of purity of an antibody various non-limiting embodiments of the invention is easily determined by well-known methods.

In some embodiments, the recombinant antibodies (or variable regions thereof) are further screened or analyzed in an immunoassay to confirm that the antibodies specifically bind to the antigen. In some embodiments, the immunoassay is a standard immunoassay such as a flow cytometry assay (e.g., a FACS scan), an enzyme-linked immunosorbent assay (ELISA), a Western blotting assay, an immunohistochemistry assay, an immunofluorescence assay, a radioimmunoassay, a neutralization assay, a binding assay, an affinity assay, or a protein or peptide immunoprecipitation assay. All of these immunoassays are well known standard assays and have been well described in standard methods books (see, e.g., Ausubel et al., supra; Coligan et al., supra; Harlow and Lane, supra).

Therapeutic Antibodies

The various non-limiting embodiments and methods of the invention are useful, for example, in isolating antibodies that have therapeutic value. For example, in the course of a normal immune response in an animal to a pathogen, antibodies with the highest specificity to an antigen of the pathogen may take weeks to arise. This is because the B lymphocyte producing the antibody must first be stimulated by the appropriate T lymphocyte that also recognize the antigen presented on an antigen presenting cell in context of the major histocompatibility complex expressed by every nucleated cell of an animal. B lymphocytes initially responding to the antigen produce antibodies that specifically bind to the antigen. However, the highest affinity antibodies are actually those that are produced by B lymphocytes that have bound their antigen (through cell surface expressed immunoglobulin complexed with other cell surface antigens to form the B cell receptor) and, upon stimulation through the B cell receptor and other cells (including T lymphocytes), undergo affinity maturation to produce antibodies with high affinity for their specific antigen. Such a B lymphocyte that has undergone affinity maturation (or its progeny with the same antibody specificity) is available in the animal to quickly produce high affinity antibody should the animal encounter the same pathogen again.

This tight regulation of T lymphocytes and B lymphocytes responding to an antigen the first time that antigen is seen (e.g., the first time the animal is infected with a particular pathogen) is necessary to prevent autoimmune or inappropriate immune response. However, one drawback is that by the time an antigen-specific B lymphocyte is secreting antibody of the highest affinity and specificity for the antigen, a quickly growing pathogen may have grown within the animal to the extent that it can no longer be easily cleared. In some embodiments of the invention, the methods allow for the rapid development of an antigen-specific antibody that skips the time-consuming process of first isolating an antigen-specific B lymphocyte that is secreting the antibody and immortalizing that lymphocyte.

Thus, in another aspect, the invention provides a therapeutic composition comprising a recombinant antibody with a pharmaceutically acceptable carrier.

As used herein, "pharmaceutically acceptable carrier" includes any material which, when combined with an active ingredient (e.g., a recombinant antibody made in accordance with various embodiments of the invention), allows the ingredient to retain biological activity and is non-reactive with the subject's immune system and non-toxic to the subject when delivered. Examples include, but are not limited to, any of the standard pharmaceutical carriers such as a phosphate buffered saline solution, water, emulsions such as oil/water emulsion, and various types of wetting agents. Non-limiting examples of diluents for aerosol or parenteral administration are phosphate buffered saline, normal (0.9%) saline, Ringer's solution and dextrose solution. The pH of the solution may be from about 5 to about 8, or from about 7 to about 7.5. Further, carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered. Compositions comprising such carriers are formulated by well known conventional methods (see, for example, *Remington's Pharmaceutical Sciences,* 18th edition, A. Gennaro, ed., Mack Publishing Co., Easton, Pa., 1990; and *Remington, The Science and Practice of Pharmacy,* 20th Ed. Mack Publishing, 2000).

While any suitable carrier known to those of ordinary skill in the art may be employed in the pharmaceutical compositions of this invention, the type of carrier will vary depending on the mode of administration. In various embodiments of the invention, numerous delivery techniques for the non-limiting pharmaceutical compositions described herein (e.g., containing a binding agent or a binding agent-encoding polynucleotide) are well known in the art, such as those described by Rolland, 1998, *Crit. Rev. Therap. Drug Carrier Systems* 15:143-198, and references cited therein.

Methods of Treatment

In another aspect, the invention provides a method a treating an animal having or suspected of having disease a characterized by a disease antigen, wherein the method comprising administering an effective amount of a therapeutic composition comprising an immunoglobulin that specifically binds to an antigen made in accordance with the methods of various embodiments of the invention, wherein the antigen specifically bound by the immunoglobulin of the therapeutic composition and the disease antigen are the same.

In some embodiments, the animal is a human or a domesticated animal (e.g., a dog, cat, cow, goat, sheep, chicken, turkey, llama, emu, elephant, or ostrich).

As used herein, the phrase "characterized by" with respect to a disease and indicated disease antigen (e.g., an HIVgp120 antigen from AIDS) is meant a disease in which the indicated disease antigen is present in an animal with that disease. In some embodiments, the disease antigen is encoded by nucleic acid from the disease's etiological agent (e.g., a virus). In some embodiments, the disease antigen is encoded by the animal's genome (e.g., the BCR-ABL fusion disease antigen encoded by the Philadelphia chromosome in patients with chronic myelogenous leukemia (CML).

By "treating" is meant halting, retarding, or inhibiting progression of a disease or preventing development of disease in an animal. Methods of detecting whether the treatment is successful are known. For example, where the disease is a solid tumor, progression of the disease is inhibited, halted, or retarded if there is a regression of the tumor, reduction in metastases, reduction in tumor size and/or reduction in tumor cell count following administration of the effective amount of a therapeutic composition comprising a recombinant immunoglobulin produced using the methods of various embodiments of the invention.

As used herein, by an "effective amount" is an amount or dosage sufficient to effect beneficial or desired results including halting, slowing, halting, retarding, or inhibiting progression of a disease in an animal or preventing development of disease in an animal. An effective amount will vary depending upon, e.g., an age and a body weight of a subject to which the therapeutic composition comprising the recombinant immunoglobulin is to be administered, a severity of symptoms and a route of administration, and thus administration is determined on an individual basis. In general, the daily adult dosage for oral administration is about 0.1 to 1000 mg, given as a single dose or in divided doses. For continuous intravenous administration, the compositions can be administered in the range of 0.01 ug/kg/min to 1.0 ug/kg/min, desirably 0.025 ug/kg/min to 0.1 ug/kg/min.

An effective amount can be administered in one or more administrations. By way of example, an effective amount of a recombinant immunoglobulin produced using the methods of various embodiments of the invention, is an amount sufficient to ameliorate, stop, stabilize, reverse, slow and/or delay progression of a disease (e.g., a cancer) in an animal or is an amount sufficient to ameliorate, stop, stabilize, reverse, slow and/or delay growth of a diseased cell (e.g., a biopsied cancer cell) in vitro. As is understood in the art, an effective amount of a recombinant antibody of various embodiments of the invention may vary, depending on, inter alia, the animal's medical history as well as other factors such as the isotype (and/or dosage) of the recombinant antibody.

Effective amounts and schedules for administering the compositions comprising a non-limiting recombinant antibody of various embodiments of the invention may be determined empirically, and making such determinations is within the skill in the art. Those skilled in the art will understand that the dosage that must be administered will vary depending on, for example, the animal that will receive the compositions of various embodiments of the invention, the route of administration, the particular type of compositions used (e.g., the isotype of the recombinant antibody within the composition) and other drugs being administered to the animal. Where the animal (e.g., a human patient) is administered a composition comprising an antibody, guidance in selecting appropriate doses for antibody is found in the literature on therapeutic uses of antibodies, e.g., *Handbook of Monoclonal Antibodies*, Ferrone et al., eds., Noges Publications, Park Ridge, N.J., 1985, ch. 22 and pp. 303-357; Smith et al., Antibodies in Human Diagnosis and Therapy, Haber et al., eds., Raven Press, New York, 1977, pp. 365-389.

A typical daily dosage of an effective amount of an antibody used alone might range from about 1 ug/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 ug/kg body weight; at least about 500 ug/kg body weight; at least about 250 ug/kg body weight; at least about 100 ug/kg body weight; at least about 50 ug/kg body weight; at least about 10 ug/kg body weight; at least about 1 ug/kg body weight, or more, is administered. In some embodiments, a dose of a binding agent (e.g., antibody) provided herein is between about 0.01 mg/kg and about 50 mg/kg, between about 0.05 mg/kg and about 40 mg/kg, between about 0.1 mg and about 30 mg/kg, between about 0.1 mg and about 20 mg/kg, between about 0.5 mg and about 15 mg, or between about 1 mg and 10 mg. In some embodiments, the dose is between about 1 mg and 5 mg. In some alternative embodiments, the dose is between about 5 mg and 10 mg.

The methods described herein (including therapeutic methods) can be accomplished by a single direct injection at a single time point or multiple time points to a single or multiple sites. Administration can also be nearly simultaneous to multiple sites. Frequency of administration may be determined and adjusted over the course of therapy, and is base on accomplishing desired results. In some cases, sustained continuous release formulations of the recombinant immunoglobulins of various embodiments of the invention may be appropriate. Various formulations and devices for achieving sustained release are known in the art.

Compositions comprising the recombinant antibodies of present invention may be formulated for any appropriate manner of administration, including for example, systemic, topical, oral, nasal, intravenous, intracranial, intraperitoneal, subcutaneous or intramuscular administration, or by other methods, such as infusion, which ensure its delivery to the bloodstream in an effective form. The composition may also be administered by isolated perfusion techniques, such as isolated tissue perfusion, to exert local therapeutic effects. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. In some embodiments, for oral administration, the formulation of the compositions is resistant to decomposition in the digestive tract, for example, as microcapsules encapsulating the recombinant immunoglobulin of various embodiments of the invention within liposomes. Biodegradable microspheres (e.g., polylactate polyglycolate) may also be employed as carriers for the therapeutic compositions of this invention. Suitable biodegradable microspheres are disclosed, for example, in U.S. Pat. Nos. 4,897,268 and 5,075,109.

In some embodiments of the invention, compositions may also comprise buffers (e.g., neutral buffered saline or phosphate buffered saline), carbohydrates (e.g., glucose, mannose, sucrose or dextran), mannitol, proteins, polypeptides or amino acids such as glycine, antioxidants, chelating agents such as EDTA or glutathione, adjuvants (e.g., aluminum hydroxide) and/or preservatives. Alternatively, non-limiting compositions of various embodiments of the present invention may be formulated as a lyophilizate.

In some embodiments of the invention, the recombinant immunoglobulins also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 18th edition, A. Gennaro, ed., Mack Publishing Co., Easton, Pa., 1990; and Remington, The Science and Practice of Pharmacy 20th Ed. Mack Publishing, 2000. To increase the serum half life of the recombinant immunoglobulin of various embodiments of the invention, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, and IgG4) that is responsible for increasing the in vivo serum half-life of the IgG molecule.

In some embodiments of the invention, the recombinant immunoglobulins may also be formulated as liposomes. Liposomes containing the recombinant immunoglobulins are prepared by methods known in the art, such as described in Epstein et al., 1985, Proc. Natl. Acad. Sci. USA 82:3688; Hwang et al., 1980, *Proc. Natl. Acad. Sci. USA* 77:4030; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. In addition, antibodies of various embodiments of the invention (including antigen binding domain fragments such as Fab' fragments) can be conjugated to the liposomes as described in Martin et al., 1982, *J. Biol. Chem.* 257:286-288, via a disulfide interchange reaction. Administration of the recombinant antibodies of various embodiments of the invention includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908, 6,413,942, and 6,376,471.

In another aspect, the invention provides a method of reducing the likelihood of occurrence in an animal of a disease characterized by the presence in the animal of a disease antigen, wherein the method comprising administering an effective amount of a therapeutic composition comprising a recombinant immunoglobulin of various embodiments of the invention, wherein the antigen specifically bound by the immunoglobulin of the therapeutic composition and the disease antigen are the same.

Vaccine preparation is generally described in *Vaccine Design* ("The subunit and adjuvant approach" (eds Powell M. F. & Newman M. J., (1995) Plenum Press New York).

In another aspect, the invention provides a kit for determining the amino acid sequence of an antibody from an animal comprising (a) a means for obtaining nucleic acid sequences encoding immunoglobulin chain variable regions of multiple immunoglobulins from an animal, and (b) instructions for correlating mass spectra information from an antibody analyzed by mass spectrometry with predicted mass spectra information derived from the nucleic acid sequences to determine the amino acid sequence of the antibody.

The methods disclosed herein can be used to monitor circulating antibodies over time, e.g., in a subject immunized with an antigen. In these embodiments, samples can be taken from the subject at a plurality of time points (e.g., before and after immunization) and the methods disclosed herein used to identify circulating antibodies at each time point. The composition of circulating antibodies can be compared at the plurality of time points to determine the efficacy and/or time course of the vaccination. This can be useful for monitoring immune responses in individual subjects and also in the development of vaccines.

The following examples are provided to illustrate, but not to limit, the various aspects and embodiments of the invention.

Example 1

Identifying Individual Antibody Heavy Chains from a Polyclonal Population of Antibodies that Specifically Bind an Antigen In this example, multiple monoclonal antibodies were derived from a polyclonal population of antibodies that specifically bound an antigen. Using the methods of various embodiments of the invention, the information from the genetic material database generated from nucleic acid molecules from the animal whose sera comprised the starting polyclonal population were compared to peptide database information from analysis of the monoclonal antibodies.

The nucleic acid sequences were obtained from splenocytes from an animal immunized with the antigen according to the methods described herein using primers specific for rabbit immunoglobulin chain-encoding sequences (see, for example, the primer sequences in Example 6 below). The CDR3 regions from the heavy chains of the polyclonal antibodies were ranked based on the number of times they appeared in the database and the percentage of times each CDR3 appeared among all of the CDR3 regions in the database. Table 2 shows the top 25 CDR3 regions and their frequencies. These results show that the same CDR3 sequences were found in many different antibodies in the polyclonal mixture. This information shows that antibodies that specifically bind to the same antigen often share sequences in their CDR3 regions (and presumably in the other CDR regions). This information shows that the methods described herein will be able to identify and isolate those immunoglobulin chains (or fragments thereof) that will specifically bind to the antigen.

TABLE 2

| SEQ ID NO: | CDR3 | Count | Percent |
|---|---|---|---|
| 29 | GVKF | 582 | 7.90% |
| 30 | GVSTNV | 530 | 7.20% |
| 31 | DPYDDPTYRGYGMDL | 372 | 5.05% |
| 32 | NPAVNTYAS | 345 | 4.69% |
|  | GGL | 198 | 2.69% |
| 33 | HLFLHF | 196 | 2.66% |
| 34 | HLFLNL | 172 | 2.34% |
|  | GNV | 169 | 2.30% |
|  | GNI | 143 | 1.94% |
| 35 | HLFLNF | 129 | 1.75% |
| 36 | GLGYVGSSVYIVKYINL | 126 | 1.71% |
| 37 | DLIRVAGDTFYDGAFNL | 113 | 1.53% |
| 38 | GRYNGWGYSNDL | 113 | 1.53% |
| 39 | GGGTTLYTYFDL | 111 | 1.51% |
| 40 | GLGYVGSDVYIVKYINL | 105 | 1.43% |
| 41 | GGYGYGYGNTDFNL | 93 | 1.26% |
| 42 | DDGGVRVDFDL | 87 | 1.18% |
| 43 | VDDSGWMPFKL | 85 | 1.15% |
| 44 | NVGSSSHYNLNL | 76 | 1.03% |
| 45 | DGTDHGFNIDL | 72 | 0.98% |
| 46 | STFRNSYARLAL | 69 | 0.94% |
| 47 | IPYGWYSGGGAAPYFDL | 65 | 0.88% |
| 48 | NAAIL | 62 | 0.84% |
| 49 | AVSDNGYGMYWFNL | 61 | 0.83% |
| 50 | ELAGYDVGVEF | 59 | 0.80% |

For the creation of the peptide database, the following methods were used.

Proteolytic Digestion of Antibodies

Approximately 10 ug of the polyclonal population of antibodies was concentrated and buffer exchanged by ultrafiltration (0.5 ml 10K Amicon: Millipore). The initial volume was first concentrated, then exchanged by adding 400 ul of 200 mM Hepes at pH 8. Samples were denatured by resuspending in 80 ul of 8M urea in pH 8 Hepes for 15 min at room temperature. Antibodies were reduced in 10 mM DTT at room temperature for 40 min. Alkylation was performed for 1 hour with 20 mM IAA. Urea concentration was reduced to a final concentration of 2M. Samples were then divided equally by five and digested separately overnight at 37 C with Trypsin, Lys-C, Glu-C, Pepsin, or Chymotrypsin respectively. For Pepsin digests, samples were concentrated and exchanged with 3M acetic acid and digested at RT for 1 hour. Digests were quenched by adding 20% TFA and purified using Sep-Pack cartridges (Waters). Cleaned samples were lyophilized and resuspended for analysis on an LTQ Orbitrap Velos mass spectrometer.

Mass Spectrometry

Peptide mixtures produced by digesting the antibody fraction with the proteases Lys-C, trypsin, chymotrypsin, Pepsin, or Glu-C (i.e., peptides were produced by digesting the antibody fraction with each of these proteases individually) were analyzed by LC-MS/MS individually using the LTQ Orbitrap Velos (Thermo-Fisher) hybrid mass spectrometer. Samples were loaded for 15 min using a Famos autosampler (LC Packings) onto a hand-poured fused silica capillary column (125 um internal diameter 18 cm) packed with MagicC18aQ resin (5 m, 200 Å) using an Agilent 1100 series binary pump with an in-line flow splitter. Chromatography was developed using a binary gradient at 400 nl/min of 8-30% solvent B for 35 min (Solvent A, 0.25% formic acid (FA); Solvent B, 0.1% FA, 97% acetonitrile). As peptides eluted from the liquid chromatography column into the mass spectrometer, they were ionized and the peptide ion mass-to-charge ratios were measured to generate an MS1 spectrum. The mass spectrometer then selected the 20 most abundant peptide ions eluting at that moment and that had not been subjected to MS2 spectrum acquisition in the past 35 seconds, then isolated and fragmented, in turn, each of those 20 precursor peptide ions to produce 20 MS2 product ion spectra. An entire cycle of acquiring one MS1 spectrum of precursor ions followed by acquiring 20 MS2 product ion spectra in a data-dependent manner was accomplished in about 1.6 seconds, and then repeated continuously as peptides eluted from the liquid chromatography column. Charge-state screening was used to reject singly charged species, and a threshold of 500 counts was required to trigger an MS/MS spectrum. When possible, the LTQ and Orbitrap were operated in parallel processing mode.

Database Searching and Data Processing.

MS/MS spectra were searched using the SEQUEST algorithm against a genetic database. Search parameters included full enzyme specificity for Chymotrypsin, Glu-C, Lys-C, and trypsin, and no enzyme specificity for pepsin with a parent mass tolerance of 50 p.p.m., a static modification of 57.0214 on cysteine and dynamic modifications of 15.9949 on methionine. HCD spectra were searched with a fragment ion tolerance of ±0.02 Da, while OD spectra were searched with a fragment ion tolerance of ±1 Da. Peptides were filtered to a 1% peptide FDR via the target-decoy approach, using a linear discriminant function to score each peptide based on parameters such as Xcorr, ΔCn, and precursor mass error.

Results

FIG. 4 schematically depicts the method followed in this example. The nucleic acid sequences were analyzed using the Kabat rules (see Kabat, E. A. et al., Sequences of Proteins of Immunological Interest, National Institutes of Health, Bethesda, Md., (1987) and Wu, T. T. and Kabat, E. A. J. Exp. Med. 132: 211-250 (1970)) to determine where the variable and CDR3 region (and the sequences thereof) were located within the sequences. Next, the percent coverage of CDR3 regions of the heavy chain of multiple monoclonal antibodies identified by Mass spectrometry was elucidated. As shown below in Table 3, sixteen different peptide sequences from the MS-analyzed polyclonal antibody mixture were identified, where each of the sixteen peptides comprised the entirety (i.e., 100%) of the CDR3 region of the corresponding sequence from the nucleic acid sequences collected from the animal.

TABLE 3

| SEQ ID NO: | CDR3 | % CDR3 coverage |
|---|---|---|
|  | GNL | 100 |
|  | GNV | 100 |
| 29 | GVKF | 100 |
| 30 | GVSTNV | 100 |
| 51 | SRSTSYYINL | 100 |
| 45 | DGTDHGFNIDL | 100 |
| 52 | DGSDHGFNIDL | 100 |
| 53 | GADSIYRIYFDL | 100 |
| 54 | NVGSSSYYNLNL | 100 |
| 55 | GGDAGYGYFDAFGP | 100 |
| 56 | GGDAGYGSFDAFGP | 100 |
| 57 | GLGYVGSSVYISKYINL | 100 |
| 58 | VPWTGGSGDARLTRLDL | 100 |
| 36 | GLGYVGSSVYIVKYINL | 100 |
| 59 | DLGYASYIGYGYPSYYFKL | 100 |
| 60 | DLGYASYRGYGYPSYYFKL | 100 |

Of the peptides listed in Table 3, five of the most frequent-occurring observed peptides by mass spectrometry were also seen as theoretical mass spectra derived from the information from the nucleic acid sequences. Thus, this experiment proved that by comparing and correlating the predicted mass spectra (and underlying sequences) derived from the nucleic acid sequences with the observed mass spectra from the actual peptide fragments from the polyclonal antibodies, the sequences of multiple monoclonal antibodies (or at least the heavy chains thereof) were readily obtained.

Example 2

Development of an Influenza Antigen-Specific Recombinant Human Antibody

During the winter of 2009-2010, a strain of H1N1 influenza virus infected a large number of humans, causing death and permanent injury. Using the non-limiting methods of various embodiments of the invention, neutralizing antibodies may be cloned from humans previously exposed to a similar virus strain, and used as a composition to treat human patients currently suffering from the disease.

Accordingly, elderly individuals who were known to have been exposed to the influenza virus during the 1918 influenza epidemic are screened for the presence of serum antibodies that can neutralize the 1918 virus. To do this, the method described in Yu et al., *Nature* 455: 532-536, 2008 (and online supplement; article and supplement incorporated herein by reference in their entirety) is followed.

Patients whose blood serum and/or plasma contains virus-neutralizing antibodies are identified, and blood is taken from these patients and separated into cells and serum and/or plasma.

From the blood cells, B lymphocytes are isolated according to standard methods (see, for example, the methods described here) and nucleic acid molecules from the B lymphocytes are obtained. Immunoglobulin chain-encoding nucleic acid molecules are isolated from these cells by PCR amplifying genomic DNA using primers that hybridize to regions upstream and downstream of the human immunoglobulin heavy (VH)- and light (VL)-chain variable-region genes. Methods for making such primers are standard in the field of immunology (see, e.g., the methods described in Marks and Bradbury, "PCR Cloning of Human Immunoglobulin Genes" in *Antibody Engineering: Methods and Protocols,* 248: 117-134, 2003, incorporated herein by reference).

These nucleic acid molecules obtained by using these primers for PCR amplification are used to populate the genetic material database. Within the genetic database, the nucleic acid sequences are further manipulated using standard software packages to determine the amino acid sequence of the polypeptide encoded by each nucleic acid sequence, and the encoded polypeptides are virtually digested with trypsin, where the predicted resulting peptides generated from such digest are used to generate predicted mass spectra.

From the blood from the patients, serum and/or plasma is collected. Antibodies present in the serum and/or plasma are isolated by standard methods. For example, serum proteins are passed through a protein A sepharose column, to which immunoglobulins adhere and non-immunoglobulin proteins do not. Because the individuals whose blood is collected are not newly exposed to the 1918 influenza virus, their serum antibodies are further enriched for antibodies that specifically bind to a 1918 viral antigen by passing the serum antibodies over a second column coated with 1918 virus (e.g., attenuated virus or fragments thereof). The bound antibodies are next treated with a protease (e.g., papain) or chemical protein cleavage reagent that specifically cuts near the hinge region of the immunoglobulin, and the non-adherent Fc portions removed. Finally, the bound Fab or Fab2 fragments are treated with trypsin to generate peptide fragments, and all fragments are then fractionated using liquid chromatography, with the fragments then being analyzed by mass spectrometry. Using an algorithm such as the Sequest program, the observed tandem mass spectra of the peptides are correlated with the predicted mass spectra from the nucleic acid sequences extracted from the patients' B lymphocytes. Using this process, at least one peptide found within the predicted amino acid sequence of a unique immunoglobulin chain of the genetic material database may be identified. The nucleic acid sequence encoding this immunoglobulin chain (or variable region thereof) is then retrieved from the genetic database and synthesized using standard DNA synthesis methods. The synthesized DNA sequences are then subcloned into expression vectors which are then transfected into CHO cells. The recombinant antibodies produced by the cells are next isolated and tested for the ability to bind to the 1918 virus (or fragments thereof).

Recombinant antibodies produced using this method are then combined with a pharmaceutically acceptable carrier and administered to patients suffering from H1N1 virus infection. Because these recombinant antibodies are wholly human in origin, it is not expected that they will be rejected by the patients' immune systems.

Example 3

Obtaining Nucleic Acid Sequences

This protocol uses next generation sequencing (NGS), and is based on 454 NGS platform (FLX+, FLX or junior;

commercially available from 454 Life Sciences, a Roche company, Branford, Conn.). Slight modifications will be needed for other high throughput NGS platforms and will be based on NGS manufacturing's instructions.

Mice are immunized with antigen of interest (peptide(s), recombinant proteins, virus, toxin, etc) with standard immunization protocols (see, e.g., Coligan et al., supra). Immune responses are monitored by plasma immunoglobulins titer against the specific antigen. Blood, spleen, bone marrow, lymph nodes, or any lymphoid organs can be collected and processed to isolate B cells according to standard methods. This isolation procedure can also be reduced if material is limited and replaced with a direct RT-PCR procedure using immunoglobulin variable domain specific PCR primers against heavy and light chains populations from the animal.

Of course in some embodiments, the nucleic acid sequences can be directly sequenced straight from the biological material (i.e., without being amplified prior to sequencing). Services and reagents for directly sequencing from nucleic acid sequences are commercially available, for example, from Helicos BioSicences Corp. (Cambridge, Mass.). For example, Helicos' True Single Molecule Sequencing allows direct sequencing of DNA, cDNA, and RNA. See also U.S. Pat. Nos. 7,645,596; 7,037,687, 7,169,560; and publications Harris et al., Science 320: 106-109, 2008; Bowers et al., Nat. Methods 6: 493-494, 2009; and Thompson and Milos, Genome Biology 12: 217, 2011 (all of which patents and publications are incorporated herein by reference in their entireties).

In some embodiments, the nucleic sequences are amplified (e.g., by polymerase chain reaction) prior to obtaining sequence information.

In one non-limiting example, an oligo dT PCR primer is used for RT-PCR. In another non-limiting example, gene-specific RT-PCR is performed using the PCR primers described below are used. In another example, PCR primers against heavy chain and light chain populations in a mouse have sequences set forth in PCT publication no. WO2010/097435, herein incorporated by reference.

With or without B cell enrichment, purified genetic materials (DNA or mRNA) will then be subjected to RT-PCR following standard procedures (see, e.g., Ausubel et al., supra). This is the library preparation stage of the genetic materials before NGS sequencing run. Reverse transcription (RT) reaction can apply oligo dT or immunoglobulin specific primers to generate cDNAs. Polymerase chain reaction procedure will apply immunoglobulin specific primers to amplify variable region of (rearranged or/and expressed) heavy and light chains from the sample.

These methods are described in further details below.

Library Preparation

Sample Preparation Example:

Blood, spleen, bone marrow, or lymph nodes are isolated after mice received final boost with antigen. Mononuclear cells are isolated by Ficoll separation as previously described above. Ficolled cells are then washed by PBS, counted, and snap frozen for total RNA preparation.

Total RNA is isolated from the cells using the Qiagen RNeasy kit (commercially available from Qiagen Inc., Hilden, Germany) according to manufacturer's instructions, and the total RNA is stored at −80° C.

For gene-specific RT-PCR or standard RT-PCR (using oligo dT), the following protocol may be used.

| | |
|---|---|
| 10 uM CST mouse RT-Ig primer or Oligo dT | 1 ul |
| 2.5 ug total RNA (splenocytes) | x ul |
| 10 mM dNTP | 2 ul |
| Sterile, distilled water | to 14 ul |

Incubate mixture at 65° C. for 5 minutes and then place on ice.

| | |
|---|---|
| 5x cDNA Synthesis Buffer | 4 ul |
| 0.1M DTT | 1 ul |
| Invitrogen Thermoscript RT (15 U/ul) | 1 ul |

Mix contents gently and incubate at 60° C. for 60 mins
Terminate reaction by heating at 85° C. for 5 mins
cDNA is ready for use in making library
cDNA will then be subjected to PCR using CST 454 specific fusion mouse primers for Heavy and Light chains. The primers will have the following sequences:
Mouse 454 Amplicon Primers
Heavy Chains (Forward and Reverse Primers)

HV1
(SEQ ID NO: 1)
CCATCTCATCCCTGCGTGTCTCCGACTCAGACGAGTGCGTGATGTGAA

GCTTCAGGAGTC

HV2
(SEQ ID NO: 2)
CCATCTCATCCCTGCGTGTCTCCGACTCAGACGCTCGACACAGGTGCA

GCTGAAGGAGTC

HV3
(SEQ ID NO: 3)
CCATCTCATCCCTGCGTGTCTCCGACTCAGAGACGCACTCCAGGTGCA

GCTGAAGCAGTC

HV4
(SEQ ID NO: 4)
CCATCTCATCCCTGCGTGTCTCCGACTCAGAGCACTGTAGCAGTTACT

CTGAAAAGAGTC

HV5
(SEQ ID NO: 5)
CCATCTCATCCCTGCGTGTCTCCGACTCAGATCAGACACGGAGGTCCA

GCTGCAACAATCT

HV6
(SEQ ID NO: 6)
CCATCTCATCCCTGCGTGTCTCCGACTCAGATATCGCGAGGAGGTCCA

GCTGCAGCAGTC

HV7
(SEQ ID NO: 7)
CCATCTCATCCCTGCGTGTCTCCGACTCAGCGTGTCTCTACAGGTCCA

ACTGCAGCAGCCT

HV8
(SEQ ID NO: 8)
CCATCTCATCCCTGCGTGTCTCCGACTCAGCTCGCGTGTCGAGGTGAA

GCTGGTGGAGTC

HV9
(SEQ ID NO: 9)
CCATCTCATCCCTGCGTGTCTCCGACTCAGTCTCTATGCGGAGGTGAA

GCTGGTGGAATC

HV10
(SEQ ID NO: 10)
<u>CCATCTCATCCCTGCGTGTCTCCGACTCAG</u>TGATACGTCTGATGTGAA

CTTGGAAGTGTC

HVFOR1
(SEQ ID NO: 11)
<u>CCTATCCCCTGTGTGCCTTGGCAGTCTCAG</u>TGCAGAGACAGTGACCAG

AGT

HVFOR2
(SEQ ID NO: 12)
<u>CCTATCCCCTGTGTGCCTTGGCAGTCTCAG</u>TGAGGAGACTGTGAGAGT

GGT

HVFOR3
(SEQ ID NO: 13)
<u>CCTATCCCCTGTGTGCCTTGGCAGTCTCAG</u>TGAGGAGACGGTGACTGA

GGT

HVFOR4
(SEQ ID NO: 14)
<u>CCTATCCCCTGTGTGCCTTGGCAGTCTCAG</u>TGAGGAGACGGTGACCGT

GGT

Kappa Chains (Forward and Reverse Primers)

KV1
(SEQ ID NO: 15)
<u>CCATCTCATCCCTGCGTGTCTCCGACTCAG</u>CATAGTAGTGGATGTTTT

GATGACCCAAACT

KV2
(SEQ ID NO: 16)
<u>CCATCTCATCCCTGCGTGTCTCCGACTCAG</u>CGAGAGATACGATATTGT

GATGACGCAGGCT

KV3
(SEQ ID NO: 17)
<u>CCATCTCATCCCTGCGTGTCTCCGACTCAG</u>ATACGACGTAGATATTGT

GATAACCCAG

KV4
(SEQ ID NO: 18)
<u>CCATCTCATCCCTGCGTGTCTCCGACTCAG</u>TCACGTACTAGACATTGT

GCTGACCCAATCT

KV5
(SEQ ID NO: 19)
<u>CCATCTCATCCCTGCGTGTCTCCGACTCAG</u>CGTCTAGTACGACATTGT

GATGACCCAGTCT

KV6
(SEQ ID NO: 20)
<u>CCATCTCATCCCTGCGTGTCTCCGACTCAG</u>TCTACGTAGCGATATTGT

GCTAACTCAGTCT

KV7
(SEQ ID NO: 21)
<u>CCATCTCATCCCTGCGTGTCTCCGACTCAG</u>TGTACTACTCGATATCCA

GATGACACAGACT

KV8
(SEQ ID NO: 22)
<u>CCATCTCATCCCTGCGTGTCTCCGACTCAG</u>ACGACTACAGGACATCCA

GCTGACTCAGTCT

KV9
(SEQ ID NO: 23)
<u>CCATCTCATCCCTGCGTGTCTCCGACTCAG</u>CGTAGACTAGCAAATTGT

TCTCACCCAGTCT

KVFOR1
(SEQ ID NO: 24)
<u>CCTATCCCCTGTGTGCCTTGGCAGTCTCAG</u>CCGTTTCAGCTCCAGCTTG

KVFOR2
(SEQ ID NO: 25)
<u>CCTATCCCCTGTGTGCCTTGGCAGTCTCAG</u>CCGTTTTATTCCAGCTTGGT

KVFOR3
(SEQ ID NO: 26)
<u>CCTATCCCCTGTGTGCCTTGGCAGTCTCAG</u>CCGTTTTATTTCCAACTTTG

Lambda Chains (Forward and Reverse Primers)

LV
(SEQ ID NO: 27)
<u>CCATCTCATCCCTGCGTGTCTCCGACTCAG</u>TACGAGTATGCAGGCTGT

TGTGACTCAGGAA

LVFOR
(SEQ ID NO: 28)
<u>CCTATCCCCTGTGTGCCTTGGCAGTCTCAG</u>CTTGGGCTGACCTAGGAC

AGT

In all of the above sequences, the underlined sequences are for the 454 sequencing, the bolded sequences are barcodes for multiplexing, and the regular font sequences are mouse-specific sequences.

The primers are used to amplify the above-described libraries as follows:

Heavy Chain PCR:

| | |
|---|---|
| CST454 mouse heavy chain primers mix | 1 ul |
| cDNA | 1 ul |
| 2x Phusion Master Mix | 12.5 ul |
| H2O | 10.5 ul |

Light Chain PCR:

| | |
|---|---|
| CST454 mouse light chain primers mix | 1 ul |
| cDNA | 1 ul |
| 2x Phusion Master Mix | 12.5 ul |
| H2O | 10.5 ul |

The PCR condition cycle conditions may be as follows in Table 4:

TABLE 4

| Step | Temperature | Time (in minutes) |
|---|---|---|
| 1: Denaturing Step | 98° C. | 01:30 |
| 2: Denaturing Step | 98° C. | 00:10 |
| 3: Annealing Step | 60° C. | 00:30 |
| 4: Extension step | 72° C. | 00:30 |

20 cycles are applied of steps 2-4 are applied. PCR products will then be subjected to Agencourt Ampure DNA purification (commercially available from Beckman Coulter Genomics, Danvers, Mass.) 2 times, following manufacture's protocol (see, e.g., the protocols of Beckman Coulter Genomics' Agencourt AMPure XP system).

Once the PCR/genetic library is prepared, all subsequent steps will follow 454 manufacturing protocols for emPCR and sequencing reactions. See publications by 454 Life Sciences Corp., a Roche Company, Branford, Conn. 06405 entitled, "Sequencing Method Manual, GS Junior Titanium Series" (May 2010 (rev. June 2010)) and "emPCR Amplification Method Manual—Lib-L, GS junior Titanium Series (May 2010 (rev. June 2010)), both of which are hereby incorporated by reference in their entirety.

Multiple samples can be combined at this stage into a single sequencing run. They will be distinguished by a unique barcode (or MID from 454 platform). For example, a barcode is incorporated into the PCR primer.

In some embodiments, the emPCR Amplification Method Manual—Lib-L, GS junior Titanium Series (May 2010 (rev. June 2010); 454 Life Sciences Corp.) is followed. In some embodiments, the Sequencing Method Manual, GS Junior Titanium Series" (May 2010 (rev. June 2010); 454 Life Sciences Corp.) is next followed.

Sequencing data can be produced as FASTA files (or any standard file formats) and stored in a genetic material database. These sequence data will be used to generate the predicted mass spectra database to analyze the observed peptide mass spectra generated from the same animal's serum and/or plasma immunoglobulins. Standard programs can be used to do this. In this example, the predicted mass spectra were generated by the Sequest software package.

Example 4

Identifying Individual Antibody Chains from a Polyclonal Population

The methods described herein were next used to identify the sequence of individual antibodies from several different polyclonal populations. The methods of this example are shown schematically in FIGS. 2 and 4.

Using the methods described above in Example 2, three different polyclonal populations of antibodies that specifically bind to three different antigens were made into three different libraries. Deep sequencing using the 454 sequencing methods described above were performed using primers specific for rabbit immunoglobulin chain-encoding sequences to obtain three different genetic material databases.

Correspondingly, the genetic material databases were used to generate three different protein databases using the methods described in Example 3 above.

The results for the first antigen are shown in Tables 5 (light chain) and 6 (heavy chain); the second antigen are shown in Tables 7 (light chain) and 8 (heavy chain) and the third antigen are shown in Tables 9 (light chain) and 10 (heavy chain).

TABLE 5

| CDR3 | CDR3 count | CDR3 coverage | Total Peptides | Unique Peptides | CDR3 peptide |
|---|---|---|---|---|---|
| QGEFSCRDFDCTV (SEQ ID NO: 61) | 16 | 100 | 58 | 30 | CQGEFSCRDFDCTVF (SEQ ID NO: 62) |
| AGGYKSSGDTVS (SEQ ID NO: 63) | 15 | 100 | 48 | 24 | YCAGGYKSSGDTVSF (SEQ ID NO: 64) |
| AGGYKSTTDGSA (SEQ ID NO: 65) | 9 | 100 | 29 | 17 | CAGGYKSTTDGSAF (SEQ ID NO: 66) |
| QQGRRSVDVDNV (SEQ ID NO: 67) | 8 | 100 | 25 | 12 | CADAATYYCQQGRRSVDVDNVFGGGTE (SEQ ID NO: 68) |
| QGEFNCDGVGCTT (SEQ ID NO: 69) | 2 | 100 | 17 | 9 | YCQGEFNCDGVGCTTF (SEQ ID NO: 70) |

TABLE 6

| CDR3 | CDR3 count | CDR3 coverage | Total Peptides | Unique Peptides | CDR3 peptide |
|---|---|---|---|---|---|
| GVRDWGDALDL (SEQ ID NO: 71) | 5 | 100 | 42 | 22 | GVRDWGDALDLWGQGTLVTVSSGQPK (SEQ ID NO: 72) |
| LYNSVVGDDI (SEQ ID NO: 73) | 10 | 100 | 38 | 20 | LYNSVVGDDIWGPGTLVTVSLGQPK (SEQ ID NO: 74) |
| LYNSVVGDDM (SEQ ID NO: 75) | 4 | 100 | 37 | 21 | LYNSVVGDDMWGPGTLVTVSLGQPK (SEQ ID NO: 76) |
| GMPGSTSGNSNI (SEQ ID NO: 77) | 2 | 100 | 34 | 20 | GMPGSTSGNSNIWGPGTLVTVSLGQPK (SEQ ID NO: 78) |
| LYNSLVGDDI (SEQ ID NO: 79) | 2 | 100 | 30 | 15 | LYNSLVGDDIWGPGTLVTVSLGQPK (SEQ ID NO: 80) |

TABLE 6-continued

| CDR3 | CDR3 count | CDR3 coverage | Total Peptides | Unique Peptides | CDR3 peptide |
|---|---|---|---|---|---|
| KGDPGHPNGLFFTM (SEQ ID NO: 81) | 3 | 100 | 22 | 19 | KGDPGHPNGLFFTMWGPGTLVTVSFGQPK (SEQ ID NO: 82) |
| GGGSHSGSAIYDMDP (SEQ ID NO: 83) | 2 | 100 | 20 | 14 | GGGSHSGSAIYDMDPWGPGTLVTVSSGQPK (SEQ ID NO: 84) |
| GTSRGSDYRLDL (SEQ ID NO: 85) | 2 | 100 | 15 | 11 | GTSRGSDYRLDLWGQGTLVTVSSGQPK (SEQ ID NO: 86) |
| GMPASTSGNSNI (SEQ ID NO: 87) | 2 | 100 | 14 | 14 | GMPASTSGNSNIWGPGTLVTVSLGQPK (SEQ ID NO: 88) |
| DAIANI (SEQ ID NO: 89) | 2 | 100 | 10 | 8 | DAIANIWGPGTLVTVSLGQPK (SEQ ID NO: 90) |
| DKWMVFGDLRL (SEQ ID NO: 91) | 2 | 100 | 9 | 4 | DKWMVFGDLRLWGPGTLVTVSSGQPK (SEQ ID NO: 92) |

TABLE 7

| CDR3 | CDR3 count | CDR3 coverage | Total Peptides | Unique Peptides | CDR3 peptide |
|---|---|---|---|---|---|
| QQGRTYSDVANV (SEQ ID NO: 93) | 1 | 66.67 | 42 | 20 | TYSDVANVFGGGTEVVVK (SEQ ID NO: 94) |
| QQGYSSYNVDNA (SEQ ID NO: 95) | 2 | 41.67 | 75 | 20 | NVDNAFGGGTEVVVK (SEQ ID NO: 96) |
| QQGYSSSNVDNA (SEQ ID NO: 97) | 2 | 41.67 | 41 | 19 | NVDNAFGGGTEVVVK (SEQ ID NO: 98) |
| LGTYDCRSADCNA (SEQ ID NO: 99) | 2 | 46.15 | 33 | 18 | SADCNAFGGGTEVVVK (SEQ ID NO: 100) |
| QHGYYSNVDNA (SEQ ID NO: 101) | 2 | 45.45 | 46 | 18 | NVDNAFGGGTEVVVK (SEQ ID NO: 102) |
| QQGFSSRNVDNA (SEQ ID NO: 103) | 2 | 41.67 | 24 | 18 | NVDNAFGGGTEVVVK (SEQ ID NO: 104) |
| QQGYSSVNVDNA (SEQ ID NO: 105) | 2 | 41.67 | 26 | 18 | NVDNAFGGGTEVVVK (SEQ ID NO: 106) |
| QQGYTYNNVDNA (SEQ ID NO: 107) | 2 | 41.67 | 27 | 16 | NVDNAFGGGTEVVVK (SEQ ID NO: 108) |
| LGTYDCRSGDCNV (SEQ ID NO: 109) | 1 | 46.15 | 25 | 15 | SGDCNVFGGGTEVVVK (SEQ ID NO: 110) |
| QQGYTSNVDNA (SEQ ID NO: 111) | 2 | 45.45 | 26 | 15 | NVDNAFGGGTEVVVK (SEQ ID NO: 112) |
| QQGQTPENVDNA (SEQ ID NO: 113) | 2 | 41.67 | 22 | 14 | NVDNAFGGGTEVVVK (SEQ ID NO: 114) |
| QQGSTYSDVANV (SEQ ID NO: 115) | 1 | 66.67 | 29 | 14 | TYSDVANVFGGGTEVVVK (SEQ ID NO: 116) |
| QQGATYSDVANV (SEQ ID NO: 117) | 1 | 66.67 | 63 | 13 | TYSDVANVFGGGTEVVVK (SEQ ID NO: 118) |
| QQGTTYSDVANV (SEQ ID NO: 119) | 1 | 66.67 | 25 | 13 | TYSDVANVFGGGTEVVVK (SEQ ID NO: 120) |
| QQGYTRSNVDNA (SEQ ID NO: 121) | 2 | 41.67 | 21 | 11 | NVDNAFGGGTEVVVK (SEQ ID NO: 122) |
| AGYKSYGNADID (SEQ ID NO: 123) | 4 | 66.67 | 24 | 10 | SYGNADIDFGGGTEVVVK (SEQ ID NO: 124) |
| QQGYTSSNVDNA (SEQ ID NO: 125) | 2 | 41.67 | 17 | 9 | NVDNAFGGGTEVVVK (SEQ ID NO: 126) |

TABLE 7-continued

| CDR3 | CDR3 count | CDR3 coverage | Total Peptides | Unique Peptides | CDR3 peptide |
|---|---|---|---|---|---|
| LVSYDCSSADCNA (SEQ ID NO: 127) | 2 | 46.15 | 51 | 8 | SADCNAFGGGTEVVVK (SEQ ID NO: 128) |
| QQAYTSSNVDNA (SEQ ID NO: 129) | 2 | 41.67 | 4 | 3 | NVDNAFGGGTEVVVK (SEQ ID NO: 130) |

TABLE 8

| CDR3 | CDR3 count | CDR3 coverage | Total Peptides | Unique Peptides | CDR3 peptide |
|---|---|---|---|---|---|
| DGGL (SEQ ID NO: 131) | 2 | 100 | 11 | 6 | DGGLWGPGTLVTVSSGQPK (SEQ ID NO: 132) |
| DPYDTNTSLDAL (SEQ ID NO: 133) | 2 | 100 | 10 | 4 | DPYDTNTSLDALWGPGTLVTVSSGQPK (SEQ ID NO: 134) |
| EGSDDDSFDL (SEQ ID NO: 135) | 4 | 100 | 10 | 5 | EGSDDDSFDLWGPGTLVTVSSGQPK (SEQ ID NO: 136) |
| GGDL (SEQ ID NO: 137) | 2 | 100 | 9 | 5 | GGDLWGQGTLVTVSSGQPK (SEQ ID NO: 138) |
| GHWSAGATLYGYFSL (SEQ ID NO: 139) | 2 | 100 | 11 | 5 | GHWSAGATLYGYFSLWGPGTLVTVSSGQPK (SEQ ID NO: 140) |

TABLE 9

| CDR3 | CDR3 count | CDR3 coverage | Total Peptides | Unique Peptides | CDR3 peptide |
|---|---|---|---|---|---|
| LANYDCSSGDCSV (SEQ ID NO: 141) | 1 | 100 | 28 | 18 | CLANYDCSSGDCSVF (SEQ ID NO: 142) |
| QGNFDCSSADCSA (SEQ ID NO: 143) | 2 | 100 | 37 | 21 | CQGNFDCSSADCSAF (SEQ ID NO: 144) |
| QGNFDCTSADCSA (SEQ ID NO: 145) | 2 | 100 | 37 | 21 | CQGNFDCTSADCSAF (SEQ ID NO: 146) |

TABLE 10

| CDR3 | CDR3 count | CDR3 coverage | Total Peptides | Unique Peptides | CDR3 Peptide |
|---|---|---|---|---|---|
| DGTDHGFNIDL (SEQ ID NO: 45) | 8 | 100 | 38 | 22 | DGTDHGFNIDLWGPGTLVTVSSGQPK (SEQ ID NO: 147) |
| GNV | 2 | 100 | 36 | 21 | TSTTVTLQMTSLTAADTATYFCASGNVWGPGTLVTVSSGQPK (SEQ ID NO: 148) |
| GVSTNV (SEQ ID NO: 30) | 6 | 100 | 29 | 19 | GVSTNVWGPGTLVTVSSGQPK (SEQ ID NO: 149) |
| GVKF (SEQ ID NO: 29) | 4 | 100 | 30 | 18 | FCTRGVKF (SEQ ID NO: 150) |
| DGSDHGFNIDL (SEQ ID NO: 52) | 6 | 100 | 29 | 16 | DGSDHGFNIDLWGPGTLVTVSSGQPK (SEQ ID NO: 151) |
| NAAIL (SEQ ID NO: 152) | 10 | 100 | 34 | 16 | NAAILWGPGTLVTVSSGQPK (SEQ ID NO: 153) |

TABLE 10-continued

| CDR3 | CDR3 count | CDR3 coverage | Total Peptides | Unique Peptides | CDR3 Peptide |
|---|---|---|---|---|---|
| SRSTSYYINL (SEQ ID NO: 154) | 12 | 100 | 33 | 15 | SRSTSYYINLWGPGTLVTVSSGQPK (SEQ ID NO: 155) |
| GGDAGYGSFDAFGP (SEQ ID NO: 56) | 6 | 100 | 30 | 14 | GGDAGYGSFDAFGPWGPGTLVTVSSGQPK (SEQ ID NO: 156) |
| GVSTDV (SEQ ID NO: 157) | 2 | 100 | 25 | 14 | GVSTNVWGPGTLVTVSSGQPK (SEQ ID NO: 158) |
| NVGSSSYYNLNL (SEQ ID NO: 54) | 6 | 100 | 28 | 14 | NVGSSSYYNLNLWGPGTLVTVSSGQPK (SEQ ID NO: 159) |
| GVSTSV (SEQ ID NO: 160) | 2 | 100 | 24 | 13 | GVSTNVWGPGTLVTVSSGQPK (SEQ ID NO: 161) |
| GGYAGAGYFDAFNP (SEQ ID NO: 162) | 2 | 100 | 21 | 12 | GGYAGAGYFDAFNPWGPGTLVTVSSGQPK (SEQ ID NO: 163) |
| NYNL (SEQ ID NO: 164) | 6 | 100 | 26 | 12 | NYNLWGPGTLVTVSSGQPK (SEQ ID NO: 165) |
| RDGFSTDRYFNL (SEQ ID NO: 166) | 7 | 91.67 | 25 | 12 | DGFSTDRYFNLWGPGTLVTVSSGQPK (SEQ ID NO: 167) |
| DRGTGSGDYTPFNL (SEQ ID NO: 168) | 5 | 71.43 | 26 | 12 | GSGDYTPFNLWGPGTLVTVSSGQPK (SEQ ID NO: 169) |
| DAAIL (SEQ ID NO: 170) | 8 | 100 | 27 | 11 | NAAILWGPGTLVTVSSGQPK (SEQ ID NO: 171) |
| GPYVDSTYYNL (SEQ ID NO: 172) | 6 | 100 | 23 | 11 | GPYVDSTYYNLWGPGTLVTVSSGQPK (SEQ ID NO: 173) |
| GSGDYTPFNL (SEQ ID NO: 174) | 6 | 100 | 23 | 11 | GSGDYTPFNLWGPGTLVTVSSGQPK (SEQ ID NO: 175) |
| YYDGADYHTYNL (SEQ ID NO: 176) | 6 | 100 | 21 | 11 | YYDGADYHTYNLWGPGTLVTVSSGQPK (SEQ ID NO: 177) |
| EFGNNGWNIDL (SEQ ID NO: 178) | 6 | 100 | 21 | 10 | EFGNNGWNIDLWGPGTLVTVSSGQPK (SEQ ID NO: 179) |
| VEYGNDWGNL (SEQ ID NO: 180) | 6 | 100 | 20 | 10 | VEYGNDWGNLWGPGTLVTVSSGQPK (SEQ ID NO: 181) |
| YFDGADYHTYNL (SEQ ID NO: 182) | 6 | 100 | 20 | 10 | YFDGADYHTYNLWGPGTLVTVSSGQPK (SEQ ID NO: 183) |
| RFSGGGYGYDL (SEQ ID NO: 184) | 5 | 90.91 | 25 | 10 | FSGGGYGYDLWGPGTLVTVSSGQPK (SEQ ID NO: 185) |
| DRDL (SEQ ID NO: 186) | 6 | 100 | 19 | 9 | DRDLWGPGTLVTVSSGQPK (SEQ ID NO: 187) |
| GLDL (SEQ ID NO: 188) | 5 | 100 | 19 | 9 | YGLDLWGPGTLVTVSSGQPK (SEQ ID NO: 189) |
| YDVDSVSAYDL (SEQ ID NO: 190) | 6 | 100 | 24 | 9 | YDVDSVSAYDLWGPGTLVTVSSGQPK (SEQ ID NO: 191) |
| EVVGYDYSGDL (SEQ ID NO: 192) | 6 | 100 | 18 | 8 | EVVGYDYSGDLWGPGTLVTVSSGQPK (SEQ ID NO: 193) |
| DPYDDPTY (SEQ ID NO: 194) | 2 | 100 | 10 | 6 | DPYDDPTYR (SEQ ID NO: 195) |
| GGL (SEQ ID NO: 196) | 1 | 100 | 3 | 3 | GGLVKPGASLTL (SEQ ID NO: 196) |

Tables 5-10 show peptides identified with high confidence (>99% certainty) by mass spectrometry (CDR3 peptide) that correspond to sequences (specifically the CDR3 region) generated by deep sequencing from the antibody repertoire of the animal. CDR3 count shows the number of times a peptide was identified from the polyclonal antibody mixture that matched the CDR3 region. CDR3 coverage indicated the percent of those amino acids in the CDR3 region (shown in the CDR3 column) that appear in the peptides identified by mass spectrometry relative to the total amino acids of the CDR3 region. Total peptides represent the total number of peptides by sequence identified by mass spectrometry corresponding to the full length variable region sequence determined by deep sequencing. Unique peptides represent the number of unique peptides by sequence identified by mass spectrometry corresponding to the full length variable region sequence determined by deep sequencing.

Example 5

In another example, the following protocols can be used to generate the nucleic acid sequences and the polyclonal antibodies. The results show success in generating an antigen-specific antibody using these methods.

In these protocols, mice were immunized with an immunogenic P-ERK antigen. The genetic material database and peptide database can be generated using the following methods.

I. Genetic Material Database:
Cell Isolation.

Spleens from immunized mice were flushed 5 times with 5 mL of RPMI/10% FCS using a syringe and 21 G needle. Cells were frozen in 90% FCS/10% DMSO. A total of 50-100×10^6 cells were isolated from each spleen.
RNA Isolation and cDNA Synthesis.

Total RNA was isolated from Splenocytes according to manufacturer's protocol using QIAshredder (Qiagen cat#79654) and RNeasy mini kit (Qiagen, Hilden, Germany; cat#74104). RNA was DNAse treated on column as per a standard next generation sequencing protocol. Total RNA concentration was measured using an ND-1000 spectrophotometer (NanoDrop; commercially available from Thermo Scientific, Wilmington, Del.).

The isolated RNA was used for first-strand cDNA synthesis by reverse transcription using Thermoscript RT-PCR system (Invitrogen (part of Life Technologies), Carlsbad, Calif. cat#11146-024). cDNA was synthesized using 1.5 ug of RNA and oligo dT primer according to manufacturer's protocol.

$V_H$ and $V_L$ Amplification.

A two-step PCR reaction was used to amplify the $V_H$ and $V_L$ genes. A mix of degenerate sense and anti-sense primers was used for the first round of PCR and a set of universal primers was used for the second round of PCR. Due to the large number of sense degenerate primers the heavy chain PCR is divided up into 8 separate reactions. The sequences of the primers used are shown below.
First Round Primers, Universal Tail is Underlined
Heavy Chain Sense Primers:

$V_H1.1$:
(SEQ ID NO: 197)
ACGAGCTACGCACGAACTGCAGGTRTCCACTCC (SEQ ID NO: 198)
ACGAGCTACGCACGAATAGCAGGTGTCCACTCC (SEQ ID NO: 199)
ACGAGCTACGCACGARGTACAGGTGTCCACTCC (SEQ ID NO: 200)
ACGAGCTACGCACGAGCYACAGMTGTCCACTCC (SEQ ID NO: 201)
ACGAGCTACGCACGAACTGCAGGTGTCCWMTCC $V_H1.2$:
(SEQ ID NO: 202)
ACGAGCTACGCACGARCTRCAGGTGTKCACTCC (SEQ ID NO: 203)
ACGAGCTACGCACGAGCTAWMGGTGTCCACTCC (SEQ ID NO: 204)
ACGAGCTACGCACGACCTCAGGTGTCCACTCC (SEQ ID NO: 205)
ACGAGCTACGCACGAGCTACAGGTGCTCACTCC (SEQ ID NO: 206)
ACGAGCTACGCACGAACTGCAGGTGTCCTCTCT $V_H1.3$:
(SEQ ID NO: 207)
ACGAGCTACGCACGAAYTGCAGGTGTCCAYTGC (SEQ ID NO: 208)
ACGAGCTACGCACGAGCTAMMGGTGTCCACTTC (SEQ ID NO: 209)
ACGAGCTACGCACGACTCCTGTCAKTAACTKCAGGT (SEQ ID NO: 210)
ACGAGCTACGCACGAAACTGCAGGTGTCTCTCT (SEQ ID NO: 211)
ACGAGCTACGCACGARCTRCAGGYGTCCACTCT $V_H2$:
(SEQ ID NO: 212)
ACGAGCTACGCACGACCAAGCTGTATCCTTTCC (SEQ ID NO: 213)
ACGAGCTACGCACGACCAAGCTGTGTCCTRTCC $V_H3$:
(SEQ ID NO: 214)
ACGAGCTACGCACGATGTTGACAGYCVTTCCKGGT (SEQ ID NO: 215)
ACGAGCTACGCACGATGTTCACAGCCTTTCCTGGT $V_H4$:
(SEQ ID NO: 216)
ACGAGCTACGCACGATTTAAAAGGGGTCCAGTGT $V_H5$:
(SEQ ID NO: 217)
ACGAGCTACGCACGATAYTTTAAAARGTGTCMAGTGT (SEQ ID NO: 218)
ACGAGCTACGCACGAGTTTTAAAAGGTGTCCTGTG $V_H6-8$:
(SEQ ID NO: 219)
ACGAGCTACGCACGACTYTTAAAAGGKGTCCAGWG (SEQ ID NO: 220)
ACGAGCTACGCACGACYTTTAMATGGTATCCAGTGT (SEQ ID NO: 221)
ACGAGCTACGCACGACTTTTACATGGTTTCAAGTGT (SEQ ID NO: 222)
ACGAGCTACGCACGAYTGTCCCTGCATATGTCYT $V_H9-15$:
(SEQ ID NO: 223)
ACGAGCTACGCACGAATGGCAGCWGCYCCAAG (SEQ ID NO: 224)
ACGAGCTACGCACGATTTATCAAGGTGTGCATTGT (SEQ ID NO: 225)
ACGAGCTACGCACGACTTTTAAAAGWTGTCCAGKGT

```
                                             (SEQ ID NO: 226)
ACGAGCTACGCACGAGTGACAGTCCTTCCTGGTAG (SEQ ID NO: 227)
ACGAGCTACGCACGACTTCCTGATGGCAGTGGTT (SEQ ID NO: 228)
ACGAGCTACGCACGAAGCTACAGGTATCCAATCC
```

Heavy Chain Anti-Sense Primers:

```
IgG1:
                                             (SEQ ID NO: 229)
CACTGGTGTGAGTCAATGCAGACAGATGGGGGTGTCG

IgG2a:
                                             (SEQ ID NO: 230)
CACTGGTGTGAGTCAAGACCGATGGGGCTGTTGTT

IgG2b:
                                             (SEQ ID NO: 231)
CACTGGTGTGAGTCACAGACTGATGGGGGTGTTGTT

IgG3:
                                             (SEQ ID NO: 232)
CACTGGTGTGAGTCAAGACAGATGGGGCTGTTGTT
```

Kappa Chain Sense Primer:

```
                                             (SEQ ID NO: 233)
ACGAGCTACGCACGAGACATYWWGATGACCCAGTCTCC
```

Kappa Chain Anti-Sense Primer:

```
                                             (SEQ ID NO: 234)
CACTGGTGTGAGTCACAGTTGGTGCAGCATCAGCCCG
```

Second Round Primers, Universal Tail is Underlined
Heavy or Light Chain Sense Primer:

```
                                             (SEQ ID NO: 235)
CCTATCCCCTGTGTGCCTTGGCAGTCACGAGCTACGCACGA
```

Heavy Chain Anti-Sense Primers:

```
MID97:
                                             (SEQ ID NO: 236)
CCATCTCATCCCTGCGTGTCTCCGACTCAGctagtcactcCACTGGTG
TGAGTCA MID81:
                                             (SEQ ID NO: 237)
CCATCTCATCCCTGCGTGTCTCCGACTCAGAGAGCGTCACCACTGGTG
TGAGTCA MID24:
                                             (SEQ ID NO: 238)
CCATCTCATCCCTGCGTGTCTCCGACTCAGTAGAGACGAGCACTGGTG
TGAGTCA
```

Light Chain Anti-Sense Primers:

```
MID34:
                                             (SEQ ID NO: 239)
CCATCTCATCCCTGCGTGTCTCCGACTCAGcacgctacgtCACTGGTG
TGAGTCA MID66:
                                             (SEQ ID NO: 240)
CCATCTCATCCCTGCGTGTCTCCGACTCAGTCACGCGAGACACTGGTG
TGAGTCA MID57:
                                             (SEQ ID NO: 241)
CCATCTCATCCCTGCGTGTCTCCGACTCAGCGCGTATACACACTGGTG
TGAGTCA
```

In the above sequences, the underline and italic sequences are for 2 step PCR amplification, the underline sequences are for the 454 sequencing, the bolded sequences are the 454 key, the lower case sequences are barcode for multiplexing and the regular font capitalized sequences are mouse-specific sequences.

The PCR reactions were set up using the above-primers as outlined in Table 11.

TABLE 11

(First round Heavy chain PCR set-up)

| Sample | Sense primers | Anti-sense primers |
| --- | --- | --- |
| 1 | $V_H1.1$ | IgG1, IgG2a, IgG2b, IgG3 |
| 2 | $V_H1.2$ | IgG1, IgG2a, IgG2b, IgG3 |
| 3 | $V_H1.3$ | IgG1, IgG2a, IgG2b, IgG3 |
| 4 | $V_H2$ | IgG1, IgG2a, IgG2b, IgG3 |
| 5 | $V_H3$ | IgG1, IgG2a, IgG2b, IgG3 |
| 6 | $V_H5$ | IgG1, IgG2a, IgG2b, IgG3 |
| 7 | $V_H4$ & $V_H6$-8 | IgG1, IgG2a, IgG2b, IgG3 |
| 8 | $V_H9$-15 | IgG1, IgG2a, IgG2b, IgG3 |

For the first round, a 50 µL heavy chain PCR reaction contained 0.2 µM of each sense primer (5 sense primers per reaction) and 0.2 µM of each anti-sense primer (4 anti-sense primers per reaction), 10 µL of 5× Phusion HF reaction buffer (Finnzymes (part of Thermos Scientific), cat#F-518), 1 µL of cDNA, 0.2 µM dNTP (NEB, cat#N0447), 1 µL of Phusion Hot Start II DNA polymerase (Finnzymes, cat#F-549L) and 28 µL RT-PCR Grade water (Ambion (a Life Technologies company), Austin, Tex., cat#AM9935). For the first round, a 50 µL light chain PCR reaction contained 0.2 µM of the sense primer and 0.2 µM of the anti-sense primer, 10 µL of 5× Phusion HF reaction buffer (Finnzymes, cat#F-518), 1 µL of cDNA, 0.2 µM dNTP (NEB, cat#N0447), 1 µL of Phusion Hot Start II DNA polymerase (Finnzymes, cat#F-549L) and 35 µL RT-PCR Grade water (Ambion, cat#AM9935). The PCR thermocycle program was as follows: 98° C. for 2 min; 15 cycles (98° C. for 0.5 min, 55° C. for 0.5 min, 72° C. for 1 min); 72° C. for 5 min; 4° C. storage. PCR products were purified according to manufacturer's protocol using DNA clean and Concentrator-5 kit (Zymo Research Co., Irvine, Calif., cat#DR014).

For the second round, a 50 µL heavy chain PCR reaction contained 0.2 µM of universal sense and universal anti-sense primer 10 µL of 5× Phusion HF reaction buffer (Finnzymes, cat#F-518), 10 µL of the purified first round PCR product, 0.2 µM dNTP (NEB, cat#N0447), 1 µL of Phusion Hot Start II DNA polymerase (Finnzymes, cat#F-549L) and 19 µL RT-PCR Grade water (Ambion, cat#AM9935). The PCR thermocycle program was: 98° C. for 2 min; 10 cycles (98° C. for 0.5 min, 55° C. for 0.5 min, 72° C. for 1 min); 72° C. for 5 min; 4° C. storage. For the second round a 50 µL light chain PCR reaction contained 0.2 µM of universal sense and universal anti-sense primer 10 µL of 5× Phusion HF reaction buffer (Finnzymes, cat#F-518), 10 µL of the purified first round PCR product, 0.2 µM dNTP (NEB, cat#N0447), 1 µL of Phusion Hot Start II DNA polymerase (Finnzymes, cat#F-549L) and 19 µL RT-PCR Grade water (Ambion, cat#AM9935). The PCR thermocycle program was: 98° C. for 2 min; 8 cycles (98° C. for 0.5 min, 55° C. for 0.5 min, 72° C. for 1 min); 72° C. for 5 min; 4° C. storage. PCR products were purified according to manufacturer's protocol using AMPure XP (Agencourt; Beckman Coulter Genomics, Brea, Calif., cat#A63881) and analyzed using an Agilent 2100 BioAnalyzer.

The sequences of the PCR products are then translated into predicted amino acid sequences which are then theoretically digested (e.g., with a protease and/or a chemical protein cleavage reagent) to produce virtual peptide fragments. These virtual peptide fragments are then used to generate predicted mass spectra.

II. Generation of Actual Mass Spectra from Peptide Fragments of Polyclonal Antibodies:

Polyclonal antibodies are purified from the sera and/or plasma of an animal (e.g., from the sera and/or plasma of the animal from whom the nucleic acid sequences are obtained). To purify the antibodies, the following methods are used:

Protein-G Purification:

1 mL of magnetic protein-G beads (Millipore (Billerica, Mass.), cat# LSKMAGG 10) were added to each of four 15 mL conical tubes (Falcon (BD Biosciences, Franklin Lake, N.J.), cat#352097). The beads in each tube were washed twice with 10 mL of phosphate buffered saline pH7.4, 0.05% Tween-20 (PBST) and three times with 10 mL of PBS. Sera from three mice (ID 1262-2, 1262-4, 1263-4) were pooled together and diluted ten-fold to a final volume of 6 ml in PBS. 1.5 ml of the combined, diluted sera was then added to each tube of beads and incubated overnight at 4° C. The flow through was collected and put through the purification process another two times. After the flow through was collected each tube was washed two times with 10 mL PBST and three times with 10 mL of PBS. Each tube was then incubated at 4° C. for 30 minutes with 0.5 mL of 0.1M pH 2.7 glycine to elute the IgG. The elution was repeated five times. All eluates were neutralized with 1M Tris pH 8.5, dialyzed overnight against PBS and protein concentration was measured with an ND-1000 spectrophotometer (Nanodrop). In total 2.5 mg of IgG was purified.

Antigen Column Preparation:

5.0 mL of fresh streptavidin (SA) magnetic beads (Pierce, cat#88817) were washed three times with 10 mL PBS, and incubated overnight at 4° C. with 105 uL of a 20 mg/ml stock of biotin p-ERK peptide (a biotinylated form of Catalog No. 1150 commercially available from Cell Signaling Technology, Inc., Danvers, Mass.) diluted in 5.0 mL of PBS. Flow through was discarded and beads were washed three times with 10 mL of PBS and aliquoted into 10 low binding 1.7 mL tubes (Axygen (Union City, Calif.), cat# MCT-175-L-C). Aliquoted beads were placed on a magnetic rack (Invitrogen, DynaMag) and PBS was removed prior to adding the dilute seras.

Antigen-Specific Purification:

Protein-G purified IgG from above was added to the SA-magnetic beads coupled with biotin P-Erk peptide. After overnight incubation at 4° C. the flow through was collected and the beads were washed with PBS-containing buffers.

IgG was then eluted with 5 fractions of 1.5 mL 0.1M Glycine pH 3.5, then 5 fractions of 1.5 mL 0.1M Glycine pH 2.7, then 5 fractions of 1.5 mL 0.1M Glycine pH 1.8 and neutralized with 1M Tris pH 8.5. Eluates were assayed for P-ERK (i.e., phosphorylated ERK kinase, the antigen used to immunize the mice) reactivity using 96-well plates coated with p-ERK-BSA peptide. Fractions with activity were quantitated by ELISA (Thermo, cat#23300) and assayed for p-ERK reactivity by Western blot using lysates from Jurkat T cells (e.g., commercially available from the American Type Culture Collection or ATCC, Manassas, Va.) treated with either 20 uM U0126 for 1 hour or 200 nM Tetradecanoyl-Phorbol-Myristic Acid (TPA) for 15 minutes. The fractions with the cleanest p-ERK-reactivity were analyzed by mass spectrometry.

Mass Spectrometry Analysis

The antibody-containing fractions were digested with at least one protease (e.g., trypsin) and/or at least one chemical protein cleavage reaction, and the resulting peptides subjected to analysis using mass spectrometry. The mass spectrometry analysis methods used to analyze the peptides are standard and have been described before in detail. (see, e.g., U.S. Pat. No. 7,300,753; Geiger et al., Nature Methods 7: 383-385, 2010; Elias and Gygi, Nature Methods 4: 207-214, 2007; Keshishian et al., Molecular and Cellular Proteomics 6: 2212-2229, 2007, all of which are hereby incorporated by reference in their entireties).

As described above (see, e.g., Example 3), the mass spectra were analyzed using as a reference the information in the genetic material database. To do this, MS2 spectra are collected and then correlated one-by-one to predicted MS2 spectra from reference sequences (i.e., from the genetic material database) using a standard computational program that finds a match for every MS2 spectrum, even when it is not a good quality spectrum or a good match. Such programs are commercially available. For example, the Sequest software can be obtained as part of the Sorcerer software package from Sage-N Research, Inc. (Milpitas, Calif.). The spectra that are identified as being good quality spectra or good matches to the genetic material database are mapped onto the reference sequences from the genetic material database. If a peptide MS2 can be mapped to more than one distinct component of the genetic database, it is unclear which component was present in the antigen-binding polyclonal antibody fraction as it could be one or more of those identified components. Thus, the process is repeated, and with repetition, evidence can be collected to show that some components correlate with collected MS spectra better than others. In other words, much of their variable region sequences are observed as MS2 spectra after enrichment by antigen binding. These elements are assumed to encode true antigen binding antibodies, and thus their sequences are constructed (e.g., on a synthetic oligonucleotide generator), cloned into an expression plasmid (e.g., pcDNA3.1 from Invitrogen), expressed in cells, and tested for antigen binding.

Results

Figure 6:
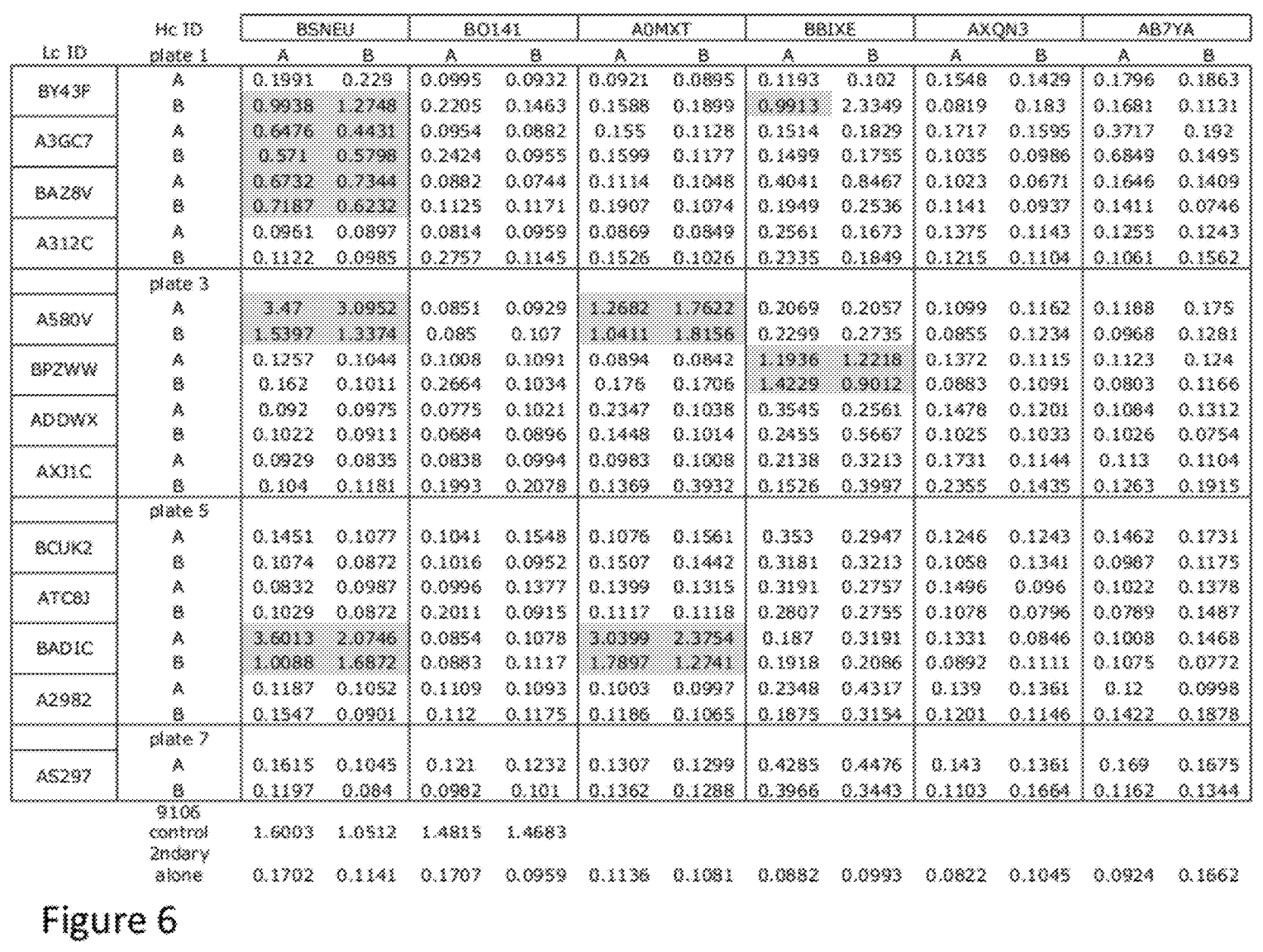

As shown in FIG. 5, the correlation of the actual mass spectrometry results from the peptide fragments with the theoretical mass spectrometry information from the nucleic acid sequences allowed the identification the sequences of heavy and light chain fragments. Those peptides that had the highest degree of confidence as far as mass spectrometry coverage is concerned and correlation to the nucleic acid sequences are shown. The nucleic acid sequence encoding the full length chain comprising the actual peptide fragments was synthesized and cloned into a recombinant expression vector. By random pairing, heavy and light chains were combined and expressed together in a cell to produce (i.e., create) recombinant antibodies (see, e.g., method of U.S. Pat. Nos. 4,816,397; 4,816,567; and US patent application no. 20110045534). FIG. 6 is a table showing the results of an ELISA experiment using pERK-coated plates. As can be seen, several pairings of the chains identified in FIG. 5 resulted in antibodies that were able to specifically bind to the p-ERK-coated plates (positive antibodies shown in yellow in FIG. 6, and the positive peptides are shown in red in FIG. 5).

Surprisingly, these results showed that neither frequency of peptide occurrence alone nor frequency of CDR3 count alone predicted usage of a particular antibody chain that specifically bound to the antigen. For example, light chain nucleic acid sequence ref. no. G623FKB01A3GC7 matched to 235 peptides from LC-MS/MS (i.e., liquid chromatography, tandem mass spectrometry) analysis and light chain nucleic acid sequence ref. no. G623FKB01AXJ1C had a sequence that appeared in 1068 times in a single NGS run (see FIG. 5, lower table). However, neither of these, when combined with a heavy chain, was actually able to form an antibody that could specifically bind to the pERK antigen. This result is very surprising and showed that method of Reddy et al., Nature Biotechnology 28(9):965-969, 2010, which relied solely on nucleic acid sequence frequency from the NGS analysis, would have missed the true antigen-binding sequence. Thus, the methods described herein can be used reliably to identify and isolate an antibody that specifically binds to a chosen antigen.

Example 6

An antigen-specific rabbit antibody was generated in accordance with the methods described herein. To do this, the following protocols were followed.

Rabbit Splenocyte RNA Purification

The p-MET antigen (Cell Signaling Technology, Inc., Danvers, Mass. Catalog #1645) was used to immunize rabbits using standard methods. Immunized rabbits who had antigen-specific sera (i.e., sera containing polyclonal antibodies that specifically bound to the immunizing antigen) were sacrificed after a final antigen injection (boost). 50 ml of blood was collected and spleen or other lymphoid organs was collected. 10 million splenocytes were used for RNA purification. Serum and/or plasma from the 50 ml collected blood was also set aside for antigen specific antibody affinity purification.

RNA was purified from splenocytes using Qiagen's RNeasy kit (Qiagen cat#74104) following the manufacturer's protocol. On column DNase I-treatment was conducted to eliminate contaminating genomic DNA by incorporating a DNase I digest step. After the RW1 buffer wash, DNase I (Qiagen cat#79254) diluted in RDD buffer was applied to the RNA purification column and incubated for 20 minutes at room temperature. The column was then washed once more with RW1 buffer, followed by two washes with RPE buffer, and the RNA was eluted with either 30 or 50 µl water. The concentration of the RNA was determined by absorbance measured on a Nanodrop spectrophotometer (Thermo Scientific) at wavelength 450 nm.

cDNA Synthesis and Generation of Amplicons by PCR

RNA isolated from rabbit splenocytes was first reverse transcribed using Invitrogen's Thermoscript reverse transcriptase (Invitrogen cat#12236-022) as shown below:

| DNase treated RNA: | 5 uL |
| Oligo dT primer(50 uM): | 1 uL |
| dNTP's (10 mM): | 2 uL |
| dI H2O: | 4 uL |

Incubate at 65° C. for 5 min, place on ice for 2 minutes, then add the following:

| 5X cDNA buffer: | 4 uL |
| 0.1 mM DTT: | 1 uL |
| RNAse OUT: | 1 uL |
| dI H2O: | 1 uL |
| ThermoScript: | 1 uL |

The mixture was incubated at 50° C. for 1 hour, followed by a heat-inactivation step at 85° C. for 5 minutes. Finally, the complementary RNA strand was eliminated from the cDNA by adding 1 µl of RNase H (Invitrogen (Carlsbad, Calif.), cat#18021-071) and incubating at 37° C. for 20 minutes.

Amplicons of heavy, kappa and lambda chain variable regions for sequencing were generated by PCR as follows.

Heavy Chain Fusion Primers:

```
Reverse
MID11
                                         (SEQ ID NO: 242)
CCATCTCATCCCTGCGTGTCTCCGACTCAGtgatacgtctGGGCCAG
TGGGAAGACTGATGG Forward
                                         (SEQ ID NO: 243)
CCTATCCCCTGTGTGCCTTGGCAGTCTCAGatcagacacgATGGAGA
CTGGGCTGCGCT
```

Kappa Chain Fusion Primers

```
Reverse
MID16
                                         (SEQ ID NO: 244)
CCATCTCATCCCTGCGTGTCTCCGACTCAGtcacgtactaGAAGAGGA
GGACAGWAGGCGC Forward
                                         (SEQ ID NO: 245)
CCTATCCCCTGTGTGCCTTGGCAGTCTCAGATGGACATGAGGGCCCCC
```

Lambda Chain Fusion Primers

```
Reverse
MID39
                                         (SEQ ID NO: 246)
CCATCTCATCCCTGCGTGTCTCCGACTCAGtacagatcgtCTTGTTGT
CCTTGAGTTCCTCAGAGGA Forward
                                         (SEQ ID NO: 247)
CCTATCCCCTGTGTGCCTTGGCAGTCTCAGATGGCCTGCACCCCG
```

In the above sequences, the underline sequences are for the 454 sequencing, the bolded sequences are 454 key, the lower case sequences are barcode for multiplexing and the regular font capitalized sequences are rabbit-specific sequences.

PCR amplification was done using Finnzyme's Phusion Hot Start II polymerase (Thermo Scientific cat# F-540S) where the reaction mix and conditions were set up as shown below:

Reaction Mixture:

| | |
|---|---|
| cDNA: | 2.5 uL |
| 5X Buffer GC: | 5 uL |
| 10 mM dNTP mix: | 0.25 uL |
| Phusion HotStart II: | 0.25 uL |
| Primers (forward + reverse) 30 uM: | 0.25 uL |
| Water: | 16.75 uL |

PCR Program:

| |
|---|
| Step 1 98° C. - 1.5 minutes |
| Step 2 98° C. - 10 seconds |
| Step 3 60° C. - 30 seconds |
| Step 4 72° C. -30 seconds |
| Step 5 Repeat steps 2 through 4, 20 times |
| Step 6 72° C. - 2 minutes |
| Step 7 - hold |

Figure 7:
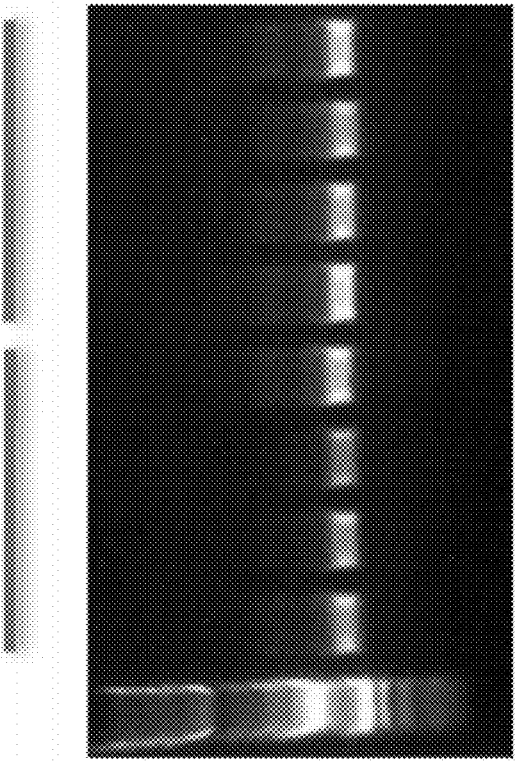
FIG. 7 is a photographic representation of an agarose gel showing the results of an RT-PCR reaction (i.e., reverse-transcriptase-polymerase chain reaction) of heavy chains and kappa and lambda light chains from cDNA generated from splenocytes of rabbits immunized with p-MET antigen.

To ensure the absence of any false amplification from contaminating template in any of the reagents, duplicate reactions were set up for each mixture (4 separate reactions for heavy chain, and one for each light chain) where the cDNA template was substituted with water. These negative control reactions with no template were run at the same time as the samples containing template. Upon completion of the PCR program, 3 μl of each reaction (including the negative controls) were analyzed by electrophoresis on a 1.5% TAE agarose gel for the presence of the amplicons when template was added to the reaction but not in the absence of cDNA. FIG. 7 shows the results of these electrophoresis gels.

Amplicon Purification, Analysis, Quantitation, and Preparation for 454 Sequencing In order to eliminate excess primers and/or primer dimmers in the PCR samples, amplicons were purified using Agentcourt Ampure magnetic beads (Beckman Coulter cat#A63881) following the manufacturer's protocol (000387v001). The eluted amplicons after Ampure purification were then analyzed for purity and absence of any contaminating DNA species on the Agilent 2100 Bioanalyzer using the high sensitivity DNA chip (Agilent Technologies cat#5067-4626) by following the manufacturer's protocol.

Once the purity of amplicons was verified, the concentration of the DNA was quantified on a fluorometer using the Quant-iT PicoGreen dsDNA Assay Kit (Invitrogen cat#P7589) as described in the manufacturer's protocol. The Lambda DNA provided in the kit was used as a concentration standard with which a standard curve was generated from 100 ng/well to 1.56 ng/well. The fluorescence of each amplicon diluted 100-fold in TE buffer was measured in duplicate, and the concentration of DNA was determined according to the linear portion of the standard curve. All fluorescence measurements were done in black 96-well plates. If the value of fluorescence was out of the linear range of the standard curve, the samples were remeasured with either larger or smaller dilutions in order to capture fluorescence values that fall within the linear range. Using the approximate size in base pairs of each chain type (heavy-540 bp, kappa-485 bp and lambda-510 bp), the following formula was used to determine the concentration:

Concentration of each amplicon(molecules/μl)= [sample conc(ng/μl)*6.022×10$^{23}$]/[656.6× 10$^9$*amplicon length(bp)]

Each amplicon was normalized to 1×10$^7$ molecules/μl, then mixed at a ratio of heavy chain:kappa chain:lambda chain at 3:3:1 by volume, vortexed, and finally diluted 1:10 to obtain a final concentration of the mixture at 1×10$^6$ molecules/μl.

Emulsion PCR Amplification, Bead Enrichment, Bead Counting and Sequencing

Emulsion PCR was conducted following the 454 published protocol: "emPCR Amplification Method Manual—Lib-L" (Edition: May 2010 (Rev. April 2011, herein incorporated by reference in its entirety) with the following modifications:

Section 3.1.3 Step 2)

| Reagent | Volume (μl) |
|---|---|
| Mol. Bio. Grade water | 458 |
| Additive | 515 |
| Amp Mix | 270 |
| Amp Primer | 32 |
| Enzyme Mix | 70 |
| PPiase | 2 |
| Total | 1347 |

Once the sequencing beads were enriched, from step 3.7 of "emPCR Amplification Method Manual—Lib-L", the beads were counted on Beckman Coulter's Z2 Particle Counter with the following settings:

| | |
|---|---|
| Aperture: | <100 μm> |
| Aperture Kd: | <60.04> |
| Set Upper cutoff: | <30.00 μm> |
| Set Lower cutoff: | <10.00 μm> |
| Count Mode: | <between> |
| Metered Volume: | <0.5 ml> |
| Resolution: | <256> |

The concentration of beads was calculated as:

Concentration of beads=[Avg. reading from particle counter*4]beads/μl

The enriched beads from the emulsion PCR were sequenced on the 454 Sequencer (Roche) following the 454 sequencing protocol for GS FLX+ or GS Junior.

The peptide fragments of the polyclonal antibodies collected from the sera of immunized rabbits were generated as described above for mice (see, for example, Example 6). Briefly, the following protocol was used.

Peptide-Affinity Purification of Rabbit IgG

1. Re-suspend the peptide-affinity resin and take 0.4 ml of the slurry into a new column (Bio-rad, 731-1550, 0.8×4 cm), and this should make 0.2 ml settled purification resin. If necessary, make a control column of either blank resin or an un-related peptide-affinity resin of equal volume. The blank resin was made with no peptide in the conjugation process.
2. Wash the column with 10 ml PBS, and let it drain completely.
3. Load the Protein-A purified total IgG. Cap the bottom first and wrap with paraffin. Add 3-5 ml of total IgG. Cap the top and wrap with paraffin.
4. Rotate on a roller for 15 min at RT.
5. Collect the flow through. Un-cap the top first, then the bottom, let the column drain completely.
6. Wash with 10 ml PBS, 3 times (wash the column wall to make sure that all the resin is packed at the bottom).
7. Wash with 10 ml 1×RIPA.
8. Wash with 10 ml 20% Acetonitrile in PBS pH7.4.
9. Wash with 10 ml 60% Ethylene glycol in PBS pH7.4.

10. Wash with 10 ml 2.0M NaCl in PBS, 017.4.
11. Elute with 5 ml 0.1M Glycine pH3.5, neutralized immediately with 70 ul 1M Tris pH8.5.
12. Elute with 5 ml 0.1M Glycine pH2.7, neutralized immediately with 300 ul 1M Tris pH8.5.
13. Elute with 5 ml 0.1M Glycine pH1.8, neutralized immediately with 800 ul 1M Tris pH8.5.
14. All or the fractions of interest are measured for IgG concentration using Rabbit IgG ELISA plates (provided by Molecular assay/ELISA group).
15. The antigen-specific activity can be assessed using ELISA and/or Western blot. The specific activity can also be assessed after normalizing all fractions to the same concentration.
16. Purified antibody materials are ready to be processed for LC-MS/MS Liquid chromatography-tandem mass spectrometry (LC-MS/MS) analysis was performed on peptides from the purified antibodies (i.e., the purified antibodies were digested and the peptides analyzed) as described above. The resulting mass spectra were correlated with the theoretical mass spectrometry data based on information in the genetic material database.

Figure 9:
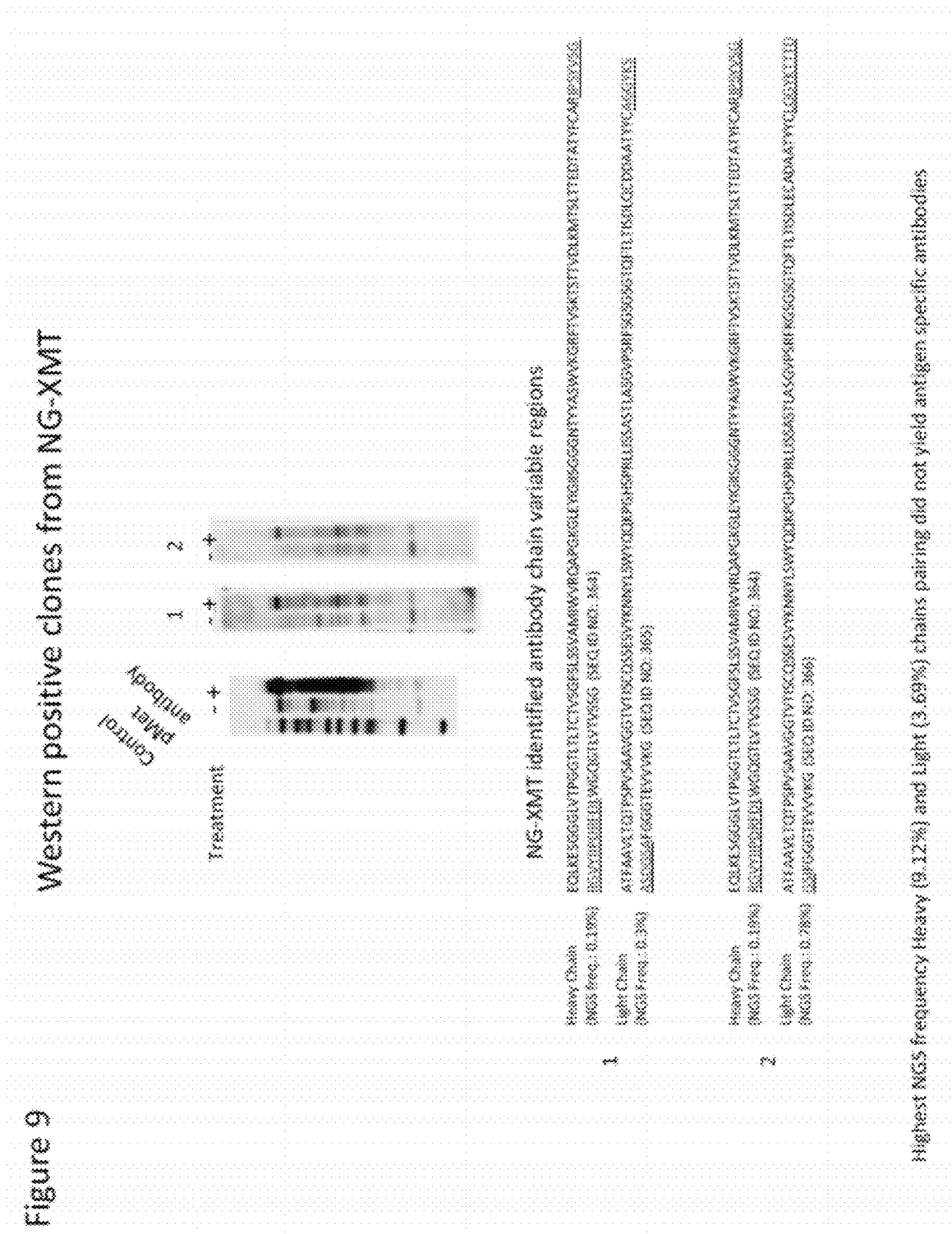
FIG. 9 is a photographic representation showing the results of a Western blotting experiment probing lysates prepared from Hela cells untreated (−lanes in all three blots) or treated with human growth factor (HGF) (+lanes in all three blots) with two different rabbit antibodies generated using a non-limiting method of the invention (blots labeled 1 and 2) and with a control antibody (left-most blots). Following positive results with Western blotting, antigen specific antibodies (heavy and light chain pairing) were then identified. As shown, the antibodies identified in both lanes 1 and 2 used the same heavy chain, but had different light chains. The amino acid sequences of the heavy and light chains of the two rabbit antibodies are shown below the Western blotting results, with the CDR3 regions of the heavy and light chains being underlined.

As shown in the table set forth in FIG. 8, a number of heavy and light chain peptides were identified by correlating the actual (i.e., observed) mass spectrometry of the peptides with the theoretical mass spectrometry data from the nucleic acid sequences. The frequency of occurrence of these peptides is shown in the right-most lane of the table. These chains were chosen based on their coverage of CDR3 (in most cases 100%), and the underlying nucleotide sequences retrieved from the genetic material database and synthesized. Six heavy chain was randomly combined with five light chain (shown in red in FIG. 8), and the resulting antibodies tested using ELISA (with antigen-coated plates) and Western blotting analysis (against Hela cells untreated (−lanes) or treated with Human Growth Factor (+lanes), where the HGF-treated cells are known to express the p-MET antigen. The results of the Western blotting analysis are shown in FIG. 9. A p-MET specific antibody (commercially available from Cell Signaling Technology, Inc., Danvers, Mass., catalog no. 3126) was used as a control. The antibodies generated in accordance with the methods described herein that showed high specific binding to the antigen in the cell lysates are shown in bold red in FIG. 8 (i.e., heavy chain ref nos. GXRYQP201BIQD2 and GXRYQP201A97DZ and light chain ref nos. GXRYQP201A291T and GXRYQP201BRIWK and GXRYQP201ALDF5). Note that FIG. 9 shows only two of the 6 different antibodies that specifically bound to antigen generated in this example (i.e., FIG. 9 shows only the two antibodies that use the GXRYQP201BIQD2 heavy chain coupled with the GXRYQP201A291T light chain and the GXRYQP201BRIWK light chain.

Again, as observed with the mouse antibody, the chains with the highest frequency did not result in formation of an antigen-specific antibody (compare heavy chain GXRYQP201A1C3B, which had a frequency of 9.12% but did not specifically bind antigen with heavy chain GXRYQP201 BIQD2 which had a frequency of only 0.19% but did specifically bind antigen).

Example 7

This Example describes generation of monoclonal antibodies from rabbits immunized with four different antigens and from mice immunized with an additional different antigen (Table 12) using the approach described hereinabove, further demonstrating that the present approach is robust and reproducible in at least two laboratory animal species.

TABLE 12

Functionally relevant monoclonal antibodies against multiple targets identified by the NGS/LC-MS/MS platform tested by ELISA and Western blot (WB).

| Antigen | Immunized species | High confidence heavy + light chains | Unique ELISA+ clones | Unique WB+ clones |
| --- | --- | --- | --- | --- |
| PR A/B | Rabbit | 8 + 10 | 12 | 6 |
| pMET | Rabbit | 11 + 10 | 6 | 4 |
| Lin28A | Rabbit | 7 + 4 | 5 | 5 |
| Sox1 | Rabbit | 9 + 5 | 12 | 1 |
| p-p44/42 | Mouse | 12 + 13 | 15 | 3 |

Figure 10A:
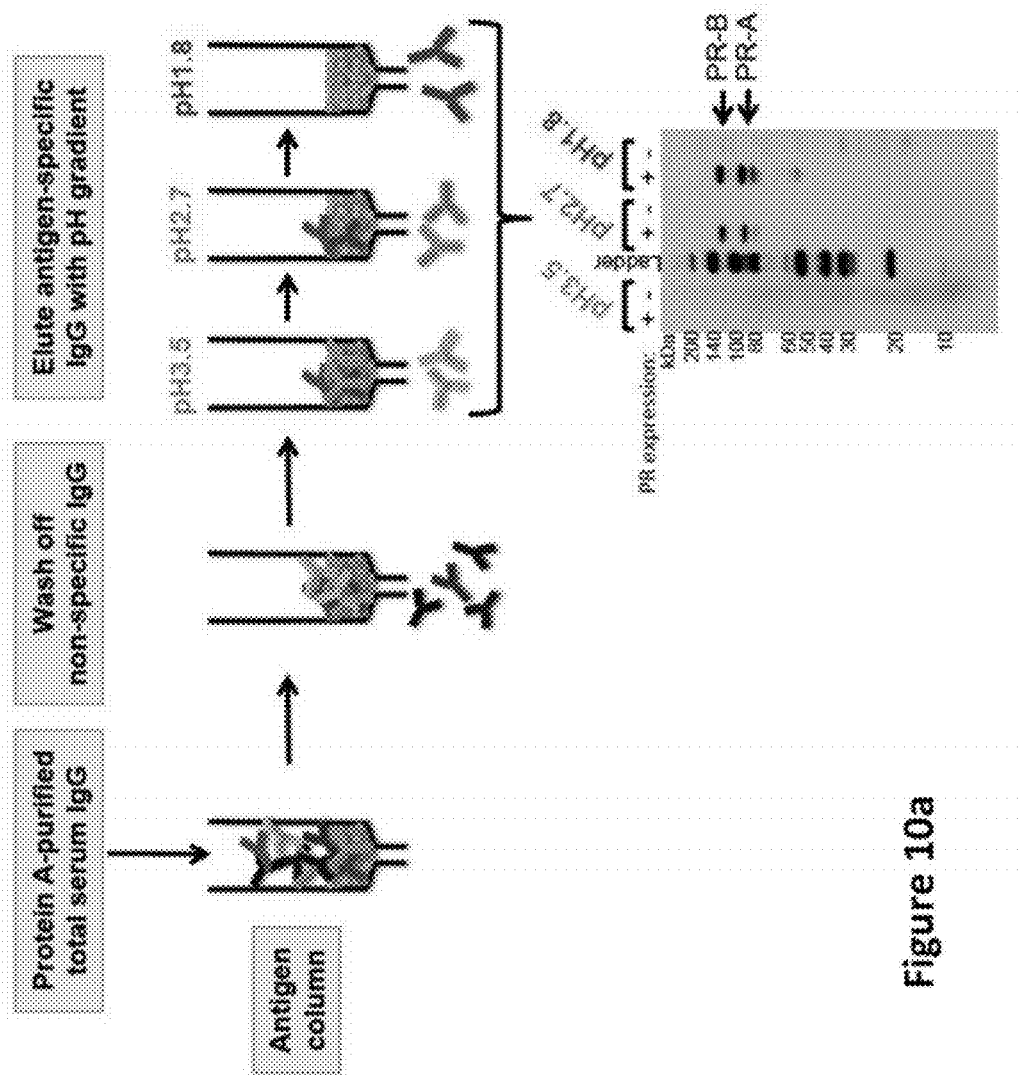

New Zealand white rabbits were immunized with human Progesterone Receptor A/B specific (PR A/B) peptides conjugated to keyhole limpet hemocyanin (KLH). Antigen-specific antibody activity in the crude serum of each animal was screened to select the rabbit with the highest ELISA and Western blot signals to PR A/B. Serum from this animal was collected from 20 mL of blood, and RNA was obtained from splenic B cells. Total γ immunoglobulin (IgG) was isolated from the serum using a protein A sepharose column, and antigen-specific polyclonal antibodies were purified by affinity chromatography using a custom column consisting of antigen-specific peptide conjugated to sepharose beads. Bound IgGs were washed extensively with PBS then subjected to sequential elutions with progressively acidic buffers (pH 3.5, pH 2.7 and pH 1.8) (FIG. 10a). Fractions from each elution were collected, neutralized, and screened by antigen specific ELISA and Western blotting of lysate from the PR A/B expressing cell line T47D and the PR A/B negative cell line HT1080 (FIG. 10a). It was found that PR A/B Western blot specific activity was greatly enriched in the pH 1.8 fraction, to a lesser extent in the pH 2.7 fraction, and was undetectable in the pH 3.5 fraction when the polyclonal fraction was concentration matched. The pH1.8 fraction was therefore used for LC-MS/MS analysis.

To generate a custom database of Ig V-region sequences by NGS, RNA was isolated from total splenocytes collected from the same animal that showed strong specific activity to PR A/B. Ig heavy and light chain variable region amplicons were generated using rabbit Ig-specific γ and κ chain primers to amplify the entire V-region. Primers contained barcodes and followed the specific requirements for 454 titanium fusion primer design for the Roche 454 NGS platform. To increase the number of V-region sequences collected, we combined three 454 GS Junior sequencing runs consisting of γ and κ chains that resulted in a total of 80,000 passed filter reads, of which 44,363 contained the entire V-region and provided the basis for the proteomic approach described below. Sequences collected included 5,279 unique γ chain complementarity determining region 3 (CDR3) sequences and 11,681 unique κ chain CDR3 sequences of varying length that followed a Gaussian distribution. Consistent with previous data, this rabbit preferentially used VH1 (V1S69+V1S40>64%) followed by VH4 (V1S44+V1S45~30%) in heavy chain VDJ rearrangement (Becker et al., *Eur J Immunol* 20: 397-402, 1990, Knight, *Annu Rev Immunol* 10: 593-616, 1992, Mage et al., *Dev Comp Immunol* 30: 137-153, 2006).

Figure 10C:
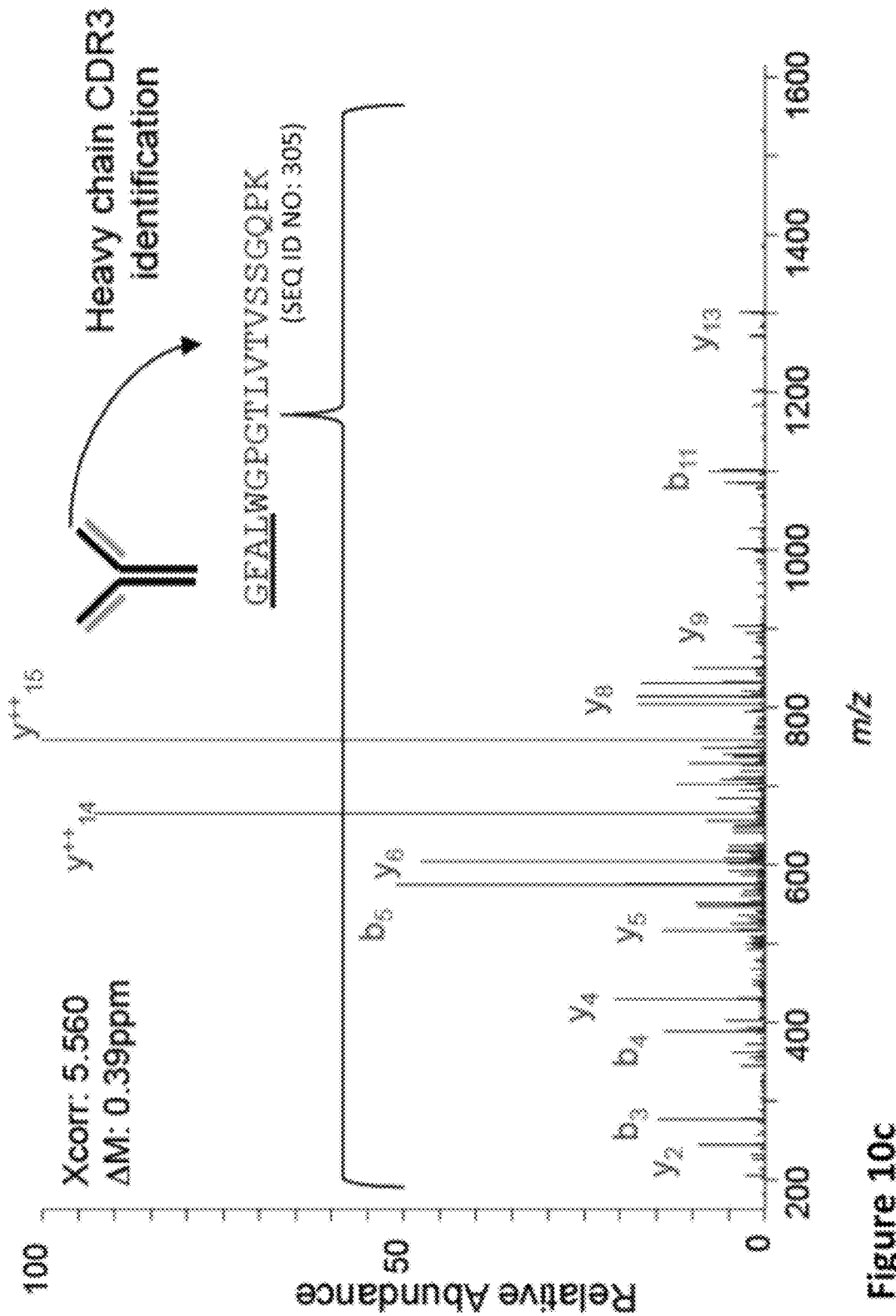

Next, the pH 1.8 fraction was examined by LC-MS/MS based on its previous activity (FIG. 10a). To maximize sequence coverage, 5 ug of polyclonal antibody was divided evenly and digested separately by chymotrypsin, elastase, pepsin and trypsin. A total of four LC-MS/MS runs using a 45-minute gradient were collected using an Orbitrap Velos (Thermo Fisher), producing an average of 10,000 spectra per run (FIG. 10b). To estimate the false-discovery rate (FDR), the target/decoy approach was used by generating a composite database of forward and reverse-oriented sequences (Elias et al., *Nat Methods* 4: 207-214, 2007), and each LC-MS/MS run was searched using the SEQUEST (Yates et al., *Anal Chem* 67: 1426-1436, 1995) program. Peptide spectral matches (PSMs) were filtered to a final FDR of ≤2% using a linear discriminant analysis (Huttlin et al., *Cell* 143: 1174-1189, 2010) taking into account enzyme specificity when possible (chymotrypsin/trypsin). An example of a high confidence heavy chain CDR3 peptide identified using this method is shown in FIG. 10c. Individual runs were combined and a total of 2,356 V-region PSMs were identified with a FDR of 1.8%.

Figure 10D:
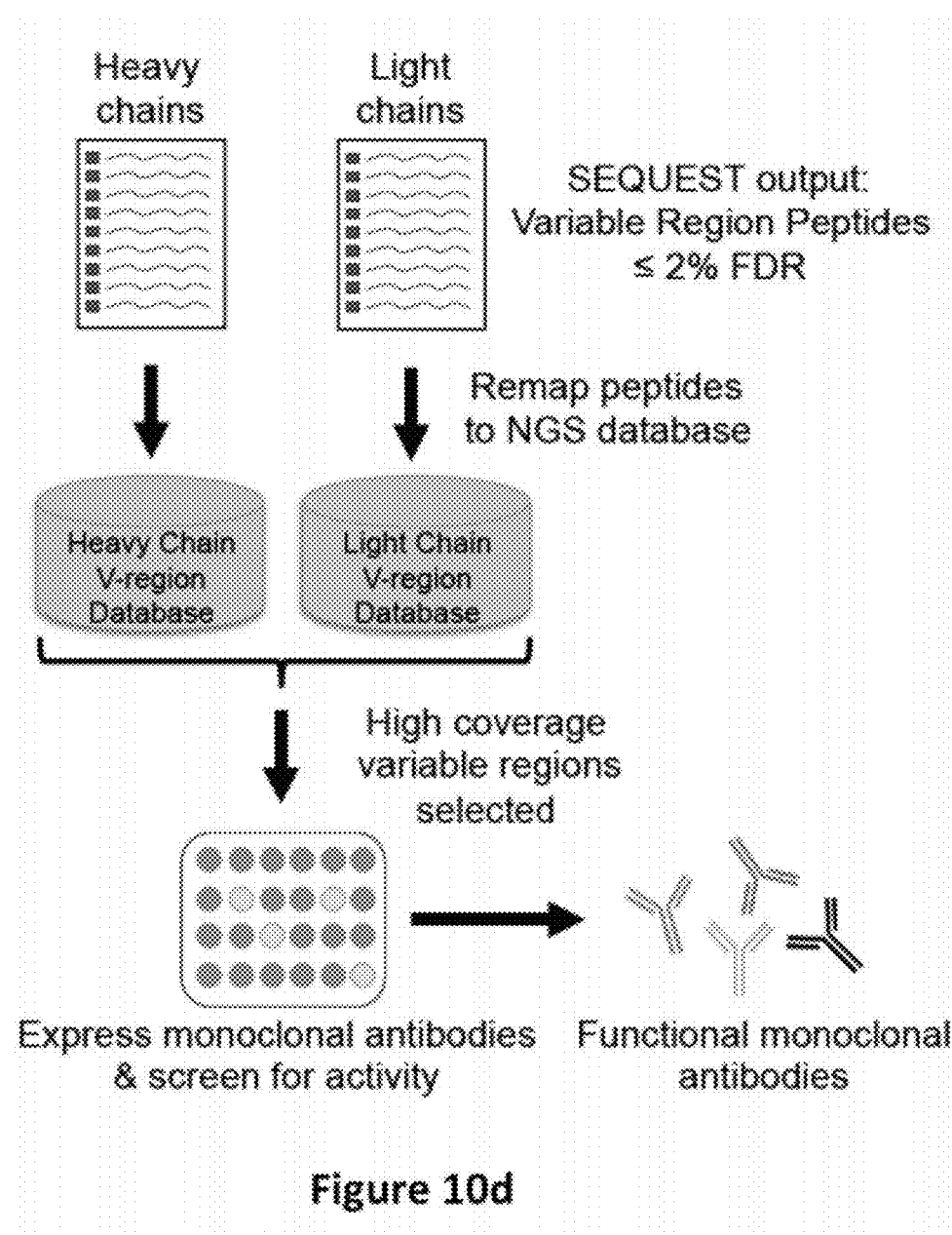
Figure 10E:
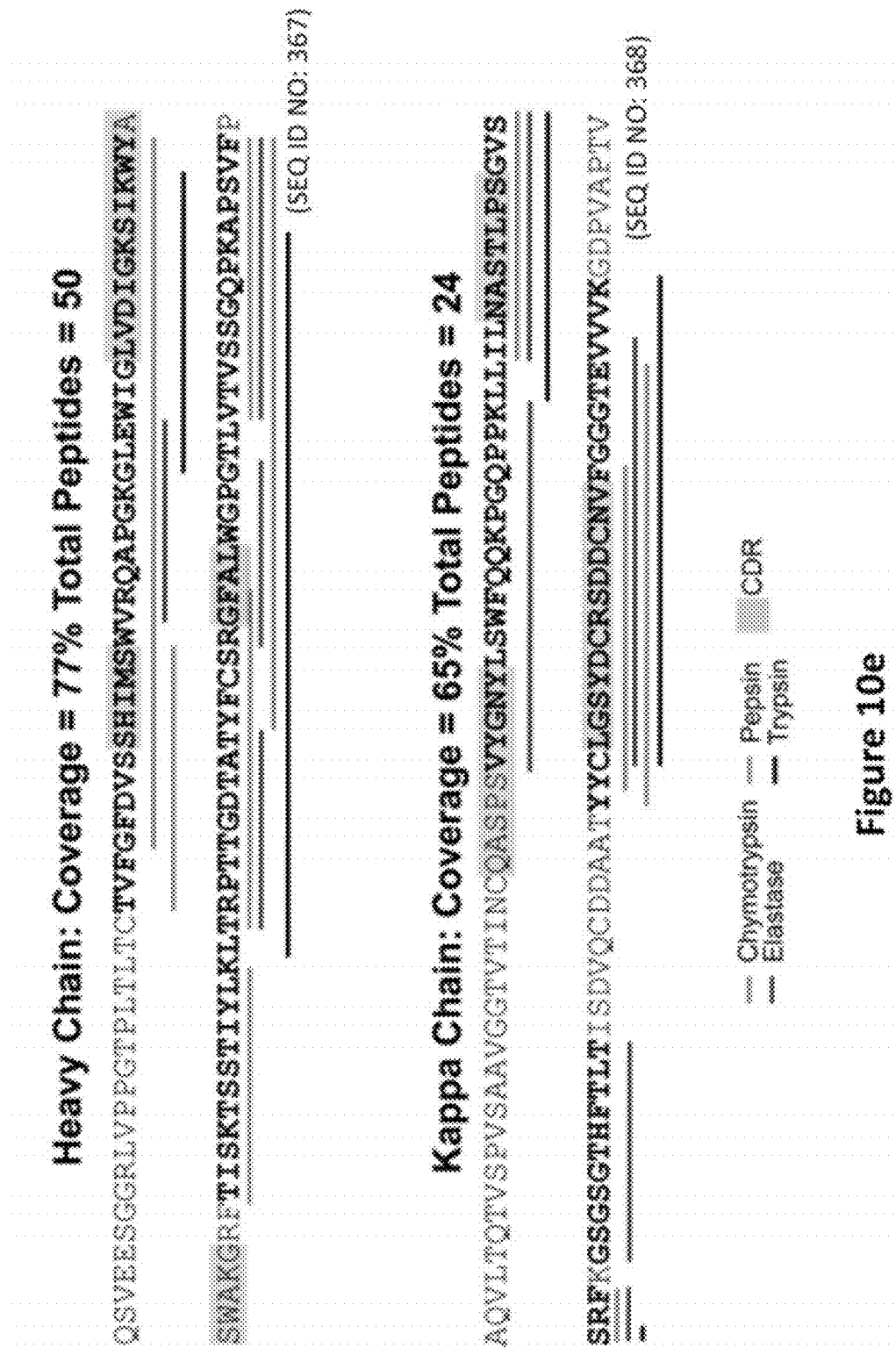

A database of antibody V-region sequences is analogous to a database of protein isoforms. As a result, traditional approaches using shotgun sequencing by LC-MS/MS in which only a few peptides are often used to confidently identify a protein are insufficient for identifying an antibody V-region sequence in a polyclonal antibody mixture. In addition, since antibody V-region sequences can vary by as little as one amino acid, high mass accuracy helped provide additional confidence in PSMs. Each V-region PSM with a mass error ≥−5 and ≤5 ppm as determined by SEQUEST was mapped back to the entire V-region database to address PSM redundancy and coverage across the dataset (FIG. 10d). After remapping, the total number of peptides, the unique number of peptides, spectrum share (total peptides mapping to sequence/total V-region PSMs), total V-region sequence coverage, and CDR3 coverage were determined for each V-region sequence. In order to identify V-region sequences with high confidence that are likely to be enriched from the polyclonal mixture, empirically stringent criteria were applied in the proteomics analysis including: a) overall high coverage (≥65%), b) at least 12 unique peptides due to high degree of homology of V-region sequences, and c) high hyper-variable region coverage, specifically, ≥95% coverage of CDR3. Although V-region sequences could be identified using one protease alone, it was found that because of the high degree of variability in V-region sequences along with the unpredictable complexity of a polyclonal mixture, it was advantageous to use multiple proteases to increase V-region coverage. For example, as shown in FIG. 10e, multiple overlapping peptide fragments from different proteases contributed to the identification of the entire CDR3 of both heavy and light chain sequences. Identifying unique PSMs across multiple runs from multiple proteases that map to the same V-region sequence increased spectral counts and coverage across the entire V-region sequence, provided higher confidence that specific V-region sequences were present in the polyclonal mixture, and further increased confidence in the NGS sequence quality (Kircher et al., *Bioessays* 32: 524-536, 2010). Using the filtering criteria described above, a total of ten γ and eight κ chain sequences of high confidence were identified from the pH 1.8 elution fraction (Table 13).

TABLE 13

Identification of high confidence heavy and light chains. Heavy and light chains with 100% CDR3 spectrtun coverage and overall ≥65% variable region coverage were identified and ranked in order of confidence as measured by total peptide count. CDR3 sequence identity and rabbit germline determination are also indicated. Heavy and light chains were chosen for gene synthesis, cloning, and expression of combinatorial antibodies for characterization. NGS rank indicates the frequency ranking of the given CDR3 sequence identified in the NGS database for each chain.

100% CDR3 Coverage and ≥65% V-region Coverage

| NGS Ref. # | Total Peptide Count | % Variable Region Coverage | CDR3 Sequence | SEQ ID NO: | NGS rank by CDR3 frequency | Germline V(D)J |
|---|---|---|---|---|---|---|
| γ chain | | | | | | |
| G2JXQJ001A2Q81 | 101 | 95.69 | KLGL | 396 | 212 | IGHV1S45, D4-2, J4 |
| G2JXQJ001AGJSJ | 91 | 92.04 | GFSL | 397 | 76 | IGHV1S69, *, J4 |
| G2JXQJ001BJE8R | 78 | 98.26 | DLGDL | 398 | 423 | IGHV1S45, D3-1, J4 |
| G2JXQJ001BT2NA | 70 | 86.21 | DLGNL | 399 | 461 | IGHV1S45, D4-1,14 |
| G2JXQJ001AFBNC | 61 | 87.27 | GNL | | 58 | IGHV1S44, D4-1, J4 |
| G2JXQJ001AL49Y | 59 | 87.72 | DFHL | 400 | 237 | IGHV1S45, *, J4 |
| G2JXQJ001BWR23 | 56 | 89.17 | GSLGTLPL | 401 | 103 | IGHV1S45, D8-1, J2 |
| G2JXQJ001BN8MH | 50 | 82.14 | GFAL | 402 | 109 | IGHV1S69, *, J4 |
| G2JXQJ001BPNUG | 48 | 81.51 | GHDDGYNYVYKL | 403 | 123 | IGHV1S69, D6-1, J4 |
| G2JXQJ001BZA42 | 35 | 95.54 | GFTL | 404 | 1417 | IGHV1S69, *, J4 |

TABLE 13-continued

Identification of high confidence heavy and light chains.
Heavy and light chains with 100% CDR3 spectrtun coverage and overall ≥65%
variable region coverage were identified and ranked in order of confidence
as measured by total peptide count. CDR3 sequence identity and rabbit
germline determination are also indicated. Heavy and light chains
were chosen for gene synthesis, cloning, and expression of combinatorial
antibodies for characterization. NGS rank indicates the frequency
ranking of the given CDR3 sequence identified in the NGS database
for each chain.

100% CDR3 Coverage and ≥65% V-region Coverage

| NGS Ref. # | Total Peptide Count | % Variable Region Coverage | CDR3 Sequence | SEQ ID NO: | NGS rank by CDR3 frequency | Germline V(D)J |
|---|---|---|---|---|---|---|
| κ chain | | | | | | |
| G2JXQJ001BJ8KJ | 93 | 87.27 | LAGYDCTTGDCFA | 405 | 2769 | IGKV1S15, J1-2 |
| G2JXQJ001BQM6D | 47 | 95.5 | LGGYDCDNGDCFT | 406 | 85 | IGKV1S15, J1-2 |
| G2JXQJ001A9VP3 | 33 | 92.79 | LGTYDCRRADCNT | 407 | 5654 | IGKV1S19, J1-2 |
| G2JXQJ001BQJFD | 28 | 98.15 | QSTLYSSTDEIV | 408 | 86 | IGKV1S10, J1-2 |
| G2JXQJ001BJCLS | 28 | 96.23 | QCSYVNSNT | 409 | 4518 | IGKV1S44, J1-2 |
| G2JXQJ001AG4TB | 24 | 65.45 | LGSYDCRSDDCNV | 411 | 179 | IGKV1S2, J1-2 |
| G2JXQJ001AIZ32 | 17 | 86.11 | LGAYDDAADNS | 411 | 252 | IGKV1S19, J1-2 |
| G2JXQJ001BJYR5 | 15 | 72.07 | LGTYDCNSADCNV | 412 | 1128 | IGKV1S15, J1-2 |

* indicates that no possible D gene can be identified.

Figure 11A:
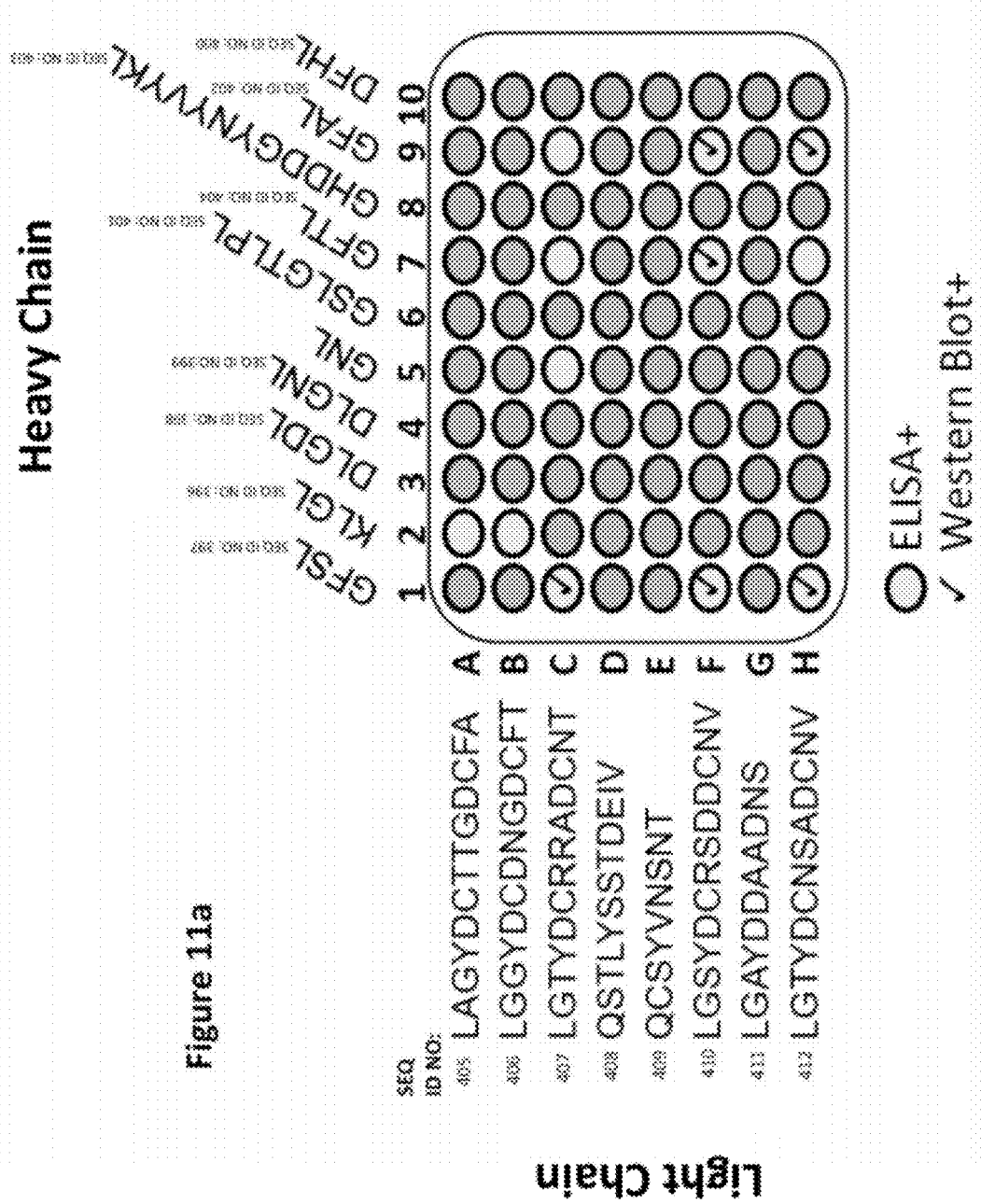
Figure 11C:
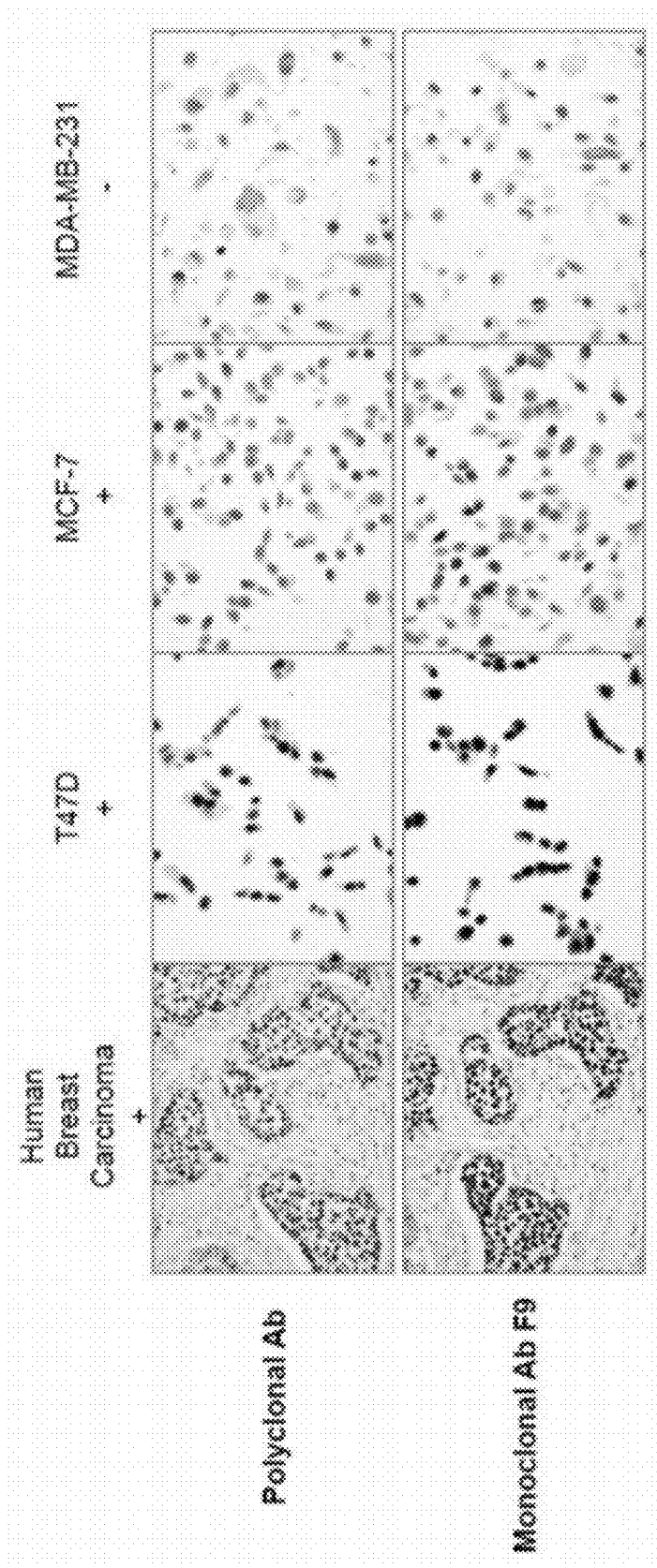
Figure 11D:
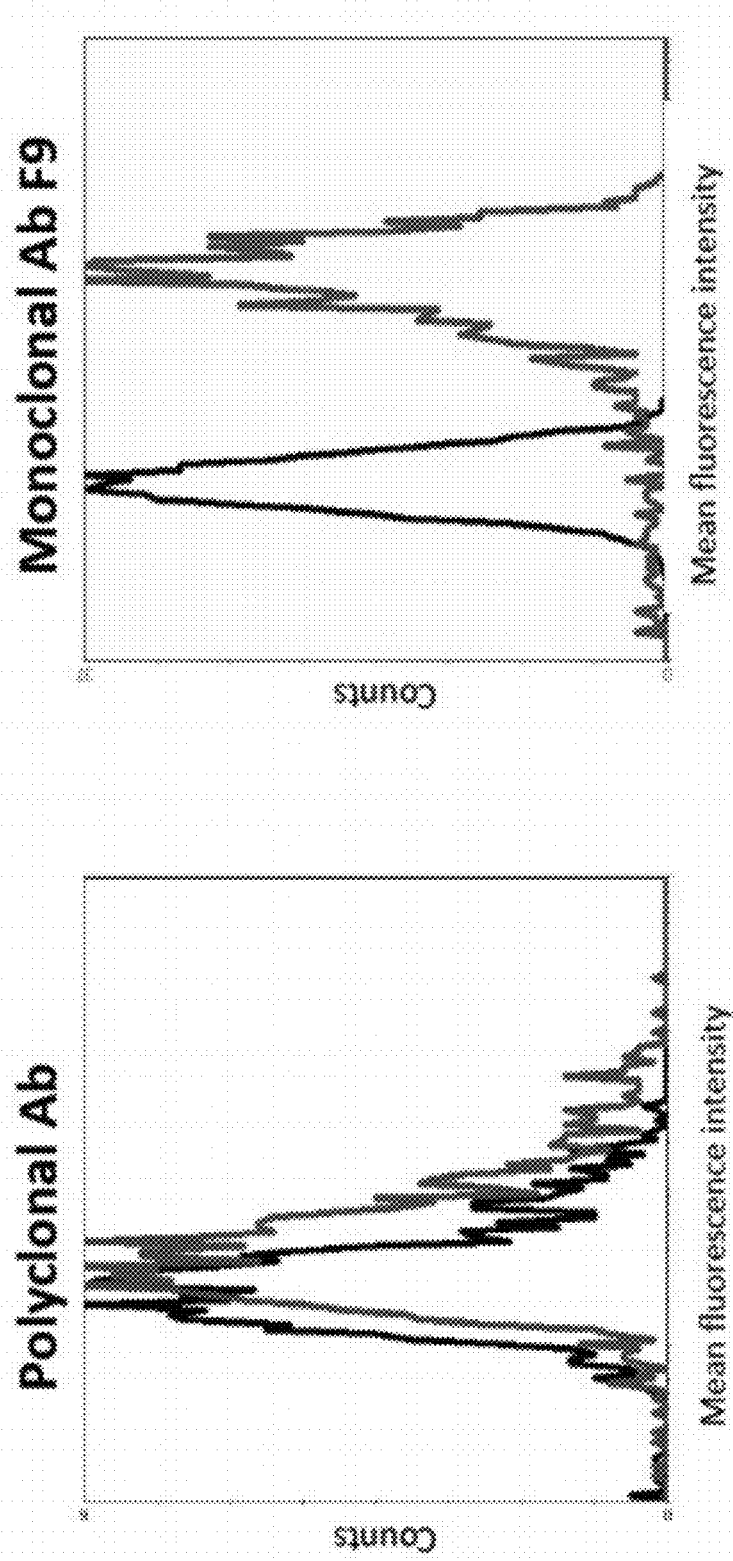
Figure 11E:
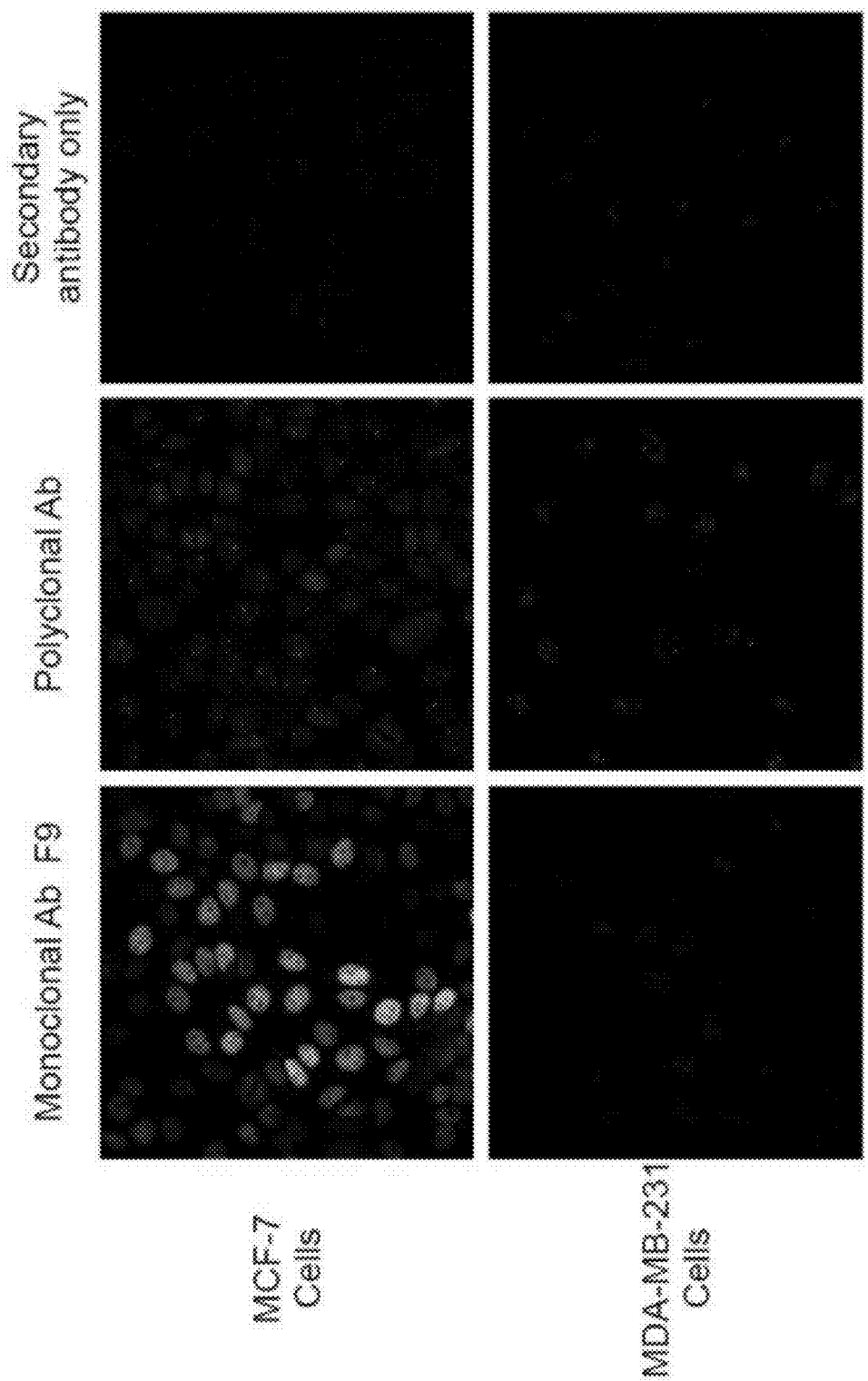

Despite providing evidence for the existence of high confidence V-region sequences present in affinity purified serum, direct information on cognate heavy and light chain pairing is absent from LC-MS/MS data due to proteolysis and the reduction of disulfide bonds during sample preparation. As a result, all possible combinations of heavy and light chain pairings were expressed (8×10 matrix for a total of 80 antibodies, in one 96-well plate transfection) in addition to the highest rank heavy and light sequences observed by NGS frequency and screened for antigen-specific binding activity to PR A/B peptide by ELISA. A total of 12 heavy and light chain pairs were positive by antigen-specific ELISA (FIG. 11a). Each antigen-specific ELISA-positive clone was then tested by Western blot for specificity against endogenously expressed PR A/B in cell lysates (FIG. 11b). Six clones were found that specifically bound to PR A/B (FIG. 11b); two clones showed a much stronger signal compared to the original polyclonal mixture when assayed at the same antibody concentration. Antigen-specific clones positive by Western blot were further characterized in additional assays. One monoclonal antibody, clone F9 and clone C1, exhibited superior signal and specificity in Western blotting and immunohistochemistry (IHC) (FIG. 11b-c) and also reacted specifically in flow cytometry (FC) and immunofluorescence (IF) assays where the polyclonal mixture failed (FIG. 11d-e). In contrast, γ and κ chains selected by virtue of their highest NGS rank did not yield antigen-specific antibodies. CDR3 containing peptides were not observed from the highest NGS rank γ and κ chains, and none of the CDR3 sequences from the 30 highest rank γ or κ chains was identified with high confidence by our proteomics approach. It could not be ruled out that the absence of activity may be due to a lack of cognate pairing, but the fact that none of these chains was observed by LC-MS/MS suggests none of the highest rank NGS chains was specific against the antigen. Thus, in these experiments antigen-specific antibodies could not be identified relying on NGS rank alone.

In order to visualize clonal diversity, phylogenetic analysis (Dereeper et al., Nucleic Acids Res 36: W465-469, 2008) was performed on high confidence heavy and light chain V-region sequences shown in Table 13. Closely related sequences for either heavy or light chain clustered into discrete groups. Interestingly, all PR A/B-specific monoclonal antibodies discovered in this report clustered closely together in the phylogenetic tree, most likely due to clonal expansion from closely related B cells during immunization. Germline usage also supported this observation (Table 13). Similar observations were made in an independent experiment with a different antigen (Lin28A, FIG. 12).

The methods used in the experiments described in this Example are as follows.

Immunization and Handling of Animals.

New Zealand white rabbits were immunized by intradermal injection with four separate doses, each 3 weeks apart, with a mixture of keyhole limpet hemocyanin-conjugated peptides derived from the amino acid sequence of different regions of each human protein antigen. Peptides were conjugated to Imject maleimide-activated KLH (Thermo-Pierce). Mouse immunizations were carried out in the same manner, except the route of immunization was intraperitoneal and the injections were 2 weeks apart. Blood was drawn at 3 days after the final boost. Whole spleen from each animal was harvested at time of euthanasia following confirmation of desired polyclonal activity.

Next Generation DNA Sequencing of Rabbit and Mouse B Cell Repertoires.

Splenocytes from hyperimmunized rabbits and mice were harvested and lysed for total RNA purification using Qiagen's RNeasy kit following the manufacturer's protocol.

The RNA was on-column treated with DNase I (Qiagen cat#79254) to eliminate genomic DNA using the provided protocol. To generate heavy and light chain amplicon libraries from this material to be sequenced with 454 Life Sciences platform (Roche), RT-PCR was carried out as follows. cDNA was generated from the splenocyte total RNA as template using Thermoscript reverse transcriptase (Invitrogen cat#12236014) with oligo dT as primer. For rabbit IgG sequencing, variable regions of γ, κ1, κ2, and λ chains were amplified with sequence specific 454 fusion primers (hybridizing to the leader on the 5' end and containing sequences on the 3' end required for identification and bar-coding in the Lib-L format of 454 sequencing platform) using Phusion® Hot Start II High-Fidelity DNA Polymerase (Finnzymes Oy, Finland) with the following steps: denaturation-98° C. for 90 seconds; 20 cycles of [denaturation-98° C. for 10 seconds; annealing-60° C. for 30 seconds; extension-72° C. for 30 seconds]. For mouse IgG sequencing, heavy and light chain amplicons were generated by a two-step PCR process. In the first step γ or κ chain variable regions were amplified (15 cycles with the same conditions as described above for rabbit) with a mixture of gene family-specific degenerate oligonucleotides as sense primers, and anti-sense primers that hybridize to a highly conserved region at the start of the constant region, each sense and antisense primer containing distinct adaptor sequences at its 5' end. Each reaction from the first round was column-purified with a commercial kit (Qiagen cat#28104) then further amplified by an additional 10 (γ chain) and 8 cycles (κ chain) in the second step using adaptor sequence-specific primers that contain sequences on the 3' end required for identification and bar-coding in the Lib-L format of 454 sequencing platform. For either species all light chain amplification reactions for each animal were pooled. Excess primers for heavy and light chain samples were eliminated using Agencourt AMPure XP DNA purification system following the provided protocol. The quality and purity of the amplicon pool after primer elimination was verified on Agilent Bioanalyzer 2100 (Agilent Technologies), and the concentration of the DNA was accurately quantified on a fluorometer using Quant-iT PicoGreen dsDNA Assay Kit (Invitrogen). Following the Lib-L LV, GS FLX Titanium Series protocol from 454 Life Sciences, emulsion PCR and bead enrichment was carried out. Bead number was counted on Beckman Coulter Z2 Particle Counter, and the library was sequenced on 454 GS Junior (Roche).

Affinity Purification of Antigen-Specific IgG.

Total IgG from the serum of the hyperimmunized rabbits (New Zealand white) was purified using Protein A sepharose beads (GE Healthcare), then was incubated rotating for 15 minutes in a column with the immunogen peptide covalently coupled to sepharose beads. By gravity flow, the unbound fraction was drained, and the column was washed extensively with 1× phosphate-buffered saline (PBS) to eliminate non-specific IgG. Antigen-specific polyclonal IgG pool was eluted sequentially with 0.1M glycine/HCl buffer at pH 3.5, followed by pH 2.7, and finally pH 1.8. Each elution was immediately neutralized with 1M Tris buffer (pH 8.5). Total IgG from the serum of the hyperimmunized mice was purified using Protein-G magnetic beads (Millipore, cat# LSKMAGG10), then incubated rotating overnight at 4° C. with immunogen peptide immobilized on magnetic beads (Pierce, cat#88817). Using a magnetic tube rack (Invitrogen, cat#12321D) beads were extensively washed with PBS, then antibody bound to the column was sequentially eluted with progressively acidic pH as described for the rabbit IgG purification.

Protease Digestion of Affinity-Purified Antibody.

Polyclonal antibody was denatured in 8 M urea in 20 mM HEPES pH 8 then reduced in 10 mM DTT for 1 hour at 55° C. Reduced polyclonal was cooled to room temperature (RT) and alkylation was performed in the presence of 20 mM iodoacetamide for 1 hour. Chymotrypsin, elastase, and trypsin digestion was performed in the presence 2 M Urea in 20 mM HEPES pH 8.0 overnight at 37° C. at an enzyme to substrate ratio of 1:50. Pepsin digestion was performed in the presence of 3 M acetic acid at RT overnight at an enzyme to substrate ratio of 1:50. Digested peptides were desalted by STAGE-TIPS as published previously (Rappsilber et al., Anal Chem 75: 663-670, 2003), and analyzed by LC-MS/MS.

Mass Spectrometry.

LC-MS/MS was performed using the LTQ Orbitrap Velos (Thermo-Fisher) mass spectrometer. The samples were loaded for 7 min using a Famos autosampler (LC Packings) onto a hand-poured fused silica capillary column (125 µm internal diameter×20 cm) packed with Magic C18aQ resin (5 µm, 200 Å) using an Agilent 1100 series binary pump with an in-line flow splitter. Chromatography was developed using a binary gradient at 400 nl/min of 5-30% solvent B for 45 min (Solvent A, 0.25% formic acid (FA); Solvent B, 0.1% FA, 97% acetonitrile). Twenty MS/MS spectra were acquired in a data-dependent fashion from a preceding master spectrum in the Orbitrap (300-1,500 m/z at a resolution setting of $6\times10^4$) with an automatic gain control (AGC) target of $10^6$. Charge-state screening was used to reject singly charged species, and a threshold of 500 counts was required to trigger an MS/MS spectrum. When possible, the LTQ and Orbitrap were operated in parallel processing mode.

Database Searching and Data Processing.

MS/MS spectra were searched using the SEQUEST algorithm (version 28 rev 12) (Yates et al., Anal Chem 67: 1426-1436, 1995) against a custom hybrid database composed of 21,932 full length gamma and 22,431 full length kappa V-region sequences and gamma and kappa constant region sequences concatenated to 6,358 yeast proteins (S. cerevisiae, NCBI) and 42 common contaminants, including several human keratins, trypsin and chymotrypsin. Since V-region sequences are highly related, the yeast proteome artificially contributed more diverse sequences to the reference database (Beausoleil et al., Nat Biotechnol 24: 1285-1292, 2006) and provided another source of confidence after filtering the final dataset since filtered data should not include peptides identified from yeast. Search parameters included partial specificity for chymotrypsin and trypsin and no specificity for elastase and pepsin, a mass tolerance of ±50 ppm, a static modification of 57.0214 on cysteine, and dynamic modification of 15.9949 on methionine. False discovery rate in the dataset was estimated using the target/decoy approach (Elias et al., Nat Methods 4: 207-214, 2007). Datasets were filtered to an FDR of ≤2% using a linear discriminant analysis (Huttlin et al., Cell 143: 1174-1189, 2010). Although the mass accuracy of the Orbitrap greatly exceeds 50 ppm, when searched with a wider precursor ion tolerance, correct peptide identifications result in small precursor mass errors (±1 ppm), while incorrect peptide identifications distribute across the entire 50 ppm window. As a result, stringent precursor mass filters selectively remove many incorrect PSMs from the dataset.

Post acquisition analysis was performed as described in the text. Briefly, passing peptides derived from V-region sequences were re-mapped to the NGS Ig database. For peptides that arose from chymotryptic and tryptic digests, matches were limited to those arising from expected cleavages (KR for trypsin, YWFLMA for chymotrypsin). CDR coverage was determined by identifying CDRs using the rules defined by Kabat (Wu et al., *J Exp Med* 132: 211-250, 1970). In all cases, coverage was defined as the total number of amino acids identified from high confidence peptides divided by the number of amino acids in the mature V-region sequence.

Cloning, Expression and Characterization of Identified Immunoglobulin Chains.

γ and κ chains identified through the mass spectrometry analysis of the affinity-purified polyclonal IgG pool were cloned and expressed as follows. For each identified chain, the nucleic acid sequence encoding the entire variable domain from FWR1 through FWR4 were synthesized (Integrated DNA Technologies, Coralville Iowa). Using overlap PCR, each heavy-light chain combination permutation was expressed with a viral 2A sequence that uses a ribosomal skip mechanism to generate two polypeptides from a single open reading frame (Doronina et al., *Mol Cell Biol* 28: 4227-4239, 2008, Donnelly et al., *J Gen Virol* 82: 1027-1041, 2001). A single open reading frame cassette of, in order from 5' to 3', light chain variable and constant regions, 2A peptide sequence from Thosea asigna virus, and heavy chain variable domain was cloned into a CMV-promoter driven mammalian expression plasmid containing in-frame rabbit γ chain leader sequence and rabbit γ chain constant regions, 5' and 3' of the cloning site, respectively. HEK293 were transfected with plasmid preps encoding each light-heavy chain combination assembled in this manner using polyethylenimine (Boussif et al., *Proc Natl Acad Sci USA* 92: 7297-7301, 1995). The supernatant was screened 2 to 5 days post-transfection for secretion of antigen-specific antibody by ELISA using the immunogen peptide as the coating antigen, and light-heavy chain permutations that showed reactivity were further characterized. For mouse antibody expression, constant regions were of mouse IgG2a.

Characterization of Polyclonal and Monoclonal Antibodies by ELISA, Western Blotting, Flow Cytometry, Immunofluorescence and Immunohistochemistry.

Detailed protocols of ELISA, Western blotting, flow cytometry, immunofluorescence and immunohistochemistry can be found online at the web site of Cell Signaling Technology Inc. Costar cat#3369 certified high binding polystyrene 96-well plates were used for ELISA. Antigens used for ELISA analysis for each target were the same peptides used for immunizations. For Progesterone Receptor antibodies, Western blotting was performed on T47D (PR+), MDA-MB-231 cells (PR−) and HT-1080 (PR−) cell lysate, flow cytometry analysis on T47D (PR+) and MDA-MB-231 cells (PR−), confocal immunofluorescence analysis on MCF-7 cells (PR+) compared with MDA-MB-231 cells (PR−), and immunohistochemical analysis on paraffin-embedded primary human breast carcinoma sections, T47D and paraffin-embedded MCF-7 cells (PR+) compared with MDA-MB-231 cells (PR−). For phospho-p44/42 MAPK mouse antibodies, Western blotting was performed on lysate from Jurkat cells treated with either U1026 (Cell Signaling Technology, Inc. cat#9903) or 12-O-Tetradecanoylphorbol-13-Acetate (TPA) (Cell Signaling Technology, Inc. cat#4174). For Lin28A antibodies, Western blotting was performed on total lysate from NCCIT, NTERTA, MES and IGROV1 cell lines, confocal immunofluorescence and flow cytometry analyses on NTERA (Lin28A+) and HeLa (Lin28A−) cells. For phospho-Met (pMet) antibodies, lysates from MKN45 cells untreated (pMet+) and treated (pMet−) with SU11274 Met kinase inhibitor were used. For Sox1 antibodies, mouse brain extract (Sox1+) and lysate from NIH-3T3 (Sox1−) cells were used.

Example 8

In this Example, human monoclonal antibodies specific for the Hepatitis B virus small surface antigen (HBsAg) were generated in accordance with the methods described herein. To do this, the following protocol was followed to generate the genetic material database. Polyclonal antibodies were purified as described below and were analyzed following the mass spectrometry analysis as described above for mouse and rabbit.

I. Generation of the Nucleic Acid Sequences.
Antigen-Specific, Memory and Total B-Cell Isolation and RNA Purification Peripheral blood mononuclear cells (PBMC) were isolated from fresh, whole human blood collected in heparin vacuum tubes, using a Ficoll gradient. In a Greiner Leucocep 50 ml conical tube (Sigma Aldrich cat# Z642843) containing 20 ml of Histopaque 1077 (Sigma Aldrich cat#10771) at the bottom, up to 25 ml of blood was applied on top, then the tubes were centrifuged for 20 minutes at 1500×g at room temperature. The leukocytes (buffy coat) were collected using a sterile pipette, washed in RPMI medium twice by resuspending the cells in 50 ml of RPMI, then centrifuged at 300×g for 10 minutes at 4° C. After the washes, the PBMC were either cryopreserved in 20% DMSO in fetal bovine serum or processed immediately for B-cell isolation.

For B-cell isolation, a negative selection method was used to eliminate all non-B-cells from the PBMC using Invitrogen's Dynabeads Untouched B-cell Isolation kit (Invitrogen cat#113-51D) following the manufacturer's protocol. The resulting unlabeled B-cell population was further processed to isolate either antigen-specific or memory B-cells.

For antigen-specific B-cell isolation, total unlabeled B-cells were incubated with biotinylated antigen that is immobilized on streptavidin magnetic beads (Pierce-Thermo Scientific cat#88816) on a rotator at room temperature for 20 minutes. The beads containing any antigen-binding B-cells were then washed twice with 1×PBS. The washed beads were then resuspended in Qiagen's RNeasy kit RLT lysis buffer (supplemented with 1% β-mercaptoethanol) for RNA isolation.

For memory B-cell isolation, $CD27^+$ and surface $IgG^+$ cells were isolated from total unlabeled B-cells using Miltenyi's MACS kits for $CD27^+$ and surface $IgG^+$ cell isolation (Miltenyi Biotec (Auburn, Calif.) cat#130-051-601 and 130-047-501). In order to simultaneously isolate $CD27^+$ and $sIgG^+$ B-cells, magnetic bead-conjugated antibodies to both cell surface markers were added at the same time during the incubation step. Upon purification, memory B-cells were spun down at 300×g for 10 minutes, and then lysed in RLT buffer for RNA as described above for RNA isolation.

RNA was purified from selected cells using Qiagen's RNeasy kit (Qiagen cat#74104) following the manufacturer's protocol. On column DNase I-treatment was conducted to eliminate contaminating genomic DNA by incorporating a DNase I digest step. After the RW1 buffer wash, DNase I (Qiagen cat#79254) diluted in RDD buffer was applied to the RNA purification column and incubated for 20 minutes at room temperature. The column was then washed once more with RW1 buffer, followed by two washes with RPE buffer, and the RNA was eluted with either 30 or 50 μl water. The concentration of the RNA was determined by absorbance measured on a Nanodrop spectrophotometer (Thermo Scientific) at wavelength 450 nm.

cDNA Synthesis and Generation of Amplicons by PCR

RNA isolated from memory or antigen-specific B-cells was first reverse transcribed using Invitrogen's Thermoscript reverse transcriptase (Invitrogen cat#12236-022) as shown below:

| | |
|---|---|
| DNase treated RNA: | 5 uL |
| Oligo dT primer(50 uM): | 1 uL |
| dNTP's (10 mM): | 2 uL |
| dI H2O: | 4 uL |

Incubated at 65° C. for 5 min, placed on ice for 2 minutes, then added the following:

| | |
|---|---|
| 5X cDNA buffer: | 4 uL |
| 0.1 mM DTT: | 1 uL |
| RNAse OUT: | 1 uL |
| dI H2O: | 1 uL |
| ThermoScript: | 1 uL |

The mixture was incubated at 50° C. for 1 hour, followed by a heat-inactivation step at 85° C. for 5 minutes. Finally, the complementary RNA strand was eliminated from the cDNA by adding 1 μl of RNase H (Invitrogen cat#18021-071) and incubating at 37° C. for 20 minutes.

Amplicons of heavy, kappa and lambda chain variable regions for sequencing were generated by PCR as follows. For amplification of heavy chain, 4 independent reactions (each one specific to gene families of $V_H1$ and 7; $V_H2$, 5 and 6; $V_H3$; and $V_H4$) were run for each cDNA sample using the below listed primers in order to preserve the natural distribution of $V_H$ gene transcript frequency in the pool of B-cells. For kappa and lambda chain amplification, single reaction for each chain was run for each cDNA sample. For each reaction, an equimolar mixture of forward primers was used with the same concentration of reverse primer(s) as indicated below. Amplification was performed with fusion primers compatible for 454 Sequencing (Roche) by the Lib-L platform. Reverse primers were designed to hybridize to the 5' end of the constant region of each chain. These primers contain the Lib-L primer B and MID sequences so that sequencing reads would begin from the extreme 5' end of each constant region (in reverse sense) and into the 3' end of the variable region. For heavy and kappa chains, a single reverse primer was used for each MID, whereas for lambda chain, two distinct reverse primers were required for each MID.

Heavy Chain Fusion Primers:

```
Reverse oli551   CCA TCT CAT CCC TGC GTG TCT CCG AC tcag CTGTGCGTCGCA gaa gac    MID136
         Sga TGG GCC CTT GGT GGA (SEQ ID NO: 248)

oli555   CCA TCT CAT CCC TGC GTG TCT CCG AC tcag ACGCGAGTAT gaa gac Sga  MID27
         TGG GCC CTT GGT GGA (SEQ ID NO: 249)

oli602   CCA TCT CAT CCC TGC GTG TCT CCG AC tcag CACGCTACGT gaa gac Sga  MID34
         tgg gcc ctt ggt gga (SEQ ID NO: 250)

oli606   CCA TCT CAT CCC TGC GTG TCT CCG AC tcag TGAGTCAGTAT gaa gac sga MID70
         tgg gcc ctt ggt gga (SEQ ID NO: 251)

oli670   CCA TCT CAT CCC TGC GTG TCT CCG AC tcag ATCTACTGACatgat gaa gac MID88
         Sga tgg gcc ctt ggt gga (SEQ ID NO: 252)

oli671   CCA TCT CAT CCC TGC GTG TCT CCG AC tcag AGTAGTGATCtcaca gaa gac MID83
         Sga tgg gcc ctt ggt gga (SEQ ID NO: 253)

Forward
VH1/7 oli621   CCT ATC CCC TGT GTG CCT TGG CAG TC tcag ATG GAC TGG ACC TGG AGV ATC
         (SEQ ID NO: 254)

oli622   CCT ATC CCC TGT GTG CCT TGG CAG TC tcag ATG GAC TGG ATT TGG AGG RTC
         (SEQ ID NO: 255)

oli623   CCT ATC CCC TGT GTG CCT TGG CAG TC tcag ATG GAC TGC ACC TGG AGG ATC
         (SEQ ID NO: 256)

oli624   CCT ATC CCC TGT GTG CCT TGG CAG TC tcag ATG GAC TGG ACC TGG AGG KTC
         (SEQ ID NO: 257)

VH2/5/6 oli618   CCT ATC CCC TGT GTG CCT TGG CAG TC tcag ATG GAC ATA CTT TGT TCC ACG C
         (SEQ ID NO: 258)

oli619   CCT ATC CCC TGT GTG CCT TGG CAG TC tcag ATG GAC ACA CTT TGC TAC ACA C
         (SEQ ID NO: 259)

oli620   CCT ATC CCC TGT GTG CCT TGG CAG TC tcag ATG TCT GTC TCC TTC CTC ATC T
         (SEQ ID NO: 260)

oli629   CCT ATC CCC TGT GTG CCT TGG CAG TC tcag ATG GGG TCA ACC GCC ATC CTC
         (SEQ ID NO: 261)
```

VH3

| | |
|---|---|
| oli625 | CCT ATC CCC TGT GTG CCT TGG CAG TC tcag ATG GAG TTK GGR CTG AGC TGG (SEQ ID NO: 262) |
| oli626 | CCT ATC CCC TGT GTG CCT TGG CAG TC tcag ATG GAG TTT KGG CTK AGC TGG (SEQ ID NO: 263) |
| oli627 | CCT ATC CCC TGT GTG CCT TGG CAG TC tcag ATG GAA CTG GGG CTC CGC TGG (SEQ ID NO: 264) |
| oli628 | CCT ATC CCC TGT GTG CCT TGG CAG TC tcag ATG GAR TTG GGG CTG WGC TGG (SEQ ID NO: 265) |

VH4

| | |
|---|---|
| oli617 | CCT ATC CCC TGT GTG CCT TGG CAG TC tcag ATG AAR CAY CTG TGG TTC TTC CT (SEQ ID NO: 266) |

Kappa Chain Fusion Primers

Reverse

| | | |
|---|---|---|
| oli552 | CCA TCT CAT CCC TGC GTG TCT CCG AC tcag ACGACAGCTC gaa gat gaa gac aga tgg tgc agc cac (SEQ ID NO: 267) | MID77 |
| oli556 | CCA TCT CAT CCC TGC GTG TCT CCG AC tcag TCGATCACGT gaa gat gaa gac aga tgg tgc agc cac (SEQ ID NO: 268) | MID42 |
| oli603 | CCA TCT CAT CCC TGC GTG TCT CCG AC tcag TACACACACT GAA GAT GAA GAC AGA TGG TGC AGC cac (SEQ ID NO: 269) | MID37 |
| oli607 | CCA TCT CAT CCC TGC GTG TCT CCG AC tcag TGTAGTGTGAT GAA GAT GAA GAC AGA TGG TGC AGC cac (SEQ ID NO: 270) | MID71 |

Forward

| | |
|---|---|
| oli630 | CCT ATC CCC TGT GTG CCT TGG CAG TC tcag ATG GAC ATG AGG GTS CCY GCT CAG CTC (SEQ ID NO: 271) |
| oli631 | CCT ATC CCC TGT GTG CCT TGG CAG TC tcag ATG GAC ATG AGR GTC CTC GCT CAG CTC (SEQ ID NO: 272) |
| oli632 | CCT ATC CCC TGT GTG CCT TGG CAG TC tcag ATG GAA GCC CCA GCD CAG CTT CTC (SEQ ID NO: 273) |
| oli633 | CCT ATC CCC TGT GTG CCT TGG CAG TC tcag ATG GAA ACC CCA GCG CAG CTT CTC (SEQ ID NO: 274) |
| oli634 | CCT ATC CCC TGT GTG CCT TGG CAG TC tcag ATG GTG TTG CAG ACC CAG GTC TTC (SEQ ID NO: 275) |
| oli635 | CCT ATC CCC TGT GTG CCT TGG CAG TC tcag ATG GGG TCC CAG GTT CAC CTC CTC (SEQ ID NO: 276) |
| oli636 | CCT ATC CCC TGT GTG CCT TGG CAG TC tcag ATG AGG CTC CYT GCT CAG CTC CTG (SEQ ID NO: 277) |

Lambda Chain Fusion Primers

Reverse

| | | |
|---|---|---|
| oli604 | CCA TCT CAT CCC TGC GTG TCT CCG AC tcag CGTAGACTAG AGG GCG GGA ACA GAG TGA CMG TGG (SEQ ID NO: 278) | MID21 |
| oli605 | CCA TCT CAT CCC TGC GTG TCT CCG AC tcag CGTAGACTAG AGG GYG GGA ACA GAG TGA CCG AKG (SEQ ID NO: 279) | MID21 |
| oli608 | CCA TCT CAT CCC TGC GTG TCT CCG AC tcag TCTAGCGACTAT AGG GCG GGA ACA GAG TGA CMG TGG (SEQ ID NO: 280) | MID45 |

-continued

| | | |
|---|---|---|
| oli609 | CCA TCT CAT CCC TGC GTG TCT CCG AC tcag TCTAGCGACTAT AGG GYG GGA ACA GAG TGA CCG AKG (SEQ ID NO: 281) | MID45 |
| oli553 | CCA TCT CAT CCC TGC GTG TCT CCG AC tcag TAGCGCGCGCT agg gcg gga aca gag tga cMg tgg (SEQ ID NO: 282) | MID101 |
| oli554 | CCA TCT CAT CCC TGC GTG TCT CCG AC tcag TAGCGCGCGCT agg gYg gga aca gag tga ccg aKg (SEQ ID NO: 283) | MID101 |
| oli557 | CCA TCT CAT CCC TGC GTG TCT CCG AC tcag ATAGAGTACT agg gcg gga aca gag tga cMg tgg (SEQ ID NO: 284) | MID33 |
| oli558 | CCA TCT CAT CCC TGC GTG TCT CCG AC tcag ATAGAGTACT agg gYg gga aca gag tga ccg aKg (SEQ ID NO: 285) | MID33 |

Forward

| | |
|---|---|
| oli637 | CCT ATC CCC TGT GTG CCT TGG CAG TC tcag ATG ACC TGC TCC CCT CTC CTC CTC A (SEQ ID NO: 286) |
| oli638 | CCT ATC CCC TGT GTG CCT TGG CAG TC tcag ATG GCC GGC TTC CCT CTC CTC CTC A (SEQ ID NO: 287) |
| oli639 | CCT ATC CCC TGT GTG CCT TGG CAG TC tcag ATG GCC TGG TCT CCT CTC CTC CTC A (SEQ ID NO: 288) |
| oli640 | CCT ATC CCC TGT GTG CCT TGG CAG TC tcag ATG GCC TGG ACY CCT CTC CTC CTC M (SEQ ID NO: 289) |
| oli641 | CCT ATC CCC TGT GTG CCT TGG CAG TC tcag ATG CCC TGG GCT CTG CTS CTC CTS A (SEQ ID NO: 290) |
| oli642 | CCT ATC CCC TGT GTG CCT TGG CAG TC tcag ATG CCC TGG GTC ATG CTC CTC CTG A (SEQ ID NO: 291) |
| oli643 | CCT ATC CCC TGT GTG CCT TGG CAG TC tcag ATG GCC TGG ACT CCT CTC TTT CTG T (SEQ ID NO: 292) |
| oli644 | CCT ATC CCC TGT GTG CCT TGG CAG TC tcag ATG GAG AAG AAG AGG AGA CCT GGG G (SEQ ID NO: 293) |
| oli645 | CCT ATC CCC TGT GTG CCT TGG CAG TC tcag ATG GCC TGG ACC GCT CTC CTT CTG A (SEQ ID NO: 294) |
| oli646 | CCT ATC CCC TGT GTG CCT TGG CAG TC tcag ATG GCC TGG ACC GTT CTC CTC CTC G (SEQ ID NO: 295) |
| oli647 | CCT ATC CCC TGT GTG CCT TGG CAG TC tcag ATG GCA TGG ATC CCT CTC TTC CTC G (SEQ ID NO: 296) |
| oli648 | CCT ATC CCC TGT GTG CCT TGG CAG TC tcag ATG GCC TGG ATC CCT CTA CTT CTC C (SEQ ID NO: 297) |
| oli649 | CCT ATC CCC TGT GTG CCT TGG CAG TC tcag ATG GCC TGG AYC CCT CTC CTG CTC C (SEQ ID NO: 298) |
| oli650 | CCT ATC CCC TGT GTG CCT TGG CAG TC tcag ATG GCA TGG GCC ACA CTC CTG CTC C (SEQ ID NO: 299) |
| oli651 | CCT ATC CCC TGT GTG CCT TGG CAG TC tcag ATG GCC TGG ACC CCT CTC TGG CTC A (SEQ ID NO: 300) |
| oli652 | CCT ATC CCC TGT GTG CCT TGG CAG TC tcag ATG GCC TGG GTC TCC TTC TAC CTA C (SEQ ID NO: 301) |
| oli653 | CCT ATC CCC TGT GTG CCT TGG CAG TC tcag ATG GCC TGG ACC CCA CTC CTC CTC C (SEQ ID NO: 302) |
| oli654 | CCT ATC CCC TGT GTG CCT TGG CAG TC tcag ATG GCC TGG GCT CCT CTG CTC CTC A (SEQ ID NO: 303) |
| oli655 | CCT ATC CCC TGT GTG CCT TGG CAG TC tcag ATG GCC TGG GCT CCA CTA CTT CTC A (SEQ ID NO: 304) |

PCR amplification was done using Finnzyme's Phusion Hot Start II polymerase (Thermo Scientific cat# F-540S) where the reaction mix and conditions were set up as shown below:

Reaction Mixture:

| | |
|---|---|
| cDNA: | 2.5 uL |
| 5X Buffer GC: | 5 uL |
| 10 mM dNTP mix: | 0.25 uL |
| Phusion HotStart II: | 0.25 uL |
| Primers (forward + reverse) 30 uM: | 0.25 uL |
| Water: | 16.75 uL |

PCR Program:

| |
|---|
| Step 1 98° C. - 2 minutes |
| Step 2 98° C. - 10 seconds |
| Step 3 60° C. - 30 seconds |
| Step 4 72° C. -30 seconds |
| Step 5 Repeat steps 2 through 4 |
| Step 6 72° C. - 2 minutes |
| Step 7 - hold |

For heavy chain amplification, 25 or 30 cycles (step 5 repeated either 24 or 29 times), and for kappa and lambda chains, 20 or 30 cycles were run when amplifying cDNA template generated from either memory B-cells or from antigen-specific B-cells, respectively, as 5 extra cycles were required for sufficient amplification from antigen-specific B-cell cDNA for each chain. To ensure the absence of any false amplification from contaminating template in any of the reagents, duplicate reactions were set up for each mixture (4 separate reactions for heavy chain, and one for each light chain) where the cDNA template was substituted with water. These negative control reactions with no template were run at the same time as the samples containing template. Upon completion of the PCR program, 3 µl of each reaction (including the negative controls) were analyzed by electrophoresis on a 1.5% TAE agarose gel for the presence of the amplicons (approximately 540 bp for heavy chain, approximately 485 bp for kappa chain and approximately 510 bp for lambda chain) when template was added to the reaction but not in the absence of cDNA.

Amplicon Purification, Analysis, Quantitation, and Preparation for 454 Sequencing In order to eliminate excess primers and/or primer dimmers in the PCR samples, amplicons were purified using Agentcourt Ampure magnetic beads (Beckman Coulter cat#A63881) following the manufacturer's protocol (000387v001). For heavy chain, all four reactions (VH1/7, VH2/5/6, VH3, VH4) were pooled and purified as one sample, thus a total of 3 amplicon samples (heavy, kappa and lambda chains) were purified for each cDNA amplification. The protocol for ampure purification was modified in that purifications were done in single 1.5 ml microtubes using a generic magnetic rack that is suitable for 1.5 ml tubes instead of in a 96-well plate format. All volumes and other procedures were as described in the protocol. The eluted amplicons after Ampure purification were then analyzed for purity and absence of any contaminating DNA species on the Agilent 2100 Bioanalyzer using the high sensitivity DNA chip (Agilent Technologies cat#5067-4626) by following the manufacturer's protocol.

Once the purity of amplicons was verified, the concentration of the DNA was quantified on a fluorometer using the Quant-iT PicoGreen dsDNA Assay Kit (Invitrogen cat#P7589) as described in the manufacturer's protocol. The Lambda DNA provided in the kit was used as a concentration standard with which a standard curve was generated from 100 ng/well to 1.56 ng/well. The fluorescence of each amplicon diluted 100-fold in TE buffer was measured in duplicate, and the concentration of DNA was determined according to the linear portion of the standard curve. All fluorescence measurements were done in black 96-well plates. If the value of fluorescence was out of the linear range of the standard curve, the samples were remeasured with either larger or smaller dilutions in order to capture fluorescence values that fall within the linear range. Using the approximate size in base pairs of each chain type (heavy-540 bp, kappa-485 bp and lambda-510 bp), the following formula was used to determine the concentration:

Concentration of each amplicon(molecules/µl)= [sample conc(ng/µl)*$6.022\times10^{23}$]/[656.6× $10^9$*amplicon length(bp)]

Each amplicon was normalized to $1\times10^7$ molecules/µl, then mixed at a ratio of Hc:Kc:Lc at 3:3:1 by volume, vortexed, and finally diluted 1:10 to obtain a final concentration of the mixture at $1\times10^6$ molecules/µl.

Emulsion PCR Amplification, Bead Enrichment, Bead Counting and Sequencing

Emulsion PCR was conducted following the 454 published protocol: "emPCR Amplification Method Manual—Lib-L" (Edition: May 2010 (Rev. April 2011)) with the following modifications:

Section 3.1.3 Step 2)

| Reagent | Volume (µl) |
|---|---|
| Mol. Bio. Grade water | 458 |
| Additive | 515 |
| Amp Mix | 270 |
| Amp Primer | 32 |
| Enzyme Mix | 70 |
| PPiase | 2 |
| Total | 1347 |

Once the sequencing beads were enriched, from step 3.7 of "emPCR Amplification Method Manual—Lib-L", the beads were counted on Beckman Coulter's Z2 Particle Counter with the following settings:

| | |
|---|---|
| Aperture: | <100 µm> |
| Aperture Kd: | <60.04> |
| Set Upper cutoff: | <30.00 µm> |
| Set Lower cutoff: | <10.00 µm> |
| Count Mode: | <between> |
| Metered Volume: | <0.5 ml> |
| Resolution: | <256> |

The concentration of beads was calculated as:

Concentration of beads=[Avg. reading from particle counter*4]beads/µl

The enriched beads from the emulsion PCR were sequenced on the 454 Sequencer (Roche) following the 454 sequencing protocol: "Sequencing Method Manual—GS Junior Titanium Series"—May 2010 (Rev. June 2010), herein incorporated by reference in its entirety.

II. Generation of Peptide Fragments:

Purification of Antigen-Specific IgG from Human Donor Plasma

Donor Plasma Isolation and Screening for Reactivity to Specific Antigens.

Whole blood from human volunteers was collected following IRB guidelines in heparin tubes. During ficoll-gradient separation of PBMC (as described above), plasma samples were collected simultaneously and stored at −80° C. Reactivity of plasma IgG to various antigens was tested by ELISA. Briefly, high-binding 96-well plates (Costar cat#) were coated 100 μl/well of antigen at 2 μg/ml dissolved in carbonate buffer at 37° C. for two hours or 4° C. overnight. The plates were rinsed three times with PBS-Tween (0.1%), then blocked with 300 μl/well of 5% non-fat dry milk in PBS-Tween at 37° C. for 1 hour. Plasma samples were diluted at 1/100, 1/500 and 1/1000 and 1/2000 in 5% milk PBS-Tween, and 100 μl of each dilution was added in duplicates of blocked wells of the 96-well plate and incubated for 2 hours at 37° C. The plates were washed 3 times with 1×PBS-Tween, and horseradish peroxidase-conjugated anti-human IgG antibody (Southern Biotech 2040-05) diluted 1/4000 in PBS-Tween was added to each well (100 μl) and incubated at 37° C. for one hour. The plates were washed 6 times with PBS-Tween and developed by addition of 50 μl TMB substrate solution (BioFX cat#TMBW-1000-01), followed by 50 μl of stop solution (BioFX cat# STPR1000-01). The signals were measured at optical density of 450 nm. Donors whose plasma showed significant signal at 1/500 or greater dilution were selected for screening by NG-XMT procedure.

Hepatitis B virus small surface antigen (HBsAg) adw subtype was purchased from Prospec (Rehovot, Israel, cat# HBS-872).

Purification of Antigen-Specific IgG from Total Plasma IgG
Protein G Purification 1. 5 ml of bead slurry (2.5 ml bead bed volume) of Protein G Sepharose 4 Fast Flow (GE Healthcare cat#17-0618-05) were applied to a gravity flow column and washed with 1×PBS twice.
2. 5 ml of human plasma diluted with 1×PBS to 15 ml was applied to the column with beads, and the column was incubated on a rotator overnight at 4 C, or room temperature for 2 hours.
3. The column was washed 4 times with 20 ml of 1×PBS.
4. IgG was eluted with 20 ml of pH2.7 0.1M glycine/HCl buffer and collected in a tube containing 1.2 ml of 1M Tris pH8.5 for neutralization.
5. 10 ml of 1×PBS (pH7.4) was added to the neutralized eluate to minimize precipitation due to high concentration of IgG.
6. Purified IgG was dialyzed twice against 4 liters of 1×PBS in a 10 kDa cut-off dialysis cassette (Pierce cat#66456).
7. IgG concentration was determined by measuring the absorbance at 280 nm on a Nanodrop photospectrometer (Thermo Scientific).

Affinity Purification

1. HBsAg was conjugated with biotin (Pierce Cat #20217) following the manufacturer's protocols. The conjugated antigen was dialyzed extensively in 1×PBS.
2. 2 mg of biotin-conjugated antigen was incubated with 5 ml of magnetic streptavidin beads (Thermo Scientific cat#8816) overnight at 4° C. or for two hours at room temperature on a rotator. The beads were rinsed with 1×PBS twice, then divided into nine 1.5 ml tubes.
3. The efficiency of immobilization of antigen to beads was evaluated by HBsAg Elisa and consistently showed greater than 80% binding.
4. To each tube containing immobilized antigen, 1 mg of protein G-purified IgG from a single donor was added, the beads were resuspended fully by vortexing and incubated rotating at room temperature for 15 minutes.
5. The tubes were placed in a magnetic rack, the supernatant was removed, and the beads were washed 5 times with 1 ml 1×PBS.
6. After the last wash step, 0.9 ml of 0.1M glycine-HCl buffer at pH1.8 was applied to one tube, vortexed and incubated at room temperature for 5 minutes. After 5 minutes, the first tube was placed on the magnetic rack, then the acidic buffer in the tube was removed and placed into a second tube. This procedure was repeated until all nine tubes were incubated with the acidic buffer. Eluted IgG was finally collected in a tube containing 0.14 ml of 1M Tris pH8.5 for neutralization.
7. After each tube underwent elution, the beads were washed with 1×PBS twice before restarting the purification from the step where 1 mg of protein G-purified IgG was added to the beads. The procedure was repeated multiple times to generate sufficient material for protease treatment prior to MS analysis.

III. Mass Spectrometry

Mass spectrometry analysis was performed as described above. Briefly, following digestion with a protease (e.g., trypsin) and/or a chemical protein cleavage reagent (e.g., cyanogen bromide), mass spectrometry analysis was performed on the peptides. The resulting MS2 spectra was correlated to the theoretical MS2 spectra derived from the information in the genetic material database, in order to identify the genetic sequences that encode antibodies that specifically bind to the Hepatitis B virus small surface antigen.

IV. Expression and Identification of Monoclonal Antibodies 24 distinct heavy (gamma) chain variable region clones, 20 distinct kappa chain variable region clones and 10 distinct lambda chain variable region clones were expressed in a combinatorial format and screened for antigen-specific binding activity (See FIG. 14, where gamma chain clones are indicated in the left most vertical column and light chain clones are indicated in the top horizontal row). Each gamma chain was paired with every light (kappa and lambda) chain to express antibodies by transient transfection of HEK293E cells in standard 96-well tissue culture plates.

Antibody that was secreted from the transfected cells in each well was screened for binding to purified, recombinant hepatitis B surface antigen (HBsAg-adw subtype purchased from Prospec, Ness-Ziona, ISRAEL) by enzyme-linked immunosorbant assay (ELISA). High binding 96-well ELISA plates (Costar-3369) were coated with 50 μl/well of HBsAg diluted in carbonate buffer at 2 μg/ml by incubating at 37° C. for two hours then blocked with 300 μl/well of 5% powdered milk in phosphate-buffered saline (PBS) by incubating at 37° C. for one hour. The supernatant from the transiently transfected HEK293E cells were diluted five-fold in 5% milk in PBS with 0.05% Tween 20 (PBS-T), then 50 μl of the diluted supernatant was applied to each well of HBsAg-coated ELISA plates. To assess non-specific binding, the same supernatant was also applied to plates coated only with 5% milk in PBS. After addition of supernatant, the ELISA plates were incubated at 37° C. for 2 hours followed by 3 washes with 250 μl/well of PBS-T. To detect any binding of antibody, 50 μl/well of horse radish peroxidase (HRP)-conjugated anti-human IgG (Southern Biotech) diluted 4000-fold in PBS-T was added to each well and incubated at 37° C. for one hour. The plates were washed 6 times as described above, and then 50 μl/well of a chromogenic substrate for HRP, 3,3',5,5'-Tetramethylbenzidine, was added, which was neutralized with 50 μl/well of acid approximately 10 minutes later. The signal from the chromogenic substrate neutralized with acid was measured by absorbance (optical density) at 450 nm.

FIG. 14 shows the values obtained from the absorbance of HBsAg plates from which the absorbance of the milk only plates in each well was subtracted. The following supernatant samples were used as controls (values are averages of two independent wells in each case): positive=supernatant from transfection of anti-HBsAg human antibody heavy and light chain; negative=supernatant from cells transfected with PEI only. Wells with signal greater than the negative control signal by 10-20-fold, 20-40-fold and higher than 40-fold are indicated in increasing shades of grey. 30 heavy-light permutations exhibited strong reactivity to HBsAg, greater than 40-fold over background in two or more out of four wells, 26 were between 20 to 40-fold over background, and 18 were between 10 to 20-fold over background (one of the 18, expressed as a combination of EVUGG gamma chain, shown with * on the table, and AKUOL lambda chain was later found to be non-reactive). Thus, out of 24 distinct variable region gamma chain clones tested, 17 expressed HBsAg-specific antibody when paired with at least one of the 30 light chain clones tested.

Example 9

In this Example, a human subject is administered a vaccine comprising an antigen of interest, and blood samples are taken before vaccination (week 0) and then at weeks 1 and 2. Subsequent samples are taken at 4-week intervals up to week 52. PBMC are isolated as described in Example 8 and either cryopreserved in 20% DMSO in fetal bovine serum or processed immediately for B-cell isolation. Plasma samples are stored at −80° C. for later analysis by mass spectrometry. For each sample, the PBMC and plasma are processed as described below to assess the antigen-specific antibody population over time following vaccination.

I. Generation of the Nucleic Acid Sequences.
Antigen-Specific, Memory and Total B-Cell Isolation and RNA Purification For B-cell isolation, a negative selection method is used to eliminate all non-B-cells from the PBMC using Invitrogen's Dynabeads Untouched B-cell Isolation kit (Invitrogen cat#113-51D) following the manufacturer's protocol. The resulting unlabeled B-cell population is further processed to isolate either antigen-specific or memory B-cells.

For antigen-specific B-cell isolation, total unlabeled B-cells are incubated with biotinylated antigen that is immobilized on streptavidin magnetic beads (Pierce-Thermo Scientific cat#88816) on a rotator at room temperature for 20 minutes. The beads containing any antigen-binding B-cells are then washed twice with 1×PBS. The washed beads are then resuspended in Qiagen's RNeasy kit RLT lysis buffer (supplemented with 1% β-mercaptoethanol) for RNA isolation.

For memory B-cell isolation, CD27$^+$ and surface IgG$^+$ cells are isolated from total unlabeled B-cells using Miltenyi's MACS kits for CD27$^+$ and surface IgG$^+$ cell isolation (Miltenyi Biotec (Auburn, Calif.) cat#130-051-601 and 130-047-501). To simultaneously isolate CD27$^+$ and sIgG$^+$ B-cells, magnetic bead-conjugated antibodies to both cell surface markers are added at the same time during the incubation step. Upon purification, memory B-cells are spun down at 300×g for 10 minutes, and then lysed in RLT buffer for RNA as described above for RNA isolation.

RNA is purified from selected cells using Qiagen's RNeasy kit (Qiagen cat#74104) following the manufacturer's protocol. On-column DNase I-treatment is conducted to eliminate contaminating genomic DNA by incorporating a DNase I digest step. After the RW1 buffer wash, DNase I (Qiagen cat#79254) diluted in RDD buffer is applied to the RNA purification column and incubated for 20 minutes at room temperature. The column is then washed once more with RW1 buffer, followed by two washes with RPE buffer, and the RNA is eluted with either 30 or 50 μl water. The concentration of the RNA is determined by absorbance measured on a Nanodrop spectrophotometer (Thermo Scientific) at wavelength 450 nm.

cDNA Synthesis and Generation of Amplicons by PCR

RNA isolated from memory or antigen-specific B-cells is first reverse transcribed as described in Example 8. Amplicons of heavy, kappa and lambda chain variable regions for sequencing are generated by PCR as follows. For amplification of heavy chain, four independent reactions (each one specific to gene families of $V_H1$ and 7; $V_H2$, 5 and 6; $V_H3$; and $V_H4$) are run for each cDNA sample using the primers described in Example 8 to preserve the natural distribution of $V_H$ gene transcript frequency in the pool of B-cells. For kappa and lambda chain amplification, a single reaction for each chain is run for each cDNA sample. For each reaction, an equimolar mixture of forward primers is used with the same concentration of reverse primer(s). Amplification is performed with fusion primers compatible for 454 Sequencing (Roche) by the Lib-L platform. Reverse primers are designed to hybridize to the 5' end of the constant region of each chain. These primers contain the Lib-L primer B and MID sequences so that sequencing reads begin from the extreme 5' end of each constant region (in reverse sense) and into the 3' end of the variable region. For heavy and kappa chains, a single reverse primer is used for each MID, whereas for lambda chain, two distinct reverse primers were required for each MID.

PCR amplification is performed using Finnzyme's Phusion Hot Start II polymerase (Thermo Scientific cat# F-540S) where the reaction mix and conditions are set up as described in Example 8.

To ensure the absence of any false amplification from contaminating template in any of the reagents, duplicate reactions are set up for each mixture (four separate reactions for heavy chain, and one for each light chain) where the cDNA template is substituted with water. These negative control reactions with no template are run at the same time as the samples containing template. Upon completion of the PCR program, 3 μl of each reaction (including the negative controls) is analyzed by electrophoresis on a 1.5% TAE agarose gel for the presence of the amplicons (approximately 540 bp for heavy chain, approximately 485 bp for kappa chain and approximately 510 bp for lambda chain) when template is added to the reaction but not in the absence of cDNA.

To preserve cognate pairing of antibody chains during sequencing, the isolated B cells are subjected to single cell encapsulation using single-cell microdroplet encapsulation (Raindance Technologies, Inc., Lexington, Mass.). The encapsulated B cells are then fused with a single cell RT-PCR reagent (the reagent sold by Qiagen, as Cat #210210) with amplification primers to generate linked heavy and light chain PCR products from each single B cell. Overlap PCR (Meijer P. J. et al., J. Mol. Biol. 358(3):764-72, 2006) is used to stitch the heavy and light chain PCR products into one DNA for preservation of antibody chain pairs through downstream sequencing.

Amplicon Purification, Analysis, Quantitation, and Preparation for 454 Sequencing To eliminate excess primers and/or primer dimers in the PCR samples, amplicons are purified using Agentcourt Ampure magnetic beads (Beckman Coulter cat#A63881) following the manufacturer's protocol (000387v001). For heavy chain, all four reactions (VH1/7, VH2/5/6, VH3, VH4) are pooled and purified as one sample, thus a total of three amplicon samples (heavy, kappa and lambda chains) are purified for each cDNA amplification. The protocol for Ampure purification is modified in that purifications are done in single 1.5 ml microtubes using a generic magnetic rack that is suitable for 1.5 ml tubes instead of in a 96-well plate format. All volumes and other procedures are as described in the protocol. The eluted amplicons after Ampure purification are then analyzed for purity and absence of any contaminating DNA species on the Agilent 2100 Bioanalyzer using the high sensitivity DNA chip (Agilent Technologies cat#5067-4626) by following the manufacturer's protocol.

Once the purity of amplicons is verified, the concentration of the DNA is quantified on a fluorometer using the Quant-iT PicoGreen dsDNA Assay Kit (Invitrogen cat#P7589) as described in the manufacturer's protocol. The Lambda DNA provided in the kit is used as a concentration standard with which a standard curve was generated from 100 ng/well to 1.56 ng/well. The fluorescence of each amplicon diluted 100-fold in TE buffer is measured in duplicate, and the concentration of DNA is determined according to the linear portion of the standard curve. All fluorescence measurements are done in black 96-well plates. Using the approximate size in base pairs of each chain type (heavy-540 bp, kappa-485 bp and lambda-510 bp), the following formula is used to determine the concentration:

Concentration of each amplicon(molecules/µl)= [sample conc(ng/µl)*$6.022 \times 10^{23}$]/[$656.6 \times 10^9$*amplicon length(bp)]

Each amplicon is normalized to $1 \times 10^7$ molecules/µl, then mixed at a ratio of Hc:Kc:Lc at 3:3:1 by volume, vortexed, and finally diluted 1:10 to obtain a final concentration of the mixture at $1 \times 10^6$ molecules/µl.

Emulsion PCR Amplification, Bead Enrichment, Bead Counting and Sequencing

Emulsion PCR is conducted following the 454 published protocol: "emPCR Amplification Method Manual—Lib-L" (Edition: May 2010 (Rev. April 2011)) with the modifications described in Example 8.

Once the sequencing beads are enriched, from step 3.7 of "emPCR Amplification Method Manual—Lib-L", the beads are counted on Beckman Coulter's Z2 Particle Counter, and the concentration of beads is calculated as:

Concentration of beads=[Avg. reading from particle counter*4]beads/µl

The enriched beads from the emulsion PCR are sequenced on the 454 Sequencer (Roche) following the 454 sequencing protocol: "Sequencing Method Manual—GS Junior Titanium Series"—May 2010 (Rev. June 2010), herein incorporated by reference in its entirety.

II. Generation of Peptide Fragments:
Purification of Antigen-Specific IgG from Human Donor Plasma
Screening for Reactivity to Antigen.

Reactivity of plasma IgG to the antigen(s) of interest is tested by ELISA. Briefly, high-binding 96-well plates (Costar cat#) are coated 100 µl/well of antigen at 2 µg/ml dissolved in carbonate buffer at 37° C. for two hours or 4° C. overnight. The plates are rinsed three times with PBS-Tween (0.1%), then blocked with 300 µl/well of 5% non-fat dry milk in PBS-Tween at 37° C. for 1 hour. Plasma samples are diluted at 1/100, 1/500 and 1/1000 and 1/2000 in 5% milk PBS-Tween, and 100 µl of each dilution is added in duplicates of blocked wells of the 96-well plate and incubated for 2 hours at 37° C. The plates are washed three times with 1×PBS-TWEEN and horseradish peroxidase-conjugated anti-human IgG antibody (Southern Biotech 2040-05) diluted 1/4000 in PBS-Tween is added to each well (100 µl) and incubated at 37° C. for one hour. The plates are washed 6 times with PBS-Tween and developed by addition of 50 µl TMB substrate solution (BioFX cat#TMBW-1000-01), followed by 50 µl of stop solution (BioFX cat# STPR1000-01). The signals are measured at optical density of 450 nm. Serum titers are observed to generally increase with time following vaccination.

Purification of Antigen-Specific IgG from Total Plasma IgG

Total IgG are purified from each serum sample using Protein G as described in Example 8. The purified IgG are dialyzed twice against 4 liters of 1×PBS in a 10 kDa cut-off dialysis cassette (Pierce cat#66456), and the IgG concentration is determined by measuring the absorbance at 280 nm on a Nanodrop photospectrometer (Thermo Scientific). The Protein G-purified IgG are then affinity purified using beads bound to the antigen as described in Example 8. The affinity-purified antibodies from each sample are collected for mass spectrometry analysis.

III. Mass Spectrometry

Mass spectrometry analysis is performed as described above. Briefly, following digestion with a protease (e.g., trypsin) and/or a chemical protein cleavage reagent (e.g., cyanogen bromide), mass spectrometry analysis is performed on the peptides. The resulting MS2 spectra are correlated to the theoretical MS2 spectra derived from the information in the genetic material database, in order to identify the genetic sequences that encode antibodies that specifically bind to the antigen of interest. By determining the sequences of the antibodies in the samples, the composition of the antigen-specific antibody population in the subject at multiple points in time following vaccination is determined.

Example 10

This Example describes the production of antigen-specific human antibodies using a transgenic animal that expresses human antibody genes.

XENOMOUSE strain XMG1-KL mice (Amgen, Thousand Oaks, Calif.) have their endogenous mouse antibody machinery inactivated and contain human immunoglobulin heavy and light chain loci (Jakobovits et al., 2007, Nature Biotechnol., 25:1134-43). These mice produce fully human IgG1κ and IgG1λ antibodies. The mice are immunized with a human antigen of interest, and a genetic material database and peptide database are generated using the following methods.

I. Genetic Material Database:
Cell Isolation.

Spleens from immunized mice are flushed 5 times with 5 mL of RPMI/10% FCS using a syringe and 21 G needle. Cells are frozen in 90% FCS/10% DMSO. A total of 50-100×10^6 cells are isolated from each spleen.

RNA Isolation and cDNA Synthesis.

Total RNA is isolated from Splenocytes according to manufacturer's protocol using QIAshredder (Qiagen cat#79654) and RNeasy mini kit (Qiagen, Hilden, Germany;

cat#74104). RNA is DNAse treated on column as per a standard next generation sequencing protocol. Total RNA concentration is measured using an ND-1000 spectrophotometer (NanoDrop; commercially available from Thermo Scientific, Wilmington, Del.).

The isolated RNA is used for first-strand cDNA synthesis by reverse transcription using Thermoscript RT-PCR system (Invitrogen (part of Life Technologies), Carlsbad, Calif. cat#11146-024). cDNA is synthesized using 1.5 ug of RNA and oligo dT primer according to manufacturer's protocol.
$V_H$ and $V_L$ amplification.

Amplicons of heavy, kappa and lambda chain variable regions for sequencing are generated by PCR as follows using primers specific for human antibody sequences as described in Example 8. For amplification of heavy chain, four independent reactions (each one specific to gene families of $V_H1$ and 7; $V_H2$, 5 and 6; $V_H3$; and $V_H4$) are run for each cDNA sample to preserve the natural distribution of $V_H$ gene transcript frequency in the pool of B-cells. For kappa and lambda chain amplification, a single reaction for each chain is run for each cDNA sample. For each reaction, an equimolar mixture of forward primers is used with the same concentration of reverse primer(s). Amplification is performed with fusion primers compatible for 454 Sequencing (Roche) by the Lib-L platform. Reverse primers are designed to hybridize to the 5' end of the constant region of each chain. These primers contain the Lib-L primer B and MID sequences so that sequencing reads begin from the extreme 5' end of each constant region (in reverse sense) and into the 3' end of the variable region. For heavy and kappa chains, a single reverse primer is used for each MID, whereas for lambda chain, two distinct reverse primers were required for each MID.

PCR amplification is performed using Finnzyme's Phusion Hot Start II polymerase (Thermo Scientific cat# F-540S) where the reaction mix and conditions are set up as described in Example 8.

To ensure the absence of any false amplification from contaminating template in any of the reagents, duplicate reactions are set up for each mixture (four separate reactions for heavy chain, and one for each light chain) where the cDNA template is substituted with water. These negative control reactions with no template are run at the same time as the samples containing template. Upon completion of the PCR program, 3 µl of each reaction (including the negative controls) is analyzed by electrophoresis on a 1.5% TAE agarose gel for the presence of the amplicons (approximately 540 bp for heavy chain, approximately 485 bp for kappa chain and approximately 510 bp for lambda chain) when template is added to the reaction but not in the absence of cDNA. PCR products are purified according to manufacturer's protocol using AMPure XP (Agencourt; Beckman Coulter Genomics, Brea, Calif., cat#A63881) and analyzed using an Agilent 2100 BioAnalyzer.

The sequences of the PCR products are then translated into predicted amino acid sequences, which are then theoretically digested (e.g., with a protease and/or a chemical protein cleavage reagent) to produce virtual peptide fragments. These virtual peptide fragments are then used to generate predicted mass spectra.

Generation of Actual Mass Spectra from Peptide Fragments of Polyclonal Antibodies:

Polyclonal antibodies are purified from the sera and/or plasma of the mice. To purify the antibodies, the following methods are used:

Protein-G Purification:

1 mL of magnetic protein-G beads (Millipore (Billerica, Mass.), cat# LSKMAGG10) are added to each of four 15 mL conical tubes (Falcon (BD Biosciences, Franklin Lake, N.J.), cat#352097). The beads in each tube are washed twice with 10 mL of phosphate buffered saline pH7.4, 0.05% Tween-20 (PBST) and three times with 10 mL of PBS. Sera from three mice (ID 1262-2, 1262-4, 1263-4) are pooled together and diluted ten-fold to a final volume of 6 ml in PBS. 1.5 ml of the combined, diluted sera is then added to each tube of beads and incubated overnight at 4° C. The flow through is collected and put through the purification process another two times. After the flow through is collected, each tube is washed two times with 10 mL PBST and three times with 10 mL of PBS. Each tube is then incubated at 4° C. for 30 minutes with 0.5 mL of 0.1M pH 2.7 glycine to elute the IgG. The elution is repeated five times. All eluates are neutralized with 1M Tris pH 8.5, dialyzed overnight against PBS and protein concentration was measured with an ND-1000 spectrophotometer (Nanodrop). In total, approximately 2.5 mg of IgG is purified.

Antigen Column Preparation:

5.0 mL of fresh streptavidin (SA) magnetic beads (Pierce, cat#88817) are washed three times with 10 mL PBS, and incubated overnight at 4° C. with 105 uL of a 20 mg/ml stock of the antigen of interest conjugated to biotin diluted in 5.0 mL of PBS. Flow through is discarded, and beads are washed three times with 10 mL of PBS and aliquoted into ten low binding 1.7 mL tubes (Axygen (Union City, Calif.), cat# MCT-175-L-C). Aliquoted beads are placed on a magnetic rack (Invitrogen, DynaMag), and PBS is removed prior to adding the dilute sera.

Antigen-Specific Purification:

Protein-G purified IgG from above is added to the SA-magnetic beads coupled with biotinylated antigen. After overnight incubation at 4° C., the flow through is collected and the beads are washed with a total of 10 mL of each of the following buffers, in series:

PBS

RIPA buffer (i.e., radioimmunoprecipitation assay buffer; Alcaraz et al., *J. Vet. Diagn. Invest.* 2(3): 191-196, 1990; Ngoka, L. C., *Proteome Sci.* 6(1): 30, 2008)

20% Acetonitrile in PBS

60% Ethylene glycol in PBS 0.5M NaCl in PBS

PBS (i.e., phosphate buffered saline)

IgG is then eluted with 5 fractions of 1.5 mL 0.1M Glycine pH 3.5, then 5 fractions of 1.5 mL 0.1M Glycine pH 2.7, then 5 fractions of 1.5 mL 0.1M Glycine pH 1.8 and neutralized with 1M Tris pH 8.5. Eluates are assayed for reactivity to the antigen of interest using 96-well plates coated with the antigen. Fractions with activity are quantitated by ELISA (Thermo, cat#23300) and assayed for antigen reactivity by western blot. The fractions with the cleanest reactivity are analyzed by mass spectrometry.

Mass Spectrometry

Mass spectrometry analysis is performed as described above. Briefly, following digestion with a protease (e.g., trypsin) and/or a chemical protein cleavage reagent (e.g., cyanogen bromide), mass spectrometry analysis is performed on the peptides. The resulting MS2 spectra are correlated to the theoretical MS2 spectra derived from the information in the genetic material database, in order to identify the genetic sequences that encode antibodies that specifically bind to the antigen of interest.

Expression and Identification of Monoclonal Antibodies

Distinct heavy (gamma) chain variable region clones, kappa chain variable region clones and lambda chain variable region clones are expressed in a combinatorial format and screened for antigen-specific binding activity. Each gamma chain is paired with every light (kappa and lambda) chain to express antibodies by transient transfection of HEK293E cells in standard 96-well tissue culture plates.

Antibody that is secreted from the transfected cells in each well is screened for binding to purified, recombinant antigen by enzyme-linked immunosorbant assay (ELISA), as described above. Several pairings of the heavy and light chains result in antibodies that specifically bind to the antigen-coated plates. These heavy and light chain pairs are selected, resulting in the production of fully human antibodies that specifically bind to the human antigen of interest.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method for obtaining nucleic acid sequences or amino acid sequences of heavy or light chains of immunoglobulins that specifically bind to an antigen of interest, comprising:

(a) providing nucleic acid sequences encoding immunoglobulin chains of white blood cells of at least one animal, and deriving predicted mass spectra information from predicted amino acid sequences encoded by said nucleic acid sequences;

(b) isolating a population of polyclonal immunoglobulins, wherein said population of polyclonal immunoglobulins is a purified population of polyclonal immunoglobulins obtained by antigen affinity purification with said antigen of interest, digesting said population of polyclonal immunoglobulins with one or more proteases to obtain peptide fragments, and performing mass spectrometry analysis to obtain mass spectra information of said peptide fragments;

(c) correlating the mass spectra information of said peptide fragments obtained in step (b) with the predicted mass spectra information in step (a), identifying nucleic acid sequences encoding immunoglobulin chains that comprise amino acid sequences corresponding to one or more of said peptide fragments, determining heavy or light variable regions and CDR3 regions of the immunoglobulin chains encoded by the identified nucleic acid sequences; and for the heavy or light variable region and the CDR3 region encoded by each identified nucleic acid sequence, calculating the amino acid sequence coverage of the heavy or light variable region by said peptide fragments, and calculating the amino acid sequence coverage of the CDR3 region by said peptide fragments;

(d) selecting nucleic acid sequences having an amino acid sequence coverage of the heavy or light variable region of at least 60% and an amino acid sequence coverage of the CDR3 region of at least 60% from the identified nucleic acid sequences to obtain nucleic acid sequences or amino acid sequences of heavy or light chains of immunoglobulins that specifically bind to said antigen of interest; and (e) producing a heavy or light chain encoded by a nucleic acid sequence obtained in step (d) by recombinant molecular biology techniques or gene synthesis techniques.

2. The method of claim 1, wherein said at least one animal of step (a) is an animal exposed to said antigen of interest.

3. The method of claim 1, wherein the nucleic acid sequences provided in step (a) are expressed nucleic acid sequences.

4. The method of claim 1, wherein the nucleic acid sequences encoding immunoglobulin chains are obtained from said white blood cells of said at least one animal by:

(1) isolating nucleic acid molecules from said white blood cells from said at least one animal; and (2) amplifying nucleic acid molecules encoding immunoglobulin chains using primers specific for polynucleotide sequences adjacent to said nucleic acid molecules encoding immunoglobulin chains, and (3) obtaining nucleic acid sequences of said amplified nucleic acid molecules encoding immunoglobulin chains.

5. The method of claim 4, wherein the nucleic acid molecules are RNA molecules and said amplification step includes an initial reverse transcription step.

6. The method of claim 4, wherein said polynucleotide sequences in step (2) are selected from the group consisting of genomic DNA flanking immunoglobulin genes, immunoglobulin chain constant region-encoding polynucleotide sequences, and immunoglobulin chain framework region-encoding polynucleotide sequences.

7. The method of claim 1, wherein the predicted mass spectra information is obtained using a method comprising the steps of:

(i) performing a theoretical digest of predicted amino acid sequences encoded by the nucleic acid sequences with one or more proteases and/or one or more chemical protein cleavage reagents to generate virtual peptide fragments; and (ii) creating predicted mass spectra of said virtual peptide fragments.

8. The method of claim 1, wherein the nucleic acid sequences of step (a), predicted amino acid sequences, and predicted mass spectra derived from said nucleic acid sequences are located within a genetic material database.

9. The method of claim 1, wherein said population of polyclonal immunoglobulins of step (b) is obtained from a body fluid sample or fraction thereof of an animal.

10. The method of claim 9, wherein said body fluid is selected from the group consisting of blood, cerebrospinal fluid, synovial fluid, peritoneal fluid, mucosal secretions, tears, nasal secretions, saliva, milk, and genitourinary secretions.

11. The method of claim 9, wherein the animal is an animal previously exposed to said antigen of interest.

12. The method of claim 11, wherein the animal previously exposed to said antigen of interest is an animal previously immunized with said antigen of interest.

13. The method of claim 9, wherein the animal from which the body fluid sample or fraction thereof is obtained is the same as said at least one animal in step (a).

14. The method of claim 1, wherein said population of polyclonal immunoglobulins of step (b) is obtained from the medium of cultured white blood cells in vitro.

15. The method of claim 1, wherein the peptide fragments of step (b) are obtained from the population of polyclonal immunoglobulins by digesting the population with multiple proteases.

16. The method of claim 1, wherein the selection in step (d) is additionally based on at least one parameter selected from the group consisting of the number of unique peptides mapped, spectrum share, total peptide count, unique peptide count, frequency of the encoding nucleic acid sequences, and clonal relatedness.

17. The method of claim 1, wherein step (e) comprises:
making a heavy chain and a light chain based on the obtained nucleic acid sequences or amino acid sequences of step (d) by recombinant molecular biology techniques or gene synthesis techniques, and
assembling said heavy chain with said light chain to create an immunoglobulin that specifically binds to said antigen of interest.

18. The method of claim 17, further comprising evaluating the immunoglobulin in an immunoassay to confirm that said immunoglobulin specifically binds to said antigen of interest.

19. The method of claim 18, wherein the immunoassay is selected from the group consisting of a flow cytometry assay, an enzyme-linked immunosorbent assay (ELISA), a Western blotting assay, an immunohistochemistry assay, an immunofluorescence assay, a radioimmunoassay, a neutralization assay, a binding assay, an affinity assay, a protein immunoprecipitation assay, and a peptide immunoprecipitation assay.

20. A method for obtaining nucleic acid sequences or amino acid sequences of immunoglobulin chain variable regions of immunoglobulins that specifically bind to an antigen of interest comprising:

(a) providing nucleic acid sequences encoding immunoglobulin chain variable regions of multiple immunoglobulins of white blood cells of at least one animal, and deriving predicted mass spectra information from predicted amino acid sequences encoded by said nucleic acid sequences;

(b) isolating a population of polyclonal immunoglobulins, wherein said population of polyclonal immunoglobulins is a purified population of polyclonal immunoglobulins obtained by antigen affinity purification with said antigen of interest, digesting said population of polyclonal immunoglobulins with one or more proteases to obtain peptide fragments of immunoglobulin chain variable regions of said population, and performing mass spectrometry analysis to obtain mass spectra information of said peptide fragments;

(c) correlating the mass spectra information of the peptide fragments obtained in step (b) with the predicted mass spectra information in step (a), identifying nucleic acid sequences encoding immunoglobulin chain variable regions that comprise amino acid sequences corresponding to one or more of said peptide fragments, determining CDR3 regions of the immunoglobulin chain variable regions encoded by the identified nucleic acid sequences; and for the immunoglobulin chain variable region and the CDR3 region encoded by each identified nucleic acid sequence, calculating the amino acid sequence coverage of the immunoglobulin chain variable region by said peptide fragments, and calculating the amino acid sequence coverage of the CDR3 region by said peptide fragments;

(d) selecting nucleic acid sequences having an amino acid sequence coverage of the immunoglobulin chain variable region of at least 60% and an amino acid sequence coverage of the CDR3 region of at least 60% from the identified nucleic acid sequences to obtain nucleic acid sequences or amino acid sequences of immunoglobulin chain variable regions of immunoglobulins that specifically bind to said antigen of interest; and (e) producing an immunoglobulin chain variable region encoded by a nucleic acid sequence obtained in (d), wherein the immunoglobulin chain variable region is a heavy or light chain variable region.

21. The method of claim 20, wherein the immunoglobulin variable regions are heavy chain variable regions.

22. The method of claim 20, wherein the immunoglobulin variable regions are light chain variable regions.

23. The method of claim 20, wherein step (e) comprises:
making a heavy chain variable region and a light chain variable region based on the obtained nucleic acid sequences or amino acid sequences of variable regions of immunoglobulins that specifically bind to said antigen of interest; and
assembling the heavy chain variable region with the light chain variable region to create an antigen binding domain of an immunoglobulin that specifically binds to said antigen of interest.

24. The method of claim 1, 17, 20, or 23, wherein the animal is a human.

25. The method of claim 1, 17, 20, or 23, wherein the animal is a rabbit or a mouse.

26. The method of claim 9, wherein the affinity purification comprises washing with 20% Acetonitrile in PBS pH7.4 wherein molecules that are separated from said antigen of interest by said washing are discarded, and obtaining said purified population of polyclonal immunoglobulins from molecules that remain bound to said antigen of interest after said washing.

27. The method of claim 9, wherein the affinity purification comprises washing with 60% Ethylene glycol in PBS pH7.4 wherein molecules that are separated from said antigen of interest by said washing are discarded, and obtaining said purified population of polyclonal immunoglobulins from molecules that remain bound to said antigen of interest after said washing.

28. The method of claim 9, wherein the affinity purification comprises washing with 2.0M NaCl in PBS pH7.4 wherein molecules that are separated from said antigen of interest by said washing are discarded, and obtaining said purified population of polyclonal immunoglobulins from molecules that remain bound to said antigen of interest after said washing.

29. The method of claim 9, wherein the affinity purification comprises washing with 20% Acetonitrile in PBS pH7.4, washing with 60% Ethylene glycol in PBS pH7.4, and washing with 2.0M NaCl in PBS pH7.4 wherein molecules that are separated from said antigen of interest by said washing steps are discarded, and obtaining said purified population of polyclonal immunoglobulins from molecules that remain bound to said antigen of interest after said washing steps.

30. The method of claim 9, wherein said population of polyclonal immunoglobulins of step (b) is obtained from a blood sample or a fraction thereof of an animal.

31. The method of claim 1, wherein the nucleic acid sequences selected in step (d) have an amino acid sequence coverage of the variable region of at last 60% and an amino acid sequence coverage of the CDR3 region of at least 75%.

32. The method of claim 20, wherein the nucleic acid sequences selected in step (d) have an amino acid sequence coverage of the variable region of at last 60% and an amino acid sequence coverage of the CDR3 region of at least 75%.

* * * * *